United States Patent
Raab et al.

(10) Patent No.: US 10,443,068 B2
(45) Date of Patent: Oct. 15, 2019

(54) PLANTS WITH ENGINEERED ENDOGENOUS GENES

(71) Applicant: Agrivida, Inc., Medford, MA (US)

(72) Inventors: R. Michael Raab, Arlington, MA (US); Michael Lanahan, Cary, NC (US); Christopher Bonin, Colchester, CT (US); Oleg Bougri, Boise, ID (US)

( * ) Notice: Subject to any disclaimer, the term of this patent is extended or adjusted under 35 U.S.C. 154(b) by 43 days.

(21) Appl. No.: 15/420,480

(22) Filed: Jan. 31, 2017

(65) Prior Publication Data

US 2017/0137836 A1      May 18, 2017

Related U.S. Application Data

(63) Continuation of application No. PCT/US2015/052940, filed on Sep. 29, 2015, and a continuation-in-part of application No. 13/793,078, filed on Mar. 11, 2013, now Pat. No. 9,598,700, which is a continuation-in-part of application No. 13/806,654, filed as application No. PCT/US2011/041991 on Jun. 27, 2011, now Pat. No. 9,434,954.

(60) Provisional application No. 62/056,852, filed on Sep. 29, 2014, provisional application No. 61/726,301, filed on Nov. 14, 2012, provisional application No. 61/358,720, filed on Jun. 25, 2010.

(51) Int. Cl.

| | | |
|---|---|---|
| *C12N 15/82* | (2006.01) | |
| *C12N 9/12* | (2006.01) | |
| *A23K 10/30* | (2016.01) | |
| *C12P 19/14* | (2006.01) | |
| *A23K 40/10* | (2016.01) | |
| *A23K 10/10* | (2016.01) | |
| *A23K 10/38* | (2016.01) | |
| *A23K 50/10* | (2016.01) | |
| *A23K 50/75* | (2016.01) | |
| *A23K 50/30* | (2016.01) | |

(52) U.S. Cl.
CPC .......... *C12N 15/8245* (2013.01); *A23K 10/10* (2016.05); *A23K 10/30* (2016.05); *A23K 10/38* (2016.05); *A23K 40/10* (2016.05); *A23K 50/10* (2016.05); *A23K 50/30* (2016.05); *A23K 50/75* (2016.05); *C12N 9/1294* (2013.01); *C12N 15/8218* (2013.01); *C12N 15/8246* (2013.01); *C12P 19/14* (2013.01); *C12Y 207/00* (2013.01); *C12Y 207/09004* (2013.01); *Y02P 60/873* (2015.11)

(58) Field of Classification Search
None
See application file for complete search history.

(56) References Cited

U.S. PATENT DOCUMENTS

| | | | |
|---|---|---|---|
| 5,432,074 A | 7/1995 | Evans et al. | |
| 5,496,714 A | 3/1996 | Comb et al. | |
| 5,654,184 A | 8/1997 | Curtiss et al. | |
| 5,780,708 A | 7/1998 | Lundquist et al. | |
| 5,834,247 A | 11/1998 | Comb et al. | |
| 5,912,415 A | 6/1999 | Olszewski et al. | |
| 5,981,835 A | 11/1999 | Austin-Phillips et al. | |
| 6,013,863 A | 1/2000 | Lundquist et al. | |
| 6,022,846 A | 2/2000 | Van Ooijen et al. | |
| 6,160,208 A | 12/2000 | Lundquist et al. | |
| 6,395,966 B1 | 5/2002 | Mumm et al. | |
| 6,521,816 B1 | 2/2003 | Frohberg | |
| 6,531,316 B1 | 3/2003 | Patten et al. | |
| 6,620,987 B1 * | 9/2003 | Allen ................. | C12N 9/00 435/320.1 |
| 6,800,792 B1 | 10/2004 | Howard et al. | |
| 6,858,775 B1 | 2/2005 | Xu et al. | |
| 7,049,485 B2 | 5/2006 | Sticklen et al. | |
| 7,102,057 B2 | 9/2006 | Lanahan et al. | |
| 7,186,898 B1 | 3/2007 | Kossmann et al. | |
| 7,361,806 B2 | 4/2008 | Lebel et al. | |
| 7,557,262 B2 | 7/2009 | Lanahan et al. | |
| 7,834,146 B2 | 11/2010 | Kovalic et al. | |
| 7,838,732 B2 | 11/2010 | Lebel et al. | |
| 7,855,322 B2 | 12/2010 | Lanahan et al. | |
| 7,906,704 B2 | 3/2011 | Raab et al. | |
| 7,919,681 B2 | 4/2011 | Lanahan et al. | |
| 7,919,682 B2 | 4/2011 | Frohberg et al. | |
| 8,101,392 B2 | 1/2012 | Nielsen et al. | |
| 8,101,393 B2 | 1/2012 | Gray et al. | |
| 8,257,502 B2 | 9/2012 | Frohberg et al. | |

(Continued)

FOREIGN PATENT DOCUMENTS

| | | |
|---|---|---|
| CN | 1564866 | 1/2005 |
| CN | 1726282 | 1/2006 |

(Continued)

OTHER PUBLICATIONS

Mikkelsen et al, 2004, Biochem. J., 377:525-532.*
Guo et al., "Protein tolerance to random amino acid change" PNAS, Jun. 22, 2004, vol. 101, No. 25, pp. 9205-9210.
Gupta et al., "Shoot Multiplication from Mature Trees of Douglas Fir and Sugar Pine" Plant Cell Reports, 1985, vol. 4, pp. 177-179.
Harrison et al., "Accumulation of Recombinant Cellobiohydrolase and Endoglucanase in the Leaves of Mature Transgenic Sugar Cane" Plant Biotechnology Journal, 2011, 9, pp. 884-896.

(Continued)

*Primary Examiner* — Jason Deveau Rosen
(74) *Attorney, Agent, or Firm* — Volpe and Koenig, P.C.

(57) ABSTRACT

Genetically engineered plants expressing altered Glucan Water Dikinase and having elevated levels of starch are provided. Methods of genetically engineering plants to express altered Glucan Water Dikinase, and genetic constructs are provided. Methods of breeding genetically engineered plants homozygous for a mutated gene encoding an altered Glucan Water Dikinase are described. Methods of agricultural processing and animal feed using the genetically engineered plants are also provided.

6 Claims, 14 Drawing Sheets

Specification includes a Sequence Listing.

(56) References Cited

U.S. PATENT DOCUMENTS

| | | | |
|---|---|---|---|
| 8,343,747 B2 | 1/2013 | Burke et al. | |
| 8,420,387 B2 | 4/2013 | Shen et al. | |
| 8,455,715 B2 | 6/2013 | Paul et al. | |
| 8,481,810 B2 | 7/2013 | Lebel et al. | |
| 2003/0159182 A1 | 8/2003 | Tackaberry et al. | |
| 2003/0167533 A1 | 9/2003 | Yadav et al. | |
| 2003/0233675 A1 | 12/2003 | Cao et al. | |
| 2004/0034888 A1 | 2/2004 | Liu et al. | |
| 2004/0096938 A1 | 5/2004 | Xu et al. | |
| 2004/0123343 A1 | 6/2004 | La Rosa et al. | |
| 2005/0125860 A1 | 6/2005 | Raab et al. | |
| 2005/0239728 A1 | 10/2005 | Pachuk et al. | |
| 2005/0283850 A1 | 12/2005 | Snell et al. | |
| 2006/0150278 A1 | 7/2006 | Frohberg | |
| 2006/0236419 A1 | 10/2006 | La Rosa et al. | |
| 2006/0272049 A1 | 11/2006 | Waterhouse et al. | |
| 2007/0192900 A1 | 8/2007 | Sticklen et al. | |
| 2007/0218530 A1 | 9/2007 | Duck et al. | |
| 2007/0250961 A1 | 10/2007 | Blaylock et al. | |
| 2008/0115243 A1 | 5/2008 | Raab et al. | |
| 2008/0220125 A1 | 9/2008 | Abbas et al. | |
| 2009/0119800 A1* | 5/2009 | Lanahan | C12N 9/00 800/284 |
| 2009/0155238 A1 | 6/2009 | Weiner et al. | |
| 2009/0193541 A1 | 7/2009 | Miles | |
| 2009/0258930 A1 | 10/2009 | Pachuk et al. | |
| 2009/0298149 A1 | 12/2009 | Wang et al. | |
| 2009/0320831 A1 | 12/2009 | Lanahan et al. | |
| 2010/0124771 A1 | 5/2010 | Sabesan et al. | |
| 2010/0143967 A1 | 6/2010 | McFarland | |
| 2010/0159494 A1 | 6/2010 | Sweeney et al. | |
| 2010/0159510 A1 | 6/2010 | Raab et al. | |
| 2011/0045127 A1 | 2/2011 | Ral et al. | |
| 2011/0053195 A1 | 3/2011 | Bauer et al. | |
| 2011/0111442 A1 | 5/2011 | Shen et al. | |
| 2012/0040409 A1 | 2/2012 | Hau et al. | |
| 2012/0054915 A1 | 3/2012 | Steffens | |
| 2012/0258503 A1 | 10/2012 | Raab et al. | |
| 2013/0269061 A1 | 10/2013 | Lessard et al. | |

FOREIGN PATENT DOCUMENTS

| | | |
|---|---|---|
| CN | 1777677 | 5/2006 |
| CN | 101910404 | 12/2010 |
| CN | 101979548 | 2/2011 |
| EP | 0602899 | 6/1994 |
| WO | 1997/01642 | 1/1997 |
| WO | 1998/21348 | 5/1998 |
| WO | 2000/011144 | 3/2000 |
| WO | 2000/036093 | 6/2000 |
| WO | 2000/052155 | 9/2000 |
| WO | 2000/071701 | 11/2000 |
| WO | 2001/059091 | 8/2001 |
| WO | 2002/086112 | 10/2002 |
| WO | 2003/050265 | 6/2003 |
| WO | 2003/071860 | 9/2003 |
| WO | 2005/030942 | 4/2005 |
| WO | 2005/095618 | 10/2005 |
| WO | 2005/095619 | 10/2005 |
| WO | 2005/097999 | 10/2005 |
| WO | 2007/146944 | 12/2007 |
| WO | 2008/064314 | 5/2008 |
| WO | 2009/067751 | 6/2009 |
| WO | 2010/060056 | 5/2010 |
| WO | 2010/099134 | 9/2010 |
| WO | 2011057159 | 5/2011 |
| WO | 2011163659 | 12/2011 |

OTHER PUBLICATIONS

Hedge et al., "Single-Step Synthesis of 4-nitrophenyl Ferulate for Spectrophotometric Assay of Feruloyl Esterases" Analytical Biochemistry, 2009, 387(1), pp. 128-129.

Hess et al., "Roadmap for Agricultural Biomass Feedstock Supply in the United States" DOE/NE-ID-11129, Nov. 2003, Revision 1.
Hiei et al., "Efficient Transformation of Rice (*Oryza sativa* L.) mediated by Agrobacterium and sequence analysis of the boundaries of the T-DNA" The Plant Journal, 1994, 6 (2), pp. 271-282.
Higgins, "Synthesis and Regulation of Major Proteins in Seeds" Annual Review of Plant Physiology, 1984, pp. 191-221.
Hirata et al., "Molecular Structure of a Gene, VMA1, Encoding the Catalytic Subunit of H+-Translocating Adenosine Triphosphatase for Vacuolar Membranes of *Saccharomyces cerevisiae*" The Journal of Biological Chemistry, Apr. 25, 1990, vol. 265, No. 12, pp. 6726-6733.
Hood et al., "Commercial Production of Avidin from Transgenic Maize: Characterization of Transformant, Production, Processing, Extraction and Purification" Molecular Breeding, 1997, pp. 291-306.
Hood et al., "Subcellular Targeting is a Key Condition for High-Level Accumulation of Cellulase Protein in Transgenic Maize Seed" Plant Biotechnology Journal, 2007, 5: pp. 709-719.
Horiguchi, "RNA silencing in plants: a shortcut to functional analysis" Differentiation, 2004, 72 (2-3): pp. 65-73.
Horsch et al, "A Simple and General Method for Transferring Genes into Plants" Science, Mar. 1985, pp. 1229-1231.
Horton et al., "Engineering hybrid genes without the use of restriction enzymes: gene splicing by overlap extension" Gene, 1989, vol. 77, 61-68.
Ingram et al., "Enteric Bacterial Catalysts for Fuel Ethanol Production" Biotechnology Progress, 1999, pp. 856-866.
Kane et al., "Protein Splicing Converts the Yeast TFP1 Gene Product to the 69-kD Subunit of the Vacuolar H+-Adenosine Triphosphatase" Science, New Series, Nov. 2, 1990, vol. 250, No. 4981, pp. 651-657.
Kavakli et al., "Generation, characterization, and heterologous expression of wild-type and up-regulated forms of *Arabidopsis thaliana* leaf ADP-glucose pyrophosphorylase" Planta, 2002, vol. 215, pp. 430-439.
Klein et al., "High-Velocity Microprojectiles for Delivering Nucleic Acids Into Living Cells" Nature, May 1987, vol. 327, pp. 70-73.
Klein-Marcuschamer et al., The Challenge of Enzyme Cost in the Production of Lignocellulosic Biofuels, 2012, 109: pp. 1083-1087.
Kötting et al., "STARCH-EXCESS4 Is a Laforin-Like Phosphoglucan Phosphatase Required for Starch Degradation in *Arabidopsis thaliana*" The Plant Cell, Jan. 2009, vol. 21, pp. 334-346.
Komari et al., "Vectors carrying two separate T-DNAs for co-transformation of higher plants mediated by Agrobacterium tumefaciens and segregations of transformants free from selection markers" The Plant Journal, Jul. 1996, 10(1): pp. 165-174.
Krishnan et al., "Mutant resources in rice for functional genomics of the grasses" Plant Physiology, 2009, vol. 149: pp. 165-170.
Lai et al., "Structural Characterization of Human Erythropoietin" The Journal of Biological Chemistry, Mar. 5, 1986, vol. 261, pp. 3116-3121.
Latif et al., "Production of Ethanol and Xylitol from Corn Cobs by Yeasts" Bioresource Technology, vol. 77, 2001, pp. 57-63.
Langeveld, et al., "Development Perspectives of the Biobased Economy: a Review" Crop Science, 2010, 50: S131-S151.
Lee et al., "Enzymatic Saccharification of Woody Biomass Micro/Nanofibrillated by Continuous Extrusion ProcessII: Effect of Hot-Compressed Water Treatment" Bioresource Technology, 2010, 101(24): pp. 9645-9649.
Lindh et al., "Production of the p24 Capsid Protein from HIV-1 Subtype C in *Arabidopsis thaliana* and Daucus carota Using an Endoplasmic Recticulum-Directing SEKDEL sequence in Protein Expression Constructs" Protein Expression and Purification, 2009, 66(1): pp. 46-51.
Linger et al., "Heterologous Expression and Extracellular Secretion of Cellulolytic Enzymes of Zymomonas mobilis" Applied and Environmental Mirobiology, 2010, 76(19): pp. 6360-6369.
Liu et al., "Enhanced Enzymatic Hydrolysis and Structural Features of Corn Stover by FeCl3 Pretreatment" Bioresource technology, 2009, 100(23): pp. 5853-5858.
Lloyd et al., "Leaf starch degradation comes out of the shadows" TRENDS in Plant Science, Mar. 2005, vol. 10, No. 3, (8 pages).

(56) References Cited

OTHER PUBLICATIONS

Lynd et al., "Biocommodity Engineering" Biotechnology Progress, vol. 15, 1999, pp. 777-793.
Majeran, et al., "Functional Differentiation of Bundle Sheath and Mesophyll Maize Chloroplasts Determined by Comparative Proteomics" The Plant Cell, Nov. 2005, vol. 17, 3111-3140.
Mansfield et al., "Substrate and Enzyme Characteristics that Limit Cellulose Hydrolysis" Biotechnology Progress, 1999, vol. 15, pp. 804-816.
Matsumoto et al., "Characterization of Human Glycoprotein (Erythropoietin) Produced in Cultured Tobacco Cells" Plant Molecular Biology, 1995, pp. 1163-1172.
Matsuoka et al., "The promoters of two carboxylases in a C4 plant (maize) direct cell-specific, light-regulated expression in a C3 plant (rice)" The Plant Journal, 1994, vol. 6 (3), pp. 311-319.
McMillan et al., "Enzymatic Conversion of Biomass for Fuels Production" ACS Symposium Series, ISBN13: 9780841229563, pp. 292-324.
Montvalvo-Rodriguez et al., "Autohydrolysis of Plant Polysaccharides Using Transgenic Hyperthermophilic Enzymes" Biotechnology and Bioengineering, 2000, vol. 2, pp. 151-159.
Morassutti et al., "Production of a Recombinant Antimicrobial Peptide in Transgenic Plants Using a Modified VMA Intein Expressing System" FEBS letters, Apr. 2002, vol. 519, Nos. 1-3, pp. 141-146.
Morris et al., "Cloning of the xynB Gene from Dictyoglomus thermophilum Rt46B.1 and Action of the Gene Product on Kraft Pulp" Applied and Envoronmental Microbiology, 1998, vol. 64(5), pp. 1759-1765.
Mosier et al., "Features of Promising Technologies for Pretreatment of Lignocellulosic Biomass" Bioresource Biotechnology, 2005, vol. 96, pp. 673-686.
Murashige et al., "A Revised Medium for Rapid Growth and Bio Assays with Tobacco Tissue Cultures" Physiologia Plantarum; vol. 15, 1962, pp. 473-497.
Negrotto et al., "The Use of Phosphomannose-Isomerase as a Selectable Marker to recover Transgenic Maize plants (*Zea mays* L) via Agrobacterium transformation" Plant Cell Reports, 2000, vol. 19 (8), pp. 798-803.
Niittyla et al., "A previously unknown maltose transporter essential for starch degradation in leaves" Science, Jan. 2, 2004, vol. 303, No. 5654, pp. 87-89.
Obana et al., "Enhanced turnover of transitory starch by expression of up-regulared ADP-glucose pyrophosphorylases in *Arabidopsis thaliana*" Plant Science, 2006, vol. 170, pp. 1-11.
Olsson et al., "Fermentation of lignocellulosic Hydrolysates for Ethanol Production" Enzyme and Microbial Technology, 1996, vol. 18, pp. 312-331.
Oparka et al., "Simple, but Not Branched, Plasmodesmata Allow the Nonspecific Trafficking of Proteins in Developing Tobacco Leaves" Cell, Jun. 1999, vol. 97, pp. 743-754.
Parsons et al., "Transformation of Poplar by Agrobacterium Tumefaciens" Biotechnology, Jun. 1986, vol. 4, pp. 533-536.
Patel et al., "Transgenic Barley Expressing a Fungal Xylanase Gene in the Endosperm of the Developing Grains" Molecular Breeding, 2000, vol. 6, pp. 113-123.
Perler, "InBase: The Intein Database" Nucleic Acids Research, 2002, vol. 30, No. 1, pp. 383,384.
Perler et al., "Protein Splicing Elements; Inteins and Exteins—A Definition of Terms and Recommended Nomenclature" Nucleic Acids Research, Feb. 24, 1994, vol. 22, No. 7, pp. 1125-1127.
Pietrokovski, "Conserved Sequence Features of Inteins (Protein Introns) and Their Use in Indentifying New Inteins and Related Proteins" Protein Science, Aug. 10, 1994, vol. 3, pp. 2340-2350.
Amould et al., 2007, Engineered I-CreI derivatives cleaving sequences from the human XPC gene can induce highly afficient gene correction in mammalian cells, J. Mol. Biol. 371: 49-65.
Amould et al., 2011, The I-CreI meganuclease and its engineered derivatives: Applications from cell modification to gene therapy, Protein Eng. Des. Sel. 24: 27-31.
Belhaj et al., 2013, Plant genome editing made easy: targeted mutagenesis in model and crop plants using the CRISPR/Cas system, Plant Methods 9: 39-48.
Boch and Bonas, 2010, Xanthomonas AvrBs3 family-type III effectors: discovery and function, Annu. Rev. Phytopathol. 48: 419-436.
Cermak et al., 2011, Efficient design and assembly of custom TALEN and other TAL effector-based constructs for DNA targeting, Nucleic Acids Res. 39: e82.
Cong et al., 2013, Multiplex genome engineering using CRISPR/Cas systems, Science 339: 819-823.
Djukanovic et al., 2013, Male-sterile maize plants produced by targeted mutagenesis of the cytochrome P450-like gene (MS26) using a re-designed I-CreI homing endonuclease, The Plant Journal 76: 888-899.
Elkonin and Pakhaomova, 2000, Influence of nitrogen and phosphorus on induction embryogenic callus of sorghum, Plant Cell Tissue and Organ Culture 61: 115-123.
Gao et al., 2005, Agrobacterium tumefaciens-mediated sorghum transformation using a mannose selection, Plant Biotechnology Journal, 3: 591-599.
Garcia-Bustos et al., 1991, Nuclear protein localization., Biochim Biophys Acta 1071: 83-101.
Gasiunas et al., 2012, Cas9-crRNA ribonucleoprotein complex mediates specific DNA cleavage for adaptive immunity in bacteria, Proc Natl Acad Sci U S A. 109 (39): 2579-2586.
Goujon M et al., 2010, A new bioinformatics analysis tools framework at EMBL-EBI, Nucleic acids research July 38 Suppl: W695-9 doi:10.1093/nar/gkq313.
Heath et al., 1997, The structure of I-CreI, a group I intron-encoded homing endonuclease, Nat. Struct. Biol. 4: 468-76.
Jinek et al., 2012, A programmable dual-RNA-guided DNA endonuclease in adaptive bacterial immunity, Science 337: 816-821.
Joung and Sander, 2013, TALENs: a widely applicable technology for targeted genome editing, Nature Reviews (Mol Cell Biol) 14: 49-55.
Kalderon et al., 1984, Sequence requirements for nuclear lócation of simian virus 40 large T antigen, Nature 311: 33-38.
Larkin et al., 2007, ClustalW and ClustalX version 2, Bioinformatics, 23(21): 2947-2948. doi:10.1093/bioinformatics/btm404.
Larson et al., 2013, CRISPR interference (CRISPRi) for sequence-specific control of gene expression, Nat. Protoc. 8(11): 2180-2196.
Leader et al., 1994, Characterisation and expression of a maize U3 snRNA gene, Biochimica et Biophysica Acta 1219: 145-147.
Liang et al., 2014, Targeted mutagenesis in *Zea mays* using TALENs and the CRISPR/Cas System, Journal of Genetics and Genomics 41: 63-68.
Li et al., 2011, TAL nucleases (TALNs): hybrid proteins composed of TAL effectors and FokI DNA-cleavage domain, Nucleic Acids Res. 39: 359-372.
Raikhel, 1992, Nuclear targeting in plants, Plant Physiol 100: 1627-1632.
Rosen et al., 2006, Homing endonuclease I-CreI derivatives with novel DNA target specificities, Nucleic Acids Res. 34: 4791-4800.
Shieh et al., 1993, Nuclear targeting of the maize R protein requires two nuclear localization sequences, Plant Physiology 101: 353-361.
Shukla et al., 2009, Precise genome modification in the crop species *Zea mays* using zinc-finger nucleases, Nature 459: 437-441.
Symington and Gautier, 2011, Double-Strand Break End Resection and Repair Pathway Choice, Annual Review of Genetics. 45: 247-271.
Upadhyay et al., 2014, RNA-guided genome editing for target gene mutations in wheat, Genes, Genomes, Genetics 3: 2233-2238.
Varagona et al., 1992, Nuclear localization signal(s) required for nuclear targeting of the maize regulatory protein Opaque-2, The Plant Cell 4: 1213-1227.
Wagner et al., 1990, Active transport of proteins into the nucleus, FEBS 275: 1-5.
Wright et al., 2005. High-frequency homologous recombination in plants mediated by zinc-finger nucleases, The Plant journal: for cell and molecular biology, 44(4), pp. 693-705.
Yon and Fried, 1989, Precise gene fusion by PCR, Nucleic Acids Res. 17 (12): 4895.

(56) References Cited

OTHER PUBLICATIONS

Poirier, "Green Chemistry Yields a Better Plastic" Nature Biotechnology, vol. 17, Oct. 1999, pp. 960-961.
Puchta et al., "Homologous recombination in plant cells is enhanced by in vivo induction of double strand breaks into DNA by a site-specific endonuclease" Nucleic Acids Research, 1993, vol. 21, No. 22, pp. 5034-5040.
Ransom et al., "Heterologous Acidothermus cellulolyticus 1,4,β-Endoglucanase E1 Produced Within the Corn Biomass converts Corn Stover Into Glucose" Applied Biochemistry and Biotechnology, 2007, vol. 36, pp. 207-220.
Ritte et al., "The starch-related R1 protein is an alpha-glucan, water dikinase" Proc. Natl Acad Sci USA, 2002, vol. 99 (10), pp. 7166-7171.
Rocha-Sosa et al., "Both Developmental and Metabolic Signals Activate the Promoter of a Class I Patatin Gene" The EMBO Journal, 1989, vol. 8, No. 1, pp. 23-29.
Ryan et al., "Genomic Sequence of a 12S Seed Storage Protein from Oilseed Rape" Nucleic Acids Research, 1989, vol. 17, No. 9, p. 3584.
Sakon et al., accession No. GUN1_ACIC1 (3 pages), 1996.
Sasaki et al., "GenBank Accession AP003620," Feb. 16, 2008 [online]; downloaded from http://www.ncbi.nlm.nih.gov/nuccore/AP003620 on Mar. 14, 2012.
Sasaki et al., "GenBank Accession AK103463," Dec. 4, 2008 [online]; downloaded from http://www.ncbi.nlm.nih.gov/nuccore/AK103463 on Mar. 14, 2012.
Satoru et al., "Involvement of alpha-amylase I-1 in starch degradation in rice chloroplasts" Plant and Cell Physiology, Jun. 2005, vol. 46, No. 6, pp. 858-869.
Sattarzadeh et al., "Transgenic maize lines with cell-type specific expression of fluorescent proteins in plastids," Plant Biotechnology Journal, 2010, vol. 8, pp. 112-125.
Scheidig et al., "Downregulation of a chloroplast-targeted beta-amylase leads to a starch-excess phenotype in leaves", Plant Journal, Jun. 2002, vol. 30, No. 5, pp. 581-591.
Schreier et al., "The Use of Nuclear-Encoded Sequences to Direct the Light-Regulated Synthesis and Transport of a Foreign Protein into Plant Chloroplasts" The EMBO Journal, 1985, vol. 4, No. 1, pp. 25-32.
Shen et al., "Engineering a thermoregulated intein-modified xylanase into maize for consolidated lignocellulosic biomass processing" Nature Biotechnology, Nov. 2012, vol. 30 (11), pp. 1131-1138.
Shill et al., "Ionic Liquid Pretreatment of Cellulosic Biomass: Enzymatc Hydrolysis and Ionic Liquid Recycle" Biotechnology and Bioengineering, 2011, 108(3): pp. 511-520.
Shingledecker et al., "Reactivity of the Cysteine Residues in the Protein Splicing Active Center of the *Mycobacterium tuberculosis* RecA Intein" Archives of Biochemistry and Biophysics, Mar. 1, 2000, vol. 375, No. 1, pp. 138-144.
Sikora et al., "Mutagenesis as a Tool in Plant Genetics, Functional Genomics, and Breeding," International Journal of Plant Genomics, 2011, vol. 2011, Article ID 314829, 13 pages.
Sijmons et al., "Production of Correctly Processed Human Serum Albumin in Transgenic Plants" Biotechnology, Mar. 1990, vol. 8, pp. 217-221.
Sivamani et al., "Expression enhancement of a rice polyubiquitin gene promoter" Plant Molecular Biology, 2006, vol. 60, pp. 225-239.
Smeekens "Protein Transport into and Within Chloroplasts" Trends in Biochemical Sciences, Feb. 1990, vol. 15, pp. 73-76.
Smith et al., "Total silencing by intron-spliced hairpin RNAs," Nature, 2000, 407:319-320.
Smith et al., "Starch mobilization in leaves" Journal of Experimental Botany, Jan. 1, 2003, vol. 54, No. 382 pp. 577-583.
Smith and Waterman, "Identification of Common Molecular Subsequences" J. Mol. Biol., 1981, vol. 147, pp. 195-197.
Smith and Zeeman, "Quantification of starch in plant tissues" Nature Protocols, 2006, vol. 1, pp. 1342-1345.
Sowinski et al., "On the mechanism of C4 photosynthesis intermediate exchange between Kranz mesophyll and bundle sheath cells in grasses" Journal of Experimental Botany, Mar. 2008, vol. 59 (6), pp. 1137-1147.
Sreenath et al., "Production of Ethanol from Wood Hydrolyzate by Yeasts" Bioresource Technology, 2000, vol. 72, No. 3, pp. 253-260.
Stahl and Simon, "Gated communities: apoplastic and symplastic signals converge at plasmodesmata to control cell fates" Journal of Experimental Botany, 2013, vol. 64 (17), pp. 5237-5241.
Staub et al., "High-Yield Production of a Human Therapeutic Protein in Tobacco Chloroplasts" Nature Biotechnology, Mar. 2000, vol. 18, pp. 333-338.
Sticklen, "Plant Genetic Engineering for Biofuel Production: Towards Affordable Cellulosic Ethanol" Nature Reviews: Genetics, 2008, vol. 9, pp. 433-443.
Stitt and Zeeman, "Starch turnover: pathways, regulation and role in growth" Current Opinion in Plant Biology, 2012, vol. 15, 282-292.
Stoutjesdijk et al., "hpRNA-mediated targeting of the *Arabidopsis* FAD2 gene gives highly efficient and stable silencing" Plant Physiology, 2002, vol. 129(4), pp. 1723-1731.
Streatfield et al., "Corn as a production system for human and animal vaccines" Vaccine 21, 2003, pp. 812-815.
Sun et al., "Protein Trans-Splicing to Produce Herbicide-Resistant Acetolactate Synthase" Applied and Environmental Microbiology, Mar. 2001, pp. 1025-1029.
Syngenta Participations AG, "International Search Report", PCT/US2008/082336, dated Feb. 17, 2009.
Syngenta Participations AG, "Written Opinion", PCT/US2008/082336, dated Feb. 17, 2009.
Tague et al., "A Short Domain of the Plant Vacuolar Protein Phytohemagglutinin Targets Invertase to the Yeast Vacuole," The Plant Cell, Jun. 1990, vol. 2, pp. 533-546.
Taylor et al., "Dry-Grind Process for Fuel Ethanol by Continuous Fermentation and Stripping" Biotechnology Progress, 2000, vol. 16, pp. 541-547.
Till et al., "Discovery of chemically induced mutations in rice by TILLING" BMC Plant Biol., 2007, vol. 7:19.
Tingey et al., "Glutamine Synthetase Genes of Pea Encode Distinct Polypeptides Which are Differentially Expressed in Leaves, Roots and Nodules" The EMBO Journal, 1987, vol. 6, No. 1, pp. 1-9.
Tokuda et al., "Metazoan cellulase genes from termites: intron/exon structures and sites of expression" Biochimica et Biophysica Acta 1447, (1999), pp. 146-159.
Ulgen et. al., "Bioconversion of Starch Into Ethanol by a Recombinant *Saccharomyces cerevisiae* Strain YPG-AB" Process Biochemistry, 2002, vol. 37, pp. 1157-1168.
UNIPROT, P77853_DICTH, Feb. 1, 1997, pp. 1-4.
Vainstein et al., "Permanent genome modifications in plant cells by transient viral vectors." Trends in Biotechnology, Aug. 2011, vol. 29, No. 8, pp. 363-369.
Van den Broeck et al., Targeting of a foreign protein to chloroplasts by fusion to the transmit peptide from the small subunit of ribulose 1,5-bisphosphate carboxylase, Nature, 1985, vol. 313 (6001), pp. 358-363.
Von Heijne "Towards a Comparative Anatomy of N-Terminal Topogenic Protein Sequences" Journal of Molecular Biology, 1986, vol. 189, pp. 239-242.
Waigmann et al., "Direct functional assay for tobacco mosaic virus cell-to-cell movement protein and identification of a domain involved in increasing plasmodesmal permeability" Proc. Nat'l Acad. Sci. USA, Feb. 1994, vol. 91, pp. 1433-1437.
Wallace et al., "The Curious Case of Protein Splicing: Mechanistic Insights Suggested by Protein Semisynthesis" Protein Science, 1993, vol. 2, pp. 697-705.
Wang et al., "Identification of an Unusual Intein in Chloroplast CipP Protease of Chlamydomonas Eugametos" Journal of Biological Chemistry, May 2, 1997, vol. 272, No. 18, pp. 11869-11873.
Warthmann et al., "Highly Specific Gene Silencing by Artificial miRNAs in Rice" PLoS ONE, 2008, vol. 3, Issue 3, e1829, pp. 1-10.
Wehrkamp-Richter et al., "Characterisation of a new reporter system allowing high throughput in planta screening for recombination events before and after controlled DNA double strand break induction" Plant Physiology and Biochemistry, 2009, vol. 47, 248-255.

(56) References Cited

OTHER PUBLICATIONS

Biswas, et al., "Expression of Biologically Active Acidothermus cellulolyticus Endoglucanase in Transgenic Maize Plants" Plant Science, 2006, pp. 617-623.
Borkhardt et al., "Autohydrolysis of Plant Xylans by Apoplastic Expression of Thermophilic Bacterial Endo-Xylanases" Plant Biotechnology Journal, 2010, vol. 8, pp. 363-374.
Herbers et al., "A Thermostable Xylanase from Clostridium thermocellum Expressed at High Levels in the Apoplast of Transgenic Tobacco Has No Detrimental Effects and Is Easily Purified" Nature Biotechnology, 1995, vol. 13, pp. 63-66.
Hyunjong et al., "Dual Targeting of Xylanase to Chloroplasts and Peroxisomes as a Means to Increase Protein Accumulation in Plant Cells" Journal of Experimental Botany, 2006, vol. 57 (1), pp. 161-169.
Ishida et al., "High Efficiency Transformation of Maize (*Zea mays* L.) Mediated by Agrobacterium Transformation" Nature Biotechnology, 1996, vol. 14, pp. 745-750.
Ishida et al., "Agrobacterium-Mediated Transformation of Maize" Nature Protocols, 2007, vol. 2(7), pp. 1614-1621.
Kimura et al., "Stable Expression of a Thermostable Xylanase of Clostridium thermocellum in Cultured Tobacco Cells" Journal of Bioscience and Bioengineering, 2003, vol. 95(4), pp. 397-400.
Oraby et al., "Enhanced Conversion of Plant Biomass Into Glucose Using Transgenic Rice-Produced Endoglucanase for Cellulosic Ethanol" Transgenic Research, 2007, vol. 16, pp. 739-749.
Park et al., "Enhancement of Growth and Cellulose Accumulation by Overexpression of Xyloglucanase in Poplar" FEBS Letters, 2004, vol. 564, pp. 183-187.
Sainz, "Commercial Cellulosic Ethanol: The Role of Plant-Expressed Enzymes" In Vitro Cellular and Developmental Biology, 2009, vol. 45: 314-329.
Shimamoto et al., Fertile Transgenic Rice Plants Regenerated from Transformed Protoplasts, Nature, vol. 338, Mar. 1989, pp. 274-276.
Verma, et al., "Microwave Assisted Pretreatment of Woody Biomass with Ammonium Molybdate Activated by H2O2" Bioresource Technology, 2011, vol. 102(4), pp. 3941-3945.
Weise et al., "Engineering starch accumulation by manipulation of phosphate metabolism of starch," Plant Biotechnology Journal, 2012, 10(5): 545-554.
Wenzler et al., "Analysis of a Chimeric Class-I Patatin-GUS Gene in Transgenic Potato Plants: High-Level Expression in Tubers and Sucrose-Inducible Expressions in Cultured Leaf and Stem Explants" Plant Molecular Biology, 1989, vol. 12, pp. 41-50.
Wilson et al., GenBank Accession AC203259 [online]; downloaded from http://www.ncbi.nlm.nih.gov/nuccore/AC203259 on May 5, 2007.
Wolf et al., "Movement protein of Tobacco Mosaic Virus Modifies Plasmodesmatal Size Exclusion Limit" Science, New Series, Oct. 1989, vol. 246 (4928), pp. 377-379.
Wood et al., "Optimized Single-Step Affinity Purification with a Self-Cleaving Intein Applied to Human Acidic Fibroblast Growth Factor" Biotechnology Progress, 2000, vol. 16, pp. 1055-1063.
Wright et al., "High-frequency homologous recombination in plants mediated by zinc-finger nucleases" The Plant Journal, 2005, vol. 44, pp. 693-705.
Wu et al., "Modes of intercellular transcription factor movement in the *Arabidopsis* apex" The Company of Biologists Ltd., 2003, vol. 130, pp. 3735-3745.
Wyman et al., "Coordinated Development of Leading Biomass Pretreatment Technologies" Bioresource Biotechnology, 2005, vol. 96, pp. 1959-1966.
Xie et al., accession No. AM181054 (also known as Q2P9Q1) (2 pages), Dec. 31, 2005.
Xu et al., "In Vitro Protein Splicing of Purified Precursor and the Identification of Branched Intermediate" Cell, Dec. 31, 1993, vol. 75, pp. 1371-1377.
Xu et al., "The Mechanism of Protein Splicing in its Modulation by Mutation" The EMBO Journal, 1996, vol. 15, No. 19, pp. 5146-5153.

Xu et al., "RNA Interference of Plant MAPK Cascades for Functional Studies" Methods in Molecular Biology, 2014, vol. 1171, pp. 91-103.
Xu and Cheng, "Pretreatment of Switchgrass for Sugar Production with the Combination of Sodium Hydroxide and Lime" Bioresource Technology, 2011, vol. 102(4), pp. 3861-3868.
Yang et al., "Intein-mediated assembly of a functional β-glucuronidase in transgenic plants", PNAS, 2003, vol. 100, No. 6, pp. 3513-3518.
Yang, et al., "Expression of Xylanase with High Specific Activity from Streptomyces olivaceoviridis A1 in Transgenic Potato Plants (*Solanum tuberosum* L.)" Biotechnology Letters, 2007, vol. 29: pp. 659-667.
Yu et al., "The *Arabidopsis* sex1 Mutant Is Defective in the R1 Protein, a General Regulator of Starch Degradation in Plants, and Not in the Chloroplast Hexose Transporter" The Plant Cell, Aug. 2001, vol. 13, pp. 1907-1918.
Yukoh Hiei and Toshihiko Komari, "Improved Protocols for Transformation of Indica Rice Mediated by Agrobacterium tumefaciens" Plant Cell Tissue and Organ Culture, 2006, vol. 85, pp. 271-283.
Zeidler et al., "Temperature Sensitive Control of Protein Activity by Conditionally Splicing Intein" Nat Biotech, 2004, vol. 22, pp. 871-876.
Ziegler, M.T. et al. "Accumulation of Thermostable Endo-1,4-β-D-Glucanase in the Apoplast of *Arabidposis thaliana* Leaves" Molecular Breeding, 2000, vol. 6, pp. 37-46.
Zeng et al., "Biological Pretreatment of Wheat Straw by Phanerochaete chrysosporium Supplemented with Inorganic Salts" Bioresource Technology, 2011, vol. 102(3), pp. 3206-3214.
Zhang et al., "A greedy algorithm for aligning DNA sequences" Journal of Computational Biology, 2000, vol. 7(1-2), pp. 203-214.
Ziegelhoffer et al., "Expression of Bacterial Cellulase Genes in Transgenic Alfalfa (*Medicago sativa* L.), potato (*Solanum tuberosum* L.) and tobacco (*Nicotiana tabacum*)" Molecular Breeding, 1999, vol. 5, pp. 309-318.
Ziegelhoffer et al., "Dramatic effects of truncation and sub-cellular targeting on the accumulation of recombinant microbial cellulase in tobacco" Molecular Breeding, 2001, vol. 8, pp. 147-158.
Ziegler et al., "Accumulation of a Thermostable Endo-1,4-β-D-glucanase in the Apoplast of *Arabidopsis thaliana* Leaves" Molecular Breeding, 2000, vol. 6, pp. 37-46.
Zhu et al., "Structural Features Affecting Biomass Enzymatic Digestability" Bioresource Biotechnology, 2008, vol. 99, pp. 3817-3828.
Zhu et al., "Pretreatment of Woody Biomass for Biofuel Production: Energy Efficiency, Technologies, and Recalcitrance" Applied Microbiology & Biotechnology, 2010, vol. 87(3), pp. 847-857.
International Search Report and Writton Opinion issued in PCT/US2015/52940.
Belhaj et al., "Plant genome editing made easy: targeted mutagenesis in model and crop plants using the CRISPR/Cas system" Plant Methods, 2013, vol. 9:39, 10 pages.
GenBank: Z29641.1, "*Zea mays* of U5E gene encoding U3snRNA" Nov. 15, 2007, (2 pages).
Abramson et al., "Plant Cell Wall Reconstruction Toward Improved Lignocellulosic Production and Processability" Plant Science, 2010, 178: pp. 61-72.
Altintas, "Improvement of Ethanol Production from Starch by Recombinant Yeast Through Manipulation of Environmental Factors" Enzyme and Microbial Technology, 2002, vol. 31, No. 5, pp. 640-647.
Alvira et al., "Pretreatment technologies for an efficient bioethanol production process based on enzymatic hydrolysis: A review" Bioresource Technology, 2010, vol. 101, pp. 4851-4861.
An et al., "Reverse genetic approaches for functional genomics of rice" Plant Molecular Biology, 2005, vol. 59, pp. 111-123.
Aspegren et al., "Secretion of Heat-Stable Fungal β-Glucanase from Transgenic, Suspension-Cultured Barley Cells" Molecular Breeding, 1995, pp. 91-99.
Banerjee and Scott-Craig, "Improving Enzymes for Biomass Conversion: A Basic Research Perspective" BioEnergy Research, 2010, 3: pp. 82-92.
Belknap et al., "pBINPLUS/ARS: an improved plant transformation vector based on pBINPLUS" BioTechniquies, May 2008, 44, pp. 753-756.

(56) References Cited

OTHER PUBLICATIONS

Birch, R.G., "Plant Transformation: Problems and Strategies for Practical Application" Annual Review of Plant Physiology and Plant Molecular Biology, Jun. 1997, vol. 48, pp. 297-326.
Bird et al., "The Tomato Polygalacturonase Gene and Ripening-Specific Expressions in Transgenic Plants" Plant Molecular Biology, 1988, pp. 651-662.
Brederode et al., "Complete Nucleotide Sequence of Alfalfa Mosaic Virus RNA 4" Nucleic Acids Research, 1980, vol. 8, No. 10, pp. 2213-2223.
Broothaerts et al., "Gene Transfer to Plants by Diverse Species of Bacteria" Nature, Feb. 2005, vol. 433, pp. 629-633.
Brunecky et al., "In planta Expression of A. celluloticus Cel5A Endocellulase Reduces Cell Wall Recalcitrance in Tobacco and Maize" Biotechnology for Biofuels, 2011, 4: 1-10.
Cameron et al., "Metabolic Engineering of Propanediol Pathways" Biotechnology Progress, 1998, pp. 116-125.
Chen et al., "Herbicide resistance from a divided EPSPS protein: the split Synechocytis DnaE intein as an in vivo affinity domain" Gene 263, (2001) p. 39-48.
Chen et al., "Identification of evolutionarily conserved amino acid residues in homeodomain of KNOX proteins for intercellular trafficking" Plant Signaling & Behavior 9, e28355, Feb. 2014, Landes Bioscience.
Cheon et al., "Ovexpression of Human Erythropoietin (EPO) Affects Plant Morphologies: Retarded Vegetative Growth in Tobacco and Male Sterility in Tobacco and *Arabidopsis*" Transgenic Research, 2004, pp. 541-549.
Chi-Ham et al., "The intellectual property landscape for gene suppression technologies in plants" Nature Biotechnology, Jan. 2010, vol. 28, No. 1, pp. 32-36.
Chih-Ching et al., "Establishment of an Efficient Medium for Anther Culture of Rice Through Comparative Experiments on the Nitrogen Sources" Scientia Sinica, 1975, vol. 18, No. 3, pp. 659-668.
Chin et al., "Single-column purification of free recombinant proteins using a self-cleavable affinity tag derived from a protein splicing element" Gene: An International Journal of Genes and Genomes, 1997, vol. 192, pp. 271-291.
Chin et al., "Protein trans-splicing in transgenic plant chloroplast: Reconstruction of herbicide resistance from split genes" PNAS, 2003, vol. 100, No. 8, pp. 4510-4515.
Chong et al., "Modulation of Protein Splicing of the *Saccharomyces cerevisiae* Vacuolar Membrane ATPase Intein" Journal of Biological Chemistry, Apr. 24, 1998, vol. 273, No. 17, pp. 10567-10577.
Chong et al., "Single-column purification of free recombinant proteins using a self-cleavable affinity tag derived from a protein splicing element" Gene: An International Journal of Genes and Genomes, 1997, vol. 192, pp. 271-281.
Christian et al, "The yield and composition of switchgrass and coastal panic grass grown as a biofuel in Southern England" Bioresource Technology 83, 2002, pp. 115-124.
Christian et al., "Targeting DNA Double-Strand Breaks with TAL Effector Nucleases" Genetics, Oct. 2010, vol. 186, pp. 757-761.
Clarke, "A Proposed Mechanism for the Self-Splicing of Proteins" Proceedings of the National Academy of Science, USA, Nov. 1994, vol. 91, pp. 11084-11088.
Coruzzi et al., "Tissue-Specific and Light-Regulated Expression of Pea Nuclear Gene Coding the Small Subunit of Ribulose-1, 5-Bisphosphate Carboxylase" The EMBO Journal, 1984, pp. 1671-1679.
Crawford and Zambryski, "Subcellular localization determines the availability of non-targeted proteins to plasmodesmatal transport" Current Biology 2000, Aug. 2000, (10), pp. 1032-1040.

Dai et al., "Expression of Acidothermus Cellulolyticus Endoglucanase E1 in Transgenic Tobacco: Biochemical Characteristics and Physiological Effects" Transgenic Research, 2000, pp. 43-54.
Dai et al., Improved Plant-Based Production of E1 Endoglucanase Using Potato: Expression Optimization and Tissue Targeting, Molecular Breeding, 2000, pp. 277-285.
Dale, "Biobased Industrial Products: Bioprocess Engineering When Costs Really Count" Biotechnology Progress, 1999, pp. 775-776.
Davis et al., "Protein Splicing: The Lengths Some Proteins Will Go to" Antonie van Leeuwenhoek, 1995, vol. 67, pp. 131-137.
Davis et al., "Novel Structure of the recA Locus of *Mycobacterium tuberculosis* Implies Processing of the Gene Product" Journal of Bacteriology, Sep. 1991, vol. 173, No. 18, pp. 5653-5662.
Davis et al., "Protein Splicing in the Maturation of M. Tuberculosis RecA Protein: A Mechanism for Tolerating a Novel Class of Intervening Sequence" Cell Press, Oct. 16, 1992, vol. 71, pp. 201-210.
Derbyshire et al., "Lightning Strikes Twice: Intron-Intein Coincidence" Proceedings of the National Academy of Science, USA, Feb. 17, 1998, vol. 95, pp. 1356-1357.
Dodd and Cann, "Enzymatic Deconstruction of Xylan for Biofuel Production" Global Change Biology Bioenergy, 2009, 1(1):2-17.
Echeverria and Boyer, "Localization of Starch Biosynthetic and Degradative Enzymes in Maize Leaves" American Journal of Botany, Feb. 1986, vol. 73 (2), pp. 167-171.
Edwards et al., "Compartmentation of photosynthesis in cells and tissues of C4 plants" Journal of Experimental Botany, Apr. 2001, vol. 52 (356) 577-590.
Evans et al., "Semisynthesis of Cytotoxic Proteins Using a Modified Protein Splicing Element" Protein Science, 1998, vol. 7: pp. 2256-2264.
Fernando et al., "Biorefineries: Current Status, Challenges, and Future Direction" Energy & Fuels, 2006, pp. 1727-1737.
Frizzi et al., "Tapping RNA silencing pathways for plant biotechnology" Plant Biotechnology Journal, 2010, vol. 8, pp. 655-677.
Galbe et al., "A Review of the Production of Ethanol from Softwood" Applied Microbiology Biotechnology, 2002, 59, pp. 618-628.
Gangopadhyay et. al., "In Vitro Splicing of Erythropoietin by the *Mycobacterium tuberculosis* RecA Intein Without Substituting Amino Acids at the Splice Junctions" Biochimica et Biophysica Acta, 2003, vol. 1619, pp. 193-200.
GenBank accession No. BAA33708, first available Oct. 8, 1999 (1 page).
Gimble, "Invasion of a Multitude of Genetic Niches by Mobile Endonuclease Genes" FEMS Microbiology Letters, Feb. 8, 2000, vol. 185, pp. 99-107.
Goodwin, "Molecular size limit for movement in the symplast of the Elodea leaf" Planta, 1983, (157), pp. 124-130.
Gordon-Kamm et al., "Transformation of Maize Cells and Regeneration of Fertile Transgenic Plants" The Plant Cell, Jul. 1990, vol. 2, pp. 603-618.
Gray et al., "Global and Grain-Specific Accumulation of Glycoside Hydrolase Family 10 Xylanases in Transgenic Maize (*Zea mays*)" Plant Biotechnology Journal, 2011, 9, pp. 1100-1108.
Grennan, "Regulation of Starch Metabolism in *Arabidopsis* Leaves" Plant Physiology, Dec. 2006, vol. 142, No. 4, pp. 1343-1345.
Gudesblat et al., "Guard cell-specific inhibition of *Arabidopsis* MPK3 expression causes abnormal stomatal responses to abscisic acid and hydrogen peroxide" New Phytologist, 2007, vol. 173, pp. 713-721.
Guilley et al., "Transcription of Cauliflower Mosaic Virus DNA: Detection of Promoter Sequences, and Characterization of Transcripts" Cell, Oct. 1982, vol. 30, pp. 763-773.

\* cited by examiner

PLANTS WITH ENGINEERED ENDOGENOUS GENES

CROSS REFERENCE TO RELATED APPLICATIONS

This application is a continuation of international patent application No. PCT/US15/52940, filed Sep. 29, 2015, which claims the benefit of U.S. provisional application No. 62/056,852, filed Sep. 29, 2014. This application is also a continuation-in-part of U.S. patent application Ser. No. 13/793,078, filed Mar. 11, 2013, which claims the benefit of U.S. provisional application No. 61/726,301, filed Nov. 14, 2012. U.S. patent application Ser. No. 13/793,078 is a continuation-in-part of U.S. patent application Ser. No. 13/806,654, filed Mar. 19, 2013, issued on Sep. 6, 2016 as U.S. Pat. No. 9,434,954, a 35 U.S.C. 371 national stage application of international patent application No. PCT/US11/041991, filed Jun. 27, 2011, which claims the benefit of U.S. provisional application No. 61/358,720, filed Jun. 25, 2010. All of these applications are incorporated herein by reference as if fully set forth.

GOVERNMENT SUPPORT STATEMENT

This invention was made with government support under award number DE-AR0000042 awarded by the Advanced Research Projects Agency-Energy, ARPA-E. The government has certain rights in the invention.

The sequence listing electronically filed with this application titled "Sequence Listing," which was created on Jan. 31, 2017 and had a size of 159,716 bytes is incorporated by reference herein as if fully set forth.

FIELD

The disclosure herein relates to genetically improved plants having optimized endogenous nucleic acid sequences encoding altered glucan water dikinase, and having elevated levels of starch. The disclosure also relates to optimized nucleic acids encoding altered glucan water dikinase, methods of optimizing endogenous nucleic acids, methods of increasing starch levels in plants, and methods of making and propagating the genetically improved plants.

BACKGROUND

Plants synthesize starch in vegetative tissues during the daytime and degrade the starch at night to mobilize the resulting sugar in order to support the energy needs of the plant. Vegetative plant cells express a series of enzymes to initiate mobilization of transitory starch during the nighttime. Glucan Water Dikinase ("GWD"), which phosphorylates starch is one of these enzymes. GWD transcript levels were shown to undergo diel fluctuation (Smith et al. Plant Phys. Preview, Apr. 29, 2014). Increasing the starch content of biomass can increase the energy content (calories) in animal feed or improve glucose extraction from biomass for the production of ethanol or other biochemicals.

Different molecular methods exist for manipulating plant characteristics. Almost all of these methods rely on inserting new, synthetic or recombinant nucleic acids into a plant through the process of transformation. The nucleic acids thus inserted may encode a ribonucleic acid (RNA) or protein, which is expressed by the transformed plant and thereby changes the plant phenotype. In many cases, the nucleic acid may encode a heterologous protein or produce more of an endogenous protein. Similarly, the transformed nucleic acids may produce RNA that through a variety of mechanisms (such as RNA interference, antisense RNA, etc.) reduce expression of an endogenous gene thereby "silencing" the gene and production of its product. In all cases the nucleic acid inserted into the plant is expressed in a dominant manner; that is, its presence has a direct effect on the plant's characteristics. More recently, it has been demonstrated that by expressing nucleic acids that encode deoxyribonucleic acid (DNA) altering proteins (such as nucleases) in an organism, the organism's genome can be permanently altered, even after the inserted nucleic acids have been removed, and endogenous genes optimized. In this way it is possible to not only generate beneficial dominant traits, but also generate very specific, targeted mutations as the basis to create beneficial recessive traits, which would have been otherwise extremely difficult to find and develop for commercial applications. Currently there are no recessive traits created using nucleases in commercial use in row crops. Recessive traits generated using nucleases have been previously demonstrated in plants and plant cells, but never in fully developed, multicellular corn and *sorghum* plants, including hybrid corn and *sorghum*. Like dominant traits, recessive traits may have commercial value and may have specific commercial advantages (security and regulatory benefits in particular) over dominant traits. Such recessive traits will require new methods of propagating, tracking, and delivering the trait, particularly in hybrid crops.

One problem with dominant traits, particularly in hybrid and cross-pollinating crops, such as corn, is that they can be readily transferred to other lines of the same species. In regions of the world where farmers generate at least part of their own seed for planting, this affords the opportunity to breed a dominant trait into a farmer's existing lines, without paying the technology owner. The established trait business model currently requires seed and trait purchasers to pay the trait provider a royalty and licenses commonly limit use of the trait to a single planting and prohibit breeding. For many traits, monitoring unlicensed breeding is nearly impossible, and substantial unlicensed trait transfer (pirating) of traits occurs in some parts of the world. Depending on the trait, pirating or transferring the trait into a useable line without paying the technology owner can be an easy task and difficult for technology providers to detect. For example, pest resistance or agronomic traits, that do not require any other materials for their use, such as an herbicide resistance or specific fertilizer, are nearly impossible to detect if they have been transferred into a different line. Subsequent generations can be generated and tracked by a breeder using commercially available test strips or phenotypically if the trait confers an easily scorable phenotype. Because the trait is dominant, it may not need to be homozygous in the progeny for farmers to use it, and thereby enables easy continued breeding and use outside of the technology licensor's awareness.

In contrast to dominant traits, a recessive trait needs to be homozygous in the crop in order to phenotypically observed or easily scored. Simple test strips may not be available to track the molecular basis of the trait, and accurate breeding of a recessive trait made through the use of a nuclease may require at least polymerase chain reaction (PCR) to detect. In this case, none of the progeny resulting from an outcross of the homozygous parent carrying the trait will display the trait and extended breeding, tracking, and in some cases hybrid crosses will be required to use such a trait. This makes pirating of the technology considerably more expensive and difficult than with dominant traits. The process of making, maintaining, and providing a recessive trait requires additional steps not necessary in the production of dominant traits, and therefore requires the use of novel processes in seed and trait production.

Recessive traits that are based on optimized genes containing a specific genetic mutation may also have regulatory advantages over dominant traits made using transgenic technologies. Because such a recessive trait may not contain any newly introduced heterologous DNA, in many parts of the world it may not be regulated as a transgenic crop.

SUMMARY

In as aspect, the invention relates to a genetically engineered plant comprising an engineered nucleic acid encoding an altered Glucan Water Dikinase, wherein the plant has an elevated level of starch in comparison to a plant of the same genetic background comprising a wild type Glucan Water Dikinase.

In an aspect the invention relates to a method for genetically engineering a plant to comprise an altered Glucan Water Dikinase. The method comprises contacting at least one plant cell comprising a target sequence in an endogenous gene encoding a Glucan Water Dikinase with a vector comprising a first nucleic acid encoding a nuclease capable of inducing a double-strand break at the target sequence. The method also comprises selecting a plant cell that includes an alteration in the target sequence. The method also comprises regenerating a genetically engineered plant including the alteration from the plant cell.

In an aspect, the invention relates to a method of increasing a starch level in a plant. The method comprises expressing a nucleic acid encoding a nuclease capable of inducing a double-strand break at a target sequence, where the target sequence is a sequence in an endogenous gene encoding a Glucan Water Dikinase. The method also comprises selecting a homozygous plant that comprises an alteration in the target sequence and has an elevated level of starch in comparison to a plant of the same genetic background comprising a wild type Glucan Water Dikinase.

In an aspect, the invention relates to a method of agricultural processing. The method comprises expressing a nucleic acid encoding a nuclease capable of inducing a double-strand break at the target sequence, where the target sequence is a sequence in an endogenous gene encoding a Glucan Water Dikinase. The method may comprise selecting a homozygous plant that includes an alteration in the target sequence and has an elevated level of starch in comparison to a plant of the same genetic background comprising a wild type Glucan Water Dikinase. The method may also comprise processing the homozygous plant.

In an aspect, the invention relates to a method of preparing animal feed. The method comprises expressing a nucleic acid encoding a nuclease capable of inducing a double-strand break at the target sequence, where the target sequence is a sequence in an endogenous gene encoding a Glucan Water Dikinase. The method may comprise selecting a homozygous plant that includes an alteration in the target sequence and has an elevated level of starch in comparison to a plant of the same genetic background comprising a wild type Glucan Water Dikinase. The method may also comprise performing at least one procedure selected from the group consisting of: harvesting, bailing, shredding, drying, ensiling, pelletizing, combining with a source of edible fiber fiber, and combining with plant biomass.

In an aspect, the invention relates to a method for producing a genetically engineered plant homozygous for an engineered nucleic acid that encodes an altered Glucan Water Dikinase comprising performing any one of the method for genetically engineering a plant comprising an altered Glucan Water Dikinase described herein.

In an aspect, the invention relates to a synthetic nucleic acid promoter having a sequence with at least with at least 70, 72, 75, 80, 85, 90, 91, 92, 93, 94, 95, 96, 97, 98, 99, or 100% identity to a reference sequence selected from the group consisting of: SEQ ID NO: 78 (MzU3.8), SEQ ID NO:79 (ZmU3), SEQ ID NO: 82 (ZmU3P1), SEQ ID NO: 84 (ZmU3P2) and SEQ ID NO: 86 (MzU3.8P).

In an aspect, the invention relates to a genetic construct comprising a first engineered nucleic acid sequence encoding a Cas9 nuclease. The Cas9 nuclease is capable of cleaving a target sequence included in an endogenous nucleic acid encoding Glucan Water Dikinase in a plant.

In an aspect, the invention relates to a kit for identifying a modified sequence of an endogenous gene encoding Glucan Water Dikinase in a sample. The kit comprises first primer and a second primer. The first primer and the second primer are capable of amplifying a target sequence included in the endogenous gene encoding Glucan Water Dikinase. The target sequence comprises a nucleic acid sequence with at least 90% identity to a reference sequence selected from SEQ ID NOS: 1-4, 75, 170-184 186, 187, 189-193. The kit may also comprise one or more component for detecting at a modification in the amplified region of the target sequence. The modification may be a modified sequence of an endogenous gene encoding Glucan Water Dikinase in any of genetically engineered plants described herein.

In an aspect, the invention relates to a method of identifying a modified sequence of an endogenous gene encoding Glucan Water Dikinase in a sample. The method comprises contacting a sample with a first primer and a second primer. The method comprises amplifying a target sequence included in the endogenous gene encoding Glucan Water Dikinase. The target sequence comprises a nucleic acid sequence with at least 90% identity to a reference sequence selected from SEQ ID NOS: 1-4, 75, 170-184 186, 187, 189-193. The method also comprises detecting modification of the target sequence. The modification may be a modified sequence of an endogenous gene encoding Glucan Water Dikinase in any of genetically engineered plants described herein.

BRIEF DESCRIPTION OF THE DRAWINGS

The following detailed description of embodiments of the present invention will be better understood when read in conjunction with the appended drawings. For the purpose of illustration, there are shown in the drawings particular embodiments. It is understood, however, that the invention is not limited to the precise arrangements and instrumentalities shown. In the drawings.

DETAILED DESCRIPTION

Figure 1:
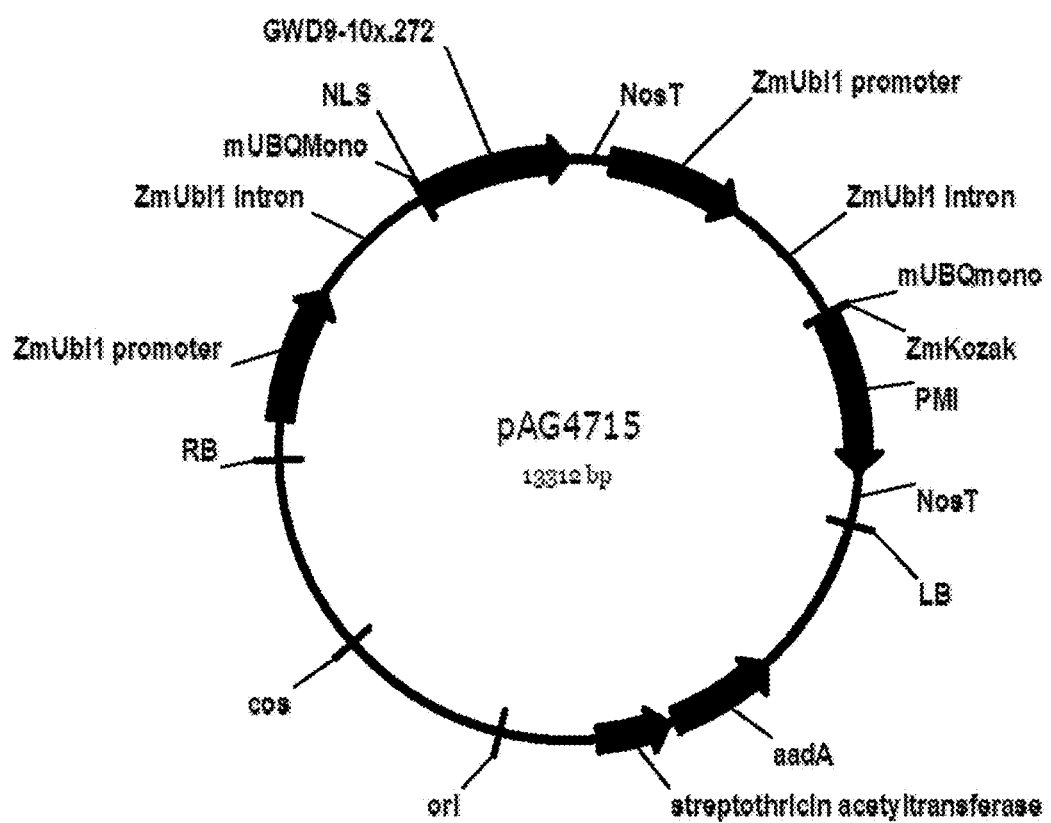
FIG. 1 illustrates the vector pAG4715 for expressing meganuclease.

Certain terminology is used in the following description for convenience only and is not limiting.

"Engineered nucleic acid sequence," "engineered polynucleotide," "engineered oligonucleotide," "engineered DNA," or "engineered RNA" as used herein refers to a nucleic acid, polynucleotide, oligonucleotide, DNA, or RNA that differs from one found in nature by having a different sequence than one found in nature or a chemical modification not found in nature. The engineered nucleic acid sequence," "engineered polynucleotide," "engineered oligonucleotide," "engineered DNA," or "engineered RNA" may be a synthetic nucleic acid sequence, synthetic polynucleotide, synthetic oligonucleotide, synthetic DNA, or synthetic RNA. The definition of engineered nucleic acid includes but is not limited to a DNA sequence created using biotechnology tools. Such tools include but are not limited to recombinant DNA technology, chemical synthesis, or directed use of nucleases (so called "genome editing" or "gene optimizing" technologies).

"Endogenous nucleic acid" as used herein refers to a nucleic acid, polynucleotide, oligonucleotide, DNA, or RNA naturally occurring in the organism or the genome. An endogenous nucleic acid may be an endogenous gene.

"Altered protein" as used herein refers to a protein, polypeptide, oligopeptide or peptide that contains at least one amino acid change, or deletion compared to the amino acid sequence contained in a naturally occurring organism, e.g., a parent organism. An altered protein may retain or lack the biological activity of the original sequence.

As used herein, "operably linked" refers to the association of two or more biomolecules in a configuration relative to one another such that the function of the biomolecules can be performed. In relation to two or more nucleotide sequences, "operably linked" refers to the association of the nucleic acid sequences in a configuration relative to one another such that the function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer sequence is operably linked to a coding sequence if it affects the transcription of the coding sequence; and a nucleic acid ribosome binding site is operably linked to a coding sequence if it is positioned so as to facilitate binding of the ribosome to the nucleic acid.

As used herein, genetic background is defined as the sum of all genes, or a collection of specific genes (e.g., all genes but for an engineered genetic modification) in a plant. Plants of the same species may be referred to as plants having the same genes or the same genetic background. A genetically engineered plant may include an engineered nucleic acid or polynucleotide described herein but otherwise have the same genes as non-genetically engineered plant of the same genetic background.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

An embodiment comprises a genetically engineered plant comprising an engineered nucleic acid encoding an altered Glucan Water Dikinase. The genetically engineered plant may have an elevated level of starch in comparison to a plant of the same genetic background but comprising a wild type (wt) GWD. The activity of the altered GWD may be reduced in comparison to wild type (wt) GWD included in a plant of the same genetic background. The level of reduction may be 20, 30, 40, 50, 60, 70, 80, 90, 91, 92, 93, 94, 95, 96, 97, 98, 99, or 100% based on the level of wt GWD. Activity of GWD may be tested by monitoring starch content in plants, for example, by using Fourier Transform Near-infrared (FT-NIR) Technique as described in Example 3 herein. The altered GWD may be inactive. Increased levels of starch indicate reduced GWD activity.

In an embodiment, the engineered nucleic acid in the genetically engineered plant may comprise an endogenous nucleic acid that includes at least one allele of a gwd gene encoding a GWD protein but having one or more modifications in comparison to the wild type plant. The modifications may be made made by genetic engineering of the plant or its ancestors. The endogenous nucleic acid may be one or more allele of the gwd gene in the engineered plant. The modifications may be in the gwd coding sequences. The endogenous nucleic acid may comprise, consist essentially of, or consist of a sequence with at least 70, 72, 75, 80, 85, 90, 91, 92, 93, 94, 95, 96, 97, 98, 99 or 100% identity to a reference sequence selected from SEQ ID NO: 1 (Zm GWD coding sequence) or SEQ ID NO: 2 (Sb GWD coding sequence). The engineered nucleic acid may include at least one mutation relative to the endogenous nucleic acid. A mutation may include an insertion of one or more nucleotides in comparison to the endogenous nucleic acid. A mutation may include a deletion of nucleotides in comparison to the native nucleic acid. A mutation may include a substitution of one or more nucleotides in comparison to the endogenous nucleic acid. A mutation may be a combination of several mutations. The at least one mutation may be within a target sequence with at least 70, 72, 75, 80, 85, 90, 91, 92, 93, 94, 95, 96, 97, 98, 99 or 100% identity to a reference sequence selected from SEQ ID NO: 1 (Zm GWD coding sequence), SEQ ID NO: 2 (Sb GWD coding sequence), SEQ ID NO: 3 (Zm GWD Exon 24+introns), SEQ ID NO: 4 (SbGWD Exon 24+introns), SEQ ID NO: 91 (GWDe1a), SEQ ID NO: 92 (GWDe24b), SEQ ID NO: 93 (GWDe24c), and SEQ ID NO: 94 (GWDe25a), SEQ ID NO:

182 (ZmGWD Exon 24), SEQ ID NO: 183 (Sb GWD Exon 24), SEQ ID NO: 184 (SbGWD Exon 7) and SEQ ID NO: 189 (Zm GWD Exon 25).

In an embodiment, the engineered nucleic acid in the genetically engineered plant may be an endogenous nucleic acid that includes at least one allele of a gwd gene encoding a GWD protein but having one or more modifications made by genetic engineering of the plant or its ancestors. The endogenous nucleic acid may be one or more allele of the gwd gene in the engineered plant. The modifications may be in the gwd coding sequences. The endogenous nucleic acid may comprise, consist essentially of, or consist of a sequence with at least 70, 72, 75, 80, 85, 90, 91, 92, 93, 94, 95, 96, 97, 98, 99 or 100% identity to a reference sequence selected from SEQ ID NO: 1 (Zm GWD coding sequence) or SEQ ID NO: 2 (Sb GWD coding sequence). The engineered nucleic acid may include at least one mutation relative to the endogenous nucleic acid. A mutation may include an insertion of one or more nucleotides in comparison to the endogenous nucleic acid. A mutation may include a deletion of nucleotides in comparison to the native nucleic acid. A mutation may include a substitution of one or more nucleotides in comparison to the endogenous nucleic acid. A mutation may be a combination of several mutations. The at least one mutation may be within a target sequence with at least 70, 72, 75, 80, 85, 90, 91, 92, 93, 94, 95, 96, 97, 98, 99 or 100% identity to a reference sequence selected from SEQ ID NO: 1 (Zm GWD coding sequence), SEQ ID NO: 2 (Sb GWD coding sequence), SEQ ID NO: 3 (Zm GWD Exon 24+introns), SEQ ID NO; 4 (SbGWD Exon 24+introns), SEQ ID NO: 91 (GWDe1a), SEQ ID NO: 92 (GWDe24b), SEQ ID NO: 93 (GWDe24c), and SEQ ID NO: 94 (GWDe25a), SEQ ID NO: 182 (ZmGWD Exon 24), SEQ ID NO: 183 (Sb GWD Exon 24), SEQ ID NO: 184 (SbGWD Exon 7) and SEQ ID NO: 189 (Zm GWD Exon 25).

In an embodiment, the engineered nucleic acid in the genetically engineered plant comprises a modified sequence of Exon 24 of the maize gwd gene. The engineered nucleic acid may comprise, consist essentially of, or consist of a polynucleotide having a sequence with at least 70, 72, 75, 80, 85, 90, 91, 92, 93, 94, 95, 96, 97, 98, 99, or 100% identity to a reference sequence selected from SEQ ID NOS: 12-40, 114-118, 119-120 and 131-146, which comprise mutations in the maize gwd gene.

In an embodiment, the engineered nucleic acid in the genetically engineered plant may comprise a modified sequence having one or more modifications within a region of the wild type Zm GWD gene (SEQ ID NO: 1) in the position from 3030 nucleotide (nt) to 3243 nt. In an embodiment, the engineered nucleic acid in the genetically engineered plant may comprise a modified sequence having one or more modifications within a region of the wild type Zm GWD gene (SEQ ID NO: 1) in the position from 3157 nt to 3213 nt. In an embodiment, the engineered nucleic acid in the genetically engineered plant may comprise a modified sequence having one or more modifications within a region of the wild type Zm GWD gene Exon 24 (SEQ ID NO: 3) in the position from 81 nt to 160 nt.

In an embodiment, the Zm GWD gene in the genetically engineered plant may comprise a modified sequence with changes in the sequence relative to wild type Zm GWD (SEQ ID NO: 1) in one of SEQ ID NOS: 12-40, 114-118, 119-120 and 131-146. The sequence of Zm GWD with the changes outside of the positions where the changes are located may have at least 70, 72, 75, 80, 85, 90, 91, 92, 93, 94, 95, 96, 97, 98, 99 or 100% identity to the corresponding regions of SEQ ID NO: 1. The changes may be the same or different from one of SEQ ID NOS: 12-40, 114-118, 119-120 and 131-146.

In an embodiment, the engineered nucleic acid in the genetically engineered plant may comprise a modified sequence of Exon 24 of the sorghum gwd gene. The engineered nucleic acid may comprise, consist essentially of, or consist of a polynucleotide having a sequence with at least 70, 72, 75, 80, 85, 90, 91, 92, 93, 94, 95, 96, 97, 98, 99, or 100% identity to a reference sequence selected from SEQ ID NO: 106 (Sb4715_1 (WT+ins)_Exon 24), and SEQ ID NO: 107 (Sb4715_2 (WT+del)_Exon 24), which are mutations in Exon 24 in the sorghum gwd gene. In an embodiment, the engineered nucleic acid in the genetically engineered plant may comprise a modified sequence having one or more modifications within a region of the wild type Sb GWD gene (SEQ ID NO: 2) in the position from 3030 nt to 3243 nt. The engineered nucleic acid in the genetically engineered plant may comprise a modified sequence having one or more modifications within a region of the wild type Sb GWD gene (SEQ ID NO: 2) in the position from 736 nt to 969 nt. The altered GWD may be encoded by any one of the engineered nucleic acids herein.

In an embodiment, a genetically engineered plant may comprise an altered Zea mays GWD (Zm GWD). The altered ZmGWD may comprise, consist essentially of, or consist of an amino acid sequence with at least 70, 72, 75, 80, 85, 90, 91, 92, 93, 94, 95, 96, 97, 98, 99 or 100% identity to a reference sequence selected from SEQ ID NOS: 45-73 (Zm GWD mutant proteins M1-M29), 121-125 (Zm GWD mutant proteins M32-M36), 126-127 (Zm GWD mutant proteins M38-M39) and 147-162 (Zm GWD mutant proteins M40-M55).

In an embodiment, the altered ZmGWD protein in the genetically engineered plant may comprise a modified sequence having one or more modifications within a region of the wild type Zm GWD protein (SEQ ID NO: 43) in the positions from 1040 amino acid (aa) to 1120 aa. The altered ZmGWD protein in the genetically engineered plant may comprise a modified sequence having one or more modifications within a region of the wild type Zm GWD protein (SEQ ID NO: 43) in the positions from 1054 aa to 1081 aa. The altered ZmGWD protein in the genetically engineered plant may comprise a modified sequence having one or more modifications within a region of the wild type Zm GWD protein (SEQ ID NO: 43) in the positions from 1011 aa to 1057 aa. The altered ZmGWD protein in the genetically engineered plant may comprise a modified sequence having one or more modifications within a region of the wild type Zm GWD protein (SEQ ID NO: 43) in the positions from 1082 aa to 1116 aa.

In an embodiment, the Zm GWD protein in the genetically engineered plant may comprise a modified sequence with changes in the sequence relative to wild type Zm GWD (SEQ ID NO: 43) in one of SEQ ID NOS: 45-73 (Zm GWD mutant proteins M1-M29), 121-125 (Zm GWD mutant proteins M32-M36), 126-127 (Zm GWD mutant proteins M38-M39) and 147-162 (Zm GWD mutant proteins M40-M55). The sequence of Zm GWD with the changes outside of the positions where the changes are located may have at least 70, 72, 75, 80, 85, 90, 91, 92, 93, 94, 95, 96, 97, 98, 99 or 100% identity to the corresponding regions of SEQ ID NO: 43. The changes may be the same or different from one of SEQ ID NOS: 45-73 (Zm GWD mutant proteins M1-M29), 121-125 (Zm GWD mutant proteins M32-M36), 126-127 (Zm GWD mutant proteins M38-M39) and 147-162 (Zm GWD mutant proteins M40-M55).

In an embodiment, a genetically engineered plant may comprise an altered *Sorghum bicolor* GWD (Sb GWD). The altered Sb GWD may comprise, consist essentially of, or consist of an amino acid sequence with at least 70, 72, 75, 80, 85, 90, 91, 92, 93, 94, 95, 96, 97, 98, 99 or 100% identity to a reference sequence selected from SEQ ID NO: 194 (Sb GWD mutant protein Sb4715_1WT+ins) and SEQ ID NO: 195 (Sb GWD mutant protein Sb4715_2 WT+del). Nucleic acids, nucleotide sequences proteins or amino acid sequences herein can be isolated, purified, synthesized chemically, or produced through recombinant DNA technology. All of these methods are well known in the art.

In an embodiment, the genetically engineered plant may be any type of plant. The genetically engineered plant may be but is not limited to a monocotyledonous plant, a dicotyledonous plant, a C4 plant, a C3 plant, corn, soybean, rice, sugar cane, sugar beet, sorghum, switchgrass, miscanthus, eucalyptus, wheat, alfalfa, willow, or poplar. The genetically engineered plant may be derived from an energy crop plant, a forage crop plant, or a food crop plant. The energy crop plant may be a corn plant, a switchgrass plant, a *sorghum* plant, a poplar plant, or a miscanthus plant. The forage crop plant may be a corn plant, an alfalfa plant, a *sorghum* plant or a soybean plant. The food crop plant may be a corn plant, a wheat plant, a soybean plant, a rice plant, or a tomato plant.

The genetically engineered plant may be a transgenic plant or a mutant plant. The genetically engineered plant may be a progeny of a transgenic plant or a mutant plant, or a descendant of a transgenic plant or a mutant plant.

The genetically engineered plant may be a conventional mutant having one or more mutations in a nucleic acid sequence of a gene encoding GWD that result in inhibited expression of the GWD or reduced activity of GWD. The mutations may be deletions, insertions or substitutions of nucleic acids in a sequence of the GWD encoding gene. The conventional mutant may have an altered level of vegetative starch compared to a non-mutant plant of the same genetic background but expressing wild type GWD.

As used herein, the genetically engineered plant may refer to a whole transgenic plant or mutant plant or a part thereof. The part may be but is not limited to one or more of leaves, stems, flowers, buds, petals, ovaries, fruits, or seeds. The part may be callus from a transgenic plant or a mutant plant. A genetically engineered plant may be regenerated from parts of a transgenic plant or a mutant plant or plants. A genetically engineered plant may be a product of sexual crossing of a first transgenic plant and a second transgenic plant or a non-transgenic plant where the product plant retains an engineered nucleic acid introduced to the first transgenic plant. A genetically engineered plant may be a product of sexual crossing of a first mutant plant and a second non-mutant plant where the product plant retains a mutation introduced to the first mutant plant. The transgenic plant or the mutant plant may be any one of the transgenic plants or mutant plants described herein.

In an embodiment, a method for genetically engineering a plant that includes an altered Glucan Water Dikinase is provided. The method may include contacting at least one plant cell that comprises a target sequence in an endogenous gene encoding a Glucan Water Dikinase with a vector. The vector may include a first nucleic acid encoding a nuclease capable of inducing a single-strand break or a double-strand break at the target sequence. The vector may be introduced by transforming or otherwise genetically engineering a plant. Transforming may be *Agrobacterium*-mediated transformation using a vector that includes a first nucleic acid encoding a nuclease. The nuclease may cleave the target sequence as described previously (Puchta et al. 1993; Wright et al. 2005; Wehrkamp-Richter et al. 2009; Cong et al., 2013; Belhaj et al., 2013, all of which are incorporated herein by reference as if fully set forth). The nuclease may be but is not limited to a meganuclease, Cas9 nuclease, a zinc finger nuclease, or a transcription activator-like effector nuclease.

As stated, the nuclease may be a meganuclease. Meganucleases may introduce single stranded or double stranded DNA breaks and have recognition sites ranging between 14 to 40 nucleotides in length providing good specificity. For use of meganucleases for targeted modification, see Rosen et al., 2006; Wehrkamp-Richter et al. 2009; Djukanovic et al., 2013, all of which are incorporated herein by reference as if fully set forth. The meganuclease may be a LAGLIDADG homing endonuclease (LHE). LAGLIDADG homing endonucleases (LHEs) are native gene-targeting proteins with their coding sequences found in introns or inteins. See Arnould et al., 2011, which is incorporated herein by reference as if fully set forth. The meganuclease may be a I-CreI homing endonuclease. As used herein, the I-CreI homing endonuclease is a meganuclease naturally occurring in chloroplasts of *Chlamydomonas reinhardtii*, and is a well characterized protein containing a single sequence motif important for nuclease enzymatic activity. See Heath et al., 1997, which is incorporated herein by reference as if fully set forth. The I-CreI endonuclease is suitable for protein engineering and was used for targeted genome modifications in several species including plants. See Rosen et al., 2006; Arnould et al., 2007; Djukanovic et al., 2013, all of which are incorporated herein by reference as if fully set forth. The meganuclease may be I-DmoI, I-SceI, E-DmeI or DmoCre. Other meganucleases may be used.

The meganuclease may be encoded by a sequence with at least 70, 72, 75, 80, 85, 90, 91, 92, 93, 94, 95, 96, 97, 98, 99, or 100% identity to a reference sequence selected from the group consisting of SEQ ID NO: 108 (4715_meganuclease) and SEQ ID NO: 109 (4716_meganuclease).

In an embodiment, the nuclease may be a Cas9 nuclease. Cas9 nuclease is the nuclease used in the Clustered Regularly Interspaced Short Palindromic Repeats (CRISPR)/CRISPR-associated protein 9 (Cas9) systems (Cong et al., 2013; Belhaj et al., 2013, both of which are incorporated herein by reference as if fully set forth. The CRISPR/Cas9 is the genome editing technology that due to its low cost, high efficiency and relative simplicity to engineer has a potential of becoming a technology of choice for genome editing in various species, but has not been demonstrated to work in multi-cellular plants by using stable transformation. The CRISPR/Cas9 system may include a Cas9 nuclease and a single guide RNA (sg RNA). The Cas9 nuclease herein may be encoded with a nucleic acid with at least 70, 72, 75, 80, 85, 90, 91, 92, 93, 94, 95, 96, 97, 98, 99, or 100% identity to a reference sequence of SEQ ID NO: 74 (Cas9 nuclease) or SEQ ID NO: 75 (ZmCas9). The nuclease may have affinity for a sequence that enables the nuclease to cleave the target sequence, or it may be guided to the target sequence by using an sgRNA. The vector herein may further include a second nucleic acid sequence encoding an sgRNA. The targeted modification of the endogenous gene may be made by expressing the Cas9 and sgRNA in a plant cell. The sgRNA chimera molecule may contain an untranslated CRISPR RNA (crRNA), a 20 bp spacer sequence complementary to the target genomic DNA sequence with a 3 bp protospacer-adjacent motif (PAM) sequence (Jinek et al., 2012, which is incorporated herein by reference as if fully set forth). The Cas9 nuclease may be expressed from PPDK, CaMV 35S, Actin, or Ubiquitin promoters in plants, such as

*Arabidopsis*, corn, tobacco, rice, wheat, and *sorghum*. The sgRNAs may be expressed from primarily RNA Polymerase III promoters U6 or U3 and from RNA polymerase II promoter CaMV E35S (Belhaj et al., 2013; Upadhyay et al., 2014, both of which are incorporated by reference herein as if fully set forth). The sgRNAs may be expressed from SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86) described herein. The promoter may have 70, 72, 75, 80, 85, 90, 91, 92, 93, 94, 95, 96, 97, 98, 99, or 100% identity to one of SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86). The promoter may have a length equal to 70, 72, 75, 80, 85, 90, 91, 92, 93, 94, 95, 96, 97, 98, 99, or 100% of the length in nucleotides of one of SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86). The percent identity of promoters shorter than SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86 may be as set forth above along the length of the shorter promoter. Cas9 nuclease may introduce a single stranded break or double stranded DNA break into an endogenous nucleic acid included in genomic DNA. Subsequently, breaks introduced by Cas9 in genomic DNA may be repaired via two distinct mechanisms NHEJ (non homologous ends joining) and HR (homologous recombination) (Symington and Gautier, 2011, which is incorporated herein by reference as if fully set forth).

In an embodiment, the nuclease may be a transcription activator-like effector nucleases (TALEN). As used herein, TALENs refer to proteins derived from *Xanthomonas*. TALENs are customizable fusion proteins comprising an engineered DNA-binding domain of TAL effectors fused to DNA cleavage domains of FokI endonuclease (Boch and Bonas, 2010; Christian et al., 2010; Joung and Sander, 2013; Li et al., 2011, all of which are incorporated herein by reference as if fully set forth). These chimeric proteins may work in pairs of two monomers for targeting FokI endonuclease to a specific DNA sequence within a genome for DNA cleavage. The TAL DNA-binding domain may be modified to recognize different sequences (Cermak et al., 2011, which is incorporated herein by reference as if fully set forth).

In an embodiment, the nuclease may be a zinc-finger nuclease. (Wright et al. 2005; Shukla et al., 2009, both of which are incorporated herein by reference as if fully set forth).

In an embodiment, the nuclease may be any other nuclease suitable for targeted modification of the target sequence.

The target sequence may be a target gene. The target gene may be an endogenous gene that is native to the plant. The target sequence may be a gwd gene of a plant The target sequence may be contained within SEQ ID NO: 1 (Zm GWD coding sequence) or SEQ ID NO: 2 (Sb GWD coding sequence). The target sequence may be any nucleic acid sequence included in an exon of an endogenous nucleic acid encoding GWD. The target sequence may be included in an exon of an endogenous nucleic acid encoding a maize GWD. The target sequence may be included in an exon of an endogenous nucleic acid encoding a *sorghum* GWD. The target sequence may be included in Exon, 1, Exon 7, Exon 24, or Exon 25 of an endogenous nucleic acid encoding GWD. The target sequence may be a target sequence for the meganuclease. The target sequence may comprise, consist essentially of, or consist of a sequence with at least 70, 72, 75, 80, 85, 90, 91, 92, 93, 94, 95, 96, 97, 98, 99, or 100% identity to SEQ ID NO: 41 (Meganuclease GWD-9/10x.272 target sequence (pAG4715)) or SEQ ID NO: 42 (Meganuclease GWD-7/8x target sequence (pAG4716)). The target sequence may be the target sequence for Cas9 nuclease. The target sequence may comprise, consist essentially of, or consist of a sequence with at least 70, 72, 75, 80, 85, 90, 91, 92, 93, 94, 95, 96, 97, 98, 99, or 100% identity to SEQ ID NO: 91 (GWDe1a), SEQ ID NO: 92 (GWDe24b), SEQ ID NO: 93 (GWDe24c), or SEQ ID NO: 94 (GWDe25a). The sgRNA may be capable of binding a target sequence selected from the group consisting of SEQ ID NO: 91 (GWDe1a), SEQ ID NO: 92 (GWDe24b), SEQ ID NO: 93 (GWDe24c), and SEQ ID NO: 94 (GWDe25a). The target sequence may be any sequence that hybridizes with the sgRNA. The nuclease may have affinity for a sequence that enables the nuclease to cleave the target sequence, or it may be guided to the target sequence by using an sgRNA.

Once expressed, the nuclease will introduce one stranded or double stranded DNA breaks in the target sequence. For example, nuclease may delete a short segment that then may be partially repaired by the cell's DNA repair mechanisms, but leaving a lesion within the target sequence. The repaired target sequence may include an alteration. The alteration may include a mutation. The mutation may be at least one of an insertion, a deletion, or a substitution of one or more nucleotides in the target sequence. The mutation may be a null mutation. As used herein, the term "null mutation" refers to a mutation in a gene that leads to its not being transcribed into RNA or translated into a functional protein. Because of the mutation in the target sequence, the native nucleic acid sequence may encode an altered GWD. The activity of the altered GWD may be reduced. The level of reduction may be 20, 30, 40, 50, 60, 70, 80, 90, 91, 92, 93, 94, 95, 96, 97, 98, 99, or 100% of the activity level of wild type GWD and may be tested by monitoring starch content in plants by using Fourier Transform Near-infrared (FT-NIR) Technique as described as described in Example 3 herein. The altered GWD may be inactive. The genetically engineered plant having the alteration or progeny thereof may have an elevated level of starch in comparison to a non-genetically engineered plant of the same genetic background.

The method may include selecting a plant cell that includes an alteration of the target sequences. The method may include regenerating the plant including the alteration from the plant cell. The genetically engineered plant may be homozygous for the alteration.

The genetically engineered plant may be heterozygous for the alteration. The genetically engineered plant herein may be heterozygous for the gene that includes the mutation. The gene may include the engineered nucleic acid encoding the altered GWD. The heterozygous plants may include alleles of the endogenous gene that encode a wild type, unaltered, GWD. The heterozygous plant may also include hemizygous plants when at least one allele of the gene encoding GWD is missing. A heterozygous plant may be phenotypically indistinguishable from the wild type plants and may not have elevated levels of starch. To produce homozygous plants with elevated levels of starch, a heterozygous genetically engineered plant may be self-crossed. Progeny may be obtained from such crosses. The progeny may include homozygous, heterozygous and wild type plants. A heterozygous plant may be phenotypically indistinguishable from the wild type plants. The method may include analyzing the progeny for the presence of the alteration and selecting a progeny plant that includes the alteration.

In an embodiment, the method may further include crossing a heterozygous genetically engineered plant to another genetically engineered plant heterozygous for the same alteration. The method may include selecting a first progeny plant that is homozygous for the alteration. The method may further include crossing the genetically engineered plant to a wild type plant of the same genetic background. Progeny may be obtained from such crosses. The progeny may include heterozygous and wild type plants. The method may include selecting a first progeny plant that is heterozygous for the alteration. The method may further include selfing the first heterozygous progeny plant and selecting a second progeny plant that is homozygous for the alteration.

A genetically engineered plant herein may be homozygous or heterozygous for the gene that includes the mutation and may include a transgene encoding a nuclease. The transgene encoding the nuclease may be segregated away during the above-described crosses.

An embodiment comprises a method for producing a genetically engineered plant homozygous for an engineered nucleic acid encoding a protein. The engineered nucleic acid may encode a recessive trait. The recessive trait may include a cleaved endogenous target sequence of a gene. The recessive trait may only be observed in plants that do not contain an unaltered, wild-type, allele of the gene. The method may comprise making an engineered nucleic acid by modifying a sequence of an endogenous nucleic acid. The method may also comprise breeding the recessive trait into other crop lines. The method may comprise maintaining the trait in the crop lines. The method may comprise generating homozygous progeny. The method may include making hybrid seed with a recessive trait.

An embodiment comprises a plant genetically engineered by any one of methods described herein is provided.

An embodiment comprises a method of increasing a starch level in a plant. The method may comprise expressing a nucleic acid encoding a meganuclease in a plant. The method may comprise expressing a nucleic acid that encodes a TALEN in a plant. The method may comprise expressing a first nucleic acid that encodes a Cas9 nuclease and a second nucleic acid that encodes a desired guide RNA that target a specific sequence. Expression of the nucleic acid(s) in the plant may alter the function or coding of an endogenous DNA sequence. Expression of the nucleic acid(s) in the plant may alter the activity of GWD and starch metabolism in the plant. The plant may be any transgenic or mutant plant herein. The plant may be a progeny of the transgenic or mutant plant. The nucleic acid(s) may be included in a genetic construct(s). The method may comprise making any genetically engineered plant herein. The genetically engineered plant or its progeny may be the plant, in which starch levels may be increased by the method herein.

A genetic construct having a nucleic acid encoding a meganuclease that inactivates or inhibits expression of the GWD protein involved in mobilization of starch in a plant in may be expressed at any point in the methods. The nucleic acid may be expressed prior to the step of processing the plant. The nucleic acid may be expressed during the step of processing the plant. The expression may be induced. Upon the expression of the nucleic acid(s), the genetically engineered plant may have an altered level of vegetative starch compared to the level of starch in a non-genetically engineered plant of the same genetic background but lacking the one or more genetic construct.

Any genetically engineered plant herein may be provided in a method of agricultural processing, a method of preparing animal feed, or a method of feeding an animal. A step of providing the genetically engineered plant may include obtaining it from another party that produced it. A step of providing may include making the genetically engineered plant. The genetically engineered plant may be a transgenic plant or mutant plant. The step of providing may include transforming the plant by contacting the plant with any one of the genetic constructs herein. The step of providing may include stable transformation of the plant by any of the methods described herein, or known methods. The step of providing may include genetically engineering the plant by cleaving a gene encoding a protein involved in starch metabolism at a cleavage site recognized by a nuclease transiently expressed in the plant after contacting the plant with a genetic construct comprising a polynucleotide encoding the nuclease. The step of providing may also include regenerating the plant from a tissue of the genetically engineered plant having an altered level of vegetative starch. The step of providing may include obtaining a progeny of the genetically engineered plant resulted from self-pollination or cross-pollination between the genetically engineered plant and non-genetically engineered plant. The step of providing may include obtaining homozygous progeny. The homozygous progeny may be inbred plants. The homozygous progeny may be hybrid plants. The genetically engineered plant may be used in a variety of subsequent methods or uses. The step of providing may include procuring the genetically engineered plant. The step of providing may include making the genetically engineered plant available for further processing steps. The step of providing may include making the genetically engineered plant available as part of an animal diet.

In the method of agricultural processing, the genetically engineered plant may be a feedstock engineered with elevated levels of starch and/or expressing one or more polysaccharide degrading enzyme. The feedstock may include any genetically engineered plant herein alone or in combination with other components. The other components may include other plant material. Agricultural processing may include manipulating or converting any agricultural feedstock including the genetically engineered plant for a particular product or use. Agricultural processing may comprise drying the genetically engineered plant. Agricultural processing may comprise fermenting the genetically engineered plant. Agricultural processing may comprise hydrolyzing the genetically engineered plant with one or more an exogenous enzymes to obtain a biochemical product. The exogenous enzymes may be lignin degrading enzymes, cellulose degrading enzymes, or hemicellulose degrading enzymes. The exogenous enzymes may be glycosidases, xylanases, cellulases, endoglucanases, exoglucanases, cellobiohydrolases, β-xylosidases, feruloyl esterases, β-glucosidases, and amylases. The exogenous enzymes may be purchased from a vendor and may comprise Accellerase® 1000, Accellerase® 1500, Accelerase® TRIO™, and Accellerase® XY available from Genencor International (Rochester, N.Y.). Exogenous enzymes may comprise Cellic, CTEC, HTEC available from Novozymes (Denmark). The exogenous enzymes may comprise starch degrading enzymes. The exogenous enzymes may comprise an amylase or an invertase. The method of agricultural processing may include simultaneous saccharification and fermentation of soluble sugars to produce ethanol.

A method of agricultural processing herein may comprise harvesting the genetically engineered plants having elevated levels of starch for use as a feedstock in agricultural processing. The method may include combining the genetically engineered plant with plant biomass. The plant biomass may include non-genetically engineered plants. The plant biomass may be genetically engineered plant biomass. The genetically engineered plant biomass may express polysaccharide degrading enzymes. By combining the genetically engineered plant with the plant biomass that express polysaccharide degrading enzyme, the method herein may not require harsh pretreatments to improve cellulose cell wall accessibility to exogenous enzymes. The methods herein may utilize any methods and compositions for consolidated pretreatment and hydrolysis of plant biomass expressing cell wall degrading enzymes described in U.S. patent application Ser. No. 13/414,627, filed Mar. 7, 2012; and International Patent Application No. PCT/US2012/028132, filed Mar. 7, 2012, which are incorporated herein by reference as if fully set forth. Plants with altered levels of elevated starch were described International Patent Application No. PCT/US2011/041991, filed Jun. 27, 2011; and U.S. patent application Ser. No. 13/806,654, filed Mar. 19, 2013; and U.S. patent application Ser. No. 13/793,078, filed Mar. 11, 2013, which are incorporated herein by reference as if fully set forth.

The genetically engineered plant may be provided in a method of preparing animal feed. Preparing animal feed may comprise combining the genetically engineered plant with animal feed stuffs, including but not limited to corn, grain, soybeans, and/or other forage. Preparing animal feed may comprise ensiling the genetically engineered plant to make silage. Preparing animal feed may comprise combining the genetically engineered plant with distillers' grains. Preparing animal feed may comprise pelletizing the genetically engineered plant into feed pellets. Preparing animal feed may comprise combining the genetically engineered plant with a source of edible fiber. Preparing animal feed may comprise combining the genetically engineered plant with a source of protein. Preparing animal feed may comprise combining the genetically engineered plant with one or more carbohydrates as a source of energy. Preparing animal feed may comprise combining the genetically engineered plant with one or more exogenous enzymes described herein.

A method of agricultural processing or or a method of preparing animal feed may also comprise at least one of the operations of harvesting, baling, grinding, milling, chopping, size reducing, crushing, extracting a component from the feedstock, purifying a component or portion of the feedstock, extracting or purifying starch, hydrolyzing polysaccharides into oligosaccharides or monosaccharides, chemical conversion, or chemical catalysis of the feedstock.

In an embodiment, animal feed formulations comprising increased levels of starch in vegetative tissues are provided. Animal feed formulations may be used for increasing milk and beef production by feeding animals plant material with increased levels of starch. Easily-fermentable sugars available in a fermentation process may be provided by embodiments herein. Production of biofuels may be enhanced by providing easily-fermentable sugars. Methods of providing easily fermentable sugars and methods of enhancing production of biofuels are provided as embodiments herein. The animal feed formulations may comprise any one or more of the genetically engineered plants herein. The animal feed formulations may comprise the products of a method of preparing animal feed herein.

Crops with elevated levels of vegetative starch may have a variety of uses and utilities. In an embodiment, biomass from plants that accumulate elevated levels of vegetative starch relative to wild type plants are provided. The biomass may be from any genetically engineered plant herein or its progeny. These plants may have added value as feedstocks for fermentation processes or animal feed applications. For example, in a typical cellulosic process, polysaccharides, such as cellulose and hemicelluloses that are present in the biomass, are hydrolyzed to simple sugars, which may then be fermented to ethanol, butanol, isobutanol, fatty acids, or other hydrocarbons by microorganisms. Because of the recalcitrance of the biomass, the release of the simple sugars from polymers, such as cellulose and hemicelluloses, often requires the use of harsh pretreatment conditions and hydrolysis with relatively expensive mixtures of enzymes. A similar situation occurs in ruminant animals that eat forage, including corn silage, as a nutrient and an energy source. In ruminant animal, the forage is masticated and moves into the rumen, where the fiber polysaccharides, such as cellulose and hemicellulose, are hydrolyzed and fermented by the microorganisms in the rumen flora. These organisms create fatty acids that are absorbed by the animal and metabolized, providing nutrition to the animal. In either ruminant digestion or biofuels processing, any starch that is present in the biomass represents an additional source of readily fermentable sugars (namely, glucose), which are less recalcitrant to hydrolysis and can be released very easily by amylases or mild chemical treatments. As a result, any increase in the amount of starch present in the biomass will simultaneously increase the amount of fermentable sugar that can be recovered. Biomass that contains elevated levels of starch may have greater value in forage applications, where the plant material is fed to livestock or dairy animals. Again, the excess starch present in this material is more easily digested by most animals than is the cellulosic material, providing more energy per unit biomass than biomass with ordinary levels of starch. Embodiments include utilizing a plant as set forth herein for any of these methods.

Methods herein, including those in the previous paragraph, may include at least one of modifying plants to create genetically engineered plants, growing the genetically engineered plants, harvesting the genetically engineered plants, processing (for example reducing the size of the forage, ensiling, treating with an inoculant, combining with other feed components, or pelleting) them for animal feed applications as one would other forage crops, or fermenting the genetically engineered plants in a manner similar to treatments that are used in cellulosic processing. Cellulosic processing steps used may comprise pretreating and hydrolyzing the polysaccharides into their component sugars by enzymatic or chemical hydrolysis or digestion. Any one step, set of steps, or all the steps set forth in this paragraph may be provided in a method herein.

An embodiment comprises a genetic construct designed to implement a strategy for modifying levels of vegetative starch in plants. The genetic construct may comprise a first engineered nucleic acid sequence that encodes a nuclease capable of cleaving a target sequence in an endogenous nucleic acid encoding GWD. The first engineered nucleic acid may encode any one of the nucleases described herein. The genetic construct may also include a second engineered nucleic acid sequence encoding an sgRNA. The second engineered nucleic acid may encode any one the sgRNAs described herein. The genetic construct may include a promoter operably linked to the first engineered nucleic acid sequence or the second engineered nucleic acid. The operably linked promoter may allow transcription of the first engineered nucleic acid sequence encoding a nuclease, or the second engineered nucleic acid sequence encoding the sgRNA. Transcription and translation of the first engineered nucleic acid sequence may be referred to as expression of the nuclease. Upon expression, the nuclease may cut the target sequence of the endogenous nucleic acid. The endogenous nucleic acid may encode GWD. Transcription of the second nucleic acid sequence may result in production of an sgRNA that recognizes a target sequence within an endogenous nucleic acid and guides Cas9 nuclease to the target for making a break.

The genetic construct may include regions encoding nuclear localization signals. As used herein, nuclear localization signals (NLS) refers the short motifs of basic amino acid sequences within nuclear proteins. Transport of certain proteins from cytoplasm into the nucleolus to perform their specific functions occurs through the nuclear envelope and involves nuclear pore complex (NPC) (Wagner et al., 1990, which is incorporated herein by reference as if fully set forth). In this process, nuclear localization signals (NLS) play an important role as they are thought to be recognized by NPC receptors to subsequently translocate proteins through the nuclear pore complex. The NLSs fall into one of several defined categories (Garcia-Bustos et al., 1991, which is incorporated herein by reference as if fully set forth). The NLS may be the SV40 NLS from simian virus 40 large T antigen, which has been used intensively in experiments for targeted genome modifications due to its activity in various organisms, including plants (Kalderon et al., 1984; Raikhel, 1992, both of which are incorporated herein by reference as if fully set forth). The SV40 NLS may be encoded by a nucleic acid sequence with at least 70, 72, 75, 80, 85, 90, 91, 92, 93, 94, 95, 96, 97, 98, 99, or 100% identity to a reference sequence of SEQ ID NO: 163. The SV NLS may comprise, consist essentially of, or consist of an amino acid sequence with at least 70, 72, 75, 80, 85, 90, 91, 92, 93, 94, 95, 96, 97, 98, 99, or 100% identity to a reference sequence of SEQ ID NO: 196. The NLS may be plant specific NLS sequences. Plant specific NLS sequences were also described, for example, in maize regulatory proteins opaque-2 and R (Varagona et al, 1992; Shieh et al, 1993, both of which are incorporated herein by reference as if fully set forth). The plant specific NLS may be encoded by a nucleic acid sequence with at least 70, 72, 75, 80, 85, 90, 91, 92, 93, 94, 95, 96, 97, 98, 99, or 100% identity to a reference sequence selected from the group of SEQ ID NOS: 164 (NLS1), 165 (NLS3), 166 (NLS4), 167 (NLSS), and 168 (NLS6). The plant specific NLS sequence may comprise, consist essentially of, or consist of an amino acid sequence with at least 70, 72, 75, 80, 85, 90, 91, 92, 93, 94, 95, 96, 97, 98, 99, or 100% identity to a reference sequence selected from the group of SEQ ID NOS: 128 (NLS1), 129 (NLS3), 130 (NLS4), 169 (NLSS), and 170 (NLS6). The NLS sequence may be a derivative NLS sequence. The NLS sequences or their derivatives may be used to target meganucleases, ZFNs, TALENs, or Cas9 proteins into plant nucleus for targeted genome modification. One or more NLS sequences may be fused with an amino acid sequence of the nuclease.

The genetic construct may further include one or more regulatory sequences (also referred to as a regulatory element) operably connected to the nucleic acid encoding the nuclease. The promoter may be any kind of promoter. The promoter may be an inducible promoter. The promoter may be a constitutive promoter. The promoter may be an inducible promoter, which initiates transcription of the nucleic acid encoding the nuclease only when exposed to a particular chemical or environmental stimulus. Examples of inducible promoters include but are not limited to alcohol inducible promoters, tetracycline inducible promoters, steroid inducible promoters, or hormone inducible promoters. The promoter may be a constitutive promoter, which provides transcription of the nucleic acids or polynucleotide sequences throughout the plant in most cells, tissues, and organs, and during many but not necessarily all stages of development. The promoter may be specific to a particular developmental stage, organ, or tissue. A tissue specific promoter may be capable of initiating transcription in a particular plant tissue. Plant tissue that may be targeted by a tissue specific promoter may be but is not limited to a stem, leaves, trichomes, anthers, or seed. A constitutive promoter herein may be the rice Ubiquitin 3 promoter (OsUbi3P) or the maize ubiquitin promoter (ZmUbi1). Other known constitutive promoters may be part of the genetic construct herein, and include but are not limited to Cauliflower Mosaic Virus (CAMV) 35S promoter, the Cestrum Yellow Leaf Curling Virus promoter (CMP) or the CMP short version (CMPS), the Rubisco small subunit promoter, the rice actin promoter (OsAct1P), and the maize phosphoenolpyruvate carboxylase promoter (ZmPepCP). The promoter may be a synthetic nucleic acid promoter from maize Zea mays. The synthetic nucleic acid promoter from maize may comprise, consist essentially of, or consist of a sequence with at least 70, 72, 75, 80, 85, 90, 91, 92, 93, 94, 95, 96, 97, 98, 99, or 100% identity to a reference sequence selected from the group consisting of: SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86). The synthetic nucleic acid promoter may have a length equal to 70, 72, 75, 80, 85, 90, 91, 92, 93, 94, 95, 96, 97, 98, 99, or 100% of the length in nucleotides of one of SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86). The percent identity of promoters shorter than SEQ ID NO: 78 (MzU3.8), SEQ ID NO: 79 (ZmU3), ZmU3P1 (SEQ ID NO: 82), ZmU3P2 (SEQ ID NO: 84), or ZmU3.8 promoter (SEQ ID NO: 86 may be as set forth above along the length of the shorter promoter. An embodiment comprises any one of the synthetic nucleic acid promoters described herein. The synthetic nucleic acid promoter may be operably connected with the first engineered nucleic acid or the second engineered nucleic acid molecule and may transcriptionally activate the first or the second engineered nucleic acid. As a result of transcriptional activation, the first or the second engineered nucleic acid may be expressed constitutively in a plant.

A regulatory element in a genetic construct herein may be a terminator. A terminator is capable of terminating transcription. A terminator sequence may be included at the 3' end of a transcriptional unit of the expression cassette. The transcriptional unit may encode the nuclease. The terminator may be derived from a terminator found in a variety of plant genes. The terminator may be a terminator sequence from the nopaline synthase (NOS) or octopine synthase (OCS) genes of Agrobacterium tumefaciens. The terminator may be the S. pyogenes Cas9 terminator (SEQ ID NO: 88). The terminator may be the ZmU3T terminator (SEQ ID NO: 89). The terminator sequence may be the CaMV 35S terminator from CaMV, or any of the 3'UTR sequences shown to terminate the transgene transcription in plants. For example, the terminator may be the maize PepC terminator (3'UTR). The genetic construct may be included in a vector. The genetic construct may be integrated into a genome of the genetically engineered plant. The genetic construct may be transiently expressed in the genetically engineered plant.

The genetic construct may be used for transformation of a plant. The genetic construct may be used for Agrobacterium-mediated transformation of a plant. The genetic construct may be used for transforming a plant by any known methods, for example, particle bombardment or direct DNA uptake. The genetic construct may be cloned and included into a vector.

An embodiment includes a vector comprising a genetic construct herein and appropriate for genetically engineering a plant. The vector may be an intermediate vector. The vector may be a transformation vector. Vectors incorporating a genetic construct herein may also include additional genetic elements such as multiple cloning sites to facilitate molecular cloning and one or more selectable markers to facilitate selection. A selectable marker that may be included in a vector may be a phosphomannose isomerase (PMI) gene from Escherichia coli, which confers to the transformed cell the ability to utilize mannose for growth. Selectable markers that may be included in a vector include but are not limited to a neomycin phosphotransferase (npt) gene, conferring resistance to kanamycin, a hygromycin phosphotransferase (hpt) gene, conferring resistance to hygromycin, or an enolpyruvylshikimate-3-phosphate synthase gene, conferring resistance to glyphosate. The vector may be any vector described in U.S. application Ser. No. 13/793,078, filed Mar. 11, 2013, which is incorporated herein by reference as if fully set forth. The vector may include a genetic construct encoding any one of the nucleases described herein. The vector may comprise a nucleic acid sequence with at least 70, 72, 75, 80, 85, 90, 91, 92, 93, 94, 95, 96, 97, 98, 99, or 100% identity to a reference sequence of SEQ ID NO: 108 (meganuclease 4715) or SEQ ID NO: 109 (meganuclease 4716). The vector may comprise a nucleic acid sequence with at least 70, 72, 75, 80, 85, 90, 91, 92, 93, 94, 95, 96, 97, 98, 99, or 100% identity to a reference sequence of SEQ ID NO: 75 (Zm Cas9). The vector may comprise a sequence with at least 70, 72, 75, 80, 85, 90, 91, 92, 93, 94, 95, 96, 97, 98, 99, or 100% identity to a reference sequence selected from the group consisting of: SEQ ID NO: 95 (ZmU3P1: sgRNA_GWDe24b), SEQ ID NO: 96 (ZmU3P2: sgRNA_GWDe24b), SEQ ID NO: 97 (ZmU3.8P: sgRNA_GWDe24b), SEQ ID NO: 98 (ZmU3P2: sgRNA_GWDe24c), SEQ ID NO: 99 (ZmU3P2: sgRNA_GWDe25a) and SEQ ID NO: 100 (ZmU3P2: sgRNA_GWDe1a). The vector or the genetic construct described herein may include an engineered nucleic acid. The vector may be pAG4715 (FIG. 1), pAG4716 (FIG. 2), or a modification thereof replacing any one of the annotated landmarks with a counterpart otherwise described herein. Routine vector elements annotated in FIG. 1 or 2 may be replaced by counterparts described herein or known in the art.

An embodiment includes an engineered nucleic acid comprising, consisting essentially of, or consisting of a sequence with at least 70, 72, 75, 80, 85, 90, 91, 92, 93, 94, 95, 96, 97, 98, 99, or 100% identity to SEQ ID NO: 41 (Meganuclease GWD-9/10x272 target sequence (pAG4715)) or SEQ ID NO: 42 (Meganuclease GWD-7/8x target sequence (pAG4716)).

An embodiment includes an engineered nucleic acid sequence comprising, consisting essentially of, or consisting of a sequence with at least 70, 72, 75, 80, 85, 90, 91, 92, 93, 94, 95, 96, 97, 98, 99 or 100% identity to a reference sequence selected from the group consisting of SEQ ID NO: 91 (GWDe1a), SEQ ID NO: 92 (GWDe24b), SEQ ID NO: 93 (GWDe24c), and SEQ ID NO: 94 (GWDe25a).

An embodiment comprises an engineered nucleic acid having a sequence as set forth in any one of the engineered nucleic acids listed herein or the complement thereof. In an embodiment, an engineered nucleic acid having a sequence that hybridizes to a nucleic acid having the sequence of any nucleic acid listed herein or the complement thereof is provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following books: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated by reference in their entirety as if fully set forth. Moderate conditions include the following: filters loaded with DNA samples are pretreated for 2-4 hours at 68° C. in a solution containing 6× citrate buffered saline (SSC; Amresco, Inc., Solon, Ohio), 0.5% sodium dodecyl sulfate (SDS; Amresco, Inc., Solon, Ohio), 5×Denhardt's solution (Amresco, Inc., Solon, Ohio), and denatured salmon sperm DNA (Invitrogen Life Technologies, Inc. Carlsbad, Calif.). Hybridization is carried in the same solution with the following modifications: 0.01 M EDTA (Amresco, Inc., Solon, Ohio), 100 µg/l salmon sperm DNA, and 5-20×10$^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.). Tm=81.5+16.61 Log$_{10}$([Na$^+$]/(1.0+0.7 [Na$^+$]))+0.41(% [G+C])−(500/n)−P−F. [Na+]= Molar concentration of sodium ions. % [G+C]=percent of G+C bases in DNA sequence. N=length of DNA sequence in bases. P=a temperature correction for % mismatched base pairs (∼1° C. per 1% mismatch). F=correction for formamide concentration (=0.63° C. per 1% formamide). Filters are exposed for development in an imager or by autoradiography. Low stringency conditions refers to hybridization conditions at low temperatures between 37° C. and 60° C., and the second wash with higher [Na$^+$] (up to 0.825M) and at a temperature 40° C. to 48° C. below Tm. High stringency refers to hybridization conditions at high temperatures over 68° C., and the second wash with [Na+]=0.0165 to 0.0330M at a temperature 5° C. to 10° C. below Tm.

An embodiment comprises an engineered nucleic acid having a sequence that has at least 70, 72, 75, 80, 85, 90, 91, 92, 93, 94, 95, 96, 97, 98, 99, or 100% identity along its length to a contiguous portion of a nucleic acid having any one of the sequences set forth herein or the complements thereof. The contiguous portion may be any length up to the entire length of a sequence set forth herein or the complement thereof.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147:195-197, which is incorporated herein by reference as if fully set forth).

An embodiment comprises engineered nucleic acids, engineered polynucleotides, or engineered oligonucleotides having a portion of the sequence as set forth in any one of the nucleic acids listed herein or the complement thereof. These engineered nucleic acids, engineered polynucleotides, or engineered oligonucleotides may have a length in the range from 10 to full length, 10 to 5000, 10 to 4900, 10 to 4800, 10 to 4700, 10 to 4600, 10 to 4500, 10 to 4400, 10 to 4300, 10 to 4200, 10 to 4100, 10 to 4000, 10 to 3900, 10 to 3800, 10 to 3700, 10 to 3600, 10 to 3500, 10 to 3400, 10 to 3300, 10 to 3200, 10 to 3100, 10 to 3000, 10 to 2900, 10 to 2800, 10 to 2700, 10 to 2600, 10 to 2500, 10 to 2400, 10 to 2300, 10 to 2200, 10 to 2100, 10 to 2000, 10 to 1900, 10 to 1800, 10 to 1700, 10 to 1600, 10 to 1500, 10 to 1400, 10 to 1300, 10 to 1200, 10 to 1100, 10 to 1000, 10 to 900, 10 to 800, 10 to 700, 10 to 600, 10 to 500, 10 to 400, 10 to 300, 10 to 200, 10 to 100, 10 to 90, 10 to 80, 10 to 70, 10 to 60, 10 to 50, 10 to 40, 10 to 35, 10 to 30, 10 to 25, 10 to 20, 10 to 15, or 20 to 30 nucleotides, or 10, 15, 20 or 25 nucleotides. An engineered nucleic acid, engineered polynucleotide, or engineered oligonucleotide having a length within one of the above ranges may have any specific length within the range recited, endpoints inclusive. The recited length of nucleotides may start at any single position within a reference sequence (i.e., any one of the nucleic acids herein) where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

An embodiment comprises a kit for identifying a modified sequence of an endogenous gene encoding Glucan Water Dikinase in a sample. The kit may comprise a first primer and a second primer. The first primer and the second primer may be capable of amplifying a target sequence included in an endogenous gene encoding Glucan Water Dikinase. The target sequence may include a nucleic acid with at least 70, 72, 75, 80, 85, 90, 91, 92, 93, 94, 95, 96, 97, 98, 99, or 100% identity to a reference sequence selected from SEQ ID NOS: 1-4, 75, 171-187, 189 and 192. The kit may further comprise one or more component for detecting modifications in the amplified region of the target sequence. The kit may comprise the first primer comprising a nucleic acid sequence selected from SEQ ID NOS: 6, 7, 9, 11, 101, 103, 105, 110, and 111. The kit may comprise the second primer comprising a nucleic acid sequence selected from SEQ ID NOS: 5, 8, 10, 102, and 104. The kit may comprise the first primer comprising the nucleic acid sequence of SEQ ID NO: 6 and the second primer comprising the nucleic sequence of SEQ ID NO: 5. The kit may comprise the first primer comprising the nucleic acid sequence of SEQ ID NO: 7 and the second primer comprising the nucleic acid sequence of SEQ ID NO: 8. The kit may comprise the first primer comprising the nucleic acid sequence of SEQ ID NO: 9 and the second primer comprising the nucleic acid sequence of SEQ ID NO: 10. The kit may comprise the first primer comprising the nucleic acid sequence of SEQ ID NO: 11 and the second primer comprising the nucleic acid sequence of SEQ ID NO: 13. The kit may comprise the first primer comprising the nucleic acid sequence of SEQ ID NO: 110 and the second primer comprising the nucleic acid sequence of SEQ ID NO: 13. The kit may comprise the first primer comprising the nucleic acid sequence of SEQ ID NO: 111 and the second primer comprising the nucleic acid sequence of SEQ ID NO: 112. The kit may comprise the first primer comprising the nucleic acid sequence of SEQ ID NO: 105 and the second primer comprising the nucleic acid sequence of SEQ ID NO: 13. The first primer and the second primer may be capable of amplifying the target sequence to produce an amplified product. The amplified product may comprise a modified target sequence. The modified target sequence may be capable of hybridizing to the sequence of the nucleic acid comprising a sequence selected of SEQ ID NO: 12-40, 106-107, 114-120, 131-146, and 188 under conditions of high stringency. The modified target sequence may be used as a probe for diagnosing the genetically engineered plants having mutations in an endogenous gene encoding the Glucan Water Dikinase. A sample may include any sample in which nucleic acids from plant matter are present. The sample may include any plant matter. The plant matter may derive from a plant or part thereof. The plant material may derive from an animal feed or food.

An embodiment provides a method of identifying a modified sequence of an endogenous gene encoding a Glucan Water Dikinase in a sample is provided. The method may include contacting a sample with a first primer and a second primer. The method may include amplifying a synthetic polynucleotide comprising a target sequence included in an endogenous gene encoding a Glucan Water Dikinase. The target sequence may be any target sequence included in the endogenous gene encoding the Glucan Water Dikinase described herein. The first primer and the second primer may be capable of amplifying the target sequence to produce an amplified product. The amplified product may be used to determine whether a plant resulted from a sexual crossing or selfing contains one or more modifications in the target sequence and diagnose specific mutants. The length of the amplified product from the sample of the mutant plant may differ from the length of the amplified product from the sample of wild type plant of the same genetic background. The amplified product from the mutant sample may be further used as probe that hybridizes to a synthetic polynucleotide comprising a specific region encoding a mutant protein under conditions of high stringency. The method may include further detecting hybridization of the at least one probe to the specific region of the target sequence.

Methods of making a genetically engineered plant, methods of increasing starch levels in plants, methods of agricultural processing, methods of preparing animal feed and methods for producing genetically engineered plants homozygous for an engineered nucleic acid that encodes an altered Glucan Water Dikinase may comprise a method of detection herein as part of making genetically engineered plants and/or identifying plants or plant biomass that comprise a genetically engineered nucleic acid herein.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

EMBODIMENTS

1. A synthetic nucleic acid promoter having a sequence with at least 70, 72, 75, 80, 85, 90, 91, 92, 93, 94, 95, 96, 97, 98, 99, or 100% identity to a reference sequence selected from the group consisting of: SEQ ID NO: 78 (MzU3.8), SEQ ID NO: 79 (ZmU3), SEQ ID NO: 82 (ZmU3P1), SEQ ID NO: 84 (ZmU3P2) and SEQ ID NO: 86 (MzU3.8P).

2. A genetic construct comprising a first engineered nucleic acid sequence encoding a Cas9 nuclease, wherein the Cas9 nuclease is capable of cleaving a target sequence in an endogenous nucleic acid encoding Glucan Water Dikinase in a plant.

3. The genetic construct of embodiment 2, wherein the first synthetic nucleic acid sequence has at least 70, 72, 75, 80, 85, 90, 91, 92, 93, 94, 95, 96, 97, 98, 99, or 100% identity to SEQ ID NO: 74 (Cas9 nuclease) or SEQ ID NO: 75 (ZmCas9).

4. The genetic construct of one or both embodiments 2 and 3, wherein the first nucleic acid is fused to a polynucleotide sequence encoding at least one nuclear localization signal (NLS).

5. The genetic construct of any one or more of embodiments 2-4, wherein the polynucleotide sequence encoding the nuclear localization signal is selected from SEQ ID NOS: 163-168.

6. The genetic construct of any one or more of embodiments 2-5 further comprising a second engineered nucleic acid sequence encoding an sgRNA, and the sgRNA is capable of binding the target sequence.

7. The genetic construct of embodiments 6, wherein the second engineered nucleic acid comprises a sequence with at least 70, 72, 75, 80, 85, 90, 91, 92, 93, 94, 95, 96, 97, 98, 99, or 100% identity to a sequence selected from SEQ ID NO: 135 (ZmU3P1:sgRNA_GWDe24b), SEQ ID NO: 136 (ZmU3P2:sgRNA_GWDe24b), SEQ ID NO: 137 (ZmU3.8P:sgRNA_GWDe24b), SEQ ID NO: 138 (ZmU3P2:sgRNA_GWDe24c), SEQ ID NO: 139 (ZmU3P2:sgRNA_GWDe25a) and SEQ ID NO: 40 (ZmU3P2:sgRNA_GWDe1a).

8. The genetic construct of any one or more of embodiments 2-7, wherein the target sequence has at least 70, 72, 75, 80, 85, 90, 91, 92, 93, 94, 95, 96, 97, 98, 99, or 100% identity to a reference sequence selected from the group consisting of SEQ ID NO: 91 (GWDe1a), SEQ ID NO: 92 (GWDe24b), SEQ ID NO: 93 (GWDe24c), and SEQ ID NO: 94 (GWDe25a).

9. The genetic construct of any one or more of embodiments 2-8 further comprising a first promoter operably linked to the first engineered nucleic acid and a second promoter operably linked to the second engineered nucleic acid.

10. The genetic construct of embodiment 9, wherein the first promoter or the second promoter is a synthetic nucleic acid promoter of embodiment 1.

11. The genetic construct of any one or more of embodiments 2-10 further comprising a terminator.

12. The genetic construct of embodiment 11, wherein the terminator comprises a nucleic acid sequence with at least 90% identity to SEQ ID NO: 88.

13. A genetic construct comprising an engineered nucleic acid sequence encoding a nuclease, wherein the nuclease is capable of cleaving a target sequence included in an endogenous nucleic acid encoding Glucan Water Dikinase.

14. The genetic construct of embodiment 13, wherein the nuclease is a meganuclease encoded by a sequence with at least 70, 72, 75, 80, 85, 90, 91, 92, 93, 94, 95, 96, 97, 98, 99, or 100% identity to a reference sequence selected from the group consisting of SEQ ID N): 164 (4715_meganuclease) and SEQ ID NO: 165 (4716_meganuclease).

15. The genetic construct of any one or more of embodiments 13-14, wherein the target sequence includes a polynucleotide of SEQ ID NO: 41 (Meganuclease GWD-9/10x272) or SEQ ID NO: 42 (Meganucleas3e GWD-7/8x.

16. The genetic construct of any one or more of embodiments 13-15 comprising at least one regulatory element, wherein the regulatory element is selected from a promoter, a terminator, and an enhancer.

17. A vector comprising a genetic construct of any one or more of embodiments 2-16.

18. A genetically engineered plant comprising an engineered nucleic acid encoding an altered Glucan Water Dikinase and having an elevated level of starch in comparison to a non-genetically engineered plant of the same genetic background.

19. The genetically engineered plant of embodiment 18, wherein the activity of the altered Glucan Water Dikinase is reduced compared to the activity of the wild type Glucan Water Dikinase in a non-genetically engineered plant of the same genetic background.

20. The genetically engineered plant of embodiment 18, wherein the altered Glucan Water Dikinase is inactive.

21. The genetically engineered plant of any one or more of embodiments 18-20, wherein the engineered nucleic acid is a modified sequence of an endogenous nucleic that is one allele of a gene encoding a Glucan Water Dikinase.

22. The genetically engineered plant of any one or embodiments 18-21, wherein all alleles of a gene encoding Glucan Water Dikinase in the plant have the sequence of the engineered nucleic acid.

23. The genetically engineered plant of any one or more of embodiments 18-22, wherein the endogenous nucleic acid includes a sequence with at least 70, 72, 75, 80, 85, 90, 91, 92, 93, 94, 95, 96, 97, 98, 99, or 100% identity to a reference sequence of SEQ ID NO: SEQ ID NO: 1 (Zm GWD coding sequence) or SEQ ID NO: 2 (Sb GWD coding sequence).

24. The genetically engineered plant of any one or more of embodiments 18-23, wherein the engineered nucleic acid comprises a mutation selected from at least one of an insertion, a deletion, or substitution of one or more nucleotides in the sequence of the endogenous nucleic acid encoding a wild type GWD.

25. The genetically engineered plant embodiment 24, wherein the mutation is within a target sequence in the endogenous nucleic acid having at least 70, 72, 75, 80, 85, 90, 91, 92, 93, 94, 95, 96, 97, 98, 99, or 100% identity to a reference sequence selected from the group consisting of SEQ ID NO: 3 (Zm GWD Exon 24+introns), SEQ ID NO; 4 (SbGWD Exon 24+introns), SEQ ID NO: 182 (ZmGWD Exon 24 no introns), SEQ ID NO: 183 (Sb GWD Exon 24), SEQ ID NO: 184 (SbGWD Exon 7) and SEQ ID NO: 189 (Zm GWD Exon 25).

26. The genetically engineered plant of any one or more of embodiments 18-25, wherein the mutation is within a target sequence in the endogenous nucleic acid having at least 70, 72, 75, 80, 85, 90, 91, 92, 93, 94, 95, 96, 97, 98, 99, or 100% identity to a reference sequence selected from the group consisting of SEQ ID NO: 91 (GWDe1a), SEQ ID NO: 92 (GWDe24b), SEQ ID NO: 93 (GWDe24c), and SEQ ID NO: 94 (GWDe25a).

27. The genetically engineered plant of any one or more of embodiments 18-26, wherein the engineered nucleic acid comprises a polynucleotide having a sequence with at least 70, 72, 75, 80, 85, 90, 91, 92, 93, 94, 95, 96, 97, 98, 99, or 100% identity to a reference sequence selected from the group of sequences consisting of SEQ ID NOS: 12-40 (Zm GWD mutations-Exon 24).

28. The genetically engineered plant of any one or more of embodiments 18-26, wherein the engineered nucleic acid comprises a polynucleotide having a sequence with at least 70, 72, 75, 80, 85, 90, 91, 92, 93, 94, 95, 96, 97, 98, 99, or 100% identity to a reference sequence selected from the group of sequences consisting of SEQ ID NOS: 114-118, 188, 131-146 (Zm GWD mutations-Exon 24), and 119-120 (Zm GWD mutations—Exon 25).

29. The genetically engineered plant of any one or more of embodiments 18-25, wherein the engineered nucleic acid comprises a polynucleotide having a sequence with at least 70, 72, 75, 80, 85, 90, 91, 92, 93, 94, 95, 96, 97, 98, 99, or 100% identity to a reference sequence selected from the group of sequences consisting of SEQ ID NO: 106 (Sb4715_1 (WT+ins)_Exon 24, and SEQ ID NO: 107 (Sb4715_2 (WT+ins)_Exon 24).

30. The genetically engineered plant of any one or more of embodiments 16-28, wherein the altered Glucan Water Dikinase comprises an amino acid sequence with at least 70, 72, 75, 80, 85, 90, 91, 92, 93, 94, 95, 96, 97, 98, 99, or 100% identity to a reference sequence selected from the group consisting of SEQ ID NOS: 45-73 (Zm GWD mutant proteins M1-M29).

31. The genetically engineered plant of any one or more of embodiments 16-25, wherein the altered Glucan Water Dikinase comprises an amino acid sequence with at least 70, 72, 75, 80, 85, 90, 91, 92, 93, 94, 95, 96, 97, 98, 99, or 100% identity to a reference sequence selected from the group consisting of SEQ ID NOS: 121-125 (Zm GWD mutant proteins M32-M36), 126-127 (Zm GWD mutant proteins M38-M39) and 147-162 (Zm GWD mutant proteins M40-M55).

32. The genetically engineered plant of any one or more of embodiments 18-26, wherein the altered Glucan Water Dikinase comprises an amino acid sequence with at least 70, 72, 75, 80, 85, 90, 91, 92, 93, 94, 95, 96, 97, 98, 99, or 100% identity to a reference sequence selected from SEQ ID NO: 82 (Sb GWD mutant protein Sb4715_1 WT+ ins) or SEQ ID NO: 83 (Sb GWD mutant protein Sb4715_2 WT+ del).

33. The genetically engineered plant of any one or more of embodiments 18-33, wherein the plant is selected from the group consisting of: a monocotyledonous plant, a dicotyledonous plant, a C4 plant, a C3 plant, tomato, sugar beet, sugar cane, eucalyptus, willow, poplar, corn, sorghum, wheat, alfalfa, soybean, rice, miscanthus, and switchgrass.

34. A genetically engineered plant comprising a genetic construct of any one or more of embodiments 2-16.

35. A method for producing a genetically engineered plant comprising:
  transforming a plant cell with a vector of embodiment 17;
  selecting a transformed plant cell that expresses nuclease and comprises an engineered nucleic acid encoding an altered Glucan Water Dikinase; and
  regenerating the genetically engineered plant from the transformed plant cell, wherein the genetically engineered plant or progeny thereof has an elevated level of starch in comparison to a non-genetically engineered plant of the same genetic background.

36. The method of embodiment 35, wherein the nuclease is a meganuclease.

37. The method of embodiment 35, wherein the nuclease is a Cas9 nuclease.

38. A method for genetically engineering a plant comprising an altered Glucan Water Dikinase comprising:
  contacting at least one plant cell comprising a target sequence in an endogenous gene encoding a Glucan Water Dikinase with a vector comprising a first nucleic acid encoding a nuclease capable of inducing a single-strand or double-strand break at the target sequence;
  selecting a plant cell that includes an alteration in the target sequence;
  regenerating a genetically engineered plant including the alteration from the plant cell.

39. The method of embodiment 38, wherein the genetically engineered plant is homozygous for the alteration.

40. The method of embodiment 38, wherein the genetically engineered plant is heterozygous for the alteration.

41. The method of embodiment 40 further comprising selfing the heterozygous genetically engineered plant, or crossing to another genetically engineered plant heterozygous for the same alteration, and selecting a first progeny plant that is homozygous for the alteration.

42. The method of embodiment 40 further comprising crossing the genetically engineered plant to a wild type plant of the same genetic background and selecting a first progeny plant that is heterozygous for the alteration.

43. The method of embodiment 42 further comprising selfing the first heterozygous progeny plant and selecting a second progeny plant that is homozygous for the alteration.

44. The method of any one or more of embodiment 38-43, wherein the alteration is a mutation selected from at least one of an insertion, a deletion, or a substitution of at least one nucleotide in the target sequence.

45. The method of embodiment 44, wherein the mutation is a null mutation.

46. The method of any one or more of embodiments 38-44, wherein the genetically engineered plant or progeny thereof has an elevated level of starch in comparison to a non-genetically engineered plant of the same genetic background.

47. The method of any one or more embodiments 38-46, wherein the nuclease is selected from the group consisting of a meganuclease, Cas9 nuclease, a zinc finger nuclease, and a transcription activator-like effector nuclease.

48. The method of embodiment 47, wherein the nuclease is the meganuclease and is encoded by a sequence with at least 90% identity to a reference sequence selected from the group consisting of SEQ ID NO: 108 (4715_meganuclease) and SEQ ID NO: 109 (4716_meganuclease).

49. The method of embodiment 48, wherein the meganuclease is capable of cutting the target sequence that comprises a polynucleotide of SEQ ID NO: 41 (target for 4715_GWD-9/10x272) or SEQ ID NO: 42 (target for 4716_3e GWD-7/8x276).

50. The method of embodiment 47, wherein the nuclease is the Cas9 nuclease.

51. The method of embodiment 50, wherein the Cas9 nuclease is encoded by a nucleic acid with at least 90% identity to SEQ ID NO: 74 (Cas9 nuclease) or SEQ ID NO: 75 (ZmCas9).

52. The method of embodiment 51, wherein the nucleic acid encoding the Cas9 nuclease is fused to at least one nuclear localization signal (NLS), and the NLS has a polynucleotide sequence selected from SEQ ID NOS: 163-168.

53. The method of any one of embodiments 38-47 and 50-52, wherein the vector further comprises a second nucleic acid sequence encoding an sgRNA.

54. The method of embodiment 53, wherein the sgRNA is capable of binding the target sequence, and the target sequence is selected from the group consisting of SEQ ID NO: 91 (GWDe1a), SEQ ID NO: 92 (GWDe24b), SEQ ID NO: 93 (GWDe24c), and SEQ ID NO: 94 (GWDe25a).

55. The method of any one or more of embodiments 53-54, wherein the second nucleic acid comprises a sequence with at least 90% identity to SEQ ID NOS: 95 (ZmU3P1: sgRNA_GWDe24b), SEQ ID NO: 96 (ZmU3P2:

sgRNA_GWDe24b), SEQ ID NO: 97 (ZmU3.8P: sgRNA_GWDe24b), SEQ ID NO: 98 (ZmU3P2: sgRNA_GWDe24c), SEQ ID NO: 99 (ZmU3P2: sgRNA_GWDe25a) and SEQ ID NO: 100 (ZmU3P2: sgRNA_GWDe1a).

56. The method of any one or more of embodiments 38-55, wherein the vector further comprises a nucleic acid promoter operably linked to the first nucleic acid or the second nucleic acid.

57. The method of embodiment 56, wherein the nucleic acid promoter comprises a sequence with at least 90% identity to a reference sequence selected from the group consisting of: SEQ ID NO: 78 (MzU3.8), SEQ ID NO: 79 (ZmU3), SEQ ID NO: 82 (ZmU3P1), SEQ ID NO: 84 (ZmU3P2) and SEQ ID NO: 86 (MzU3.8).

58. A genetically engineered plant produced by the method of any one of one of embodiments 38-57, or a progeny or descendant thereof, wherein the plant, progeny or descendant thereof comprises the alteration.

59. The genetically engineered plant of embodiment 58 having an elevated level of starch in comparison to a plant of the same genetic background comprising wild type Glucan Water Dikinase.

60. A method of increasing a starch level in a plant comprising expressing a nucleic acid in the plant that encodes a nuclease capable of inducing a double-strand break at a target sequence and selecting a homozygous plant that includes an alteration in the target sequence and has an elevated level of starch, wherein the target sequence is included in an endogenous gene encoding a Glucan Water Dikinase only.

61. A method of agricultural processing comprising:
expressing in a plant a nucleic acid encoding a nuclease capable of inducing a double-strand break at a target sequence, wherein the target sequence is included in an endogenous gene encoding a Glucan Water Dikinase;
selecting a homozygous plant that includes an alteration in the target sequence and has an elevated level of starch; and
processing the homozygous plant, wherein the processing comprises one or more procedures selected from harvesting, bailing, shredding, drying, fermenting, hydrolyzing with chemicals, hydrolyzing with exogenous enzymes and combining with plant biomass. The method may also comprise the method for producing a genetically engineered plant of any one or more of embodiments 63-71.

62. A method of preparing animal feed comprising:
expressing in a plant a nucleic acid encoding a nuclease capable of inducing a double-strand break at the target sequence, wherein the target sequence is included in an endogenous gene encoding a Glucan Water Dikinase;
selecting a homozygous plant that includes an alteration in the target sequence and has an elevated level of starch; and
performing at least one procedure selected from the group consisting of: harvesting, bailing, shredding, drying, ensiling, pelletizing, combining with a source of edible fiber, and combining with plant biomass. The method may also comprise the method for producing a genetically engineered plant of any one or more of embodiments 63-71.

63. A method for producing a genetically engineered plant comprising an engineered nucleic acid that encodes an altered Glucan Water Dikinase comprising modifying a sequence of an endogenous nucleic acid of at least one allele of a gene that encodes a Glucan Water Dikinase in a plant, wherein the modified engineered nucleic acid is an engineered nucleic acid and the modified plant is the genetically engineered plant.

64. The method of embodiment 63, wherein the genetically engineered plant is homozygous for the gene that includes the mutation and all alleles include the sequence of the engineered nucleic acid.

65. The method of embodiment 63, wherein the genetically engineered plant is heterozygous for the gene that includes the mutation.

66. The method of any one or more of embodiments 63 or 65 further comprising self-crossing the genetically engineered plant and obtaining progeny.

67. The method of any one or more of embodiments 63-65 further comprising crossing the genetically engineered plant and a non-genetically engineered plant of the same genetic background and obtaining progeny.

68. The method of any one or more of embodiments 66-67 comprising analyzing the progeny for the presence of the altered Glucan Water Dikinase and selecting a progeny plant that includes the mutation.

69. The method of embodiment 63 comprising the genetically engineered plant of any one or more of embodiments 18-34 and 58-59.

70. The method of embodiment 63, wherein the step of modifying is performed by a method of any one of embodiments 35-36.

71. The method of embodiment 63, wherein the step of modifying is performed by using a genetic construct of any one of embodiments 2-16.

72. A kit for identifying a modified sequence of an endogenous gene encoding Glucan Water Dikinase in a sample, wherein the kit comprises a first primer and a second primer, wherein the first primer and the second primer are capable of amplifying a target sequence in the endogenous gene encoding Glucan Water Dikinase and the target sequence comprises a nucleic acid sequence with at least 90% identity to a reference sequence selected from SEQ ID NOS: 1-4, 75, 171-187, 189 and 192.

73. The kit of embodiment 72 further comprising one or more component for detecting at a modification in the amplified region of the target sequence.

74. The kit of any one or more of embodiments 72-73 wherein, the first primer comprises a nucleic acid sequence selected from SEQ ID NOS: 6, 7, 9, 11, 101, 103, 105, 110, and 111.

75. The kit of any one or more of embodiments 72-74, wherein the second primer comprises a nucleic acid sequence selected from SEQ ID NOS: 5, 8, 10, 102, and 104.

76. The kit of any one or more of embodiments 72-75, wherein the first primer and the second primer are capable of amplifying the target sequence to produce an amplified product comprising a modified target sequence.

77. The kit of any one or more of embodiments 73-76, wherein the amplified target sequence comprises a sequence selected from SEQ ID NOS: 12-40, 106-107, 114-120, 131-146, and 188.

78. The kit of any one or more of embodiments 72-76, wherein the modified target sequence is capable of hybridizing to the sequence of the nucleic acid comprising a sequence selected from SEQ ID NOS: 12-40, 106-107, 114-120, 131-146, and 188 under conditions of high stringency.

79. The kit of any one or more of embodiments 72-78, wherein the sample comprises plant matter derived from a genetically engineered plant having at least one mutation in an endogenous gene encoding the Glucan Water Dikinase.

80. A method of identifying a modified sequence of an endogenous gene encoding Glucan Water Dikinase in a sample comprising:

contacting a sample with a first primer and a second primer;

amplifying a target sequence included in the endogenous gene encoding Glucan Water Dikinase and the target sequence comprises a nucleic acid sequence with at least 90% identity to a reference sequence selected from SEQ ID NOS: 1-4, 75, 171-187, 189 and 192; and detecting a modification in the target sequence.

81. The method of embodiment 79, wherein the modification in the target sequence comprises a sequence selected from SEQ ID NOS: 12-40, 106-107, 114-120, 131-146, and 188. The method of identifying may be added to any one or more of embodiments 60-71.

82. A method of preparing animal feed comprising processing a genetically engineered plant comprising a nucleic acid encoding a restricting enzyme capable of cutting a target sequence, wherein the target sequence is in an endogenous gene encoding a Glucan Water Dikinase, wherein upon the expression of the nucleic acid, the genetically engineered plant has an altered level of vegetative starch compared to the level of vegetative starch in a non-genetically engineered plant, and processing includes at least one of operation selected from the group consisting of harvesting, bailing, grinding, milling, chopping, size reducing, crushing, extracting a component from the feedstock, purifying a component or portion of the feedstock, and extracting or purifying starch.

83. The method of embodiment 82, wherein the restricting enzyme is selected from the group consisting of a meganuclease, a zinc-finger nuclease, and a TAL effector nuclease.

84. The method of embodiment 83, wherein the meganuaclease is selected from the group consisting of I-CreI, I-DmoI, I-SceI, E-DmeI, and DmoCre.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1. Meganuclease-Based Modification of GWD Gene in Maize and *Sorghum* Genomes Meganuclease constructs were designed that target GWD exon 24, which is near the predicted encoded active site of the enzyme, with the intent of introducing a mutation that inactivates GWD (null mutation). Meganuclease-induced GWD DNA mutants were identified and characterized in maize and *sorghum*.

In order to engineer I-CreI homing endonucleases with specificities against GWD genes in maize and *sorghum* genomes, two nucleotide sequences were selected from the previously annotated full length GWD genes of maize and *sorghum*. The sequence selection was based on the existence of the high nucleotide sequence identity between maize and *sorghum* sequences (95% nucleotide sequence identity) and the presence of a sequence motif in exons #24 of both crops that is required for GWD protein activity. The goal was to develop two meganuclease constructs in such a way that each of them would be specific for GWD modification in both maize and *sorghum*. Targeted genome modifications at the selected GWD sequences using the meganuclease approach would lead to expression of GWD protein variants lacking the active site (truncated proteins or modified proteins expressed from the frame shift containing coding sequences) and therefore being catalytically inactive. The selected sequences of ZmGWD (maize) and SbGWD (*sorghum*) shown below were supplied to Precision Biosciences, Inc. for designing meganucleases GWD9-10x272 and GWD7-8x.226.

The target sequence for the meganuclease GWD-9/10x.272 (pAG4715) is: ATCCTTGTGGCAAAGAGT-GTCA (SEQ ID NO: 41).

The target sequence for the meganuclease GWD-7/8x.226 target sequence (pAG4716) is: GTAGTTGGTGTAATTA-CACCTG (SEQ ID NO: 42).

The DNA sequences within exon 24 that are recognized by the designed meganucleases are underlined. The sequences in the uppercase letters show exon 24, while the sequences in lowercase letters represent flanking introns. The "CAT" codon that is double-underlined encodes a Histidine residue that is critical for GWD protein activity.

```
>ZmGWD_Exon24
                                        (SEQ ID NO: 3)
aagtgatactagtgaccctctccacaattttatgcgaaccacagaaatta ataatatattctattactctgcacctgacatctggctcctgctatcagTT

GGCAGGTTATAAGCCCGGTTGAAGTATCAGGTTATGTGGTTGTGGTTGAT

GAGTTACTTGCTGTCCAGAACAAATCTTATGATAAACCAACCATCCTTGT

GGCAAAGAGTGTCAAGGGAGAGGAAGAAATACCAGATGGAGTAGTTGGTG

TAATTACACCTGATATGCCAGATGTTCTGTCTCATGTGTCAGTCCGAGCA

AGGAATAGCAAGgtttatcttcacagctatgttgcaagatttcttgaatt ttttctcttgtattgatgttgacatactagcttttcctaat >SbGWD_Exon24
                                        (SEQ ID NO: 4)
aagtggtactagtgacctctccacagttttatgtgaaccacagaaattaa atatgataatatattctattactctgcacctgacatctggctcctgataa cagTTGGCAGGTTATAAGCCCAGTTGAAGTATCAGGTTATGTGGTTGTGG

TTGATGAGTTACTTGCTGTCCAGAACAAATCTTATGATAAACCAACCATC

CTTGTGGCAAAGAGTGTCAAGGGAGAGGAAGAAATACCAGATGGAGTAGT

TGGTGTAATTACACCTGATATGCCAGATGTTCTGTCCCATGTGTCAGTCC

GAGCAAGGAATAGCAAGgtttattttcacagttatgttgcaagctttctc agattttttttcttgtatcgatgttgacataccagttttttcctaat
```

Clustal software was used to align selected ZmGWD and SbGWD sequences. (Larkin M A et al., 2007; Goujon M et al., 2010, both of which are incorporated herein by reference as if fully set forth).

CLUSTAL 2.1 multiple sequence alignment

```
SbGWD_Exon24     aagtggtactagtgacctctccacagttttatgtgaaccacagaaattaaatatgataa    59
ZmGWD_Exon24     aagtgatactagtgacctctccacaattttatgcgaaccacagaaatta------ataa    54
                 ***** ************ ******* ******* ***************      ****

SbGWD_Exon24     tatattctattactctgcacctgacatctggctcctgataacagTTGGCAGGTTATAAGC   119
ZmGWD_Exon24     tatattctattactctgcacctgacatctggctcctgctatcagTTGGCAGGTTATAAGC   114
                 ******************************************  ** ************

SbGWD_Exon24     CCAGTTGAAGTATCAGGTTATGTGGTTGTGGTTGATGAGTTACTTGCTGTCCAGAACAAA   179
ZmGWD_Exon24     CCGGTTGAAGTATCAGGTTATGTGGTTGTGGTTGATGAGTTACTTGCTGTCCAGAACAAA   174
                 ** *********************************************************

SbGWD_Exon24     TCTTATGATAAACCAACCATCCTTGTGGCAAAGAGTGTCAAGGGAGAGGAAGAAATACCA   239
ZmGWD_Exon24     TCTTATGATAAACCAACCATCCTTGTGGCAAAGAGTGTCAAGGGAGAGGAAGAAATACA    234
                 ***********************************************************

SbGWD_Exon24     GATGGAGTAGTTGGTGTAATTACACCTGATATGCCAGATGTTCTGTCCCATGTGTCAGTC   299
ZmGWD_Exon24     GATGGAGTAGTTGGTGTAATTACACCTGATATGCCAGATGTTCTGTCTCATGTGTCAGTC   294
                 ************************************************ ************

SbGWD_Exon24     CGAGCAAGGAATAGCAAGgtttattttcacagttatgttgcaagctttctcagattttt    359
ZmGWD_Exon24     CGAGCAAGGAATAGCAAGgtttatcttcacagctatgttgcaagatttcttgaattttt    354
                 ************************ ****** ***********  **** *  *******

SbGWD_Exon24     ttcttgtatcgatgttgacataccagttttttcctaat                        397 (SEQ ID NO: 4)
ZmGWD_Exon24     ctcttgtattgatgttgacatactagcttttttcctaat                       392 (SEQ ID NO: 3)
                  ******** ************ **  **********
```

Figure 2:
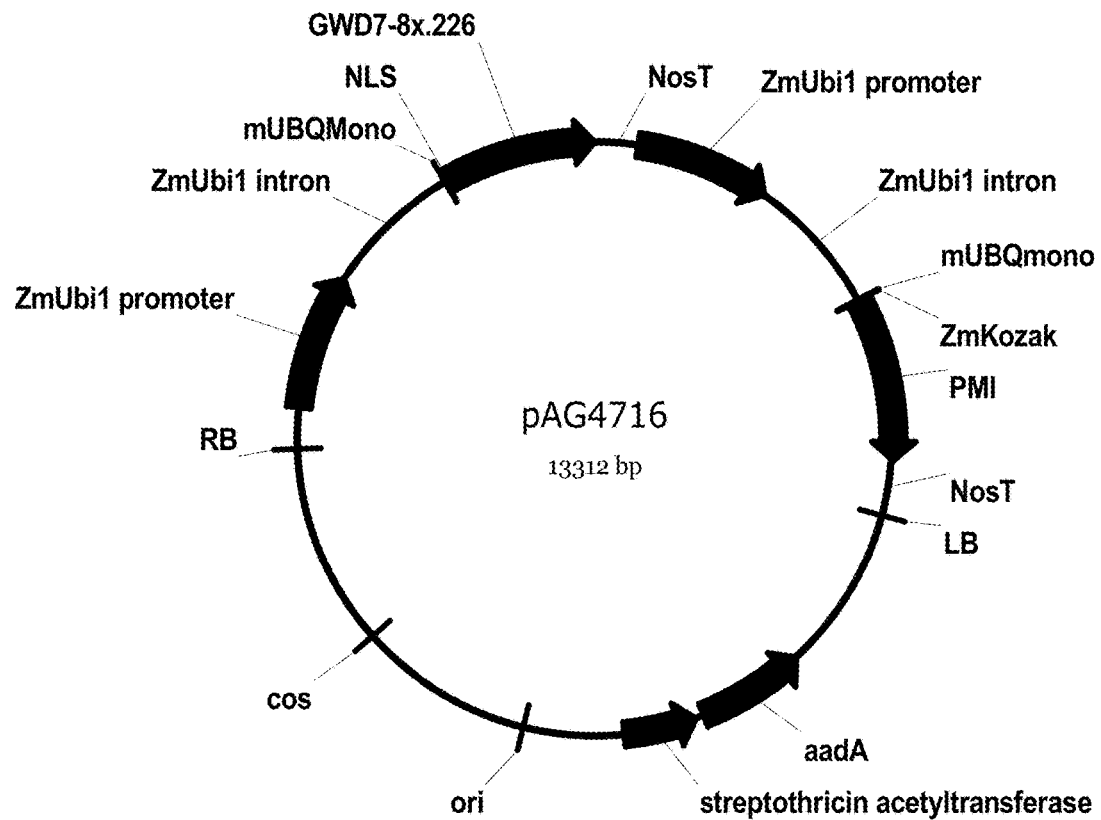
FIG. 2 illustrates the vector pAG4716 for expressing meganuclease.

Development of plant transformation vectors for expressing meganucleases:

The meganuclease sequences GWD-9/10.x272[SEQ ID NO: 108] and GWD-7/8x.226 [SEQ ID NO: 109], which were provided by Precision Biosciences, Inc., were further modified by adding BamHI restriction site at 5' and AvrII site at 3' ends using PCR approach. Subsequently, GWD-9/10x.272 and GWD-7/8x.226 nucleotide sequences were cloned into pAG4500 vector as BamHI-AvrII fragments between the maize ubiquitin 1 gene promoter and Nos transcriptional terminator sequences to generate respectively plant transformation vectors pAG4715 and pAG4716. FIG. 1 and FIG. 2 illustrate respective maps of pAG4715 and pAG4716 vectors. Referring to FIGS. 1 and 2, pAG4715 and 4716 include a maize ubiquitin promoter (ZmUbi1), a maize ubiquitin intron (ZmUbi1 intron), and a polyadenilation signal NosT serving as the transcription terminator. Both vectors also include a phosphomannose isomerase gene (PMI) as a selectable marker, At NLS (nuclear localization sequence), ZmKozak, mUBQmono, T-DNA right and left borders (RB and LB, respectively), a streptothricin acetyltransferase gene, and an aminoglycoside acetyltransferse (aadA) gene conferring resistance to streptomycin. pAG4715 includes a GWD9-10x.272 meganuclease sequence [SEQ ID NO: 108] and pAG4716 includes a GWD7-8x.226 meganuclease sequence [SEQ ID NO: 109].

pAG4715 and pAG4716 were used to generate transgenic events and mutants in maize and *sorghum*.

Sequences of the target proteins, genes, mutants and vectors used herein are listed in Table 1.

TABLE 1

| SEQ ID NO | Description | Type |
|---|---|---|
| 1 | ZmGWD coding sequence | DNA |
| 2 | SbGWD coding sequence | DNA |
| 3 | ZmGWD Exon 24 (includes introns) | DNA |
| 4 | SbGWD Exon 24 (includes introns) | DNA |

TABLE 1-continued

| SEQ ID NO | Description | Type |
|---|---|---|
| 182 | ZmGWD Exon 24 (no introns) | DNA |
| 183 | SbGWD Exon 24 (no introns) | DNA |
| 184 | SbGWD Exon 7 (no introns) | DNA |
| 5 | Mega-1 (4716) PCR Primer Reverse | DNA |
| 6 | Mega-1 (4716) PCR Primer Forward | DNA |
| 7 | Mega-2 (4715) PCR Primer Forward | DNA |
| 8 | Mega-2 (4715) PCR Primer Reverse | DNA |
| 9 | ZmGWD mega-2 PCR Primer Forward | DNA |
| 10 | ZmGWD mega-2 PCR Primer Reverse | DNA |
| 11 | SbGWD mega-2 PCR Primer Forward | DNA |
| 13 | SbGWD mega-2 PCR Primer Reverse | DNA |
| 12 | M16 (Zm GWD Exon 24 - no introns) | DNA |
| 13 | M17 (Zm GWD Exon 24 - no introns) | DNA |
| 14 | M18 (Zm GWD Exon 24 - no introns) | DNA |
| 15 | M27 (Zm GWD Exon 24 - no introns) | DNA |
| 16 | M1 (Zm GWD Exon 24 - no introns) | DNA |
| 17 | M11 (Zm GWD Exon 24 - no introns) | DNA |
| 18 | M10 (Zm GWD Exon 24 - no introns) | DNA |
| 19 | M3 (Zm GWD Exon 24 - no introns) | DNA |
| 20 | M8 (Zm GWD Exon 24 - no introns) | DNA |
| 21 | M14 (Zm GWD Exon 24 - no introns) | DNA |
| 22 | M13 (Zm GWD Exon 24 - no introns) | DNA |
| 23 | M12 (Zm GWD Exon 24 - no introns) | DNA |
| 24 | M22 (Zm GWD Exon 24 - no introns) | DNA |
| 25 | M23 (Zm GWD Exon 24 - no introns) | DNA |
| 26 | M24 (Zm GWD Exon 24 - no introns) | DNA |
| 27 | M20 (Zm GWD Exon 24 - no introns) | DNA |
| 28 | M21 (Zm GWD Exon 24 - no introns) | DNA |
| 29 | M4 (Zm GWD Exon 24 - no introns) | DNA |
| 30 | M19 (Zm GWD Exon 24 - no introns) | DNA |
| 31 | M26 (Zm GWD Exon 24 - no introns) | DNA |
| 32 | M25 (Zm GWD Exon 24 - no introns) | DNA |
| 33 | M15 (Zm GWD Exon 24 - no introns) | DNA |
| 34 | M5 (Zm GWD Exon 24 - no introns) | DNA |
| 35 | M2 (Zm GWD Exon 24 - no introns) | DNA |
| 36 | M28 (Zm GWD Exon 24 - no introns) | DNA |
| 37 | M6 (Zm GWD Exon 24 - no introns) | DNA |
| 38 | M9 (Zm GWD Exon 24 - no introns) | DNA |
| 39 | M7 (Zm GWD Exon 24 - no introns) | DNA |
| 40 | M29 (Zm GWD Exon 24 - no introns) | DNA |
| 106 | Mutant Sb4715_1 (Wt + ins) | DNA |
| 107 | Mutant Sb4715_2 (WT + del) | DNA |

TABLE 1-continued

Description of Sequences

| SEQ ID NO | Description | Type |
|---|---|---|
| 41 | Meganuclease GWD-9/10x.272 target sequence (pAG4715) | DNA |
| 42 | Meganuclease GWD-7/8x target sequence (pAG4716) | DNA |
| 43 | ZmGWD (wild type protein) | Amino acid |
| 44 | SbGWD (wild type protein) | Amino acid |
| 45 | ZmGWD M1 (mutant GWD protein) | Amino acid |
| 46 | ZmGWD M2 (mutant GWD protein) | Amino acid |
| 47 | ZmGWD M3 (mutant GWD protein) | Amino acid |
| 48 | ZmGWD M4 (mutant GWD protein) | Amino acid |
| 49 | ZmGWD M5 (mutant GWD protein) | Amino acid |
| 50 | ZmGWD M6 (mutant GWD protein) | Amino acid |
| 51 | ZmGWD M7 (mutant GWD protein) | Amino acid |
| 52 | ZmGWD M8 (mutant GWD protein) | Amino acid |
| 53 | ZmGWD M9 (mutant GWD protein) | Amino acid |
| 54 | ZmGWD M10 (mutant GWD protein) | Amino acid |
| 55 | ZmGWD M11 (mutant GWD protein) | Amino acid |
| 56 | ZmGWD M12 (mutant GWD protein) | Amino acid |
| 57 | ZmGWD M13 (mutant GWD protein) | Amino acid |
| 58 | ZmGWD M14 (mutant GWD protein) | Amino acid |
| 59 | ZmGWD M15 (mutant GWD protein) | Amino acid |
| 60 | ZmGWD M16 (mutant GWD protein) | Amino acid |
| 61 | ZmGWD M17 (mutant GWD protein) | Amino acid |
| 62 | ZmGWD M18 (mutant GWD protein) | Amino acid |
| 63 | ZmGWD M19 (mutant GWD protein) | Amino acid |
| 64 | ZmGWD M20 (mutant GWD protein) | Amino acid |
| 65 | ZmGWD M21 (mutant GWD protein) | Amino acid |
| 66 | ZmGWD M22 (mutant GWD protein) | Amino acid |
| 67 | ZmGWD M23 (mutant GWD protein) | Amino acid |
| 68 | ZmGWD M24 (mutant GWD protein) | Amino acid |
| 69 | ZmGWD M25 (mutant GWD protein) | Amino acid |
| 70 | ZmGWD M26 (mutant GWD protein) | Amino acid |
| 71 | ZmGWD M27 (mutant GWD protein) | Amino acid |
| 72 | ZmGWD M28 (mutant GWD protein) | Amino acid |
| 73 | ZmGWD M29 (mutant GWD protein) | Amino acid |
| 74 | Mutant protein Sb4715_1 (WT + ins) | Amino acid |
| 75 | Mutant protein Sb4715_2 (WT + del) | Amino acid |

Example 2. Application of TALENs for Targeted Modification of GWD Gene in Sorghum Genome Two pairs of DNA sequences were selected in each of the exons 7 and 24 of the *sorghum* GWD gene (SbGWD) for development of four custom TAL DNA-binding domains that will be fused to a truncated FokI nuclease sequence. The *sorghum* exon 24 was selected because it contains the GWD active site and to compare with other endogenous DNA editing technologies in maize, such as meganuclease and CRISP/Cas9 technologies. The *sorghum* exon 7 was chosen in the upstream region of the GWD gene sequence for producing shorter truncated versions of the GWD protein. Selection of the sequences for DNA-binding domains was performed on Life Technologies web site using a proprietary program. The two pairs of TAL DNA binding domains fused to truncated FokI endonuclease for targeted *sorghum* genome modifications in exons 7 and 24 of the GWD gene are being constructed by Life Technologies. Each pair of TALENs will recognize top and bottom strands of genomic DNA sequence at the respective GWD sites to target FokI nuclease for DNA cleavage.

SbGWD nucleotide sequences selected for TALENs-based GWD modification. The SbGWD_exon7 sequence is positioned within nt 736-969 the SbGWD coding sequence (SEQ ID NO: 2):

```
>SbGWD_exon7
                                       (SEQ ID NO: 184)
GAGGAGTATGAAGCTGCACGAGCTGAGTTAATAGAGGAATTAAATAGAG

GTGTTTCTTTAGAGAAGCTTCGAGCTAAATTGACAAAAACACCTGAAGCA

CCTGAGTCAGATGAACGTAAATCTCCTGCATCTCGAATGCCCGTTGATAA

ACTTCCAGAGGACCTTGTACAGGTGCAGGCTTATATAAGGTGGGAGAAAG

CGGGCAAGCCAAATTATCCTCCTGAGAAGCAACTG
```

The SbGWD_exon24 sequence is positioned within nt 3030-3243 the SbGWD coding sequence (SEQ ID NO: 2):

```
>SbGWD_exon24
                                       (SEQ ID NO: 183)
TTGGCAGGTTATAAGCCCAGTTGAAGTATCAGGTTATGTGGTTGTGGTTG

ATGAGTTACTTGCTGTCCAGAACAAATCTTATGATAAACCAACCATCCTTG

TGGCAAAGAGTGTCAAGGGAGAGGAAGAAATACCAGATGGAGTAGTTGG

TGTAATTACACCTGATATGCCAGATGTTCTGTCCCATGTGTCAGTCCGAG

CAAGGAATAGCAAG
```

Underlined sequences in each exon represent selected TAL DNA binding sites with the left sequence being specific for the upper DNA strand and the right sequence targeting the bottom DNA strand. A codon encoding catalytically important Histidine residue for GWD protein activity is double-underlined and in bold within exon 24. The TALENs specific for exon 7 or exon 24 will be cloned as respective pairs into pAG4500-based plant transformation vector.

Example 3. Plant Transformation and Analysis

Maize and *Sorghum* Transformation:
DNA from *Agrobacterium* was extracted using the protocol described in the Plasmid pSB1 operating manual. Plant DNA was extracted using Qiagen DNeasy Plant Mini kit (69140). Maize and *sorghum* embryos were transformed with GWD meganuclease targeting constructs pAG4715 and/or pAG4716 according to Negrotto D et al. 2000 Plant Cell Rep 19: 798; Ishida Y et al. 1996 Nat Biotech 14: 74, which is incorporated herein by reference as if fully set forth. Briefly, embryogenic callus from wild-type A×B maize was inoculated with LBA4404 *Agrobacterium* cells harboring the appropriate transformation plasmid. *Agrobacterium*-mediated transformation of immature maize embryos was performed as described on Negrotto D et al. The expression cassettes for GWD meganucleases were cloned into the KpnI-EcoRI sites of an intermediate vector capable of recombining with the pSB1 vector in triparental mating in *Agrobacterium tumefaciens* strain LBA4404 using procedures reported previously (Ishida Y et al. 1996 Nat Biotech 14: 745; Hiei Y et al. 1994 Plant J 6: 271; Hiei Y and Komari T 2006 Plant Cell Tissue Organ Cult. 85:27; Komari T et al. 1996 Plant J 10:165). Maize (*Zea mays* cultivars HiII, A188 or B73) stock plants were grown in a greenhouse under 16 hours of daylight at 28° C. Immature zygotic embryos were isolated from the kernels and inoculated with the *Agrobacterium* solution containing the genes of interest. After inoculation immature embryos were grown in a tissue culture process for 10-12 weeks. Well-developed seedlings with leaves and roots were sampled for PCR analysis to identify transgenic plants containing the genes of interest. PCR positive and rooted plants were rinsed with water to wash off the agar medium, and transplanted to soil and grown in the greenhouse to generate seeds and stover.

*Sorghum* transformation was carried according to the protocol of Gao et al., 2005. Regeneration of the transgenic plants was performed according to Elkonin and Pakhomova, 2000.

DNA from *Agrobacterium* was extracted using the protocol described in the Plasmid pSB1 operating manual. Plant DNA was extracted using Qiagen DNeasy Plant Mini kit (69140).

10×TE+Sarkosyl—Plant DNA Isolation for 96 Well Plates:

Briefly, a COSTAR grinding block was filled with ¾ leaf samples, one 5 mm steel bead was added to each well with a sample and the storage mat block was applied using a storage mat applicator to seal the block. Samples were stored at −80° C. for at least 30 min before grinding or until processing time. For processing, samples were ground for 45 sec using the Klecko Pulverizer & Secure grinder at maximum speed. Sealing was removed and discarded. Three hundred microliters of 10×TE+Sarkosyl buffer (5 mL 1M Tris, 1 mL 0.5M EDTA, 0.5 g sarkosyl, 46 mL ddH$_2$O) was added to each sample using a multichannel pipette and a sterile solution basin. The plate was incubated on a shaker for 10 min at 300 rpm, and spun for 3 min at 4000 rpm. Supernatant was removed and discarded, and the pellets were resuspended in 1×TE buffer. One hundred fifty microliter sample aliquots were added to the 96 well PCT plate. The PCR plate was sealed with aluminum foil. For best results, DNA isolation and PCR were performed on the same date.

Transgenic Diagnostic PCR Reaction Setup:

The "complete" PCR reaction mix was as follows: 15 µl 2× GoTaq MM (GoTaq Green Master Mix (PROMEGA #M712), 3 µl of combined forward and reverse primers specific to the gene of interest (each mixed at 10 µM), 2 µl DNA prep, and water to adjust volume to 30 µl. Twenty eight microliters of the "complete" PCR reaction mix per well were aliquoted into a PCR plate (FISHER, #14230236). Two microliters plant DNA sample were aliquoted into each well of the PCR plate. Positive control and no template negative control were used in each PCR reaction. Control *Agrobacterium* DNA was diluted 1:100 in TE buffer to yield clear bands. The PCR plate was sealed with a sealing mat (COSTAR #6555) and roller. PCR was performed at BIORAD PTC-100 thermocycler. The thermocycler programs were as follows: 1) 95° C.-3 min; 30 cycles 95° C.-30 sec, 5° C.-30 sec, 72° C.-45 sec; 72° C.-5 min; 10° C. (hold), and 2) 90° C. for 30 min and 10° C. (hold). Twelve microliters of each PCR reaction was loaded onto Ready Agarose 96 Plus gel −3% (BIORAD #161-3062) and ran at approximately 100V for 20 minutes before viewing with a BIORAD gel doc system equipped with Quantity One software. Quick-Load 50 bp DNA Ladder (NEB N04735) was used to identify the size of the PCR fragments. 10×TBE Buffer (Promega V4251) was used.

In Line Monitor of Starch Content in Living Corn Leaf Using Fourier Transform Near-Infrared (FT-NIR) Technique:

The starch content in corn leaf tissue is an important factor for animal feed and biofuel production. The commonly used GOPOD assay is not applicable for real-time monitoring in living tissue because the assay is invasive, requiring physical tissue samples, and labor intensive. Predictive models of starch content based on the FT-NIR spectra of dry blends of native and maize leaf starches or corn flour (wet and dry) were developed using partial least squares regression. Three key factors determine a successful application of FT-NIR techniques for fast chemical characterization: accurate and repeatable NIR spectral acquisition, reliable calibration data, and robust chemometric analysis. For analysis, the following materials were used: a spectrophotometer (Perkin Elmer Spectrum One NTS Waltham, Mass.), Unscrambler® (Version 10.2., Camo Software Inc., Woodbridge, N.J.), an oven, Hi-maize resistant starch (Honeyville, Brigham City, Utah), and Starch (Product No. S516-500, Fisher Scientific). All blank and test samples were diluted 10× using deionized water and the unreacted starch content was determined using a glucose oxidase-peroxidase (GOPOD) colorimetric assay (Megazyme International, Wicklow, Ireland).

Sample Preparation:

A total of 56 dry starch blend samples with 0-33% starch content were prepared by mixing weight proportions of HI-MAIZE® resistant starch (Honeyville, Brigham City, Utah) with starch (Product No. S516-500, Fisher Scientific). The Honeyville product contains HI-MAIZE® 260 (Ingredion, Bridgewater, N.J.) resistant starch that has been isolated from high amylose corn hybrids produced through traditional plant breeding, and contains 33% digestible, or glycemic starch.

One hundred fifty green leaf samples from different living maize plants at certain age or with different starch accumulation were collected. One hundred samples were oven-dried and 50 samples were left undried ("wet"). Leaf samples were ground to 0.5 mm and stored in plastic sample bags for moisture equilibration. Moisture content was measured using standard methods.

Starch Determination:

The starch content was analyzed for starch blends, wet and dry green tissue or corn flour sample using GOPOD assay.

Scanning, Processing and Analyses of FT-NIR Spectra:

Scanning-Approximately a 5 g milled sample was poured in a smaller NIRA cup, leveled, and scanned 16 times with a manual rotation between each scan. This procedure was repeated five times with separate subsamples and the resulting spectral scans were averaged. A total of 56 samples of starch blends were used to create starch models. 36 samples were used in the calibration set, 14 samples were used in the validation set, and six samples were used in the test set. The dry ground green tissue or flour models were made using 100 samples of corn leaf or seeds. For calibration, validation, and testing, 72, 20, and 8 samples were used, respectively. The wet ground corn models were made using 49 samples of corn leaf or corn seeds. 36 samples were used for calibration, 10 samples were used for validation, and three samples were used for the test set.

Processing and Analyses of FT-NIR Spectra—

Unscrambler® (Version 10.2., Camo Software Inc., Woodbridge, N.J.) was used to process and analyze the spectral data, build and validate the calibration, and test the regression models. Multiplicative scatter correction (MSC) and a $2^{nd}$ derivative-based smoothing technique, such as the Savitzky-Golay (SG) technique, were used for data pretreatment. Partial least squares models using a combination of MSC with SG second derivate pretreated spectral data were developed for starch blends and milled green tissue or ground corn. Examples of measured and predicted (MSC+ $2^{nd}$ Derivative Model) starch content of calibration, validation, and test samples are shown in Table 2.

TABLE 2

Measured and Predicted (MSC + $2^{nd}$ Derivative Model) Starch Content of Calibration, Validation, and Test Samples

| Starch content | Starch blends | | Dry corn flour | | Wet corn flour | |
|---|---|---|---|---|---|---|
| | Measured (%) | Predicted (%) | Measured (%) | Predicted (%) | Measured (%) | Predicted (%) |
| Calibration | 2.50 | 2.52 | 5.0 | 6.5 | 5.0 | 5.2 |
| | 5.00 | 4.89 | 7.5 | 7.4 | 10.0 | 7.9 |
| | 10.0 | 10.1 | 10.0 | 10.2 | 12.5 | 12.0 |
| | 15.0 | 15.6 | 15.0 | 14.5 | 13.2 | 13.5 |
| | 20.0 | 20.0 | | | | |
| Validation | 4.75 | 4.7 | 7.5 | 7.6 | 7.5 | 7.5 |
| | 10.0 | 9.8 | 12.5 | 12.4 | 10.0 | 10.0 |
| | 15.7 | 16.0 | 17.5 | 17.5 | 12.0 | 12.5 |
| | 18.9 | 18.9 | | | | |
| Test | 6.5 | 6.55 | 5.0 | 6.5 | 7.2 | 7.3 |
| | 12.5 | 12.45 | 11.5 | 12.5 | 11.2 | 11.5 |
| | 17.5 | 18.2 | 14.5 | 13.2 | 12.2 | 13.5 |

$R^2$: Starch blends: Calibration: 0.98, Validation: 0.97, Prediction: 0.97
Dry corn flour: Calibration: 0.86, Validation: 0.80, Prediction: 0.80
Wet corn flour: Calibration: 0.94, Validation: 0.80, Prediction: 0.75

Example 4. Identification and Characterization of Meganuclease-Induced DNA Mutations in the *Zea mays* and *Sorghum* Bicolor GWD Genes Identification of Gene of Interest (GOI) Positive Maize and *Sorghum* Transformants:

Leaves from maize and *sorghum* plants transformed with pAG4715 or pAG4716 were sampled, DNA was extracted, and screened for the presence of the meganuclease transgenes included in pAG4715 or pAG4716.

Screening of Maize and *Sorghum* Transformants:

Plants carrying pAG4715 or pAG4716 transgenes referred to as 4715 or 4716 plants, respectively, were screened for GWD mutations using sequence analysis of PCR-amplified GWD DNA sequences.

PCR Amplification of GWD:

DNA sequences surrounding the meganuclease targeting region on exon 24 were amplified using the ZmGWDmega-2 and SbGWDmega-2 primers shown in Table 3.

TABLE 3

Primers for Genotyping 4715 and 4716 Plants

| Primer Set | Primer Name | Forward or Reverse | Sequence | Product size (bp) |
|---|---|---|---|---|
| Mega-1 (4716) | Mega-1R | Reverse | TGATCTTCAGCACGAG GTTG (SEQ ID NO: 5) | 265 |
| Mega-1 (4716) | Mega-1F | Forward | GGCTCCATCTATGCCTG TATC (SEQ ID NO: 6) | 265 |
| Mega-2 (4715) | Mega-2F | Forward | GAGCTCAGTTTCGCTGT CTATC (SEQ ID NO: 7) | 209 |
| Mega-2 (4715) | Mega-2R | Reverse | ATGATCTTCAGCACGA GGTTG (SEQ ID NO: 8) | 209 |
| ZmGWD mega-2 | ZmGWD mega-2F | Forward | GGTTATAAGCCCGGTT GAAGTA (SEQ ID NO: 9) | 204 |
| ZmGWD mega-2 | ZmGWD mega-2R | Reverse | CTATTCCTTGCTCGGAC TGAC (SEQ ID NO: 10) | 204 |
| SbGWD mega-2 | SbGWD mega-2f | Forward | GGCAGGTTATAAGCCC AGTT (SEQ ID NO: 11) | 208 |
| ZmGWD mega-2 | SbGWD mega-2r | Reverse | CTATTCCTTGCTCGGAC TGAC (SEQ ID NO: 10) | 208 |

Primer sets were diluted to a final concentration of 5 μM in nuclease-free water. PCR reaction was performed as described above.

PCR samples were run on an Eppendorf Mastercycler proS (Eppendorf) using our PMI55 program (95° C., 2 min; 30 cycles [950° C., 30 sec; 55° C., 30 sec; 72° C., 45 sec]; 720° C., 8 min)

PCR samples were separated on Bio-Rad ReadyAgarose 96 Plus Gels, TBE (#161-3062) and visualized with a Bio-Rad gel imaging system.

Figure 3:
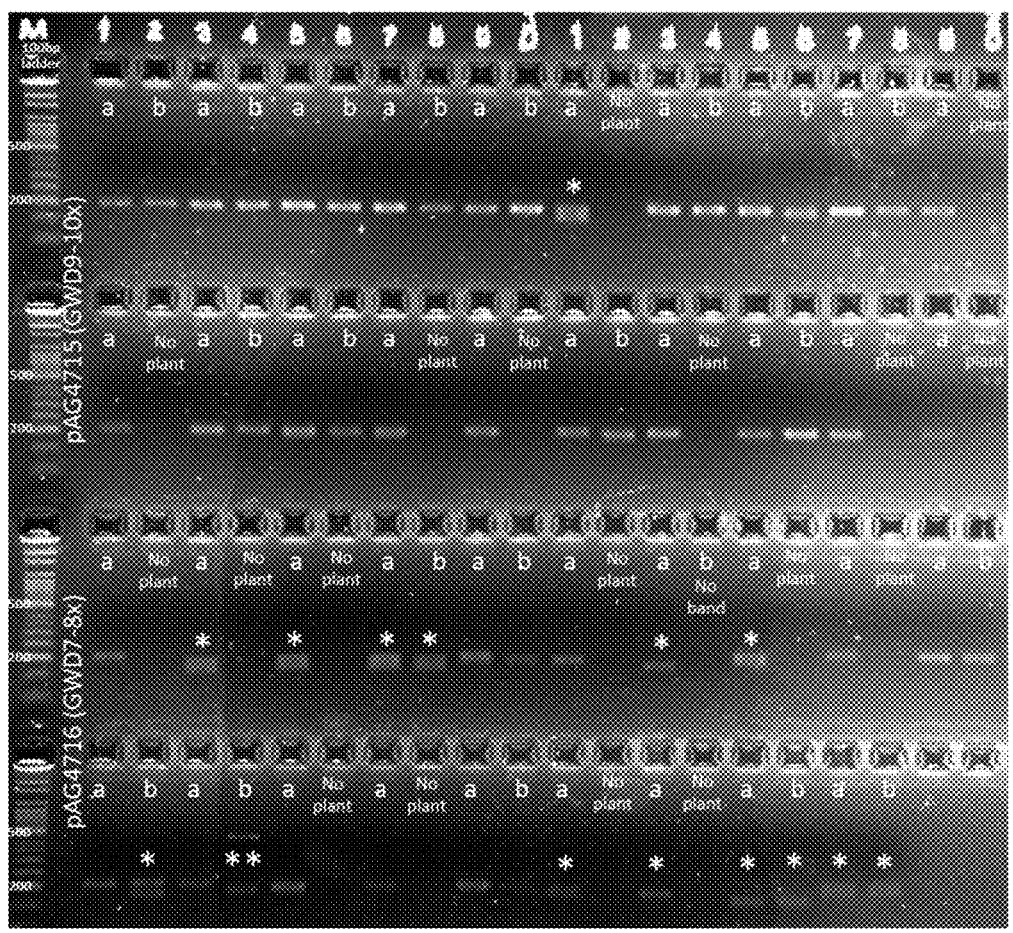
FIG. 3 illustrates PCR detection of mutants.

FIG. 3 illustrates an example of a gel showing bands of 4715 and 4716 events or successful incorporation of transgenes from pAG4715 or pAG4716, respectively. Referring to this figure, shifted GWD bands indicate potential insertions and deletions (indels) at the GWD meganuclease targeting site and are marked by asterisks.

DNA Sequence Characterization of the GWD Indel Alleles:

Sequencing of Initial GWD PCR Products—

PCR products were sequenced at Beckman Coulter Genomics (36 Cherry Hill Dr, Danvers, Mass. 01923) using the same primers used for amplification (ZmGWDmega-2 or SbGWDmega-2). Sequencing allowed differentiation between three different genetic outcomes for the GWD locus, wild type, homozygous mutant, and heterozygous mutant. Wild type had no mutation within the 204 or 208 bp GWD PCR fragment, homozygous carried an indel mutation, and heterozygous carried an unresolvable sequence region (indicating at least one indel) of the GWD PCR fragment.

Cloning and Sequencing of Individual GWD Alleles.

To initiate cloning, GWD was amplified with PCR using the same primer sets as above (ZmGWDmega-2 or SbG-WDmega-2) from DNA derived from heterozygous plants to characterize the individual GWD alleles. PCR amplification was confirmed by running 8 μl of PCR product on agarose gels as described above and the remaining 22 μl of PCR reaction was purified with a Qiagen PCR Purification Kit (28104; Qiagen, Md., USA) and eluted in 30 μl of Elution Buffer (EB).

Purified PCR products were cloned using a TOPO® TA Cloning Kit with One Shot® TOP10 Competent E. coli (K4500-01; Life Technologies) according to the protocol. For cloning procedure, 4 μl of purified PCR product was used for the ligation, ligations were incubated on ice for at least 10 min, and 50 μl of each transformation reaction was plated on LB carbenicillin (50 μg/ml) X-gal plates.

Eight E. coli colonies from each reaction were picked using a sterile pipet tip and transferred into 20 μl of sterile liquid LB with carbenicillin. GWD was then amplified by PCR using the same primer sets as above (ZmGWDmega-2 or SbGWDmega-2) and 2 μl of each diluted E. coli clone culture. PCR products were confirmed and sent for sequencing as described above.

Table 4 describes ZmGWD meganuclease events zygosity, mutation types and locations. In Table 4, ZmGWD mutations were numbered 1-28. The wild type (WT) plant refers to two GWD wild type alleles. Hemizygous event refers to one GWD mutant allele and one GWD wild type allele. Heterozygous event refers to two different GWD mutant alleles. Homozygous event refers to two identical GWD mutant alleles.

TABLE 4

ZmGWD Meganuclease Event Zygosity and Mutations

| Construct/Event | Zygosity | Mutation Locus # (1) | Mutation Type Locus # (1) | Mutation Locus # (2) | Mutation Type Locus # (2) |
|---|---|---|---|---|---|
| 4715_5 | Hemi | M18 | 1 bp del | | |
| 4715_6 | WT | | GWD wild type | | |
| 4715_11 | Hemi | M17 | 10 bp del | | |
| 4715_13 | Hemi | M16 | 24 bp del | | |
| 4715_14 | Hemi | M17 | 10 bp del | | |
| 4715_15 | Hemi | M18 | 1 bp del | | |
| 4715_18 | WT | | GWD wild type | | |
| 4715_20 | Homo or Hetero | | two mutant alleles | | |
| 4715_25 | Hemi | M17 | 10 bp del | | |
| 4715_28 | Hemi | M27 | 16 bp del | | |
| 4716_1 | Hemi | M1 | 4 bp sub | | |
| 4716_2 | Homo | M15 | 40 bp del | | |
| 4716_3 | Hetero | M9 | 15 bp del | M6 | 1 bp del |
| 4716_4 | Hetero | M11 | 17 bp del | M12 | 38 bp del |
| 4716_5 | Hetero | M7 | 4 bp del | M11 | 17 bp del |
| 4716_6 | Hetero | M4 | 9 bp del | M14 | 25 bp del |
| 4716_7 | Hemi | M1 | 4 bp sub | | |
| 4716_8 | Homo | M11 | 17 bp del | | |
| 4716_9 | WT | | GWD wild type | | |
| 4716_10 | Hetero | M11 | 17 bp del | M10 | 1 bp ins |
| 4716_11 | Hetero | M11 | 17 bp del | M10 | 1 bp ins |
| 4716_12 | Hetero | M3 | 15 bp del | M8 | 6 bp del |
| 4716_13 | Homo | M14 | 25 bp del | | |
| 4716_14 | Homo | M13 | 36 bp del | | |
| 4716_15 | Hetero | M11 | 17 bp del | M12 | 38 bp del |
| 4716_18 | Hemi | M20 | 1 bp del | | |
| 4716_20 | WT | | GWD wild type | | |
| 4716_22 | Hetero | M5 | 211 bp ins | M11 | 17 bp del |
| 4716_23 | Homo | M15 | 40 bp del | | |
| 4716_24 | Hetero | M2 | 6 bp del | M14 | 25 bp del |
| 4716_25 | Hetero | M10 | 1 bp ins | M28 | 27 bp del |
| 4716_26 | Hetero | M11 | 17 bp del | M12 | 38 bp del |
| 4716_27 | Hetero | M11 | 17 bp del | M10 | 1 bp ins |
| 4716_151 | Hemi | M10 | 1 bp ins | | |
| 4716_152 | Hetero | M22 | 10 bp del | M23 | 8 bp del + 15 bp ins (7 bp ins) |
| 4716_153 | WT | | GWD wild type | | |
| 4716_154 | Hetero | M22 | 10 bp del | M23 | 8 bp del + 15 bp ins (7 bp ins) |
| 4716_155 | Homo | M4 | 9 bp del | | |
| 4716_157 | Hemi | M24 | 1 bp del | | |
| 4716_158 | Hemi | M20 | 1 bp del | | |
| 4716_159 | Homo | M20 | 1 bp del | | |
| 4716_160 | Hemi | M10 | 1 bp ins | | |
| 4716_161 | Hetero | M4 | 9 bp del | M21 | 33 bp del (57 bp del + 17 bp ins) |
| 4716_162 | Hetero | M20 | 1 bp del | M19 | 4 bp del |
| 4716_163 | Hemi | M26 | 211 bp ins | | |
| 4716_164 | Hemi | M20 | 1 bp del | | |
| 4716_165 | Homo | M4 | 9 bp del | | |
| 4716_166 | Homo | M4 | 9 bp del | | |
| 4716_167 | Hetero | M13 | 36 bp del | M25 | 2 bp del |
| 4716_201 | Homo | M29 | 2 bp del | | |

DNA sequences for each clone were compared to wild type (WT) GWD using Vector NTI Advance (Version 11.5; Life Technologies). DNA sequences for wild type ZmGWD and SbGWD and transgenic events were compared and shown in the following files: ZmGWD meganuclease mutant DNA sequence alignments; ZmGWD meganuclease mutant protein sequence alignments; SbGWD meganuclease mutant DNA sequence alignments; SbGWD meganuclease mutant protein sequence alignments.

As shown below, an alignment of the sequences from three PCR products demonstrates insertions and deletions that distinguish maize mutants M5 and M26 from wild type sequence ZmGWD Exon24.

CLUSTAL O (1.2.1) multiple sequence alignment for ZmGWD for maize mutants M5 and M26:

```
ZmGWDExon24
            TTGGCAGGTTATAAGCCCGGTTGAAGTATCAGGTTATGTGGTTGTGGTTGATGAGTTACT    60
M5          TTGGCAGGTTATAAGCCCGGTTGAAGTATCAGGTTATGTGGTTGTGGTTGATGAGTTACT    60
M26         TTGGCAGGTTATAAGCCCGGTTGAAGTATCAGGTTATGTGGTTGTGGTTGATGAGTTACT    60
            ************************************************************

ZmGWDExon24
            TGCTGTCCAGAACAAATCTTATGATAAACCAACCATCCTTGTGGCAAAGAGTGTCAAGGG   120
M5          TGCTGTCCAGAACAAATCTTATGATAAACCAACCATCCTTGTGGCAAAGAGTGTCAAGGG   120
M26         TGCTGTCCAGAACAAATCTTATGATAAACCAACCATCCTTGTGGCAAAGAGTGTCAAGGG   120
            ************************************************************

ZmGWDExon24
            AGAGGAAGAAATACCAGATGGAGTA---------------------------------   145
M5          AGAGGAAGAAATACCAGATGGAGTAGTTGCAGAATTATTGAATTCTTTCATAATTGAACT   180
M26         AGAGGAAGAAATACCAGATGGAGCAGTGTGCTCGGGTACAGCTTCTTATTTCAATGTCTC   180
            ***********************  *

ZmGWDExon24
            ------------------------------------------------------------   145
M5          CTATGATGATGCTTTACTT--GATTGTATTATATTGATGCTCAATCATATATTGATGATT   238
M26         CAGTGGGCGTCTTACCTCTATGTTTGTGTTTTTTT-TTAAGTGCAGAAATAGAGAAAGTT   239

ZmGWDExon24
            ------------------------------------------------------------   145
M5          GTTGGAACTTGCTCTCCGATGCAAGGTGATCCAACGGGGGTGTGTCGCAACGTAAACAGG   298
M26         CTTGCAAATATCTACTCTATGAAAAGGACAGCTATTTGGAAATA------TGTGAACAGA   293

ZmGWDExon24
            ------------------------------------------------------------   145
M5          GTTTTCG-CACGAGATGGCAATAGCTCTGT-T---AACCTAGCCTCTCACGGGCACTGTG   353
M26         ACTATCCCCAGTTGCTGGGAAAAACCAAGAAGAAAGTTCCTTCAAATATCTACTCCATGA   353

ZmGWDExon24
            ---GTTGGTGTAATTACACCTGATATGCCAGATGTTCTGTCTCATGTGTCAGTCCGAGCA   202
M5          CGGGGGTATTTAATTACACCTGATATGCCAGATGTTCTGTCTCATGTGTCAGTCCGAGCA   413
M26         CGACAAGTGTCTATTACACCTGATATGCCAGATGTTCTGTCTCATGTGTCAGTCCGAGCA   413
               *************************************************

ZmGWDExon24
            AGGAATAGCAAG                                                   214  (SEQ ID NO: 182)
M5          AGGAATAGCAAG                                                   425  (SEQ ID NO: 34)
M26         AGGAATAGCAAG                                                   425  (SEQ ID NO: 31)
            ************
```

The below alignment of the sequences from twenty eight PCR products demonstrates modifications, such as deletions and insertions, that distinguish maize mutants M1-M4, M6-M25 and M27-M29 from the wild type sequence ZmG-WDExon24 (nt 3030 3243 of SEQ ID NO: 1 (ZmGWD)):

CLUSTAL O(1.2.1) multiple sequence alignment for maize mutants M1-M4, M6-M25 and M27-M29:

```
ZmGWDexon24
             TTGGCAGGTTATAAGCCCGGTTGAAGTATCAGGTTATGTGGTTGTGGTTGATGAGTTACT    60

M1           TTGGCAGGTTATAAGCCCGGTTGAAGTATCAGGTTATGTGGTTGTGGTTGATGAGTTACT    60

M2           TTGGCAGGTTATAAGCCCGGTTGAAGTATCAGGTTATGTGGTTGTGGTTGATGAGTTACT    60

M3           TTGGCAGGTTATAAGCCCGGTTGAAGTATCAGGTTATGTGGTTGTGGTTGATGAGTTACT    60

M4           TTGGCAGGTTATAAGCCCGGTTGAAGTATCAGGTTATGTGGTTGTGGTTGATGAGTTACT    60

M6           TTGGCAGGTTATAAGCCCGGTTGAAGTATCAGGTTATGTGGTTGTGGTTGATGAGTTACT    60

M7           TTGGCAGGTTATAAGCCCGGTTGAAGTATCAGGTTATGTGGTTGTGGTTGATGAGTTACT    60

M8           TTGGCAGGTTATAAGCCCGGTTGAAGTATCAGGTTATGTGGTTGTGGTTGATGAGTTACT    60
```

-continued

| | | |
|---|---|---|
| M9 | TTGGCAGGTTATAAGCCCGGTTGAAGTATCAGGTTATGTGGTTGTGGTTGATGAGTTACT | 60 |
| M10 | TTGGCAGGTTATAAGCCCGGTTGAAGTATCAGGTTATGTGGTTGTGGTTGATGAGTTACT | 60 |
| M11 | TTGGCAGGTTATAAGCCCGGTTGAAGTATCAGGTTATGTGGTTGTGGTTGATGAGTTACT | 60 |
| M12 | TTGGCAGGTTATAAGCCCGGTTGAAGTATCAGGTTATGTGGTTGTGGTTGATGAGTTACT | 60 |
| M13 | TTGGCAGGTTATAAGCCCGGTTGAAGTATCAGGTTATGTGGTTGTGGTTGATGAGTTACT | 60 |
| M14 | TTGGCAGGTTATAAGCCCGGTTGAAGTATCAGGTTATGTGGTTGTGGTTGATGAGTTACT | 60 |
| M15 | TTGGCAGGTTATAAGCCCGGTTGAAGTATCAGGTTATGTGGTTGTGGTTGATGAGTTACT | 60 |
| M16 | TTGGCAGGTTATAAGCCCGGTTGAAGTATCAGGTTATGTGGTTGTGGTTGATGAGTTACT | 60 |
| M17 | TTGGCAGGTTATAAGCCCGGTTGAAGTATCAGGTTATGTGGTTGTGGTTGATGAGTTACT | 60 |
| M18 | TTGGCAGGTTATAAGCCCGGTTGAAGTATCAGGTTATGTGGTTGTGGTTGATGAGTTACT | 60 |
| M19 | TTGGCAGGTTATAAGCCCGGTTGAAGTATCAGGTTATGTGGTTGTGGTTGATGAGTTACT | 60 |
| M20 | TTGGCAGGTTATAAGCCCGGTTGAAGTATCAGGTTATGTGGTTGTGGTTGATGAGTTACT | 60 |
| M21 | TTGGCAGGTTATAAGCCCGGTTGAAGTATCAGGTTATGTGGTTGTGGTTGATGAGTTACT | 60 |
| M22 | TTGGCAGGTTATAAGCCCGGTTGAAGTATCAGGTTATGTGGTTGTGGTTGATGAGTTACT | 60 |
| M23 | TTGGCAGGTTATAAGCCCGGTTGAAGTATCAGGTTATGTGGTTGTGGTTGATGAGTTACT | 60 |
| M24 | TTGGCAGGTTATAAGCCCGGTTGAAGTATCAGGTTATGTGGTTGTGGTTGATGAGTTACT | 60 |
| M25 | TTGGCAGGTTATAAGCCCGGTTGAAGTATCAGGTTATGTGGTTGTGGTTGATGAGTTACT | 60 |
| M27 | TTGGCAGGTTATAAGCCCGGTTGAAGTATCAGGTTATGTGGTTGTGGTTGATGAGTTACT | 60 |
| M28 | TTGGCAGGTTATAAGCCCGGTTGAAGTATCAGGTTATGTGGTTGTGGTTGATGAGTTACT | 60 |
| M29 | TTGGCAGGTTATAAGCCCGGTTGAAGTATCAGGTTATGTGGTTGTGGTTGATGAGTTACT | 60 |
| | ************************************************************ | |
| ZmGWDexon24 | TGCTGTCCAGAACAAATCTTATGATAAACCAACCATCCTTGTGGCAAAGAGTGTCAAGGG | 120 |
| M1 | TGCTGTCCAGAACAAATCTTATGATAAACCAACCATCCTTGTGGCAAAGAGTGTCAAGGG | 120 |
| M2 | TGCTGTCCAGAACAAATCTTATGATAAACCAACCATCCTTGTGGCAAAGAGTGTCAAGGG | 120 |
| M3 | TGCTGTCCAGAACAAATCTTATGATAAACCAACCATCCTTGTGGCAAAGAGTGTCAAGGG | 120 |
| M4 | TGCTGTCCAGAACAAATCTTATGATAAACCAACCATCCTTGTGGCAAAGAGTGTCAAGGG | 120 |
| M6 | TGCTGTCCAGAACAAATCTTATGATAAACCAACCATCCTTGTGGCAAAGAGTGTCAAGGG | 120 |
| M7 | TGCTGTCCAGAACAAATCTTATGATAAACCAACCATCCTTGTGGCAAAGAGTGTCAAGGG | 120 |
| M8 | TGCTGTCCAGAACAAATCTTATGATAAACCAACCATCCTTGTGGCAAAGAGTGTCAAGGG | 120 |
| M9 | TGCTGTCCAGAACAAATCTTATGATAAACCAACCATCCTTGTGGCAAAGAGTGTCAAGGG | 120 |
| M10 | TGCTGTCCAGAACAAATCTTATGATAAACCAACCATCCTTGTGGCAAAGAGTGTCAAGGG | 120 |
| M11 | TGCTGTCCAGAACAAATCTTATGATAAACCAACCATCCTTGTGGCAAAGAGTGTCAAGGG | 120 |
| M12 | TGCTGTCCAGAACAAATCTTATGATAAACCAACCATCCTTGTGGCAAAGAGTGTCAAGGG | 120 |
| M13 | TGCTGTCCAGAACAAATCTTATGATAAACCAACCATCCTTGTGGCAAAGAGTGTCAAGGG | 120 |
| M14 | TGCTGTCCAGAACAAATCTTATGATAAACCAACCATCCTTGTGGCAAAGAGTGTCAAGGG | 120 |
| M15 | TGCTGTCCAGAACAAATCTTATGATAAACCAACCATCCTTGTGGCAAAGAGTAATTACAC | 120 |
| M16 | TGCTGTCCAGAACAAATCTTATGATAAACCAAGGGAGAGGA------------------ | 101 |
| M17 | TGCTGTCCAGAACAAATCTTATGATAAACCAACCATCCTTGTGGCAAGGG---------- | 110 |
| M18 | TGCTGTCCAGAACAAATCTTATGATAAACCAACCATCCTTGTGGCAA-GAGTGTCAAGGG | 119 |
| M19 | TGCTGTCCAGAACAAATCTTATGATAAACCAACCATCCTTGTGGCAAAGAGTGTCAAGGG | 120 |

-continued

```
M20           TGCTGTCCAGAACAAATCTTATGATAAACCAACCATCCTTGTGGCAAAGAGTGTCAAGGG    120
M21           TGCTGTCCAGAACAAATCTTATGATAAACCAACCATCCTTGTGGCAAAGAGTGTCAAAAT    120
M22           TGCTGTCCAGAACAAATCTTATGATAAACCAACCATCCTTGTGGCAAAGAGTGTCAAGGG    120
M23           TGCTGTCCAGAACAAATCTTATGATAAACCAACCATCCTTGTGGCAAAGAGTGTCAAGGG    120
M24           TGCTGTCCAGAACAAATCTTATGATAAACCAACCATCCTTGTGGCAAAGAGTGTCAAGGG    120
M25           TGCTGTCCAGAACAAATCTTATGATAAACCAACCATCCTTGTGGCAAAGAGTGTCAAGGG    120
M27           TGCTGTCCAGAACAAATCTTATGATAAACCAACCATCCTTGTGGCAAGGGAGAGAT----    116
M28           TGCTGTCCAGAACAAATCTTATGATAAACCAACCATCCTTGTGGCAAAGAGTGTCAAGGG    120
M29           TGCTGTCCAGAACAAATCTTATGATAAACCAACCATCCTTGTGGCAAAGAGTGTCAAGGG    120
              ******************************

ZmGWDexon24   AGAGGAAGAAATACCAGATGGAGTAGTTGGTGTA-------ATTACACCTGATATGCCAG    173
M1            AGAGGAAGAAATACCAGATGGAGTAGTTGGAAGA-------AATACACCTGATATGCCAG    173
M2            AGAGGAAGAAATACCAGATGGAGTAGTTGTT------------ACACCTGATATGCCAG    167
M3            AGAGGAAGAAATACCAGATGGAGCACCT---------------------GATATGCCAG    158
M4            AGAGGAAGAAATACCAGATGGAGTAA----------------TTACACCTGATATGCCAG    164
M6            AGAGGAAGAAATACCAGATGGAGTAGTTGGTAA--------ATTACACCTGATATGCCAG    172
M7            AGAGGAAGAAATACCAGATGGAGTAGTTGGT----------TTACACCTGATATGCCAG    169
M8            AGAGGAAGAAATACCAGATGGAGTAGTTGGT------------ATGCCAGATATGCCAG    167
M9            AGAGGAAGAAATACCAGATGGAGTAGTTG----------------------TATGCCAG    158
M10           AGAGGAAGAAATACCAGATGGAGTAGTTGGTGTAA------ATTACACCTGATATGCCAG    174
M11           AGAGGAAGAAATACCAGATGGAGTAGTTGGTGTCAG-----------------------    156
M12           AGAGGAAGAAATACCAGATGGAGTAGTTGGTGTCAGTCCGAGCAAGGAATAGCAAG----    176
M13           AGAGGAAGAAATACCAGATGTTCTGTCTCATGTGTC-----------------------    156
M14           AGAGGAAGAATTACA-------------------------------CCTGATATGCCAG    148
M15           CTGATATGC-----------------------------------------------CAG    132
M16           ------AGAAATACCAGATGGAGTAGTTGGT-------GTAATTACACCTGATATGCCAG    148
M17           AGAGGAAGAAATACCAGATGGAGTAGTTGGTGT-A------ATTACACCTGATATGCCAG    163
M18           AGAGGAAGAAATACCAGATGGAGTAGTTGGTGTA-------ATTACACCTGATATGCCAG    172
M19           AGAGGAAGAAATACCAGATGGAGTAGTTGGTGT--------ATTACACCTGATATGCCAG    172
M20           AGAGGAAGAAATACCAGATGGAGTAGTTGGTGT--------ATTACACCTGATATGCCAG    172
M21           CTTATGATAAACC-----------------------------------ATGCCAG    140
M22           AGAGGAAGAAATACCAGATGGAGTAGTTGGTGTGA---------------TATGCCAG    163
M23           AGAGGAAGAAATACCAGATGGAGTAGTTGGCAAAGATAAACCTTGCACCTGATATGCCAG    180
M24           AGAGGAAGAAATACCAGATGGAGTAGTTGGTGA--------ATTACACCTGATATGCCAG    172
M25           AGAGGAAGAAATACCAGATGGAGTAGTTGG---TA------ATTACACCTGATATGCCAG    171
M27           ------------ACCAGATGGAGTAGTTGG-------TGTAATTACACCTGATATGCCAG    157
M28           AGAGGAAGAAACACCTGATA---------------------------TGCCAG    146
M29           AGAGGAAGAAATACCAGATGGAGTAGTTGG---TA------ATTACACCTGATATGCCAG    171

ZmGWDexon24   ATGTTCTGTCTCATGTGTCAGTCCGAGCAAGGAATAGCAAG    214 (SEQ ID NO: 182)

M1            ATGTTCTGTCTCATGTGTCAGTCCGAGCAAGGAATAGCAAG    214 (SEQ ID NO: 16)

M2            ATGTTCTGTCTCATGTGTCAGTCCGAGCAAGGAATAGCAAG    208 (SEQ ID NO: 35)
```

-continued

| | | | |
|---|---|---|---|
| M3 | ATGTTCTGTCTCATGTGTCAGTCCGAGCAAGGAATAGCAAG | 199 | (SEQ ID NO: 19) |
| M4 | ATGTTCTGTCTCATGTGTCAGTCCGAGCAAGGAATAGCAAG | 205 | (SEQ ID NO: 29) |
| M6 | ATGTTCTGTCTCATGTGTCAGTCCGAGCAAGGAATAGCAAG | 213 | (SEQ ID NO: 37) |
| M7 | ATGTTCTGTCTCATGTGTCAGTCCGAGCAAGGAATAGCAAG | 210 | (SEQ ID NO: 39) |
| M8 | ATGTTCTGTCTCATGTGTCAGTCCGAGCAAGGAATAGCAAG | 208 | (SEQ ID NO: 20) |
| M9 | ATGTTCTGTCTCATGTGTCAGTCCGAGCAAGGAATAGCAAG | 199 | (SEQ ID NO: 38) |
| M10 | ATGTTCTGTCTCATGTGTCAGTCCGAGCAAGGAATAGCAAG | 215 | (SEQ ID NO: 18) |
| M11 | ATGTTCTGTCTCATGTGTCAGTCCGAGCAAGGAATAGCAAG | 197 | (SEQ ID NO: 17) |
| M12 | ----------------------------------------- | 176 | (SEQ ID NO: 23) |
| M13 | ------------------AGTCCGAGCAAGGAATAGCAAG | 178 | (SEQ ID NO: 22) |
| M14 | ATGTTCTGTCTCATGTGTCAGTCCGAGCAAGGAATAGCAAG | 189 | (SEQ ID NO: 21) |
| M15 | ATGTTCTGTCTCATGTGTCAGTCCGAGCAAGGAATAGCAAG | 173 | (SEQ ID NO: 33) |
| M16 | ATGTTCTGTCTCATGTGTCAGTCCGAGCAAGGAATAGCAAG | 189 | (SEQ ID NO: 12) |
| M17 | ATGTTCTGTCTCATGTGTCAGTCCGAGCAAGGAATAGCAAG | 204 | (SEQ ID NO: 13) |
| M18 | ATGTTCTGTCTCATGTGTCAGTCCGAGCAAGGAATAGCAAG | 213 | (SEQ ID NO: 14) |
| M19 | ATGTTCTGTCTCATGTGTCAGTCCGAGCAAGGAATAGCAAG | 213 | (SEQ ID NO: 30) |
| M20 | ATGTTCTGTCTCATGTGTCAGTCCGAGCAAGGAATAGCAAG | 213 | (SEQ ID NO: 27) |
| M21 | ATGTTCTGTCTCATGTGTCAGTCCGAGCAAGGAATAGCAAG | 181 | (SEQ ID NO: 28) |
| M22 | ATGTTCTGTCTCATGTGTCAGTCCGAGCAAGGAATAGCAAG | 204 | (SEQ ID NO: 24) |
| M23 | ATGTTCTGTCTCATGTGTCAGTCCGAGCAAGGAATAGCAAG | 221 | (SEQ ID NO: 25) |
| M24 | ATGTTCTGTCTCATGTGTCAGTCCGAGCAAGGAATAGCAAG | 213 | (SEQ ID NO: 26) |
| M25 | ATGTTCTGTCTCATGTGTCAGTCCGAGCAAGGAATAGCAAG | 212 | (SEQ ID NO: 32) |
| M27 | ATGTTCTGTCTCATGTGTCAGTCCGAGCAAGGAATAGCAAG | 198 | (SEQ ID NO: 15) |
| M28 | ATGTTCTGTCTCATGTGTCAGTCCGAGCAAGGAATAGCAAG | 187 | (SEQ ID NO: 36) |
| M29 | ATGTTCTGTCTCATGTGTCAGTCCGAGCAAGGAATAGCAAG | 212 | (SEQ ID NO: 40) |

The amino acid sequences of GWD from twenty nine transgenic maize events and a wild type plant were analyzed and showed deletions and insertions in the wild type ZmGW (SEQ ID NO: 185) protein in the positions of amino acids 1040-1120 that distinguish this protein from maize mutants ZmGWD_M1 (SEQ ID NO: 45), ZmGWD_M2 (SEQ ID NO: 46), ZmGWD_M3 (SEQ ID NO: 47), ZmGWD_M4 (SEQ ID NO: 48), ZmGWD_M5 (SEQ ID NO: 49), ZmGWD_M6 (SEQ ID NO: 50), ZmGWD_M7 (SEQ ID NO: 51), ZmGWD_M8 (SEQ ID NO: 52), ZmGWD_M9 (SEQ ID NO: 53), ZmGWD_M10 (SEQ ID NO: 54), ZmGWD_M11 (SEQ ID NO: 55), ZmGWD_M12 (SEQ ID NO: 56), ZmGWD_M13 (SEQ ID NO: 57), ZmGWD_M14 (SEQ ID NO: 58), ZmGWD_M15 (SEQ ID NO: 59), ZmGWD_M16 (SEQ ID NO: 60), ZmGWD_M17 (SEQ ID NO: 61), ZmGWD_M18 (SEQ ID NO: 62), ZmGWD_M19 (SEQ ID NO: 63), ZmGWD_M20 (SEQ ID NO: 4), ZmGWD_M21 (SEQ ID NO: 65), ZmGWD_M22 (SEQ ID NO: 66), ZmGWD_M23 (SEQ ID NO: 67), ZmGWD_M24 (SEQ ID NO: 68), ZmGWD_M25 (SEQ ID NO: 69), ZmGWD_M26 (SEQ ID NO: 70), ZmGWD_M27 (SEQ ID NO: 71), ZmGWD_M28 (SEQ ID NO: 72), and ZmGWD_M29 (SEQ ID NO: 73).

CLUSTAL O(1.2.1) multiple sequence alignment of ZmGWD (SEQ ID NO: 43) amino acids 1040-1120:

```
ZmGWD      PTILVAKSVKGEEEIPDGVVGVITPDMPD----------VLS---HV---------SVR-

ZmGWD_M1   PTILVAKSVKGEEEIPDGVVGRNTPDMPD----------VLS---HV---------SVR-

ZmGWD_M2   PTILVAKSVKGEEEIPDGV--VVTPDMPD----------VLS---HV---------SVR-

ZmGWD_M3   PTILVAKSVKGEEEIPDGA------PDMPD----------VLS---HV---------SVR-

ZmGWD_M4   PTILVAKSVKGEEEIPDG---VITPDMPD----------VLS---HV---------SVR-

ZmGWD_M5   PTILVAKSVKGEEEIPDGVVAELLNSFIIELYDDALLDCIILMLNHILMIVGTCSPMQGD
```

```
ZmGWD_M6       PTILVAKSVKGEEEIPDGVVGKLHLICQM----------FCL---MCQSEQGIARYCLRP

ZmGWD_M7       PTILVAKSVKGEEEIPDGVVG-LHLICQM----------FCL---MCQSEQGIARYCLRP

ZmGWD_M8       PTILVAKSVKGEEEIPDGV--VGMPDMPD----------VLS---HV---------SVR-

ZmGWD_M9       PTILVAKSVKGEEEIPDGV-----VGMPD----------VLS---HV---------SVR-

ZmGWD_M10      PTILVAKSVKGEEEIPDGVVGVNYT*----------------------------------

ZmGWD_M11      PTILVAKSVKGEEEIPDGVVGVRCSVSCVSPSKE*-------------------------

ZmGWD_M12      PTILVAKSVKGEEEIPDGVVGVSPSK-------E*-------------------------

ZmGWD_M13      PTILVAKSVKGEEEI------------PD----------VLS---HV---------SVR-

ZmGWD_M14      PTILVAKSVKGEEE---------LHLICQM----------FCL---MCQSEQGIARYCLRP

ZmGWD_M15      PTILVAKSNYT*------------------------------------------------

ZmGWD_M16      P--------RERKKYQME*-----------------------------------------

ZmGWD_M17      PTIL---VARERKKYQME*-----------------------------------------

ZmGWD_M18      PTILVARVSRERKKYQME*-----------------------------------------

ZmGWD_M19      PTILVAKSVKGEEEIPDGVVG-VHLICQM----------FCL---MCQSEQGIARYCLRP

ZmGWD_M20      PTILVAKSVKGEEEIPDGVVGVLHLICQM----------FCL---MCQSEQGIARYCLRP

ZmGWD_M21      PTILVAKSVKIL*-----------------------------------------------

ZmGWD_M22      PTILVAKSVKGEEEIPDGVVG---VICQM----------FCL---MCQSEQGIARYCLRP

ZmGWD_M23      PTILVAKSVKGEEEIPDGVVGKDKPCT*--------------------------------

ZmGWD_M24      PTILVAKSVKGEEEIPDGVVGELHLICQM----------FCL---MCQSEQGIARYCLRP

ZmGWD_M25      PTILVAKSVKGEEEIPDGVVGNYT*-----------------------------------

ZmGWD_M26      PTILVAKSVKGEEEIPDGAVCSGTASYFNVSS-GRLTSMFVFFFK-CRNRESSCKYLLYE

ZmGWD_M27      PTILVA-----RERYQME*-----------------------------------------

ZmGWD_M28      PTILVAKSVKGEEE---------TPDMPD----------VLS---HV---------SVR-

ZmGWD_M29      PTILVAKSVKGEEEIPDGVVGNYT*-----------------------------------

ZmGWD          -------ARNSKVLFATCFDHTTLSELEGYDQKLFSFKPTSADITYREITE (SEQ ID NO: 185)

ZmGWD_M1       -------ARNSKVLFATCFDHTTLSELEGYDQKLFSFKPTSADITYREITE (SEQ ID NO: 45)

ZmGWD_M2       -------ARNSKVLFATCFDHTTLSELEGYDQKLFSFKPTSADITYREITE (SEQ ID NO: 46)

ZmGWD_M3       -------ARNSKVLFATCFDHTTLSELEGYDQKLFSFKPTSADITYREITE (SEQ ID NO: 47)

ZmGWD_M4       -------ARNSKVLFATCFDHTTLSELEGYDQKLFSFKPTSADITYREITE (SEQ ID NO: 48)

ZmGWD_M5       ---PTGVCRNVNRVFARDGNSSVNLASHGHCAGVFNYT*------------ (SEQ ID NO: 49)

ZmGWD_M6       VL-TTPLYLNLKDMIRNCFPSSLLLQI*---------------------- (SEQ ID NO: 50)

ZmGWD_M7       VL-TTPLYLNLKDMIRNCFPSSLLLQI*---------------------- (SEQ ID NO: 51)

ZmGWD_M8       -------ARNSKVLFATCFDHTTLSELEGYDQKLFSFKPTSADITYREITE (SEQ ID NO: 52)

ZmGWD_M9       -------ARNSKVLFATCFDHTTLSELEGYDQKLFSFKPTSADITYREITE (SEQ ID NO: 53)

ZmGWD_M10      -------------------------------------------------- (SEQ ID NO: 54)

ZmGWD_M11      -------------------------------------------------- (SEQ ID NO: 55)

ZmGWD_M12      -------------------------------------------------- (SEQ ID NO: 56)

ZmGWD_M13      ------ ARNSKVLFATCFDHTTLSELEGYDQKLFSFKPTSADITYREITE (SEQ ID NO: 57)

ZmGWD_M14      VL-TTPLYLNLKDMIRNCFPSSLLLQI* (SEQ ID NO: 58)

ZmGWD_M15      -------------------------------------------------- (SEQ ID NO: 59)
```

```
ZmGWD_M16        ------------------------------------------------ (SEQ ID NO: 60)

ZmGWD_M17        ------------------------------------------------ (SEQ ID NO: 61)

ZmGWD_M18        ------------------------------------------------ (SEQ ID NO: 62)

ZmGWD_M19        VL-TTPLYLNLKDMIRNCFPSSLLLQI*--------------------- (SEQ ID NO: 63)

ZmGWD_M20        VL-TTPLYLNLKDMIRNCFPSSLLLQI*--------------------- (SEQ ID NO: 64)

ZmGWD_M21        ------------------------------------------------ (SEQ ID NO: 65)

ZmGWD_M22        VL-TTPLYLNLKDMIRNCFPSSLLLQI*--------------------- (SEQ ID NO: 66)

ZmGWD_M23        ------------------------------------------------ (SEQ ID NO: 67)

ZmGWD_M24        VL-TTPLYLNLKDMIRNCFPSSLLLQI*--------------------- (SEQ ID NO: 68)

ZmGWD_M25        ------------------------------------------------ (SEQ ID NO: 69)

ZmGWD_M26        KDSYLEICEQNYPQLLGKTKK--K-----VPSNIYSMTTSV---YYT*--- (SEQ ID NO: 70)

ZmGWD_M27        ------------------------------------------------ (SEQ ID NO: 71)

ZmGWD_M28        -------ARNSKVLFATCFDHTTLSELEGYDQKLFSFKPTSADITYREITE (SEQ ID NO: 72)

ZmGWD_M29        ------------------------------------------------ (SEQ ID NO: 73)
```

For *Sorghum bicolor*, two meganuclease constructs were used to create GWD mutations, 4715 and 4716. First generation (T0) transformed plants could result in homozygous GWD mutants, hemizygous (WT+ mutation) GWD mutants, or heterozygous (2 different mutations; e.g., allele 1+ allele 2) GWD mutants. The following abbreviations were used: del=deletion; ins=insertion; sub=substitution; SbGWD CDS is wild type sequence. For example, the sequence name "Sb4715_1 (WT+ins)" has the following meaning: Sb4715 is the construct in *Sorghum bicolor*; 1 is the transgenic event; WT+ins indicates that T0 event 4715_1 was hemizygous for a GWD mutation, carrying a WT GWD allele and an insertion (ins) GWD allele. The same construct was used for transformation of *Zea mays* (Zm).

CLUSTAL nucleic acid alignment between *Sorghum bicolor* (Sb) GWD sequence and *Sorghum bicolor* GWD mutants Sb475_1 (WT+ins) and Sb4715_2 (WT+del) showed alterations in the sequences of the mutants compared to wild type SbGWD sequence. The SbGWD_exon24 sequence is positioned within nt 3030-3243 the SbGWD coding sequence (SEQ ID NO: 2). The sequence of Sb475_1 (WT+ins) includes a 13 nucleotide insertion in the position 3139-3149 of SbGWD and a nucleotide substitution in the position 3133-3136 of SbGWD.

As shown below, an alignment of the sequences from the three PCR products demonstrates insertions and deletions that differentiate Sb4715_1 (WT+ins) and Sb4715_2 (WT+del) and SbGWD exon 24 regions.

CLUSTAL O(1.2.1) multiple sequence alignment:

```
SbGWD_Exon2 4        TTGGCAGGTTATAAGCCCAGTTGAAGTATCAGGTTATGTGGTTGTGGTTGATGAGTTACT    60
Sb4715_1 (WT + ins)  TTGGCAGGTTATAAGCCCAGTTGAAGTATCAGGTTATGTGGTTGTGGTTGATGAGTTACT    60
Sb4715_2 (WT + del)  TTGGCAGGTTATAAGCCCAGTTGAAGTATCAGGTTATGTGGTTGTGGTTGATGAGTTACT    60
                     ************************************************************

SbGWD_Exon24         TGCTGTCCAGAACAAATCTTATGATAAACCAACCATCCTTGTGGCAAAGA----------   110
Sb4715_1 (WT + ins)  TGCTGTCCAGAACAAATCTTATGATAAACCAACCATCCTTGTGGAGTAGTTGGTGTAGTT   120
Sb4715_2 (WT + del)  TGCTGTCCAGAACAAATCTTATGATAAACCAACCATCCTTGTGGCAAAGA----------   110
                     ********************************************  **

SbGWD_Exon24         ---GTGTCAAGGGAGAGGAAGAAATACCAGATGGAGTAGTTGGTGTAATTACACCTGATA   167
Sb4715_1 (WT + ins)  GGTGTATCAAGGGAGAGGAAGAAATACCAGATGGAGTAGTTGGTGTAATTACACCTGATA   180
Sb4715_2 (WT + del)  ---GTGTCAAGGGAGAGGAAGAAATACCAGATGGAG------------TTACACCTGATA   155
                     **  *****************************                ***********

SbGWD_Exon24         TGCCAGATGTTCTGTCCCATGTGTCAGTCCGAGCAAGGAATAGCAAG               214 (SEQ ID NO: 183)
Sb4715_1 (WT + ins)  TGCCAGATGTTCTGTCCCATGTGTCAGTCCGAGCAAGGAATAGCAAG               227 (SEQ ID NO: 106)
Sb4715_2 (WT + del)  TGCCAGATGTTCTGTCCCATGTGTCAGTCCGAGCAAGGAATAGCAAG               202 (SEQ ID NO: 107)
                     ***********************************************
```

The prediction of the meganuclease mutant protein amino acid sequences were made using the sequence wild type SbGWD (SEQ ID NO: 44).

Example 5. Mutant Plants Accumulate Elevated Levels of Green Tissue Starch

Figure 4:
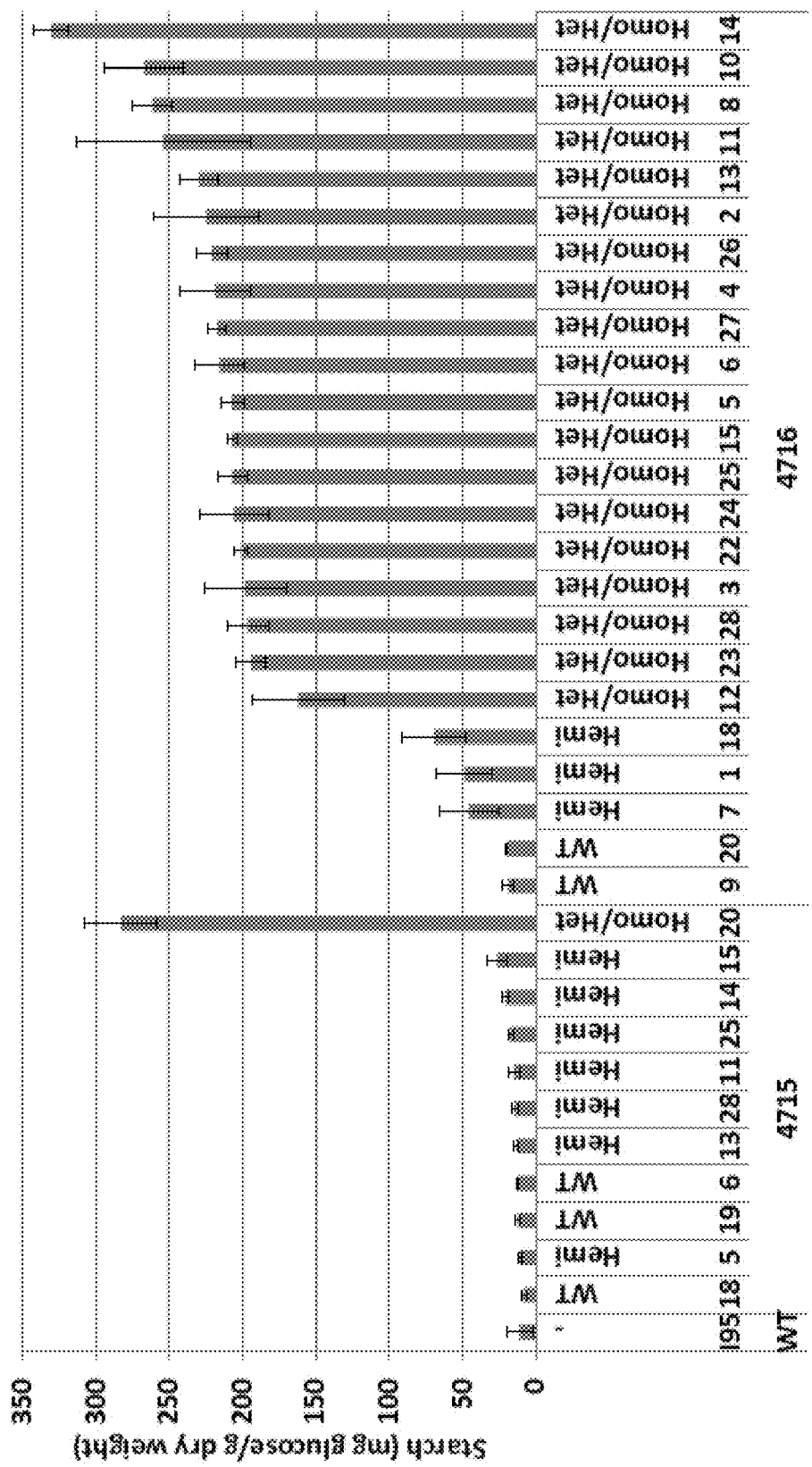
FIG. 4 illustrates a chart depicting starch content (mg starch per gram dry weight) across populations of mutant homozygous, heterozygous and hemizygous corn plants produced by using vectors pAG4715 and pAG4716. Lines 195, 20, 19, 18, 9 and 6 are control plants.

Starch was assayed in the first generation (T0) transformed maize and sorghum GWD meganuclease plants. Tissues were collected, dried and milled to a fine powder. The starch content was determined by standard methods (Smith A M and Zeeman S C, Quantification of starch in plant tissues (2006) Nat Protocols 1: 11342-1345, which is incorporated herein by reference as if fully set forth). A total starch content was assayed by adapting the protocol from Megazyme International Ireland Ltd. (Megazyme kit and reagents; cat. #K-TSTA). Briefly, 85° C. and 50° C. heat blocks were set up. From 5 to 15 mg of dry milled tissue were placed into the 1.5 ml boil-proof microcentrifuge tubes. One milliliter of 70% ethanol was added to each tube and samples were vortexed and pelleted. Four hundred microliters of solution 1 was added to each sample. Solution 1 included 1 ml of the thermostable α-amylase and 29 ml of 100 mM sodium acetate buffer, pH5.0. The samples were re-suspended and vortexed. Samples were incubated for 12 minutes at 85° C. for 12 minutes, and cooled for 5 minutes at room temperature. Three hundred microliters of the GOPOD reagent (Megazyme kit, cat. #K-TST) was pre-loaded into each well of the flat bottom 96 well assay plate. Ten microliters of samples were added to each well and compared to 1 μL, 5 μL, 10 μL, and 20 μL of glucose standard (1 mg/ml), which were also added to their respective wells. The plate was incubated at 50° C. for 20 min. Absorbance was assessed at 510 nm. Referring to FIG. 4, elevated starch is shown for mutants 4715_20 (two mutant alleles), 4716_7 (M1), 4716_1 (M1), 4716_18 (M20), 4716_12 (M3/M8), 4716_23 (M15), 4716_28 (not characterized), 4716_3 (M9/M6), 4716_22 (M5/M11), 4716_24 (M2/M14), 24716_25 (M10/M28), 4716_15 (M11/M12), 4716_5 (M7/M11), 4716_6 (M4/M14), 4716_27 (M11/M10), 4716_4 (M11/M12), 4716_26 (M11/M12), 4716_2 (M15), 4716_13 (M14), 4716_13 (M14), 4716_11 M11/M10), 4716_8 (M11), 4716_10 (M11/M10), and 4716_14 (M13) compared to wild type plants WT_195, WT_18 and WT_6. Many of the homozygous and heterozygous events exhibited greater than 20% starch increase by weight in leaves. Based on a weighted average of starch accumulation in different tissues, we estimated total plant starch (not including grain) to be approximately 10% (weight/weight).

The levels were significantly higher was observed previously in maize using RNA interference technology, despite the low transcript abundance measured in those experiments. This was a surprising result as it was anticipated that RNAi based silencing would be dominant in the plant and have the same effect as a gene deletion or knock-out strategy.

Figure 5:
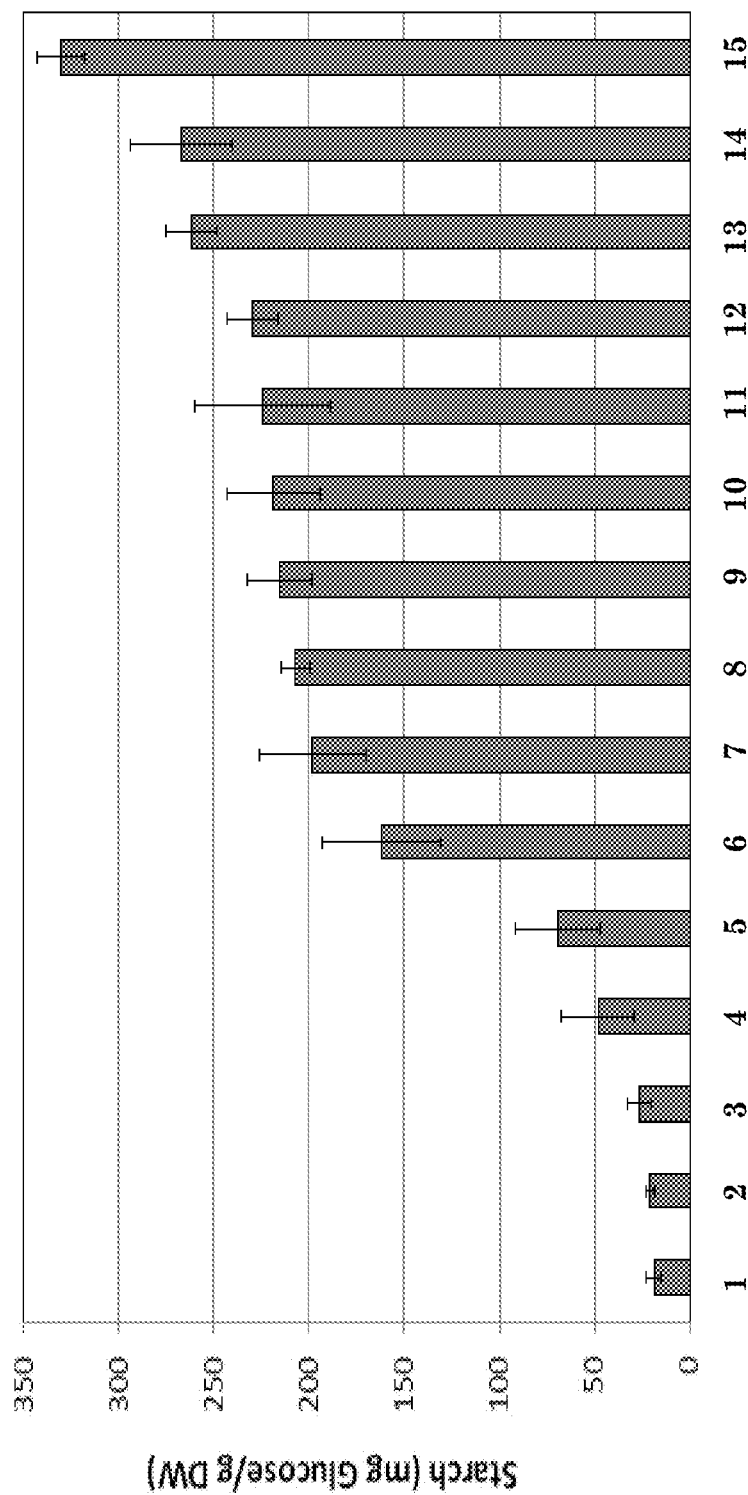
FIG. 5 illustrates starch content in green tissue of gwd knock-out corn mutants: bar 1 is wild type (WT) plant, bar 2 is M17, bar 3 is M18, bar 4 is M1, bar 5 is M20, bar 6 is M13/M12, bar 7 is M9, bar 8 is M7/M11, bar 9 is M4/M14, bar 10 is M11/M12, bar 11 is M15, bar 12 is M14, bar 13 is M11, bar 14 is M11/M10 and bar 15 is M13.

FIG. 5 illustrates green tissue starch for selected hemizygous, homozygous, and heterozygous events. FIG. 5 shows mutation type and zygosity of transgenic corn events M17 (4715_14), M18 (4715_15), M1 (4716_1), M20 (4716_18), M3/M12 (4716_12), M9 (4716_3), M7/M11 (4716_5), M4/M14 (4716_6), M11/M12 (4716_4), M15 (4716_2), M14 (4716_13), M11 (4716_8), M11/M10 (4716_10) and M13 (4716_14) have elevated levels of starch compared to non-transgenic control WT (4716_9). It was observed that several events (4716_13 (M14), 4715_15 (M11/M12) and 4716_6 (M4/M14) have greater than average biomass.

Example 6. GWD Knock-Out (GWDko) Cobs have Increased Starch Levels

T0 GWDko and wild type (wt) maize mutant lines were selfed, developed to maturity, dried, and cross-sectioned for staining. Cob sections were stained with Lugol's solution (5% KI) for 4 min and destained with H₂O overnight.

Mutant events 4716_13, 4716_26, 4716_167, 4716_164, 4716_9, and 4716-153 were analyzed for starch content. The results are shown in Table 5.

TABLE 5

| Starch Content in Mutant Lines | | | |
|---|---|---|---|
| Construct_Event | Zygosity | Green Tissue Starch | Stover Starch |
| 4716_13 | Homo | 229.7 | 38.5 |
| 4716_26 | Hetero | 220.7 | 35.3 |
| 4716_167 | Hetero | 112.0 | 31.7 |
| 4716_164 | Hemi | 30.5 | 4.0 |
| 4716_9 | WT | 18.8 | 8.4 |
| 4716_153 | WT | 5.7 | 1.2 |

Figure 6:
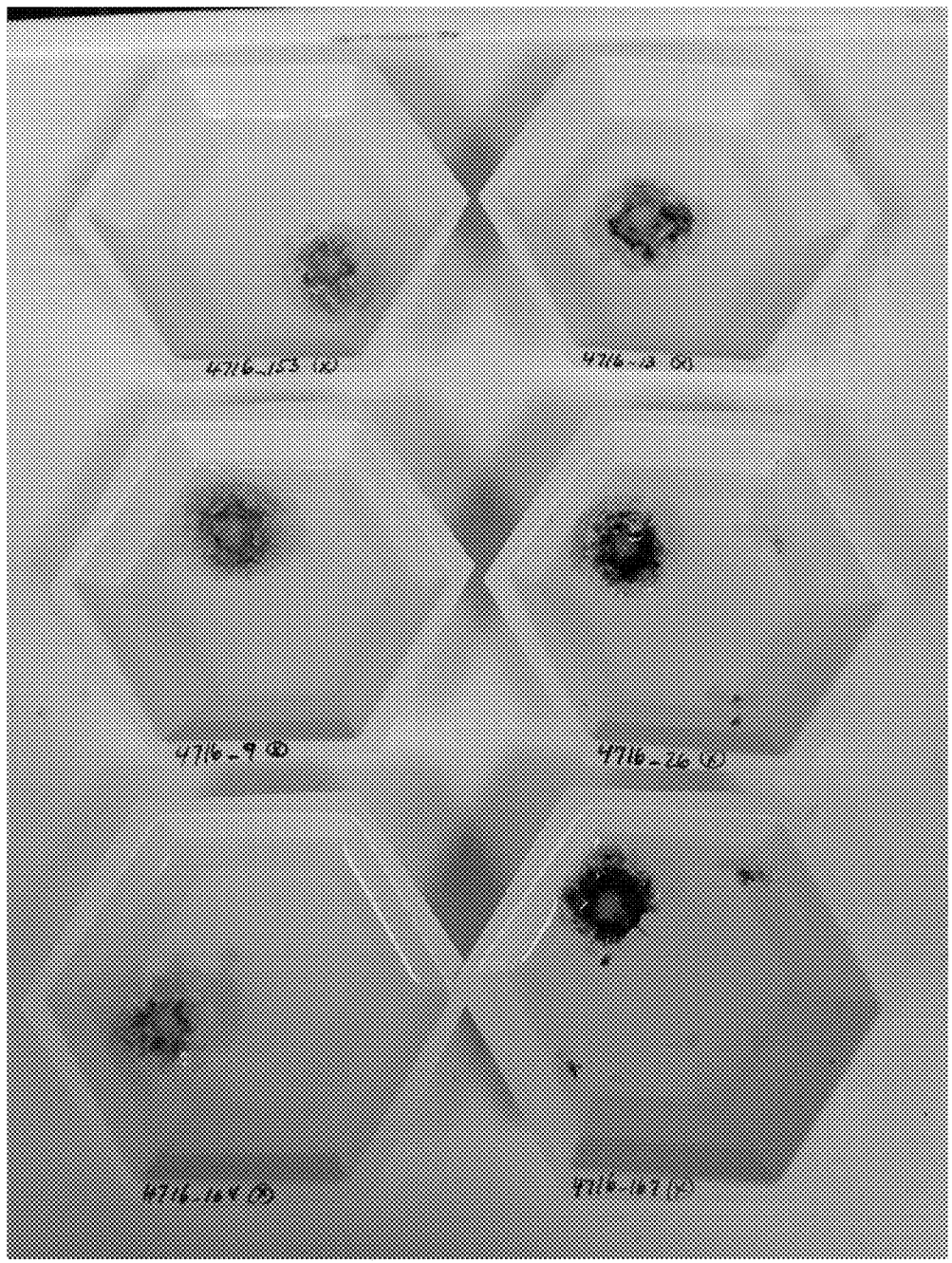
FIG. 6 illustrates starch staining in gwd knock-out (GWDko) meganuclease cobs.

Referring to Table 5 and FIG. 6, it was shown that homozygous (4716_13) and heterozygous (4716_26 and 4716_167) cobs had increased starch staining compared with hemizygous (4716_164) and wild type (4716_9 and 4716_153) cobs.

Example 7. Construction of CRISPR/Cas Maize Transformation Vectors

For constructing Cas9 expression cassette, the *S. pyogenes* Cas9 protein sequence containing N- and C-terminal At nuclear localization sequences (NLS) as well the 3×FLAG sequence positioned immediately after the first ATG codon (Jiang et al., 2013) (SEQ ID NO: 74) was chosen for expression in maize. The sequence of *S. pyogenes* Cas9 containing two SV40 nuclear localization sequences (shown in bold letters) and 3×FLAG sequence at N-terminal part (underlined sequence) for expression in maize is as follows:

(SEQ ID NO: 74)
MDYKDHDGDYKDHDIDYKDDDDKMAPKKKRKVGIHGVPAADKKYSIGLDI

GTNSVGWAVITDEYKVPSKKFKVLGNTDRHSIKKNLIGALLFDSGETAEA

TRLKRTARRRYTRRKNRICYLQEIFSNEMAKVDDSFFHRLEESFLVEEDK

KHERHPIFGNIVDEVAYHEKYPTIYHLRKKLVDSTDKADLRLIYLALAHM

IKFRGHFLIEGDLNPDNSDVDKLFIQLVQTYNQLFEENPINASGVDAKAI

LSARLSKSRRLENLIAQLPGEKKNGLFGNLIALSLGLTPNEKSNFDLAED

AKLQLSKDTYDDDLDNLLAQIGDQYADLFLAAKNLSDAILLSDILRVNTE

ITKAPLSASMIKRYDEHHQDLILLKALVRQQLPEKYKEIFFDQSKNGYAG

YIDGGASQEEFYKFIKPILEKMDGTEELLVKLNREDLLRKQRTFDNGSIP

HQIHLGELHAILRRQEDFYPFLKDNREKIEKILTFRIPYYVGPLARGNSR

FAWMTRKSEETITPWNFEEVVDKGASAQSFIERMINFDKNLPNEKVLPKH

SLLYEYFTVYNELTKVKYVTEGMRKPAFLSGEQKKAIVDLLFKINRKVIV

KQLKEDYFKKIECFDSVEISGVEDRFNASLGTYHDLLKIIKDKDFLDNEE

NEDILEDIVLILTLFEDREMIEERLKTYAHLFDDKVMKQLKRRRYTGWGR

LSRKLINGIRDKQSGKTILDFLKSDGFANRNFMQLIHDDSLIFKEDIQKA

QVSGQGDSLHEHIANLAGSPAIKKGILQTVKVVDELVKVMGRHKPENIVI

EMARENQTTQKGQKNSRERMKRIEEGIKELGSQILKEHPVENTQLQNEKL

YLYYLQNGRDMYVDQELDINRLSDYDVDHIVPQSFLKDDSIDNKVLIRSD

KNRGKSDNVPSEEVVKKMKNYWRQLLNAKLITQRKFDNLIKAERGGLSEL

DKAGFIKRQLVETRQIIKHVAQILDSRMNIKYDENDKLIREVKVITLKSK

LVSDFRKDFQFYKVREINNYHHAHDAYLNAVVGIALIKKYPKLESEFVYG

-continued

DYKVYDVRKMIAKSEQEIGKATAKYFFYSNIMNFEKTEITLANGEIRKRP

LIETNGETGEIVWDKGRDFATVRKVLSMPQVNIVKKTEVQTGGESKESIL

PKRNSDKLIARKKDWDPKKYGGFDSPIVAYSVLVVAKVEKGKSKKLKSVK

ELLGITIMERSSFEKNPIDFLEAKGYKEVKKDLIIKLPKYSLFELENGRK

RMLASAGELQKGNELALPSKYVNFLYLASHYEKLKGSPEDNEQKQLFVEQ

HKHYLDEIIEQISEFSKRVILADANLDKVLSAYNKHRDKPIREQAENIIH

LFTLINLGAPAAFKYFDTTIDRKRYTSTKEVLDATLIHQSITGLYETRID

LSQLGGDRPKKKRKVGG

The sequence was back translated and maize codon optimized to produce ZmCas9 (SEQ ID NO: 75). The optimized ZmCas9 nucleotide sequence was synthesized by Genscript. The ZmCas9 was cloned as BamHI-AvrII fragment between maize ubiquitin 1 promoter (ZmUbi1P) and nopaline synthase transcriptional terminator (NosT) sequences into pAG4500 to produce pAG4800.

The work on construction of sgRNA cassettes involved: 1) identification and isolation of a maize RNA Polymerase III promoter to drive expression of sgRNA; 2) design and synthesis of sgRNA scaffold; and 3) selection of a target gene and 20 bp specific sequences within this gene for guiding Cas9 endonuclease to its target sites.

The first description of a maize sequence encoding U3 small nuclear RNA (U3snRNA) was reported by Leader et al. in 1994, who isolated MzU3.8 gene (Genebank Accession No. Z29641) (SEQ ID NO: 76) from a maize genomic DNA library and demonstrated that the MzU3.8 U3snRNA is expressed in maize protoplasts. Using BLASTN algorithm and Z29641 sequence to search the Maize Genetics and Genomics Database we identified a homologous sequence of maize U3 that was labeled as ZmU3 (SEQ ID NO: 77).

The ZmU3 is localized on the maize chromosome 8 and is contained within a sequence with nucleotide coordinates 163620300-163621800. The CLUSTAL 2.1 multiple nucleotide sequence alignment of putative promoter regions of MzU3.8 (SEQ ID NO: 78) and ZmU3 (SEQ ID NO: 79) demonstrated 93.8% identity between the two sequences. CLUSTAL 2.1 multiple sequence alignment:

```
MzU3.8   GAATTCCATCTAAGTATCTTGGTAAAGCATGGATTAATTTGGATGCTCACTTCAGGTCTA   60
ZmU3     GAATTCCATCTAAGTATGTTGGTAAAGCATGGATTAATTTGGATGCCCACTTCAGGTCTA   60
         ***************** ************************** **************

MzU3.8   TGCAGCTCCGGTGCCTTGTGATTGTGAGTTGTGACCGATGCTCATGCTATTTTGCATTTC   120
ZmU3     TGCAGCTCCGGTGCCTTGTGATTGTGAGTTGTGACCGATGCTCATGCTATTCTGCATTTC   120
         *************************************************** ********

MzU3.8   TGCGATGTATGATGCTAGTAGATCTTCAAAACTAACAGCGCATGCCATCATCATCCACTG   180
ZmU3     TGCGATGTATGTAGCTAGTAGATCTTCAAAACTAACACCGCATGCCATCATCATCCACTG   180
         *********** ************************* **********************

MzU3.8   CTTGATTTTAGTCTCACCGCTGGCCAAAAATGTGATGATGCCAGAAACCTCAACTACCTT   240
ZmU3     CTTGATTTTAGTCTCACCGCTGGCCAAAAATGTGATGATGCCAGAAACCTCAACTACCTT   240
         ************************************************************

MzU3.8   GAATCAACACGGGCCCAGCAGTGTGATGACGACAGAAACCAAAAAAAAATGAGCCAATAG   300
ZmU3     GAATCAACACGGGCCCAACAGTGTGATGACGACAGAAAC-AAAAAAAAATGAGCCAATAG   299
         ***************** ********************* *********************

MzU3.8   TTCAGAAGGAGGCACTATGCAGAAACTACATTTCTGAAGGTGACTAAAAGGTGAGCGTAG   360
ZmU3     TTCAGAAGGAGGCACTATGCAGAAACTACATTTCTGAAGGTGACTAAAAGGTGAGCGTAG   359
         ************************************************************

MzU3.8   AGTGTACTTACTAGTAGTTTAGCCACCATTACCCAAATGCTTTCGAGCTTGTATTAAGAC   420
ZmU3     AGTGTAATTACTAGTAGTTTAGCCACCATTACCCAAATGCTTTCGAGCTTGTATTAAGAT   419
         ****** ****************************************************

MzU3.8   TTCCTAAGCTGAGCATCATCACTGATCTGCAGG--AGGGTCGCTTCGCTGCCAAGATCAA   478
ZmU3     TTCCTAAGCTGAGCATCATCACTGATCTGCAGGCCACCCTCGCTTCGCTGCCAAGATCAA   479
         *********************************  *   ********************

MzU3.8   CAGCAACCATGTGGCGGCAACATCCAGCATTGCACATGGGCTAAAGATTGAGCTCTGTGC   538
ZmU3     CAGCAACCATGTGGCGGCAACATCCAGCATTGCACATGGGCTAAAGATTGAGCTTTGTGC   539
         ****************************************************** *****

MzU3.8   CAAGTGTGAGCTGCAACCATCTAGGGATCAGCTGAGTTTATCAGTCTTTCCTTTTTTTCA   598
ZmU3     C---------------TCGTCTAGGGATCAGCTGAGGTTATCAGTCTTTCCTTTTTTTCA   584
         *                * ****************** **********************

MzU3.8   TTCTGGTGAGGCATCAAGCTACTACTGCCTCGATCGGTTGGACTTGGACCTGAAGCCCAC   658
ZmU3     TCCAGGTGAGGCATCAAGCTACTACTGCCTCGATTGGCTGGA------CCCGAAGCCCAC   638
         * * ****************************** ** ****      ** *********

MzU3.8   ATGTAGGATACCAGAATGGACCGACCCAGGACG------------------------TA   693
ZmU3     ATGTAGGATACCAGAATGGGCCGACCCAGGACGCAGTATGTTGGCCAGTCCCACCGGTTA   698
         ******************* *************                        **

MzU3.8   GTGCCACCTCGGTTG-TCACACTGCGTAGAAGCCAGCTTAAAAATTTAGCTTTGGTGACT   752
ZmU3     GTGCCATCTCGGTTGCTCACA-TGCGTAGAAGCCAGCTTAAAAATTTAGCTTTGGTAACT   757
         ****** ******** *****  ***************************** ****
```

-continued

```
MzU3.8    CACAGCA                          759 (SEQ ID NO: 78)
ZmU3      CACAGCA                          764 (SEQ ID NO: 79)
          *******
```

Using a PCR approach with the forward primer ob2297 (SEQ ID NO: 80) and reverse primer ob2299 (SEQ ID NO: 81), the 758 bp ZmU3 promoter (ZmU3P1) (SEQ ID NO: 82) was subsequently isolated from maize genomic DNA of the maize line A×B. The forward primer ob2297 included AsiSI restriction site at its 5' end to facilitate cloning an sgRNA cassette into a pAG4500-based vector. Similarly, using a forward primer ob2343 (SEQ ID NO: 83), which contained AsiSI restriction site at its 5' end, a shorter 398 bp version of the maize U3 promoter (ZmU3P2) (SEQ ID NO: 84) was isolated for testing efficiency of a truncated maize U3 promoter. An additional variant of the ZmU3P2 was amplified with the forward primer ob2351 (SEQ ID NO: 85) that has the SwaI restriction enzyme site at its 5' end. Furthermore, a 308 bp control promoter fragment ZmU3.8P (SEQ ID NO: 86) was PCR synthesized using long primers that were designed on a MzU3.8 sequence published by Leader et al. (1994), which was shown to be expressed in maize protoplasts. The ZmU3.8P sequence also included AsiSI restriction site at the 5' end. All amplified promoter variants were cloned into pCR-BluntII-TOPO vector (Life Technologies) and their integrity was confirmed by complete sequencing.

The sgRNA scaffold design herein is based on the published organization of an sgRNA chimera (Larson et al., 2013) and includes a 42 bp Cas9 handle hairpin (SEQ ID NO: 87) followed by a 41 bp *S. pyogenes* terminator (SEQ ID NO: 88). In order to improve efficiency of transcriptional termination in maize, a 37 bp putative transcription terminator sequence ZmU3T (SEQ ID NO: 89) was isolated from ZmU3 snRNA (SEQ ID NO: 77) and fused downstream of the *S. pyogenes* terminator (SEQ ID NO: 88). The 120 bp sgRNA scaffold (SEQ ID NO: 90) was synthesized by PCR using long primers and KOD Xtreme DNA Polymerase with the proof reading activity. The SnaBI or AscI restriction sites were added at the 3' end of the two PCR-amplified sgRNA backbone DNA fragments to facilitate further cloning. The sgRNA scaffold DNA fragments synthesized in this way were cloned into pCR-BluntII-TOPO vector and sequence validated.

For testing efficiency of the CRISPR/Cas system in maize, a maize gene encoding GWD was selected for the initial targeted modifications.

The maize GWD gene has been annotated earlier and was screened for the presence of $AN_{19}NGG$ target sequences on both sense and antisense DNA strands. The 5' end "A" in $AN_{19}NGG$ sequence represents a conserved "Adenine" nucleotide at the transcription start of the U3 RNA Polymerase III promoter, the 3' end positioned "NGG" sequence corresponds to the required for CRISPR/Cas system activity protospacer-adjacent motif (PAM) sequence. The candidate target sequences identified in exons 1, 24, and 25 as well as in their flanking introns were further screened against Maize GDB in order to eliminate sequences that have multiple identity hits within the maize genome. This work has been done to minimize chances for off-target activity of the CRISPR/Cas system. In this analysis, only the seed sequence (12 bp) of the target sequence plus two adjacent PAM nucleotides were used in BLASTN program as it was proposed by Larson et al. (2013). Exon 1 was selected for producing an almost complete GWD knockout, while exons 24 and 25 were chosen to generate GWD variants lacking an active site that is encoded by exon 24. A list of the final 19 bp GWD target sequences (SEQ ID NOS: 131-134), which were identified for sgRNA development, is compiled in Table 6.

TABLE 6

GWD Gene Target Sequences With Their Corresponding SEQ ID NOS

| SEQ ID NO | Sequence name | Sequence | GWD strand |
|---|---|---|---|
| 91 | GWDe1a | GGCATGAGGTGCTTACGTC | antisense |
| 92 | GWDe24b | CATAACCTGATACTTCAAC | antisense |
| 93 | GWDe24c | TCTGGCTCCTGCTATCAGT | sense |
| 94 | GWDe25a | TCTGCAGAAGTAGGCTTGA | antisense |

Each of the three variants of the maize U3 promoter, selected GWD target sequences and sgRNA backbone were assembled together by the means of fusion PCR using KOD Xtreme DNA Polymerase to construct six sgRNA expression cassettes (SEQ ID NOS: 135-140). The PCR-amplified fragments were cloned into pCR-BluntII-TOPO vector and the integrity of the synthesized sgRNA expression cassettes was verified through sequencing. The list of the PCR-synthesized sgRNA cassettes is presented in Table 7.

TABLE 7

The Synthesized sgRNA Expression Cassettes with Their Corresponding SEQ ID NOS

| SEQ ID NO | sgRNA cassette | Flanking restriction sites |
|---|---|---|
| 95 | ZmU3P1:sgRNA_GWDe24b | AsiSI-SnaBI |
| 96 | ZmU3P2:sgRNA_GWDe24b | AsiSI-SnaBI |
| 97 | ZmU3.8P:sgRNA_GWDe24b | AsiSI-SnaBI |
| 98 | ZmU3P2:sgRNA_GWDe24c | AsiSI-SnaBI |
| 99 | ZmU3P2:sgRNA_GWDe25a | SwaI-AscI |
| 100 | ZmU3P2:sgRNA_GWDe1a | AsiSI-SnaBI |

Assembled sgRNA cassettes were subsequently cloned as AsiSI-SnaBI fragments into pAG4800 to develop vectors pAG4804-4809 (Table 8).

TABLE 8

Vectors Developed for Maize CRISPR/Case System with SEQ ID NOS

| Plasmid | Genetic elements |
|---|---|
| pAG4800 | Ubi1P:Cas9 |
| pAG4804 | U3P1:sgRNA_GWDe24b + Ubi1P:ZmCas9 |
| pAG4805 | U3P2:sgRNA_GWDe24b + Ubi1P:ZmCas9 |
| pAG4806 | U3.8P:sgRNA_GWDe24b + Ubi1P:ZmCas9 |
| pAG4807 | U3P2:sgRNA_GWDe24c + Ubi1P:ZmCas9 |
| pAG4808 | U3P2:sgRNA_GWDe1a + Ubi1P:ZmCas9 |
| pAG4809 | U3P2:sgRNA_GWDe25a + Ubi1P:ZmCas9 |
| pAG4817 | U3P2:sgRNA_GWDe25a + U3P2:sgRNA_GWDe24c + Ubi1P:ZmCas9 |

One additional vector pAG4817 containing two sgRNA expression cassettes was constructed by cloning ZmU3P2:sgRNA_GWDe25a cassette as SwaI-AscI fragment into pAG4807. This vector was developed for complete removal of the GWD exon 24 by targeting Cas9 endonuclease to two different sites that are located 364 bp apart within the maize GWD gene and flank exon 24.

Figure 7:
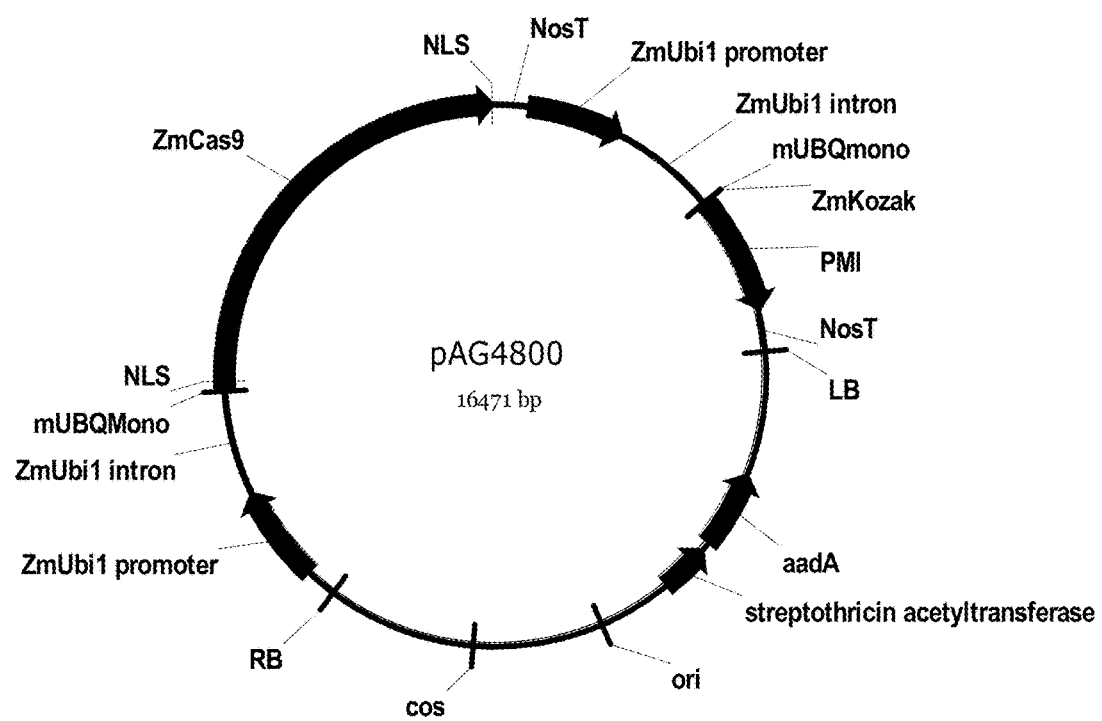
FIG. 7 illustrates the vector pAG4800 for expressing ZmCas9.
Figure 8:
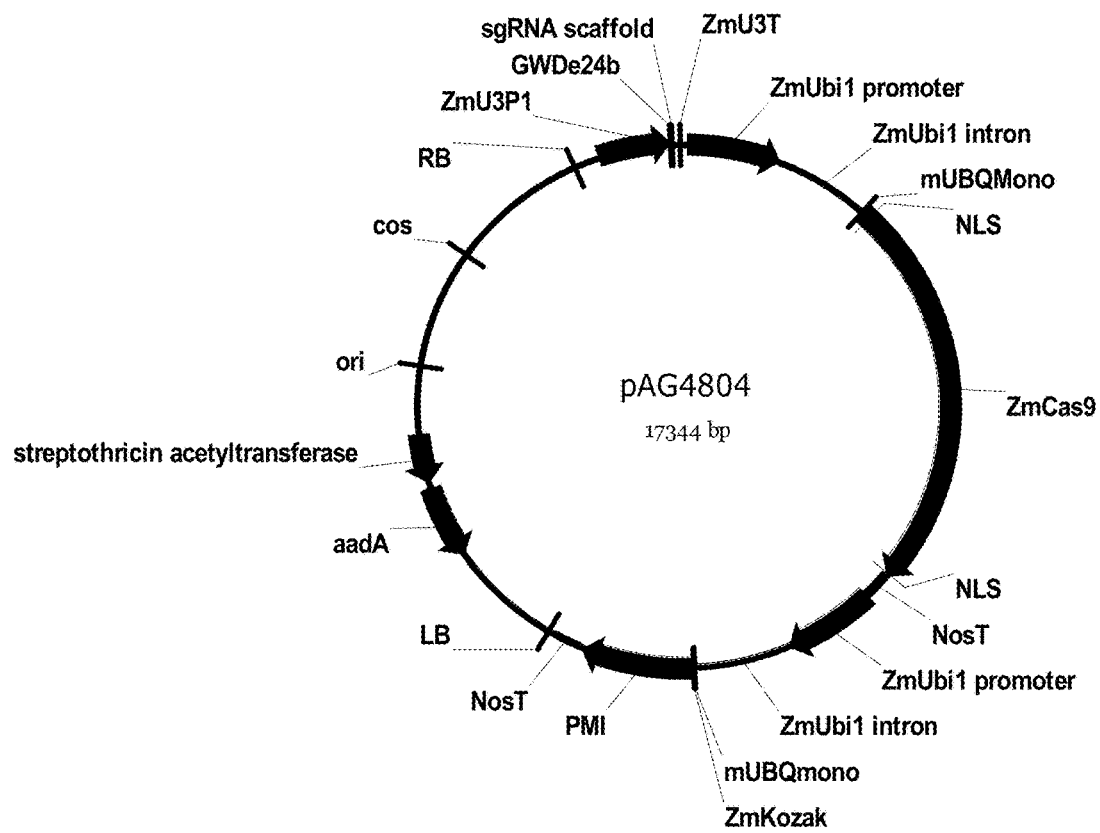
FIG. 8 illustrates the vector pAG4804 for expressing sgRNA scaffold and ZmCas9.

The maps of the plant transformation vectors pAG4800 and pAG4804, which were constructed for development of CRISP/Cas system for maize are shown on FIGS. 7-8. Referring to FIG. 7, the pAG4800 vector includes the Cas9 expression cassette and the PMI expression cassette. The Cas9 expression cassette comprises a nucleotide sequence of ZmCas9 (SEQ ID NO: 75). ZmCas9 is a maize codon optimized sequence of the S. pyogenes gene encoding Cas9 fused to two At NLS at 5' and 3' ends and 3×FLAG sequence immediately after the first ATG codon. Zm Cas9 encodes the S. pyogenes Cas9 protein (SEQ ID NO: 74) containing two At nuclear localization sequences and 3×FLAG sequence at N-terminal part for expression in maize. The Cas9 cassette also includes the Zm Ubi1 promoter, Zm Ubi1 intron, mUBQMono leader, and the NosT terminator. The PMI cassette includes the PMI gene, ZmUbi1 promoter, mUBQ-Mono, ZmKozak leaders and the NosT terminator. Referring to FIG. 8, the pAG4804 vector includes the GWDe24b-sgRNA scaffold cassette, the Cas9 expression cassette, and the PMI expression cassette. The GWDe24b-sgRNA scaffold cassette includes ZmU3P1 promoter, GWDed24 sequence, the sgRNA scaffold and ZmU3T terminator. The Cas9 expression cassette comprises ZmCas9 fused to two At NLS at 5' and 3' ends and 3×FLAG sequence immediately after the first ATG codon. The Cas9 cassette also includes the Zm Ubi1 promoter, Zm Ubi1 intron, mUBQMono leader, and the NosT terminator. The PMI cassette includes the PMI gene, ZmUbi1 promoter, mUBQMono, ZmKozak leaders and the NosT terminator.

Example 8. Generation of CRISPR/Cas-Induced Mutant Plants

Identification and Characterization of CRISPR/Cas and Maize NLS Meganuclease-induced Mutations in the Maize GWD Gene Maize plant transformation was performed according to the protocol described in Example 3. Screening of CRISPR/Cas-induced mutations was similar to screening of meganuclease-induced mutations methods that has been described in Example 3 with the exception of primers for genotyping and identifying mutations.

Table 9 describes primers for genotyping CRISPR/Cas plants that include 4804-4806, 4804-6 primer set; 4809, 4817, and 4804-6 primer set substituting GWDe24a-F for GWD24b-F and primers for amplifying DNA sequences surrounding the GWD meganuclease targeting region that include 4804-4807, 4804-7mut primers; 4817, 2856/2858 primers; 4837-4839, 371/429 primers.

TABLE 9

Primers for genotyping 4804, 4805, 4806, 4817, 4837, 4838, and 4839 plants and amplifying DNA sequences surrounding the GWD exon 24 targeting region

| Primer Set | Primer Name | Forward or Reverse | Sequence | SEQ ID NO | Product size (bp) |
| --- | --- | --- | --- | --- | --- |
| 4804-6 | GWDe24b-F | Forward | CTCACAGCACATAACCTGATACT | 101 | 100 |
| 4804-6 | sgRNA-R | Reverse | CGACTCGGTGCCACTTT | 102 | 100 |
| 4804-6 | ZmCas9-F | Forward | AGAATCAGACCACGCAGAAG | 103 | 186 |
| 4804-6 | ZmCas9-R | Reverse | GCTCCTGGTCCACATACATATC | 104 | 186 |
| 4809/4817 | GWDe24a-F | Forward | TGCAGAAGTAGGCTTGAGTTT | 110 | 89 |
| 4804-7mut | GWDex23-F | Forward | TGCTCTTCTGAACCGATTTGA | 105 | 560 |
| 4804-7mut | ZmGWD mega-2R | Reverse | CTATTCCTTGCTCGGACTGAC | 10 | 560 |
| 4817 | 2856 | Forward | GAAGGGGATTGAGAGGAAG | 111 | 613 |
| 4817 | 2858 | Reverse | CATGACGTTCAAATAGCCTCA | 112 | 613 |
| 4837-4839 | ZmGWD mega-2F | Forward | GGTTATAAGCCCGGTTGAAGTA | 9 | 381 |
| 4837-4839 | 429 | Reverse | GCAGAAGTAGGCTTGAAGGAA | 113 | 381 |

Similar to previous analyses, DNA sequences for each mutant were compared to WT GWD using Vector NTI Advance (Version 11.5; Life Technologies). Mutant DNA sequences are described in Table 10.

Transgenic maize plants carrying gene editing constructs that target regions of the GWD gene have been produced and are being analyzed for mutations in the target regions of the GWD gene. GWD mutations and predicted proteins are listed in Tables 11-14. In these tables, events carrying two different GWD mutant alleles (heterozygotes) are labeled with −1 or −2, to indicate the individual alleles. Intronic sequences are presented in lowercase letters and exons 24 or 25 are shown in uppercase letters. Since pAG4817 is targeting two different locations within ZmGWD, two mutations are provided for 4817_2 and 4817_52. The first target sequence is located just upstream of the 5'end of the exon 24 and an extra "T" that is inserted into this target location is shown as a capital letter "T" within lowercase letters specific to intron 23 (see M37 sequence). M37 is an identical modification in 4817_2 and 4817_52.

All modifications introduced by CRISPR/Cas9 are highlighted (bold black=insertion; gray=deletion) and missing nucleotides are shown by dots. Corresponding numbers of deleted or inserted nucleotides are presented in the last columns of Tables 11 and 12.

Similarly, all changes to deduced protein sequences for M32-M39 are highlighted. In the cases of translation reading frame shifts and early termination of translation, all amino acids differing from wild type GWD are also highlighted and the end of protein is indicated by an asterisk (*).

TABLE 10

CRISPR/Cas9 induced mutations in individual transgenic 4804, 4806, and 4817 events

| Mutation | Events and alleles |
|---|---|
| M32 | 4804_2, 4804_3-2, 4804_4-1, 4804_5-2, 4806_1 |
| M33 | 4804_3-1, 4804_5-1, 4804_7-1 |
| M34 | 4804_4-2 |
| M35 | 4804_6 |
| M36 | 4804_7-2 |
| M37, M38 | 4817_2 |
| M37, M39 | 4817_52 |

TABLE 11

Nucleotide sequences of CRISPR/Cas9 induced mutations in individual 4804 and 4806 events

| Sequence Description | DNA sequence | SEQ ID NO | Del/Ins number |
|---|---|---|---|
| WT ZmGWD Exon 24* | gctcctgctatcagTTGGCAGGTTATAAGCCCGGTTGAAGTATCAGGTTATGTGGTTGTGGTTGATGAGTTACTTG | 186 | None |
| M32 | gctcctgctatcagTTGGCAGGTTATAAGCCCGGTTTGAAGTATCAGGTTATGTGGTTGTGGTTGATGAGTTACTTG | 114 | +1 |
| M33 | gctcctgctatcagTTGGCAGGTTATAAGCCCGGTT...AGTATCAGGTTATGTGGTTGTGGTTGATGAGTTACTTG | 115 | −2 |
| M34 | gctcctgctatcagTTGGCAGGTTATAAGCCCGGTT....GTATCAGGTTATGTGGTTGTGGTTGATGAGTTACTTG | 116 | −3 |
| M35 | gctcctgctatcagTTGGCAGGTTATAAGCCCGGT.GAAGTATCAGGTTATGTGGTTGTGGTTGATGAGTTACTTG | 117 | −1 |
| M36 | gctcctgctatcagTT.....................................GGTTGTGGTTGATGAGTTACTTG | 118 | −37 |

*WT ZmGWD is a region of nt 81-160 of Exon 24 (SEQ ID NO: 3)

TABLE 12

Nucleotide sequences of CRISPR/Cas9 induced mutations in individual 4817 events

| Sequence Description | DNA sequence | SEQ ID NO | Del/Ins number |
|---|---|---|---|
| Wt ZmGWD Exon 24* | gctcctgctatcagTTGGCAGGTTATAAGCCCGGTTGAAGTATCAGGTTATGTGGTTGTGGTTGATGAGTTACTTG | 187 | None |
| M37 | gctcctgctatcTagTTGGCAGGTTATAAGCCCGGTTGAAGTATCAGGTTATGTGGTTGTGGTTGATGAGTTACTTG | 188 | +1 |

TABLE 12-continued

Nucleotide sequences of CRISPR/Cas9 induced mutations in individual 4817 events

| Sequence Description | DNA sequence | SEQ ID NO | Del/Ins number |
|---|---|---|---|
| Wt ZmGWD Exon 25 | CACTCTATCTGAACTTGAAGGATATGATCAGAAAC TGTTTTCCTTCAAGCCTACTTCTGCAGATATA | 189 | None |
| M38 | CACTCTATCTG................................ ................................CAGATATA | 119 | −48 |
| M39 | CACTCTATCTGAACTTGAAGGATATGATCAGAAAC TGTTTTCCTTCAÇAGCCTACTTCTGCAGATATA | 120 | +1 |

*WT ZmGWD is a region of nt 81-160 of Exon 24 (SEQ ID NO: 3)

TABLE 13

Partial deduced protein sequences of exon 24 in CRISPR/Cas9 mutants 4804 and 4806

| Sequence Description | Protein sequence | SEQ ID NO |
|---|---|---|
| WT ZmGWD Exon 24* | WQVISPVEVSGYVVVVDELLAVQNKSYDKPTILVAKSVKGEEEIPDG | 190 |
| M32 | WQVISPV* | 121 |
| M33 | WQVISPVSIRLCGCG* | 122 |
| M34 | WQVISPV VSGYVVVVDELLAVQNKSYDKPTILVAKSVKGEEEIPDG | 123 |
| M35 | WQVISPVKYQVMWLWLMSYLLSRTNLMINQPSLWQRVSRERKKYQME* | 124 |
| M36 | WLWLMSYLLSRTNLMINQPSLWQRVSRERKKYQME* | 125 |

*WT ZmGWD Exon 24 is a region of aa 1011-1057 of WT ZmGWD (SEQ ID NO: 43)

TABLE 14

Partial deduced protein sequences of exon 25 in CRISPR/Cas9 mutants 4817

| Sequence Description | Protein sequence | SEQ ID NO |
|---|---|---|
| WT ZmGWD Exon 25* | VLFATCFDHTTLSELEGYDQKLFSFKPTSADIT YR | 191 |
| M38 | VLFATCFDHTTLS...................ADITYR | 126 |
| M39 | VLFATCFDHTTLSELEGYDQKLFSFTAYFCRY NL* | 127 |

**WT ZmGWD Exon 25 is a region of aa 1082-1116 of WT ZmGWD (SEQ ID NO: 43)

Characterization of Maize NLS Meganuclease-Induced Mutations

To develop maize NLS meganuclease constructs pAG4837-4839, the viral SV40 NLS sequence in pAG4716 was replaced with the maize NLS sequences derived from Opaque2 (Hicks et al., PNAS, 1995) (Table 15). A large variation of the induced mutations in exon 24 of the maize GWD gene was observed. These mutations included substitutions, deletions, and insertions from 1 to 114 nucleotides (Tables 16-17). Indirectly assessed efficiencies of the NLS variants were estimated as the number of events containing any modifications in the target region of the GWD gene divided by the total number of analyzed events (Table 15). Each evaluated NLS sequence supported production of the induced mutations with the NLS3 and NLS4 being the most efficient.

TABLE 15

Meganuclease constructs containing plant-derived NLS sequences

| Construct | Expression cassette | NLS number | Protein sequence | SEQ ID NO | Relative efficiency (%) |
|---|---|---|---|---|---|
| pAG4837 | ZmUbi1P:NLS1: GWD7-8x.226 | NLS1 | MPTEERVRKRKES NRESARRSRYRKA AHLKEL | 128 | 59.1 |
| pAG4838 | ZmUbi1P:NLS3: GWD7-8x.226 | NLS3 | MARKRKESNRESA RRSRYRKAAHLKE L | 129 | 75.0 |
| pAG4839 | ZmUbi1P:NLS4: GWD7-8x.226 | NLS4 | MARKRKESNRESA RRSRRSRYRKV | 130 | 71.4 |

TABLE 16

List of representative mutations induced by maize NLS meganucleases in exon 24 of the ZmGWD gene in 4837, 4838, and 4839 events

| Sequence Description | Mutation | DNA sequence | SEQ ID NO | Del/Ins |
|---|---|---|---|---|
| WT ZmGWD* | None | GAAATACCAGATGGAGTAGTTGGTGTAATTA CACCTGATATGCCAGATGTTCTGTCT | 192 | None |
| 4837_12 | M40 | GAAATACCAGATGGAGTAGTTG....TAATTA CACCTGATATGCCAGATGTTCTGTCT | 131 | −3 |
| 4837_12 | M41 | GAAATACCAGATGGAGTAGTTGTATAAATT ACACCTGATATGCCAGATGTTCTGTCT | 132 | −2/+3 |
| 4837_16 | M42 | GAAATACCAGATGGAGTAGTTGTGTA..TTA CACCTGATATGCCAGATGTTCTGTCT | 133 | −1 |
| 4837_19 | M43 | GAAATACCAGATGGAGTAGTTGGTGTAGAGT AATAACACCTGATATGCCAGATGTTCTGTCT | 134 | −3/+8 |
| 4837_53 | M44 | GAAATACCAGATGGAGTAGTTGGTGT........ ............TCTGTCT | 135 | −24 |
| 4838_1 | M45 | GAAATACCAGATG................... ............TTCTGTCT | 136 | −36 |
| 4838_51 | M46 | GAAATACCAGATGGAGTAGTTGGTGTATGAA CACGTAATTACACCTGATATGCCAGATGTTC TGTCT | 137 | +10 |
| 4838_53 | M47 | GAAATACCAGATGGAGTAGTTGGTGT........ ............CT | 138 | −29 |
| 4839_1 | M48 | GAAATACCAGATGGAGTAGTTGGTG....TTA CACCTGATATGCCAGATGTTCTGTCT | 139 | −3 |
| 4839_3 | M49 | GAAATACCAGATGGAGTAGTTGGTGTAAATT ACACCTGATATGCCAGATGTTCTGTCT | 140 | +1 |
| 4839_54 | M50 | GAAATACCAGATGG............... ........GATATGCCAGATGTTCTGTCT | 141 | −22 |

TABLE 16-continued

List of representative mutations induced by maize NLS meganucleases in exon 24 of the ZmGWD gene in 4837, 4838, and 4839 events

| Sequence Description | Mutation | DNA sequence | SEQ ID NO | Del/Ins |
|---|---|---|---|---|
| 4839_57 | M51 | GAAATACCAGATGGAGTAGTTGGTGTCTCAT GCCAGATGTGAAGAAATTACACCTGATATGC CAGATGTTCTGTCT | 142 | +19 |
| 4839_58 | M52 | GAAATACCAGATGGAGTAGTTGGTG░░░░░ ░░░░░░░░░░░░ATGTTCTGTCT | 143 | −21 |
| 4839_58 | M53 | GAAATACCAGATGGAGTAGTTGGTGT░░░░ ░CAGATATGCCAGATGTTCTGTCT | 144 | −9/+2 |
| 4839_61 | M54 | GAAATACCAGATGGAGTAGTTGGTGCATTTA CTCATATTTTCTGTGATTGAATATTCTTTTC CAGATGGAGTGTCAAGGGAGAGGAAGAAATA CCAGATGGAGTGTCAAGGGAGAGGAAGAAAT ACCAGATGAAGGAAATACACCTGATATGCCA GATGTTCTGTCT | 145 | −4/+114 |
| 4839_61 | M55 | GAAATACCAGATGGAGT░░░░░░░░░░TA CACCTGATATGCCAGATGT | 146 | −12 |

*WT ZmGWD is a region of nt 3157-3213 of SEQ ID NO: 1.

TABLE 17

Partial deduced protein sequences of exon 24 in CRISPR/Cas9 mutants 4837, 4838, and 4839

| Sequence Description | Protein sequence | SEQ ID NO |
|---|---|---|
| WT ZmGWD Exon 24* | IPDGVVGVIT PDMPDVLSHVSVRARNSK | 193 |
| M40 | IPDGVV░VITPDMPDVLSHVSVRARNSK | 147 |
| M41 | IPDGVVGINYT* | 148 |
| M42 | IPDGVVGVLHLICQMFCLMCQSEQGIARYCL RPVLTTPLYLNLKDMIRNCFPSSLLL* | 149 |
| M43 | IPDGVVGVE* | 150 |
| M44 | IPDGVVGV░░░░░░LSHVSVRARNSK | 151 |
| M45 | IPD░░░░░░░░VLSHVSVRARNSK | 152 |
| M46 | IPDGVVGV* | 153 |
| M47 | IPDGVVGVSCVSPSKE* | 154 |
| M48 | IPDGVVGV░TPDMPDVLSHVSVRARNSK | 155 |
| M49 | IPDGVVGVNYT* | 156 |
| M50 | IPDGICQMFCLMFQSEQGIARYCLRPVLTTP LYLNLKDMIRNCFPSSLLLQI* | 157 |

TABLE 17-continued

Partial deduced protein sequences of exon 24 in CRISPR/Cas9 mutants 4837, 4838, and 4839

| Sequence Description | Protein sequence | SEQ ID NO |
|---|---|---|
| M51 | IPDGVVGVSCQM* | 158 |
| M52 | IPDGVVG░░░░░DVLSHVSVRARNSK | 159 |
| M53 | IPDGVVGVRYARCSVSCVSPSKE* | 160 |
| M54 | IPDGVVGAFTHIFCD* | 161 |
| M55 | IPDGV░░░░░TPDMPDVLSHVSVRARNSK | 162 |

*WT ZmGWD Exon 24 is a region of aa 1054-1081 of SEQ ID NO: 43.

Green Tissue Starch Assays

CRISPR/Cas and maize NLS meganuclease lines were assayed for starch in green leaf tissue. Leaf tissue harvested from 40 day old events was assayed for starch according to the protocol described in Example 3. These data confirm the efficacy of our CRISPR/Cas targeting system and maize NLS meganuclease gene editing constructs.

TABLE 18

Starch Content in CRISPR/Cas and Maize NLS Meganuclease Lines

| Vector | Event | Starch (mg glucose/100 mg DW) [% DW] | SD |
|---|---|---|---|
| WT | WT | 1.0 | 1.4 |
| 4804 | 58 | 1.1 | 0.1 |
| 4804 | 60 | 1.2 | 0.1 |
| 4804 | 59 | 1.3 | 0.2 |
| 4804 | 61 | 2.4 | 0.2 |
| 4804 | 53 | 9.3 | 1.9 |
| 4804 | 6 | 9.6 | 0.3 |
| 4804 | 4 | 11.2 | 1.4 |
| 4804 | 54 | 11.9 | 0.5 |
| 4804 | 51 | 12.4 | 0.9 |
| 4804 | 57 | 14.1 | 1.8 |
| 4804 | 62 | 16.7 | 0.4 |
| 4804 | 56 | 16.7 | 0.7 |
| 4804 | 7 | 17.0 | 0.6 |
| 4804 | 63 | 17.9 | 0.4 |
| 4804 | 5 | 18.0 | 0.2 |
| 4804 | 52 | 18.2 | 0.8 |
| 4804 | 3 | 18.5 | 0.9 |
| 4804 | 64 | 19.0 | 0.7 |
| 4804 | 2 | 19.5 | 1.2 |
| 4804 | 55 | 20.5 | 0.9 |
| 4804 | 1 | 27.8 | 1.7 |
| 4805 | 1 | 1.2 | 0.3 |
| 4805 | 103 | 11.2 | 0.7 |
| 4805 | 53 | 11.5 | 1.0 |
| 4805 | 56 | 11.7 | 0.7 |
| 4805 | 55 | 13.8 | 2.3 |
| 4805 | 101 | 14.2 | 0.4 |
| 4805 | 104 | 15.0 | 1.2 |
| 4805 | 51 | 15.0 | 1.2 |
| 4805 | 54 | 15.6 | 1.0 |
| 4805 | 2 | 16.4 | 0.7 |
| 4806 | 204 | 0.9 | 0.1 |
| 4806 | 203 | 0.9 | 0.1 |
| 4806 | 202 | 0.9 | 0.1 |
| 4806 | 201 | 1.0 | 0.1 |
| 4806 | 2 | 1.2 | 0.1 |
| 4806 | 52 | 1.2 | 0.6 |
| 4806 | 101 | 1.4 | 0.2 |
| 4806 | 53 | 1.7 | 0.2 |
| 4806 | 154 | 2.0 | 0.3 |
| 4806 | 57 | 2.2 | 0.7 |
| 4806 | 152 | 2.7 | 0.9 |
| 4806 | 1 | 3.3 | 0.3 |
| 4806 | 205 | 4.0 | 1.0 |
| 4806 | 207 | 4.6 | 0.6 |
| 4806 | 209 | 5.9 | 1.0 |
| 4806 | 210 | 7.1 | 0.9 |
| 4806 | 208 | 7.4 | 0.6 |
| 4806 | 155 | 7.5 | 1.0 |
| 4806 | 55 | 8.6 | 1.4 |
| 4806 | 56 | 9.4 | 1.8 |
| 4806 | 206 | 10.1 | 1.4 |
| 4806 | 54 | 11.0 | 0.9 |
| 4806 | 151 | 15.7 | 1.4 |
| 4807 | 1 | 0.7 | 0.0 |
| 4807 | 6 | 0.7 | 0.1 |
| 4807 | 5 | 0.7 | 0.1 |
| 4807 | 2 | 0.7 | 0.0 |
| 4807 | 4 | 1.0 | 0.1 |
| 4807 | 3 | 2.1 | 0.4 |
| 4809 | 1 | 10.1 | 0.8 |
| 4809 | 2 | 10.6 | 0.5 |
| 4809 | 4 | 13.3 | 0.7 |
| 4809 | 3 | 17.8 | 1.3 |
| 4817 | 54 | 14.2 | 0.7 |
| 4817 | 55 | 18.0 | 1.1 |
| 4817 | 51 | 19.2 | 0.8 |
| 4817 | 1 | 19.4 | 0.8 |
| 4817 | 53 | 20.7 | 0.5 |
| 4817 | 52 | 20.9 | 0.8 |

TABLE 19

Starch Content in CRISPR/Cas and Maize NLS Meganuclease 4837, 4838 and 4839 Lines

| Vector | Event | Starch (mg glucose/100 mg DW) [% DW] | SD |
|---|---|---|---|
| WT | 1 | 1.0 | 0.2 |
| 4837 | 8 | 1.3 | 0.2 |
| 4837 | 51 | 1.8 | 0.5 |
| 4837 | 7 | 1.8 | 0.3 |
| 4837 | 16 | 2.2 | 0.5 |

TABLE 19-continued

Starch Content in CRISPR/Cas and Maize NLS Meganuclease 4837, 4838 and 4839 Lines

| Vector | Event | Starch (mg glucose/100 mg DW [% DW] | SD |
|---|---|---|---|
| 4837 | 4 | 2.3 | 0.2 |
| 4837 | 1 | 2.3 | 0.2 |
| 4837 | 15 | 2.5 | 0.1 |
| 4837 | 53 | 3.3 | 0.5 |
| 4837 | 9 | 3.6 | 0.5 |
| 4837 | 3 | 4.7 | 1.0 |
| 4837 | 12 | 6.2 | 1.4 |
| 4837 | 17 | 16.5 | 0.5 |
| 4837 | 11 | 17.0 | 0.7 |
| 4837 | 14 | 18.2 | 0.6 |
| 4837 | 2 | 18.6 | 1.1 |
| 4837 | 5 | 19.3 | 1.3 |
| 4837 | 19 | 20.0 | 1.1 |
| 4837 | 18 | 20.4 | 0.4 |
| 4837 | 10 | 22.7 | 2.1 |
| 4837 | 6 | 23.3 | 0.9 |
| 4837 | 52 | 24.7 | 1.4 |
| 4838 | 4 | 1.2 | 0.1 |
| 4838 | 3 | 1.7 | 0.4 |
| 4838 | 53 | 1.8 | 0.7 |
| 4838 | 2 | 3.3 | 0.4 |
| 4838 | 54 | 6.9 | 1.2 |
| 4838 | 51 | 19.3 | 1.4 |
| 4838 | 52 | 19.9 | 1.2 |
| 4838 | 1 | 20.0 | 1.4 |
| 4839 | 53 | 1.1 | 0.1 |
| 4839 | 63 | 1.1 | 0.1 |
| 4839 | 62 | 1.3 | 0.1 |
| 4839 | 52 | 1.4 | 0.2 |
| 4839 | 54 | 2.1 | 0.4 |
| 4839 | 56 | 2.3 | 0.2 |
| 4839 | 51 | 2.4 | 1.1 |
| 4839 | 57 | 2.7 | 0.3 |
| 4839 | 58 | 2.8 | 0.8 |
| 4839 | 55 | 22.8 | 1.7 |
| 4839 | 61 | 23.5 | 1.1 |
| 4839 | 60 | 24.5 | 1.1 |
| 4839 | 59 | 28.0 | 3.3 |

Referring to Tables 18 and 19, it was observed that many of the events exhibited high starch, which ranged approximately 3%-27.8%.

Example 10. Green Tissue Starch Assays

Figure 9:
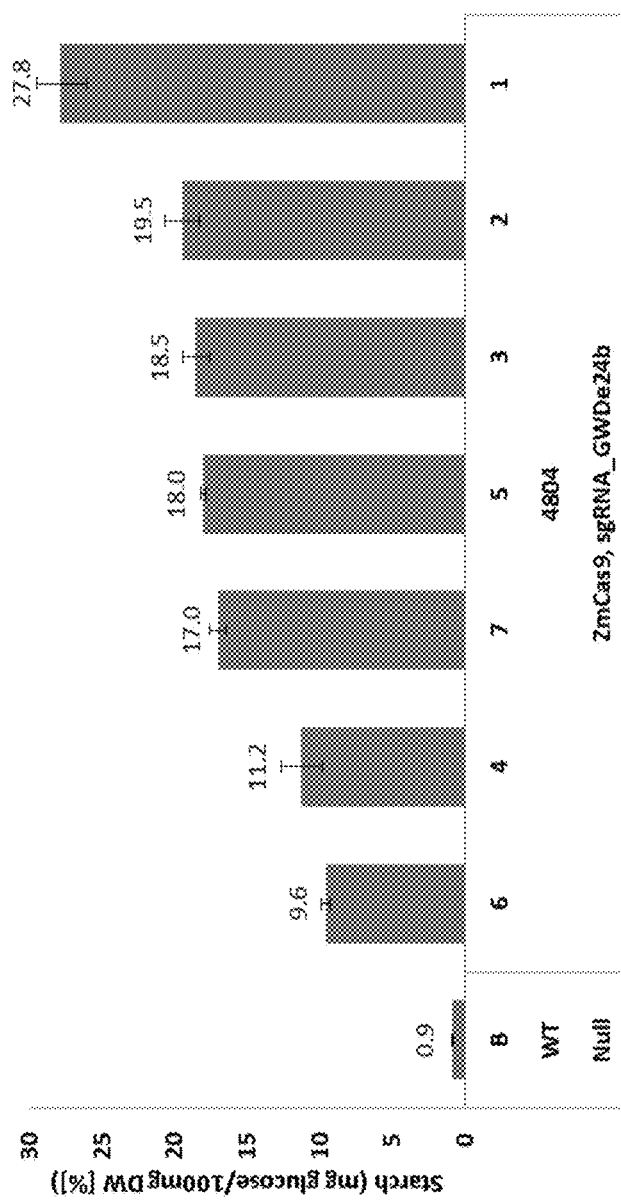
FIG. 9 illustrates starch accumulation in the pAG4804 maize events.
Figure 10:
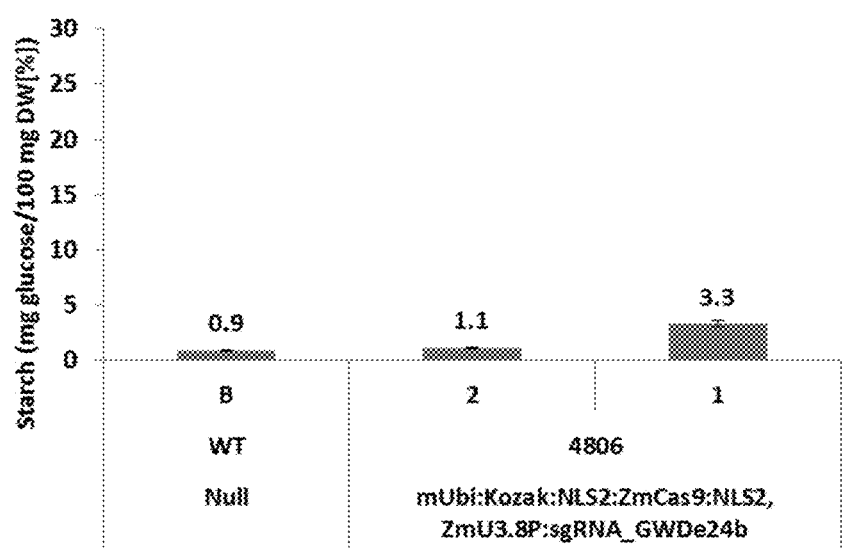
FIG. 10 illustrates starch accumulation in the pAG4806 maize events.

All of the CRISPR/Cas lines were assayed for starch in green leaf tissue as well as in dried stover leaves, stalks, and cobs. Leaf tissue harvested from 40 day old CRISPR/Cas events were assayed for starch according to our protocol described in Example 3. FIG. 9 illustrates starch accumulation in the pAG4804 maize events. Referring to FIG. 9, all seven T0 maize 4804 events had high starch, which ranged 9.6-27.8%, indicating that all currently unresolved GWD sequences were the result of two different GWD mutations rather than one wild type and one mutant allele (hemizygote). FIG. 10 illustrates starch accumulation in the pAG4806 maize events. Referring to FIG. 10, both T0 maize 4806 events had low starch, suggesting that the one unresolved GWD sequence is a hemizygote. These data confirm the efficacy of the CRISPR/Cas targeting system herein, which includes new GWD guide RNA targeting sequences and new U3 promoters used for expression of the guide RNAs.

Example 11. Breeding Recessive Mutations for Elite Inbred Introgression and Testing The advent of new methods for precision DNA engineering and mutagenesis provides a means of generating targeted recessive and dominant mutations for the development of new and beneficial plant traits. Some of these methods include targeting specific regions of genes with meganucleases, Talens, and the CRISPR/Cas system. Tracking and advancing targeted mutations present a new challenge for trait development, because, unlike traditional transgenic plant traits, they do not carry dominant T-DNA expression cassettes and selectable markers. Generation of targeted mutations in maize and *sorghum* using TALENS, ZFN, meganuclease and CRISPR/Cas methods described herein can lead to the creation of new methods for screening and breeding these unique plant traits.

Example 12. Tracking and Breeding Targeted Mutations

Transformation (T0) Generation Genotypes:

Gene-specific mutations identified using the described methods resulted in first generation transformed (T0) plants with one of three different genotypes: 1) one wild type gene allele and one mutant allele, 2) two different mutant alleles, or 3) two identical mutant alleles. These mutant allele combinations were designated as hemizygous, heterozygous, and homozygous, respectively.

Molecular Methods for Tracking Targeted Mutations:

The specific sequence characteristics of a targeted DNA mutation (e.g., substitution, deletion, insertion, or combination) relative to the wild type sequence were, and may be, tracked using methods described herein when breeding the mutation into other lines, or expanding the existing lines through breeding. To differentiate wild type, hemizygous, heterozygous, and homozygous lines in a T0 and T1+ (progeny derived from T0 parental lines and beyond) segregating populations, at least five methods could be used. These methods include: 1) PCR of the mutation site with gel electrophoresis for size separation, 2) PCR with restriction enzyme digestion and gel electrophoresis to generate a mutation specific restriction pattern, 3) PCR with direct sequencing, 4) PCR with cloning and sequencing, and 5) PCR using primers that bind or do not bind to mutation sites.

Homozygous DNA sequences from either wild type or engineered, altered, or optimized endogenous nucleic acids would be easily analyzed by PCR, size determination, and, or DNA sequencing in the targeted or mutated region. In contrast, DNA sequences that possess different alleles may result in a portion of sequence that would be difficult to analyze using sequencing, PCR or size determination due to differences in the two allelic sequences (e.g., a wild type and a mutant or two different mutant sequences). PCR products from these types of targeted events would require cloning to isolate and effectively sequence each allele.

Once the sequence of the targeted mutation has been confirmed, a mutation-specific molecular strategy for tracking is established. As mentioned previously, this strategy will be dependent on the characteristics of the mutation. In tracking the gwd mutations generated herein, PCR specific reactions were developed for each of the mutations and engineered endogenous (optimized) nucleic acids described herein.

Breeding Crosses and Selfing:

A main goal of developing traits with targeted mutations induced with transgenes is to isolate the mutations by separating the desired mutation from the transgene. This can be accomplished through genetic crosses and is most effective through outcrosses (higher frequency of recovered mutant plants that are transgene negative), which involves crossing T0 pollen to the female component of a non-transgenic plant. This can also be accomplished at a lower frequency using selfing, which involves self-pollinating (using T0 pollen to pollinate the same T0 plant). Sibbing is another option and involves crosses between two genetically identical plants, which would be expected to have the same outcome as a self-cross.

T0 plants carrying targeted mutations can be selfed to generate homozygous plants and would result in different numbers and types of progeny depending on the T0 zygosity. Homozygous T0 plants would generate 100% homozygous progeny, hemizygous T0 plants would segregate 1:2:1 (homozygous: hemizygous: wild type) for the mutant allele, and heterozygous T0 plants would segregate 1:2:1 (homozygous targeted allele 1:heterozygous:homozygous targeted allele 2).

T0 plants carrying targeted mutations can also be outcrossed into other lines and would result in different numbers and types of progeny depending on the T0 zygosity. Homozygous T0 plants would generate 100% hemizygous progeny, hemizygous T0 plants would generate 50% hemizygous progeny and 50% wild type progeny, and heterozygous T0 plants would generate hemizygous progeny, 50% with targeted allele 1 and 50% with targeted allele 2.

Because all T0 plants would be carrying transgenes, the transgene insertion location is most commonly different, and the number of transgene insertions could differ, the segregation patterns for the transgenes have the potential to vary considerably between each T0 transformation event/plant. To identify transgene-negative plants, PCR would be applied to the progeny from any cross (self, sib, or outcross) with T0 plants. Transgene-negative plants would be identified by the absence of a transgene-specific PCR product. The transgene-negative plants would then be screened for the targeted mutation using the molecular diagnostics approach defined during the initial characterization of the T0 plants.

Targeted mutations isolated from the transgene can then be maintained and bred for testing and introgressions with the continued use of the trait-specific molecular diagnostics protocol.

An Example Tracking and Breeding Procedure for a Targeted Mutation:

The molecular tracking and breeding procedure for a targeted mutation is described herein. Tracking of the GWD gene from maize (M20, ZmGWD_M20 from event 4716_164) is described herein. Generation and initial sequence characterization of this and other meganuclease-induced targeted mutations in maize and sorghum has been described in Examples herein. T0 4716_164 plants were hemizygous for the M20 mutation initially and carried an unknown number of T-DNA insertions. The M20 mutation is a recessive single base pair (bp) deletion in exon 24 of ZmGWD, which results in a mutation at an MluCI restriction enzyme site in the wild type sequence. The small size of this deletion required use of the MluCI RFLP with gel electrophoresis because it could not be differentiated from wild type with gel electrophoresis alone.

Figure 11:
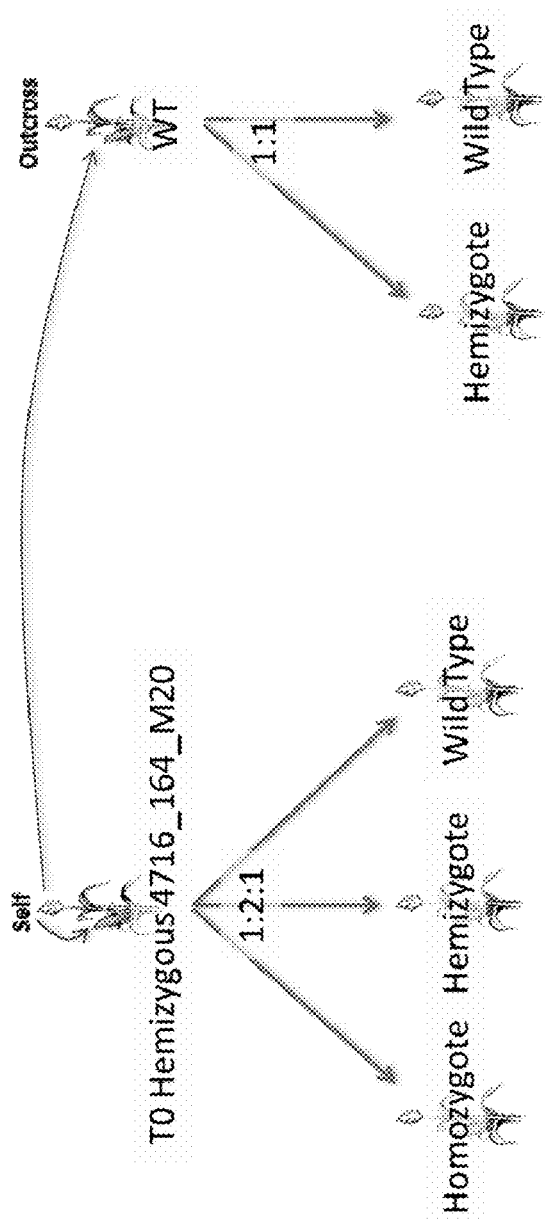
FIG. 11 illustrates a schematic drawing of selfing and outcrossing of a targeted mutation M20 derived from the maize event 4716_164.
Figure 12:
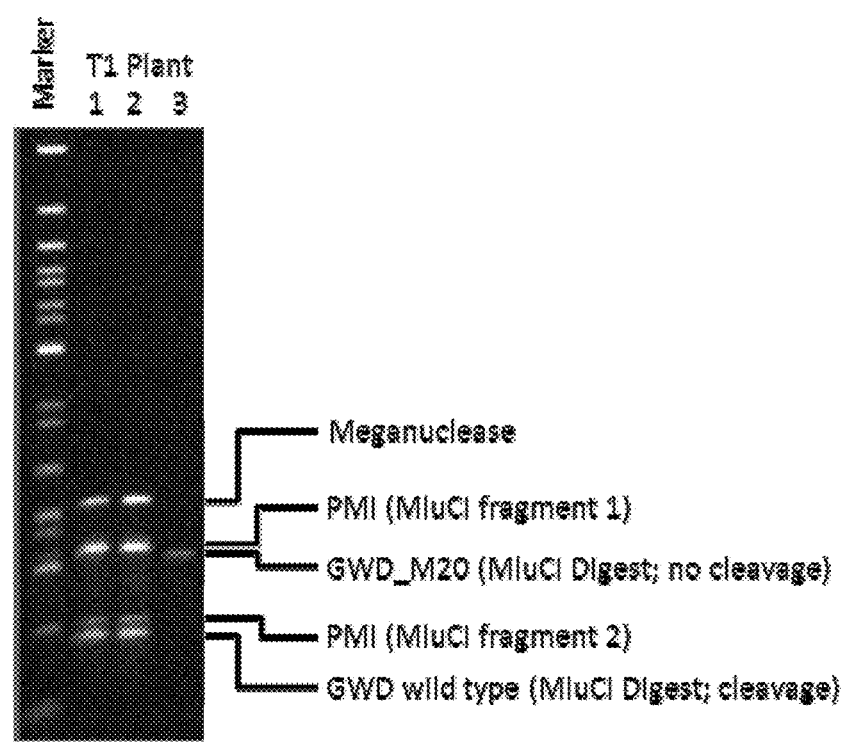
FIG. 12 illustrates genotyping of T1 progeny from the selfed T0 4716_164 M20 plant.

FIG. 11 illustrates a schematic drawing of selfing and outcrossing of a targeted mutation M20 derived from the maize event 4716_164. Referring to FIG. 11, T0 4716_164 plants were selfed and outcrossed to generate progeny for efficacy testing and introgressions, respectively. To identify homozygous M20 progeny from the T0 selfed parent, PCR with the meganuclease targeting gene and the target region of the GWD gene was performed. FIG. 12 illustrates genotyping of T1 progeny from the selfed T0 4716_164 M20 plant. Referring to FIG. 12, PCR products from meganuclease GOI and ZmGWD target region were digested with MluCI, separated on 5% polyacrylamide and stained with ethidium bromide. This revealed plants that did not carry the T-DNA (Meganuclease) but were homozygous for M20. These plants were maintained for testing.

Figure 13:
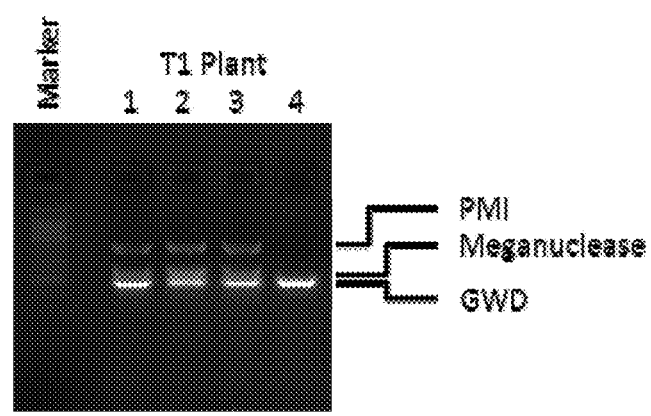
FIG. 13 illustrates genotyping of T1 progeny from the outcrossed T0 4716_164 M20 plant.
Figure 14:
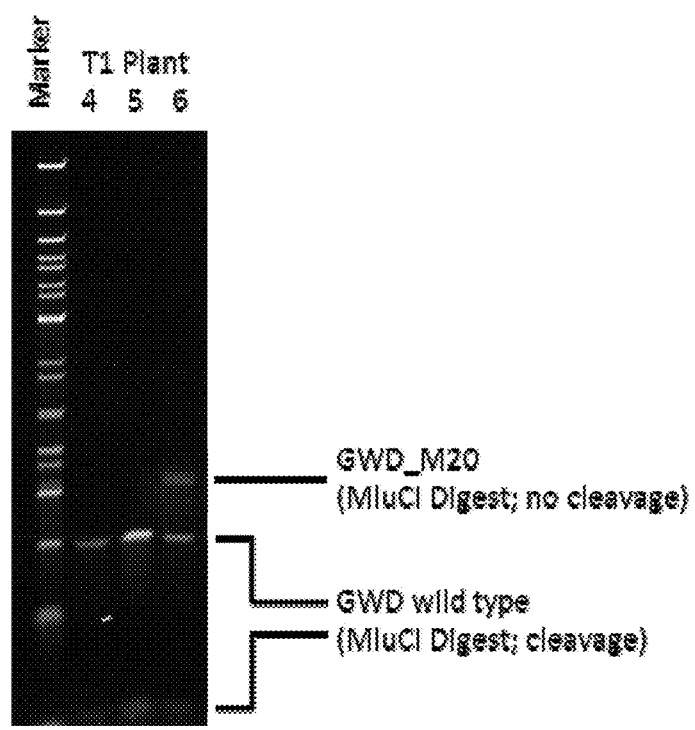
FIG. 14 illustrates genotyping of T1 progeny from the outcrossed 4716_164 M20 plant.

To identify hemizygous M20 progeny from the T0 outcrossed parent, PCR of the selectable marker gene, PMI, the meganuclease gene, and the target region was performed, followed by 3% agarose gel electrophoresis and ethidium bromide staining. This also allowed identification of T-DNA negative plants. FIG. 13 illustrates genotyping of T1 progeny from the outcrossed T0 4716_164 M20 plant. MluCI restriction digests were then performed on the same PCR products from T-DNA negative plants and separated them on a 5% polyacrylamide gel stained with ethidium bromide. FIG. 14 illustrates genotyping of T1 progeny from the outcrossed 4716_164 M20 plant. These plants were maintained for further introgressions and future testing.

REFERENCES

An, G et al., 2005. Reverse genetic approaches for functional genomics of rice. *Plant molecular biology*, 59(1), pp. 111-23.

Arnould S, Perez C, Cabaniols J P, Smith J, Gouble A, Grizot S, Epinat J C, Duclert A, Duchateau P, Paques F. (2007) Engineered I-CreI derivatives cleaving sequences from the human XPC gene can induce highly efficient gene correction in mammalian cells. J. Mol. Biol. 371: 49-65.

Arnould S, Delenda C, Grizot S, Desseaux C, Paques F, Silva G H, Smith J. (2011) The I-CreI meganuclease and its engineered derivatives: Applications from cell modification to gene therapy. Protein Eng. Des. Sel. 24: 27-31.

Belhaj K, Chaparro-Garcia A, Kamoun S, Nekrasov V. (2013) Plant genome editing made easy: targeted mutagenesis in model and crop plants using the CRISPR/Cas system. Plant Methods 9: 39-48.

Boch J. & Bonas U. (2010) *Xanthomonas* AvrBs3 family-type III effectors: discovery and function. Annu. Rev. Phytopathol. 48: 419-436.

Cermak T, Doyle E L, Christian M, Wang L, Zhang Y, Schmidt C, Baller J A, Somia N V, Bogdanove A J, Voytas D F. (2011) Efficient design and assembly of custom TALEN and other TAL effector-based constructs for DNA targeting. Nucleic Acids Res. 39: e82

Chi-Ham C L et al., 2010. The intellectual property landscape for gene suppression technologies in plants. *Nature Biotechnology*, 28 (1):32-36.

Christian, M et al., 2010. Targeting DNA double-strand breaks with TAL effector nucleases. *Genetics*, 186(2), pp. 757-61.

Cong L, Ran F A, Cox D, Lin S, Barretto R, Habib N, Hsu P D, Wu X, Jiang W, Marraffini L A, Zhang F. (2013) Multiplex genome engineering using CRISPR/Cas systems. Science 339: 819-823.

Djukanovic V, Smith J, Lowe K, Yang M, Gao H, Jones S, Nicholson M G, West A, Lape J, Bidney D, Falco S C, Jantz D, Lyznik L A. (2013) Male-sterile maize plants produced by targeted mutagenesis of the cytochrome P450-like gene (MS26) using a re-designed I-CreI homing endonuclease. The Plant Journal 76: 888-899.

Elkonin L A, Pakhaomova N V. (2000) Influence of nitrogen and phosphorus on induction embryogenic callus of *sorghum*. Plant Cell Tissue and Organ Culture 61: 115-123.

Frizzi A & Huang S, 2010. Tapping RNA silencing pathways for plant biotechnology. *Plant biotechnology journal*, 8(6), pp. 655-77.

Gao Z, Xie X, Ling Y, Muthukrishnan S, Liang G H. (2005) *Agrobacterium tumefaciens*-mediated *sorghum* transformation using a mannose selection. *Plant biotechnology journal*, 3, pp. 591-599.

Garcia-Bustos J, Heitman J, Hall M N (1991) Nuclear protein localization. Biochim Biophys Acta 1071: 83-101.

Gasiunas G, Barrangou R, Horvath P, Siksnys V. (2012) Cas9-crRNA ribonucleoprotein complex mediates specific DNA cleavage for adaptive immunity in bacteria. *Proc Natl Acad Sci USA*. 109 (39): 2579-2586.

Goujon M et al., 2010 A new bioinformatics analysis tools framework at EMBL-EBI (2010) Nucleic acids research July, 38 Suppl: W695-9

Heath P J, Stephens K M, Monnat R J Jr., Stoddard B L. (1997) The structure of I-CreI, a group I intron-encoded homing endonuclease. Nat. Struct. Biol. 4: 468-76.

Jinek M, Chylinski K, Fonfara I, Hauer M, Doudna J A, Charpentier E. (2012) A programmable dual-RNA-guided DNA endonuclease in adaptive bacterial immunity. Science 337: 816-821.

Joung J K & Sander J D. (2013) TALENs: a widely applicable technology for targeted genome editing. Nature Reviews (Mol Cell Biol) 14: 49-55.

Kalderon D, Richardson W D, Markham A F, Smith A E (1984) Sequence requirements for nuclear location of simian virus 40 large T antigen. Nature 311: 33-38.

Larkin M A et al., 2007 ClustalW and ClustalX version 2 Bioinformatics, 23(21): 2947-2948.

Larson M H, Gilbert L A, Wang X, Lim W A, Weissman J S, Qi L S. (2013) CRISPR interference (CRISPRi) for sequence-specific control of gene expression. Nat. Protoc. 8(11): 2180-2196.

Leader D J, Connelly S, Filipowicz W, Brown J W S. (1994) Characterisation and expression of a maize U3 snRNA gene. Biochimica et Biophysica Acta 1219: 145-147.

Liang Z, Zhang K, Chen K, Gao C. (2014) Targeted mutagenesis in *Zea mays* using TALENs and the CRISPR/Cas System. Journal of Genetics and Genomics 41: 63-68.

Li T, Huang S, Jiang W Z, Wright D, Spalding M H, Weeks D P, Yang B. (2011) TAL nucleases (TALNs): hybrid proteins composed of TAL effectors and FokI DNA-cleavage domain. Nucleic Acids Res. 39: 359-372.

Maniatis T, Fritsch E F and J. Sambrook J, 1982. Molecular Cloning Cold Spring Harbor Laboratory.

Puchta H, Dujon B and Hohn B, 1993. Homologous recombination in plant cells is enhanced by in vivo induction of double strand breaks into DNA by a site-specific endonuclease. *Nucleic acids research*, 21(22), pp. 5034-40.

Raikhel N V (1992) Nuclear targeting in plants. Plant Physiol 100: 1627-1632.

Rosen L E et al., (2006) Homing endonuclease I-CreI derivatives with novel DNA target specificities. Nucleic Acids Res. 34: 4791-4800.

Shieh M W et al., (1993) Nuclear targeting of the maize R protein requires two nuclear localization sequences. Plant Physiology 101: 353-361.

Shukla V K et al. (2009) Precise genome modification in the crop species *Zea mays* using zinc-finger nucleases. Nature 459: 437-441.

Sikora P et al., 2011. Mutagenesis as a tool in plant genetics, functional genomics, and breeding. *International journal of plant genomics*, 2011, p. 314829.

Smith A M and Zeeman S C, 2006. Quantification of starch in plant tissues. Nat. Protocols 1:1342-1345.

Smith T F, Waterman M S, 1981. Identification of Common Molecular Subsequences. J Mol Biol 147: 195-197.

Symington L S, Gautier J. (2011) Double-Strand Break End Resection and Repair Pathway Choice. Annual Review of Genetics. 45: 247-271.

Till B J et al., 2007 Discovery of chemically induced mutations in rice by TILLING. BMC Plant Biol. 7:19.

Upadhyay S K et al., (2014) RNA-guided genome editing for target gene mutations in wheat. Genes, Genomes, Genetics 3: 2233-2238.

Vainstein A et al., 2011. Permanent genome modifications in plant cells by transient viral vectors. *Trends in biotechnology*, 29(8), pp. 363-9.

Varagona M J et al., (1992) Nuclear localization signal(s) required for nuclear targeting of the maize regulatory protein Opaque-2. The Plant Cell 4: 1213-1227.

Wagner P et al., 1990) Active transport of proteins into the nucleus. FEBS 275: 1-5.

Wehrkamp-Richter S et al., 2009. Characterisation of a new reporter system allowing high throughput in planta screening for recombination events before and after controlled DNA double strand break induction. *Plant physiology and biochemistry☐: PPB/Sociétéfrançaise de physiologie végétale*, 47(4), pp. 248-55.

Weise, S. E. et al., (2012) Engineering starch accumulation by manipulation of phosphate metabolism of starch. *P. Biotech. J.* 10, 545-554.

Wright D et al., 2005. High-frequency homologous recombination in plants mediated by zinc-finger nucleases. *The Plant journal☐: for cell and molecular biology*, 44(4), pp. 693-705. Available at: http://www.ncbi.nlm.nih.gov/pubmed/16262717

Larkin M A et al., 2007 ClustalW and ClustalX version 2 Bioinformatics, 23(21): 2947-2948.

Goujon M et al., 2010 *A new bioinformatics analysis tools framework at EMBL-EBI* (2010) Nucleic acids research July, 38 Suppl: W695-9

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that the invention is not limited to the particular embodiments disclosed, but is intended to cover all modifications which are within the spirit and scope of the invention as defined by the appended claims; the above description; and/or shown in the attached drawings.

What is claimed is:

1. A genetically engineered plant comprising an engineered nucleic acid encoding an altered Glucan Water Dikinase, wherein the engineered nucleic acid comprises a mutation in a target nucleic acid sequence included in at least one allele of a gene encoding wild type Glucan Water Dikinase, the altered Glucan Water Dikinase comprises an amino acid sequence selected from the group consisting of SEQ ID NOS: 45-73, 121-124, 126-127, and 147-162, and the plant has an elevated level of starch in comparison to a plant of the same genetic background comprising a wild type Glucan Water Dikinase.

2. The genetically engineered plant of claim 1, wherein the altered Glucan Water Dikinase has an activity that is reduced compared to wild type Glucan Water Dikinase activity.

3. The genetically engineered plant of claim 1, wherein the altered Glucan Water Dikinase is inactive.

4. A method of preparing animal feed comprising processing a genetically engineered plant of claim 1, wherein processing includes at least one of operation selected from the group consisting of harvesting, bailing, grinding, milling, chopping, size reducing, crushing, extracting a component from the feedstock, purifying a component or portion of the feedstock, and extracting or purifying starch, wherein the animal feed comprises the engineered nucleic acid encoding the altered Glucan Water Dikinase.

5. A genetically engineered plant comprising an engineered nucleic acid encoding an altered Glucan Water Dikinase, wherein the engineered nucleic acid comprises a polynucleotide sequence selected from the group consisting of SEQ ID NOS: 12-40, 106-107, 114-120, 131-146, and 188, and the plant has an elevated level of starch in comparison to a plant of the same genetic background comprising a wild type Glucan Water Dikinase.

6. A genetically engineered plant comprising an engineered nucleic acid encoding an altered Glucan Water Dikinase, wherein the engineered nucleic acid comprises a mutation in a target nucleic acid sequence included in at least one allele of a gene encoding wild type Glucan Water Dikinase, the altered Glucan Water Dikinase comprises an amino acid sequence of SEQ ID NO: 194 or 195 and the plant has an elevated level of starch in comparison to a plant of the same genetic background comprising a wild type Glucan Water Dikinase.

* * * * *

SEQUENCE LISTING

<160> NUMBER OF SEQ ID NOS: 196

<210> SEQ ID NO 1

<211> LENGTH: 4416
<212> TYPE: DNA
<213> ORGANISM: Zea mays
<220> FEATURE:
<221> NAME/KEY: misc_feature
<222> LOCATION: (1)..(4416)
<223> OTHER INFORMATION: ZmGWD coding sequence

<400> SEQUENCE: 1

| | |
|---|---|
| atgtccggat tcagtgccgc ggccaacgca gcggcggctg agcggtgcgc gctcgcgttc | 60 |
| cgcgcacggc ccgcggcctc ctcgccagcg aagcggcagc agcagccgca gccagcgtcc | 120 |
| ctccgacgca gcggggggcca cgccgcccc acgacgctct ccgcctctag ccgcggcccc | 180 |
| gtcgtgccgc gcgccgtcgc cacgtccgcg gaccgcgcgt cccccgacct tatcggaaag | 240 |
| ttcacgctgg attccaactc cgagctccag gtcgcagtga acccagcgcc gcagggtttg | 300 |
| gtgtcagaga ttagcctgga ggtgaccaac acaagcggtt ccctgatttt gcattgggga | 360 |
| gcccttcgcc cggacaagag agattggatc ctcccgtcca gaaaacctga tggaacgaca | 420 |
| gtgtacaaga acagggctct caggacacct tttgtaaagt caggtgataa ctccactcta | 480 |
| aggattgaga tagatgatcc tggggtgcac gccattgagt tcctcatctt tgacgagaca | 540 |
| cagaacaaat ggtttaaaaa caatggccag aattttcagg ttcagttcca gtcgagccgc | 600 |
| catcagggta ctggtgcatc tggtgcctcc tcttctgcta cttctacctt ggtgccagag | 660 |
| gatcttgtgc agatccaagc ttaccttcgg tgggaaagaa gggaaagca gtcatacaca | 720 |
| ccagagcaag aaaaggagga gtatgaagct gcacgagctg agttaataga ggaagtaaac | 780 |
| agaggtgttt ctttagagaa gcttcgagct aaattgacaa agcacctga gcacctgag | 840 |
| tcggatgaaa gtaaatcttc tgcatctcga atgcccatcg gtaaacttcc agaggatctt | 900 |
| gtacaggtgc aggcttatat aaggtgggag caagcgggca agccaaacta tcctcctgag | 960 |
| aagcaactgg tagaatttga ggaagcaagg aaggaactgc aggctgaggt ggacaaggga | 1020 |
| atctctattg atcagttgag gcagaaaatt ttgaaaggaa acattgagag taaagtttcc | 1080 |
| aagcagctga agaacaagaa gtacttctct gtagaaagga ttcagcgcaa aaagagagat | 1140 |
| atcacacaac ttctcagtaa acataagcat acacttgtgg aagataaagt agaggttgta | 1200 |
| ccaaaacaac caactgttct tgatctcttc accaagtctt tacatgagaa ggatggctgt | 1260 |
| gaagttctaa gcagaaagct cttcaagttc ggcgataaag agatactggc aatttctacc | 1320 |
| aaggttcaaa ataaaacaga agttcacttg caacaaacc ataccgaccc acttattctt | 1380 |
| cactggtctt tggcaaaaaa tgctggagaa tggaaggcac cttctccaaa tatattgcca | 1440 |
| tctggttcca cattgctgga caaggcgtgt gaaactgaat ttactaaatc tgaattggat | 1500 |
| ggtttgcatt accaggttgt tgagatagag cttgatgatg gaggatacaa aggaatgcca | 1560 |
| tttgttcttc ggtctggtga acatggata aaaaataatg gttctgattt tttcctagat | 1620 |
| ttcagcaccc atgatgtcag aaatattaag gcaattttaa agggcaatgg tgatgctggt | 1680 |
| aaaggtactg ctaaggcatt gctggagaga atagcagatc tggaggaaga tgcccagcga | 1740 |
| tctcttatgc acagattcaa tattgcagca gatctagctg accaagccag agatgctgga | 1800 |
| cttttgggta ttgttgggct ttttgtttgg attagattca tggctaccag gcaactaaca | 1860 |
| tggaataaga actataatgt gaagccacgt gagataagca agcacagga taggtttaca | 1920 |
| gatgatcttg agaatatgta caagcttat ccacagtaca gagagatatt aagaatgata | 1980 |
| atggctgctg ttggtcgcgg aggtgaaggt gatgttggtc aacgcattcg tgatgagata | 2040 |
| ttagtaatac agagaaataa tgactgcaaa ggtggaatga tggaagaatg gcaccagaaa | 2100 |

```
ttgcacaaca atacaagccc agatgatgta gtgatatgcc aggccttaat tgattatatc   2160
aagagtgact tgatataag cgtttactgg gacaccttga acaaaaatgg cataaccaaa    2220
gagcgtctct tgagctatga tcgtgctatt cattcagaac caaatttcag aagtgaacag   2280
aaggcgggtt tactccgtga cctgggaaat tacatgagaa gcctaaaggc tgtgcattct   2340
ggtgctgatc ttgaatctgc tatagcaagt tgtatgggat acaaatcaga gggtgaaggt   2400
ttcatggttg gtgttcagat caatccagtg aagggtttac catctggatt tccggagttg   2460
cttgaatttg tgcttgaaca tgttgaggat aaatcagcgg aaccacttct tgagggcta   2520 ttggaagctc gagttgaact gcgcccttg cttcttgatt cgcgtgaacg catgaaagat   2580
cttatatttt tggacattgc tcttgattct accttcagga cagcaattga aaggtcatat    2640
gaggagctga atgatgcagc cccagagaaa ataatgtact tcatcagtct tgtccttgaa   2700
aatcttgcgc tttcaattga cgacaatgaa gacatcctgt attgtttaaa gggatggaac   2760
caagccttgg aaatggctaa gcaaaaagac gaccaatggg cgctctatgc taaagcattt   2820
cttgacagaa acagacttgc ccttgcgagc aagggagaac aataccataa tatgatgcag   2880
ccctctgctg agtatcttgg ctcgttactc agcatagacc aatgggcagt caatatcttc   2940
acagaagaaa ttatacgcgg tggatcagct gctactctgt ctgctcttct gaaccgattt    3000
gatcctgttt taaggaatgt tgctcacctc ggaagttggc aggttataag cccggttgaa   3060
gtatcaggtt atgtggttgt ggttgatgag ttacttgctg tccagaacaa atcttatgat    3120
aaaccaacca tccttgtggc aaagagtgtc aagggagagg aagaaatacc agatggagta   3180
gttggtgtaa ttacacctga tatgccagat gttctgtctc atgtgtcagt ccgagcaagg   3240
aatagcaagg tactgtttgc gacctgtttt gaccacacca ctctatctga acttgaagga   3300
tatgatcaga aactgttttc cttcaagcct acttctgcag atataaccta tagggagatc   3360
acagagagtg aacttcagca atcaagttct ccaaatgcag aagttggcca tgcagtacca   3420
tctatttcat tggccaagaa gaaatttctt ggaaaatatg caatatcagc cgaagaattc   3480
tctgaggaaa tggttggggc caagtctcgg aatatagcat acctcaaagg aaaagtacct   3540
tcatgggtcg gtgtcccaac gtcagttgcg ataccatttg gcacttttga aaggttttg    3600 tcagatgggc ttaataagga agtagcacag agcatagaga agcttaagat cagacttgcc   3660
caagaagatt ttagtgctct aggtgaaata agaaaagtcg tccttaatct tactgctcct   3720
atgcaattgg ttaatgagct gaaggagagg atgctaggct ctggaatgcc ctggcctggt   3780
gatgaaggag acaagcgttg ggagcaagca tggatggcta ttaaaaaggt ttgggcatca   3840
aaatggaacg aaagagcata ttttagcaca cgcaaggtga aacttgatca tgagtacctt   3900
tcgatggctg ttctcgtgca agaagttgtg aatgcagatt atgcttttgt cattcatacc   3960
acaaacccat cgtctggaga ttcttctgag atatatgctg aagtggtgaa agggcttggc   4020
gagaccctcg tgggagccta tcctggtcgt gctatgagct ttgtttgcaa aaaagatgac   4080
cttgactctc ccaagttact tggttaccca agcaagccaa ttggtctctt cataaggcaa   4140
tcaatcatct tccgttccga ctccaacggt gaggacctgg aaggttatgc tggagcagga   4200
ttatatgata gtgtaccgat ggatgaggag gatgaggtta tacttgatta tacaactgac   4260
cctcttatag tagaccgtgg attccgaagc tcaatcctct caagcatagc acgggctggc   4320
catgccatcg aggagctata tggttctcct caggacgtcg agggagtagt gaaggatgga   4380
aaaatctatg tagtccagac aagaccacag atgtag                             4416
```

<210> SEQ ID NO 2
<211> LENGTH: 4410
<212> TYPE: DNA
<213> ORGANISM: Sorghum bicolor
<220> FEATURE:
<221> NAME/KEY: misc_feature
<222> LOCATION: (1)..(4410)
<223> OTHER INFORMATION: SbGWD coding sequence

<400> SEQUENCE: 2

```
atgaccggat tcagtgccgc ggcctccgca gcagcggcgg cggagcggtg cgcgctcgcg        60
atccgcgcac ggcccgcggc ctcctcgcca gcgaagcggc agcagcagtc ggcgtccctc       120
agacgcagcg ggggccagcg ccgccccacc acgctcgctg cctcccgccg cagcccagtc       180
gtcgtgcccc cgcgccatcg cacgtccgcg accgcgcgt  cccacgacct tgtcggaaag       240
ttcacgctgg attccaactc cgagctcctg gttgcagtga accagcgcc  gcagggtttg       300
gtgtcggtga tcggcctgga ggtgaccaac acaagcggtt ccctgattct gcattgggga       360
gtccttcgcc cggacaagag agattggatc ctcccatcca gacaacctga tggaacgacg       420
gtgtacaaga cagggctct  taggacgcct tttgtaaagt ctggtgataa ctctactctt       480
agaattgaga tagatgatcc tgcggtgcaa gctattgagt cctcatcctt ggcgagaca        540
cagaacaaat ggtttaaaaa caatggccag aattttcaga ttcagctcca gtcgagccgc       600
catcaggta  atggtgcatc tggtgcctcc tcttctgcta cttctacctt ggtgccagag       660
gatcttgtgc agatccaagc ttaccttcgg tgggaaagaa agggaaagca gtcatacaca       720
ccagagcaag aaaaggagga gtatgaagct gcacgagctg agttaataga ggaattaaat       780
agaggtgttt ctttagagaa gcttcgagct aaattgacaa aaacacctga agcacctgag       840
tcagatgaac gtaaatctcc tgcatctcga atgcccgttg ataaacttcc agaggacctt       900
gtacaggtgc aggcttatat aaggtgggag aaagcgggca agccaaatta tcctcctgag       960
aagcaactgg tagaacttga ggaagcaagg aaggaactgc aggctgaggt ggacaaggga      1020
atctctattg atcaattgag gcagaaaatt ttgaaggaa  acattgagag taaagtttcc      1080
aagcagctga gaacaagaa  gtacttctct gtagaaagga ttcagcgcaa aaagagagat      1140
atcatgcaac ttctcagtaa acataagcat acagttatgg aagagaaagt agaggttgca      1200
ccaaaacaac caactgttct tgatctcttc accaagtctt acatgagaa  ggatggctgt      1260
gaagttctaa gcagaaagct cttcaagttc ggtgataaag agatactggc aatttccacc      1320
aaggttcaaa ataaaacaga agttcacttg caacaaaacc atacggagcc acttattctt      1380
cactggtctt tggcaaaaaa ggctggagaa tggaaggcac ctccttcaaa tatattgcca      1440
tctggttcca aattgctaga catggcgtgt gaaactgaat ttactagatc tgaattggat      1500
ggtttgtgtt accaggttgt tgagatagag cttgatgatg gaggatacaa aggaatgcca      1560
tttgttctta ggtctggtga acatggata  aaaaataatg gttccgattt tttcctagat      1620
ttcagcaccc gtgataccag aaatattaag ttaaggaca  atggcgatgc tggtaaaggc      1680
actgctaagg cgttgctgga gagaatagca gatctggagg aagatgccca gcgatctctt      1740
atgcataggt tcaatattgc agcagatcta gctgacgaag ccagagatgc tggactgttg      1800
ggtattgttg gacttttttgt ttggattagg ttcatggcta ccaggcaact aacatggaat      1860
aagaactata atgtgaagcc acgtgagata agcaaagcac aagataggtt tacagatgat      1920
cttgagaata tgtacagaac ttatcctcag tacagagaga tactaagaat gataatggct      1980
gctgttggtc gtggaggtga aggtgacgtt ggtcaacgca ttcgtgatga gatattagta      2040
```

```
atacagagaa ataatgactg caaaggtgga atgatggaag aatggcacca gaaattgcac    2100
aacaatacaa gcccagatga tgtagtgata tgccaggcat taattgatta tataaaaaat    2160
gattttgata taagcgttta ctgggacacc ttgaacaaaa atggcataac caaagagcgt    2220
ctcttgagct atgatcgtgc tattcattca gaaccaaatt tcagaagtga acagaaggag    2280
ggtttactcc gtgacctggg aaattacatg agaagcctaa aggctgtgca ttctggtgct    2340
gatcttgaat ctgctatagc aacttgtatg ggatacaaat cagagggtga aggtttcatg    2400
gttggcgttc agatcaatcc agtgaagggt ttgccatctg gatttcctga gttgcttgaa    2460
tttgtgcttg accatgttga ggataaatca gcagaaccac ttcttgaggg gctattggaa    2520
gctcgagttg atctgcgccc tttgcttctt gattcgcctg aacgcatgaa agatcttata    2580
tttttggaca ttgctcttga ttctaccttc aggacagcaa ttgaaaggtc atatgaggag    2640
ctcaatgatg cagccccaga gaaaataatg tacttcatca gtcttgtcct gaaaatctt    2700 gcgttttcaa ttgacgacaa tgaagacatc ctgtattgct taaagggatg gaaccaagcc    2760
ttggaaatgg ctaagcaaaa agacgaccaa tgggctcttt acgctaaagc atttcttgac    2820
agaatcagac ttgcccttgc gagcaaggga gaacagtacc ataatatgat gcagccctca    2880
gctgaatatc ttggctcgtt actcagcata gacaaatggg cagtcaatat cttcacagaa    2940
gaaattatac gcggtggatc agctgctact ctgtccgctc ttctgaaccg atttgatcct    3000
gttctaagga acgttgctaa ccttggaagt tggcaggtta taagcccagt tgaagtatca    3060
ggttatgtgg ttgtggttga tgagttactt gctgtccaga acaaatctta tgataaacca    3120
accatccttg tggcaaagag tgtcaaggga gaggaagaaa taccagatgg agtagttggt    3180
gtaattacac ctgatatgcc agatgttctg tcccatgtgt cagtccgagc aaggaatagc    3240
aaggtactgt ttgcaacctg ttttgaccat accactctgt ctgaacttga aggatatgat    3300
cagaaactgc tttccttcaa gcctacttct gcagatataa cctataggga gatcacagag    3360
agtgagcttc agcaatcaag ttctccaaat gcagaagttg gccatgcagt accatctatt    3420
tcattggcca agaagaaatt tcttggaaaa tatgcaatat cagctgaaga attcaccgag    3480
gaaatggttg gggccaagtc tcggaatata gcatacctca aaggaaaagt accttcatgg    3540
gttggtgttc aacgtcagt tgcgatacca tttggcactt ttgagaaggt tttgtcagat    3600
ggtcttaata aggaagtagc acaaaccata gagaagctta agatcaggct tgctcaagaa    3660
gattttagtg ctctaggtga aataagaaaa gccgttctta atcttactgc tcctatgcaa    3720
ttggttaatg agctgaagga gaggatgcta ggctctggaa tgccctggcc tggtgatgaa    3780
ggcaacaggc gctgggagca agcatggatg gctattaaaa aggtttgggc atcaaaatgg    3840
aatgaaagag catattttag cacacgcaag gtgaaactca atcatgagta cctttcgatg    3900
gctgttcttg tgcaagaagt tgtgaatgca gattatgctt ttgtcattca tactacaaac    3960
ccatcgtctg gagattcttc tgagatatat gctgaagtcg tgaaagggct cggagagact    4020
ctcgtgggag cctatcctgg tcgtgctatg agctttgttt gcaaaaaaga tgaccttgac    4080
tctcccaagt tacttggtta cccgagcaag ccaattggtc tcttcataag gcgatcgatc    4140
atctttcgtt ctgactccaa cggcgaggat ctggaaggtt atgccggagc aggattatat    4200
gatagtgtac cgatggatga ggaggatgaa gtcgtacttg attacacaac tgaccctctt    4260
atagtagatc gtggattccg aaattcaata ctctcaagca tcgcacgggc tggccatgcc    4320
attgaagagc tatatggttc tcctcaggac gtcgagggtg tagtgaagga tggaaaaatc    4380
```
tatgtagtcc agacaagacc acagatgtag        4410

<210> SEQ ID NO 3
<211> LENGTH: 392
<212> TYPE: DNA
<213> ORGANISM: Zea mays
<220> FEATURE:
<221> NAME/KEY: misc_feature
<222> LOCATION: (1)..(392)
<223> OTHER INFORMATION: ZmGWD Exon 24 _introns

<400> SEQUENCE: 3
aagtgatact agtgaccctc tccacaattt tatgcgaacc acagaaatta ataatatatt      60
ctattactct gcacctgaca tctggctcct gctatcagtt ggcaggttat aagcccggtt     120
gaagtatcag gttatgtggt tgtggttgat gagttacttg ctgtccagaa caaatcttat     180
gataaaccaa ccatccttgt ggcaaagagt gtcaagggag aggaagaaat accagatgga     240
gtagttggtg taattacacc tgatatgcca gatgttctgt ctcatgtgtc agtccgagca     300
aggaatagca aggtttatct tcacagctat gttgcaagat tcttgaatt tttttctcttg     360 tattgatgtt gacatactag cttttttccta at      392

<210> SEQ ID NO 4
<211> LENGTH: 397
<212> TYPE: DNA
<213> ORGANISM: Sorghum bicolor
<220> FEATURE:
<221> NAME/KEY: misc_feature
<222> LOCATION: (1)..(397)
<223> OTHER INFORMATION: SbGWD Exon 24-introns

<400> SEQUENCE: 4
aagtggtact agtgacctct ccacagtttt atgtgaacca cagaaattaa atatgataat      60
atattctatt actctgcacc tgacatctgg ctcctgataa cagttggcag gttataagcc     120
cagttgaagt atcaggttat gtggttgtgg ttgatgagtt acttgctgtc cagaacaaat     180
cttatgataa accaaccatc cttgtggcaa agagtgtcaa gggagaggaa gaaataccag     240
atggagtagt tggtgtaatt acacctgata tgccagatgt tctgtcccat gtgtcagtcc     300
gagcaaggaa tagcaaggtt tattttcaca gttatgttgc aagctttctc agattttttt     360
tcttgtatcg atgttgacat accagttttt tcctaat     397

<210> SEQ ID NO 5
<211> LENGTH: 20
<212> TYPE: DNA
<213> ORGANISM: Artificial Sequence
<220> FEATURE:
<223> OTHER INFORMATION: Synthetic construct, Mega-1(4716) PCR primer
     reverse

<400> SEQUENCE: 5
tgatcttcag cacgaggttg         20

<210> SEQ ID NO 6
<211> LENGTH: 21
<212> TYPE: DNA
<213> ORGANISM: Artificial Sequence
<220> FEATURE:
<223> OTHER INFORMATION: Synthetic construct, Mega-1 (4716) PCR primer
     forward

<400> SEQUENCE: 6
ggctccatct atgcctgtat c        21

<210> SEQ ID NO 7
<211> LENGTH: 22
<212> TYPE: DNA
<213> ORGANISM: Artificial Sequence
<220> FEATURE:
<223> OTHER INFORMATION: Synthetic construct, Mega-2 (4715) PCR primer
      forward

<400> SEQUENCE: 7
gagctcagtt tcgctgtcta tc                                              22

<210> SEQ ID NO 8
<211> LENGTH: 21
<212> TYPE: DNA
<213> ORGANISM: Artificial Sequence
<220> FEATURE:
<223> OTHER INFORMATION: Synthetic construct, Mega-2 (4715) PCR primer
      reverse

<400> SEQUENCE: 8
atgatcttca gcacgaggtt g                                               21

<210> SEQ ID NO 9
<211> LENGTH: 22
<212> TYPE: DNA
<213> ORGANISM: Artificial Sequence
<220> FEATURE:
<223> OTHER INFORMATION: Synthetic construct, ZmGWDmega-2 PCR primer
      forward

<400> SEQUENCE: 9
ggttataagc ccggttgaag ta                                              22

<210> SEQ ID NO 10
<211> LENGTH: 21
<212> TYPE: DNA
<213> ORGANISM: Artificial Sequence
<220> FEATURE:
<223> OTHER INFORMATION: Synthetic construct, ZmGWDmega-2 PCR primer
      reverse

<400> SEQUENCE: 10
ctattccttg ctcggactga c                                               21

<210> SEQ ID NO 11
<211> LENGTH: 20
<212> TYPE: DNA
<213> ORGANISM: Artificial Sequence
<220> FEATURE:
<223> OTHER INFORMATION: Synthetic construct, SbGWD mega-2 PCR primer
      forward

<400> SEQUENCE: 11
ggcaggttat aagcccagtt                                                 20

<210> SEQ ID NO 12
<211> LENGTH: 189
<212> TYPE: DNA
<213> ORGANISM: Zea mays
<220> FEATURE:
<221> NAME/KEY: misc_feature
<222> LOCATION: (1)..(189)
<223> OTHER INFORMATION: M16

<400> SEQUENCE: 12
ttggcaggtt ataagcccgg ttgaagtatc aggttatgtg gttgtggttg atgagttact     60
tgctgtccag aacaaatctt atgataaacc aagggagagg aagaaatacc agatggagta    120
gttggtgtaa ttacacctga tatgccagat gttctgtctc atgtgtcagt ccgagcaagg    180
aatagcaag                                                           189

<210> SEQ ID NO 13
<211> LENGTH: 204
<212> TYPE: DNA
<213> ORGANISM: Zea mays
<220> FEATURE:
<221> NAME/KEY: misc_feature
<222> LOCATION: (1)..(204)
<223> OTHER INFORMATION: M17

<400> SEQUENCE: 13
ttggcaggtt ataagcccgg ttgaagtatc aggttatgtg gttgtggttg atgagttact     60
tgctgtccag aacaaatctt atgataaacc aaccatcctt gtggcaaggg agaggaagaa    120
ataccagatg gagtagttgg tgtaattaca cctgatatgc agatgttct gtctcatgtg    180 tcagtccgag caaggaatag caag                                          204

<210> SEQ ID NO 14
<211> LENGTH: 213
<212> TYPE: DNA
<213> ORGANISM: Zea mays
<220> FEATURE:
<221> NAME/KEY: misc_feature
<222> LOCATION: (1)..(213)
<223> OTHER INFORMATION: M18

<400> SEQUENCE: 14
ttggcaggtt ataagcccgg ttgaagtatc aggttatgtg gttgtggttg atgagttact     60
tgctgtccag aacaaatctt atgataaacc aaccatcctt gtggcaagag tgtcaaggga    120
gaggaagaaa taccagatgg agtagttggt gtaattacac ctgatatgcc agatgttctg    180
tctcatgtgt cagtccgagc aaggaatagc aag                                213

<210> SEQ ID NO 15
<211> LENGTH: 198
<212> TYPE: DNA
<213> ORGANISM: Zea mays
<220> FEATURE:
<221> NAME/KEY: misc_feature
<222> LOCATION: (1)..(198)
<223> OTHER INFORMATION: M27

<400> SEQUENCE: 15
ttggcaggtt ataagcccgg ttgaagtatc aggttatgtg gttgtggttg atgagttact     60
tgctgtccag aacaaatctt atgataaacc aaccatcctt gtggcaaggg agagatacca    120
gatggagtag ttggtgtaat tacacctgat atgccagatg ttctgtctca tgtgtcagtc    180
cgagcaagga atagcaag                                                 198

<210> SEQ ID NO 16
<211> LENGTH: 214
<212> TYPE: DNA
<213> ORGANISM: Zea mays
<220> FEATURE:
<221> NAME/KEY: misc_feature
<222> LOCATION: (1)..(214)
<223> OTHER INFORMATION: M1

<400> SEQUENCE: 16

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg aagaaataca cctgatatgc cagatgttct   180
gtctcatgtg tcagtccgag caaggaatag caag                               214
```

<210> SEQ ID NO 17
<211> LENGTH: 197
<212> TYPE: DNA
<213> ORGANISM: Zea mays
<220> FEATURE:
<221> NAME/KEY: misc_feature
<222> LOCATION: (1)..(197)
<223> OTHER INFORMATION: M11

<400> SEQUENCE: 17

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tgtcagatgt tctgtctcat gtgtcagtcc   180
gagcaaggaa tagcaag                                                  197
```

<210> SEQ ID NO 18
<211> LENGTH: 215
<212> TYPE: DNA
<213> ORGANISM: Zea mays
<220> FEATURE:
<221> NAME/KEY: misc_feature
<222> LOCATION: (1)..(215)
<223> OTHER INFORMATION: M10

<400> SEQUENCE: 18

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tgtaaattac acctgatatg ccagatgttc   180
tgtctcatgt gtcagtccga gcaaggaata gcaag                              215
```

<210> SEQ ID NO 19
<211> LENGTH: 199
<212> TYPE: DNA
<213> ORGANISM: Zea mays
<220> FEATURE:
<221> NAME/KEY: misc_feature
<222> LOCATION: (1)..(199)
<223> OTHER INFORMATION: M3

<400> SEQUENCE: 19

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagcacctga tatgccagat gttctgtctc atgtgtcagt   180
ccgagcaagg aatagcaag                                                199
```

<210> SEQ ID NO 20
<211> LENGTH: 208
<212> TYPE: DNA
<213> ORGANISM: Zea mays
<220> FEATURE:
<221> NAME/KEY: misc_feature
<222> LOCATION: (1)..(208)
<223> OTHER INFORMATION: M8

<400> SEQUENCE: 20

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tatgccagat atgccagatg ttctgtctca   180
tgtgtcagtc cgagcaagga atagcaag                                      208
```

<210> SEQ ID NO 21
<211> LENGTH: 189
<212> TYPE: DNA
<213> ORGANISM: Zea mays
<220> FEATURE:
<221> NAME/KEY: misc_feature
<222> LOCATION: (1)..(189)
<223> OTHER INFORMATION: M14

<400> SEQUENCE: 21

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ttacacctga tatgccagat gttctgtctc atgtgtcagt ccgagcaagg   180
aatagcaag                                                           189
```

<210> SEQ ID NO 22
<211> LENGTH: 178
<212> TYPE: DNA
<213> ORGANISM: Zea mays
<220> FEATURE:
<221> NAME/KEY: misc_feature
<222> LOCATION: (1)..(178)
<223> OTHER INFORMATION: M13

<400> SEQUENCE: 22

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg ttctgtctca tgtgtcagtc cgagcaagga atagcaag     178
```

<210> SEQ ID NO 23
<211> LENGTH: 176
<212> TYPE: DNA
<213> ORGANISM: Zea mays
<220> FEATURE:
<221> NAME/KEY: misc_feature
<222> LOCATION: (1)..(176)
<223> OTHER INFORMATION: M12

<400> SEQUENCE: 23

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tgtcagtccg agcaaggaat agcaag       176
```

<210> SEQ ID NO 24
<211> LENGTH: 204
<212> TYPE: DNA
<213> ORGANISM: Zea mays
<220> FEATURE:
<221> NAME/KEY: misc_feature
<222> LOCATION: (1)..(204)
<223> OTHER INFORMATION: M22

<400> SEQUENCE: 24

```
ttggcaggtt ataagcccgg ttgaagtatc aggttatgtg gttgtggttg atgagttact    60
```
tgctgtccag aacaaatctt atgataaacc aaccatcctt gtggcaaaga gtgtcaaggg    120
agaggaagaa ataccagatg gagtagttgg tgtgatatgc cagatgttct gtctcatgtg    180
tcagtccgag caaggaatag caag                                          204

<210> SEQ ID NO 25
<211> LENGTH: 221
<212> TYPE: DNA
<213> ORGANISM: Zea mays
<220> FEATURE:
<221> NAME/KEY: misc_feature
<222> LOCATION: (1)..(221)
<223> OTHER INFORMATION: M23

<400> SEQUENCE: 25
ttggcaggtt ataagcccgg ttgaagtatc aggttatgtg gttgtggttg atgagttact     60
tgctgtccag aacaaatctt atgataaacc aaccatcctt gtggcaaaga gtgtcaaggg    120
agaggaagaa ataccagatg gagtagttgg caaagataaa ccttgcacct gatatgccag    180
atgttctgtc tcatgtgtca gtccgagcaa ggaatagcaa g                       221

<210> SEQ ID NO 26
<211> LENGTH: 213
<212> TYPE: DNA
<213> ORGANISM: Zea mays
<220> FEATURE:
<221> NAME/KEY: misc_feature
<222> LOCATION: (1)..(213)
<223> OTHER INFORMATION: M24

<400> SEQUENCE: 26
ttggcaggtt ataagcccgg ttgaagtatc aggttatgtg gttgtggttg atgagttact     60
tgctgtccag aacaaatctt atgataaacc aaccatcctt gtggcaaaga gtgtcaaggg    120
agaggaagaa ataccagatg gagtagttgg tgaattacac ctgatatgcc agatgttctg    180
tctcatgtgt cagtccgagc aaggaatagc aag                                213

<210> SEQ ID NO 27
<211> LENGTH: 213
<212> TYPE: DNA
<213> ORGANISM: Zea mays
<220> FEATURE:
<221> NAME/KEY: misc_feature
<222> LOCATION: (1)..(213)
<223> OTHER INFORMATION: M20

<400> SEQUENCE: 27
ttggcaggtt ataagcccgg ttgaagtatc aggttatgtg gttgtggttg atgagttact     60
tgctgtccag aacaaatctt atgataaacc aaccatcctt gtggcaaaga gtgtcaaggg    120
agaggaagaa ataccagatg gagtagttgg tgtattacac ctgatatgcc agatgttctg    180
tctcatgtgt cagtccgagc aaggaatagc aag                                213

<210> SEQ ID NO 28
<211> LENGTH: 181
<212> TYPE: DNA
<213> ORGANISM: Zea mays
<220> FEATURE:
<221> NAME/KEY: misc_feature
<222> LOCATION: (1)..(181)
<223> OTHER INFORMATION: M21

<400> SEQUENCE: 28
ttggcaggtt ataagcccgg ttgaagtatc aggttatgtg gttgtggttg atgagttact     60
tgctgtccag aacaaatctt atgataaacc aaccatcctt gtggcaaaga gtgtcaaaat    120
cttatgataa accatgccag atgttctgtc tcatgtgtca gtccgagcaa ggaatagcaa    180
g    181

<210> SEQ ID NO 29
<211> LENGTH: 205
<212> TYPE: DNA
<213> ORGANISM: Zea mays
<220> FEATURE:
<221> NAME/KEY: misc_feature
<222> LOCATION: (1)..(205)
<223> OTHER INFORMATION: M4

<400> SEQUENCE: 29
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg    120
agaggaagaa ataccagatg gagtaattac acctgatatg ccagatgttc tgtctcatgt    180
gtcagtccga gcaaggaata gcaag    205

<210> SEQ ID NO 30
<211> LENGTH: 210
<212> TYPE: DNA
<213> ORGANISM: Zea mays
<220> FEATURE:
<221> NAME/KEY: misc_feature
<222> LOCATION: (1)..(210)
<223> OTHER INFORMATION: M19

<400> SEQUENCE: 30
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg    120
agaggaagaa ataccagatg gagtagttgg tgtacacctg atatgccaga tgttctgtct    180
catgtgtcag tccgagcaag gaatagcaag    210

<210> SEQ ID NO 31
<211> LENGTH: 425
<212> TYPE: DNA
<213> ORGANISM: Zea mays
<220> FEATURE:
<221> NAME/KEY: misc_feature
<222> LOCATION: (1)..(425)
<223> OTHER INFORMATION: M26

<400> SEQUENCE: 31
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg    120
agaggaagaa ataccagatg gagcagtgtg ctcgggtaca gcttcttatt tcaatgtctc    180
cagtgggcgt cttacctcta tgtttgtgtt ttttttttaag tgcagaaata gagaaagttc    240
ttgcaaatat ctactctatg aaaaggacag ctatttggaa atatgtgaac agaactatcc    300
ccagttgctg ggaaaaacca agaagaaagt tccttcaaat atctactcca tgacgacaag    360
tgtctattac acctgatatg ccagatgttc tgtctcatgt gtcagtccga gcaaggaata    420
gcaag    425

<210> SEQ ID NO 32
<211> LENGTH: 212
<212> TYPE: DNA

```
<213> ORGANISM: Zea mays
<220> FEATURE:
<221> NAME/KEY: misc_feature
<222> LOCATION: (1)..(212)
<223> OTHER INFORMATION: M25

<400> SEQUENCE: 32
ttggcaggtt ataagcccgg ttgaagtatc aggttatgtg gttgtggttg atgagttact      60
tgctgtccag aacaaatctt atgataaacc aaccatcctt gtggcaaaga gtgtcaaggg     120
agaggaagaa ataccagatg gagtagttgg taattacacc tgatatgcca gatgttctgt    180
ctcatgtgtc agtccgagca aggaatagca ag                                   212

<210> SEQ ID NO 33
<211> LENGTH: 173
<212> TYPE: DNA
<213> ORGANISM: Zea mays
<220> FEATURE:
<221> NAME/KEY: misc_feature
<222> LOCATION: (1)..(173)
<223> OTHER INFORMATION: M15

<400> SEQUENCE: 33
ttggcaggtt ataagcccgg ttgaagtatc aggttatgtg gttgtggttg atgagttact      60
tgctgtccag aacaaatctt atgataaacc aaccatcctt gtggcaaaga gtaattacac    120
ctgatatgcc agatgttctg tctcatgtgt cagtccgagc aaggaatagc aag           173

<210> SEQ ID NO 34
<211> LENGTH: 425
<212> TYPE: DNA
<213> ORGANISM: Zea mays
<220> FEATURE:
<221> NAME/KEY: misc_feature
<222> LOCATION: (1)..(425)
<223> OTHER INFORMATION: M5

<400> SEQUENCE: 34
ttggcaggtt ataagcccgg ttgaagtatc aggttatgtg gttgtggttg atgagttact      60
tgctgtccag aacaaatctt atgataaacc aaccatcctt gtggcaaaga gtgtcaaggg     120
agaggaagaa ataccagatg gagtagttgc agaattattg aattctttca taattgaact    180
ctatgatgat gctttacttg attgtattat attgatgctc aatcatatat tgatgattgt    240
tggaacttgc tctccgatgc aaggtgatcc aacgggggtg tgtcgcaacg taaacagggt    300
tttcgcacga gatggcaata gctctgttaa cctagcctct cacgggcact gtgcggggat    360
atttaattac acctgatatg ccagatgttc tgtctcatgt gtcagtccga gcaaggaata    420
gcaag                                                                 425

<210> SEQ ID NO 35
<211> LENGTH: 208
<212> TYPE: DNA
<213> ORGANISM: Zea mays
<220> FEATURE:
<221> NAME/KEY: misc_feature
<222> LOCATION: (1)..(208)
<223> OTHER INFORMATION: M2

<400> SEQUENCE: 35
ttggcaggtt ataagcccgg ttgaagtatc aggttatgtg gttgtggttg atgagttact      60
tgctgtccag aacaaatctt atgataaacc aaccatcctt gtggcaaaga gtgtcaaggg     120
agaggaagaa ataccagatg gagtagttgt tacacctgat atgccagatg ttctgtctca    180
```

```
tgtgtcagtc cgagcaagga atagcaag                                          208

<210> SEQ ID NO 36
<211> LENGTH: 187
<212> TYPE: DNA
<213> ORGANISM: Zea mays
<220> FEATURE:
<221> NAME/KEY: misc_feature
<222> LOCATION: (1)..(187)
<223> OTHER INFORMATION: M28

<400> SEQUENCE: 36
ttggcaggtt ataagcccgg ttgaagtatc aggttatgtg gttgtggttg atgagttact       60
tgctgtccag aacaaatctt atgataaacc aaccatcctt gtggcaaaga gtgtcaaggg      120
agaggaagaa acacctgata tgccagatgt tctgtctcat gtgtcagtcc gagcaaggaa      180
tagcaag                                                                187

<210> SEQ ID NO 37
<211> LENGTH: 213
<212> TYPE: DNA
<213> ORGANISM: Zea mays
<220> FEATURE:
<221> NAME/KEY: misc_feature
<222> LOCATION: (1)..(213)
<223> OTHER INFORMATION: M6

<400> SEQUENCE: 37
ttggcaggtt ataagcccgg ttgaagtatc aggttatgtg gttgtggttg atgagttact       60
tgctgtccag aacaaatctt atgataaacc aaccatcctt gtggcaaaga gtgtcaaggg      120
agaggaagaa ataccagatg gagtagttgg taaattacac ctgatatgcc agatgttctg     180
tctcatgtgt cagtccgagc aaggaatagc aag                                   213

<210> SEQ ID NO 38
<211> LENGTH: 199
<212> TYPE: DNA
<213> ORGANISM: Zea mays
<220> FEATURE:
<221> NAME/KEY: misc_feature
<222> LOCATION: (1)..(199)
<223> OTHER INFORMATION: M9

<400> SEQUENCE: 38
ttggcaggtt ataagcccgg ttgaagtatc aggttatgtg gttgtggttg atgagttact       60
tgctgtccag aacaaatctt atgataaacc aaccatcctt gtggcaaaga gtgtcaaggg      120
agaggaagaa ataccagatg gagtagttgg tatgccagat gttctgtctc atgtgtcagt     180
ccgagcaagg aatagcaag                                                   199

<210> SEQ ID NO 39
<211> LENGTH: 210
<212> TYPE: DNA
<213> ORGANISM: Zea mays
<220> FEATURE:
<221> NAME/KEY: misc_feature
<222> LOCATION: (1)..(210)
<223> OTHER INFORMATION: M7

<400> SEQUENCE: 39
ttggcaggtt ataagcccgg ttgaagtatc aggttatgtg gttgtggttg atgagttact       60
tgctgtccag aacaaatctt atgataaacc aaccatcctt gtggcaaaga gtgtcaaggg      120
```

```
agaggaagaa ataccagatg gagtagttgg tttacacctg atatgccaga tgttctgtct    180
catgtgtcag tccgagcaag gaatagcaag                                      210
```

<210> SEQ ID NO 40
<211> LENGTH: 212
<212> TYPE: DNA
<213> ORGANISM: Zea mays
<220> FEATURE:
<221> NAME/KEY: misc_feature
<222> LOCATION: (1)..(212)
<223> OTHER INFORMATION: M29

<400> SEQUENCE: 40

```
ttggcaggtt ataagcccgg ttgaagtatc aggttatgtg gttgtggttg atgagttact     60
tgctgtccag aacaaatctt atgataaacc aaccatcctt gtggcaaaga gtgtcaaggg    120
agaggaagaa ataccagatg gagtagttgg taattacacc tgatatgcca gatgttctgt    180
ctcatgtgtc agtccgagca aggaatagca ag                                  212
```

<210> SEQ ID NO 41
<211> LENGTH: 22
<212> TYPE: DNA
<213> ORGANISM: Artificial Sequence
<220> FEATURE:
<223> OTHER INFORMATION: Synthetic construct, Meganuclease GWD target
      sequence pAG4715

<400> SEQUENCE: 41

```
atccttgtgg caaagagtgt ca                                              22
```

<210> SEQ ID NO 42
<211> LENGTH: 22
<212> TYPE: DNA
<213> ORGANISM: Artificial Sequence
<220> FEATURE:
<223> OTHER INFORMATION: Synthetic construct, Meganuclease target
      sequence pAG4716

<400> SEQUENCE: 42

```
gtagttggtg taattacacc tg                                              22
```

<210> SEQ ID NO 43
<211> LENGTH: 1469
<212> TYPE: PRT
<213> ORGANISM: Zea mays
<220> FEATURE:
<221> NAME/KEY: MISC_FEATURE
<222> LOCATION: (1)..(1469)
<223> OTHER INFORMATION: ZmGWD

<400> SEQUENCE: 43

```
Met Ser Gly Phe Ser Ala Ala Asn Ala Ala Ala Glu Arg Cys
1               5                  10                  15

Ala Leu Ala Phe Arg Ala Arg Pro Ala Ala Ser Ser Pro Ala Lys Arg
                20                  25                  30

Gln Gln Gln Pro Gln Pro Ala Ser Leu Arg Arg Ser Gly Gly Gln Arg
            35                  40                  45

Arg Pro Thr Thr Leu Ser Ala Ser Ser Arg Gly Pro Val Val Pro Arg
        50                  55                  60

Ala Val Ala Thr Ser Ala Asp Arg Ala Ser Pro Asp Leu Ile Gly Lys
65                  70                  75                  80

Phe Thr Leu Asp Ser Asn Ser Glu Leu Gln Val Ala Val Asn Pro Ala
                85                  90                  95
```

```
Pro Gln Gly Leu Val Ser Glu Ile Ser Leu Glu Val Thr Asn Thr Ser
            100                 105                 110

Gly Ser Leu Ile Leu His Trp Gly Ala Leu Arg Pro Asp Lys Arg Asp
            115                 120                 125

Trp Ile Leu Pro Ser Arg Lys Pro Asp Gly Thr Thr Val Tyr Lys Asn
    130                 135                 140

Arg Ala Leu Arg Thr Pro Phe Val Lys Ser Gly Asp Asn Ser Thr Leu
145                 150                 155                 160

Arg Ile Glu Ile Asp Asp Pro Gly Val His Ala Ile Glu Phe Leu Ile
                165                 170                 175

Phe Asp Glu Thr Gln Asn Lys Trp Phe Lys Asn Gly Gln Asn Phe
            180                 185                 190

Gln Val Gln Phe Gln Ser Ser Arg His Gln Gly Thr Gly Ala Ser Gly
            195                 200                 205

Ala Ser Ser Ser Ala Thr Ser Thr Leu Val Pro Glu Asp Leu Val Gln
    210                 215                 220

Ile Gln Ala Tyr Leu Arg Trp Glu Arg Arg Gly Lys Gln Ser Tyr Thr
225                 230                 235                 240

Pro Glu Gln Glu Lys Glu Glu Tyr Glu Ala Ala Arg Ala Glu Leu Ile
                245                 250                 255

Glu Glu Val Asn Arg Gly Val Ser Leu Glu Lys Leu Arg Ala Lys Leu
            260                 265                 270

Thr Lys Ala Pro Glu Ala Pro Glu Ser Asp Glu Ser Lys Ser Ser Ala
            275                 280                 285

Ser Arg Met Pro Ile Gly Lys Leu Pro Glu Asp Leu Val Gln Val Gln
    290                 295                 300

Ala Tyr Ile Arg Trp Glu Gln Ala Gly Lys Pro Asn Tyr Pro Pro Glu
305                 310                 315                 320

Lys Gln Leu Val Glu Phe Glu Glu Ala Arg Lys Glu Leu Gln Ala Glu
                325                 330                 335

Val Asp Lys Gly Ile Ser Ile Asp Gln Leu Arg Gln Lys Ile Leu Lys
            340                 345                 350

Gly Asn Ile Glu Ser Lys Val Ser Lys Gln Leu Lys Asn Lys Lys Tyr
            355                 360                 365

Phe Ser Val Glu Arg Ile Gln Arg Lys Lys Arg Asp Ile Thr Gln Leu
    370                 375                 380

Leu Ser Lys His Lys His Thr Leu Val Glu Asp Lys Val Glu Val Val
385                 390                 395                 400

Pro Lys Gln Pro Thr Val Leu Asp Leu Phe Thr Lys Ser Leu His Glu
                405                 410                 415

Lys Asp Gly Cys Glu Val Leu Ser Arg Lys Leu Phe Lys Phe Gly Asp
            420                 425                 430

Lys Glu Ile Leu Ala Ile Ser Thr Lys Val Gln Asn Lys Thr Glu Val
            435                 440                 445

His Leu Ala Thr Asn His Thr Asp Pro Leu Ile Leu His Trp Ser Leu
    450                 455                 460

Ala Lys Asn Ala Gly Glu Trp Lys Ala Pro Ser Pro Asn Ile Leu Pro
465                 470                 475                 480

Ser Gly Ser Thr Leu Leu Asp Lys Ala Cys Glu Thr Glu Phe Thr Lys
                485                 490                 495

Ser Glu Leu Asp Gly Leu His Tyr Gln Val Val Glu Ile Glu Leu Asp
            500                 505                 510
```

```
Asp Gly Gly Tyr Lys Gly Met Pro Phe Val Leu Arg Ser Gly Glu Thr
            515                 520                 525
Trp Ile Lys Asn Asn Gly Ser Asp Phe Phe Leu Asp Phe Ser Thr His
530                 535                 540
Asp Val Arg Asn Ile Lys Leu Lys Gly Asn Gly Asp Ala Gly Lys Gly
545                 550                 555                 560
Thr Ala Lys Ala Leu Leu Glu Arg Ile Ala Asp Leu Glu Glu Asp Ala
                565                 570                 575
Gln Arg Ser Leu Met His Arg Phe Asn Ile Ala Ala Asp Leu Ala Asp
            580                 585                 590
Gln Ala Arg Asp Ala Gly Leu Leu Gly Ile Val Gly Leu Phe Val Trp
        595                 600                 605
Ile Arg Phe Met Ala Thr Arg Gln Leu Thr Trp Asn Lys Asn Tyr Asn
610                 615                 620
Val Lys Pro Arg Glu Ile Ser Lys Ala Gln Asp Arg Phe Thr Asp Asp
625                 630                 635                 640
Leu Glu Asn Met Tyr Lys Ala Tyr Pro Gln Tyr Arg Glu Ile Leu Arg
                645                 650                 655
Met Ile Met Ala Ala Val Gly Arg Gly Gly Glu Gly Asp Val Gly Gln
            660                 665                 670
Arg Ile Arg Asp Glu Ile Leu Val Ile Gln Arg Asn Asn Asp Cys Lys
        675                 680                 685
Gly Gly Met Met Glu Glu Trp His Gln Lys Leu His Asn Asn Thr Ser
690                 695                 700
Pro Asp Asp Val Val Ile Cys Gln Ala Leu Ile Asp Tyr Ile Lys Ser
705                 710                 715                 720
Asp Phe Asp Ile Ser Val Tyr Trp Asp Thr Leu Asn Lys Asn Gly Ile
                725                 730                 735
Thr Lys Glu Arg Leu Leu Ser Tyr Asp Arg Ala Ile His Ser Glu Pro
            740                 745                 750
Asn Phe Arg Ser Glu Gln Lys Ala Gly Leu Leu Arg Asp Leu Gly Asn
        755                 760                 765
Tyr Met Arg Ser Leu Lys Ala Val His Ser Gly Ala Asp Leu Glu Ser
770                 775                 780
Ala Ile Ala Ser Cys Met Gly Tyr Lys Ser Glu Gly Glu Gly Phe Met
785                 790                 795                 800
Val Gly Val Gln Ile Asn Pro Val Lys Gly Leu Pro Ser Gly Phe Pro
                805                 810                 815
Glu Leu Leu Glu Phe Val Leu Glu His Val Gly Asp Lys Ser Ala Glu
            820                 825                 830
Pro Leu Leu Glu Gly Leu Leu Glu Ala Arg Val Glu Leu Arg Pro Leu
        835                 840                 845
Leu Leu Asp Ser Arg Glu Arg Met Lys Asp Leu Ile Phe Leu Asp Ile
850                 855                 860
Ala Leu Asp Ser Thr Phe Arg Thr Ala Ile Glu Arg Ser Tyr Glu Glu
865                 870                 875                 880
Leu Asn Asp Ala Ala Pro Glu Lys Ile Met Tyr Phe Ile Ser Leu Val
                885                 890                 895
Leu Glu Asn Leu Ala Leu Ser Ile Asp Asp Asn Glu Asp Ile Leu Tyr
            900                 905                 910
Cys Leu Lys Gly Trp Asn Gln Ala Leu Glu Met Ala Lys Gln Lys Asp
        915                 920                 925
Asp Gln Trp Ala Leu Tyr Ala Lys Ala Phe Leu Asp Arg Asn Arg Leu
```

-continued

```
            930             935             940
Ala Leu Ala Ser Lys Gly Glu Gln Tyr His Asn Met Met Gln Pro Ser
945             950             955             960

Ala Glu Tyr Leu Gly Ser Leu Leu Ser Ile Asp Gln Trp Ala Val Asn
        965             970             975

Ile Phe Thr Glu Glu Ile Ile Arg Gly Gly Ser Ala Ala Thr Leu Ser
            980             985             990

Ala Leu Leu Asn Arg Phe Asp Pro Val Leu Arg Asn Val Ala His Leu
        995             1000            1005

Gly Ser Trp Gln Val Ile Ser Pro Val Glu Val Ser Gly Tyr Val
    1010            1015            1020

Val Val Val Asp Glu Leu Leu Ala Val Gln Asn Lys Ser Tyr Asp
    1025            1030            1035

Lys Pro Thr Ile Leu Val Ala Lys Ser Val Lys Gly Glu Glu Glu
    1040            1045            1050

Ile Pro Asp Gly Val Val Gly Val Ile Thr Pro Asp Met Pro Asp
    1055            1060            1065

Val Leu Ser His Val Ser Val Arg Ala Arg Asn Ser Lys Val Leu
    1070            1075            1080

Phe Ala Thr Cys Phe Asp His Thr Thr Leu Ser Glu Leu Glu Gly
    1085            1090            1095

Tyr Asp Gln Lys Leu Phe Ser Phe Lys Pro Thr Ser Ala Asp Ile
    1100            1105            1110

Thr Tyr Arg Glu Ile Thr Glu Ser Glu Leu Gln Gln Ser Ser Ser
    1115            1120            1125

Pro Asn Ala Glu Val Gly His Ala Val Pro Ser Ile Ser Leu Ala
    1130            1135            1140

Lys Lys Lys Phe Leu Gly Lys Tyr Ala Ile Ser Ala Glu Glu Phe
    1145            1150            1155

Ser Glu Glu Met Val Gly Ala Lys Ser Arg Asn Ile Ala Tyr Leu
    1160            1165            1170

Lys Gly Lys Val Pro Ser Trp Val Gly Val Pro Thr Ser Val Ala
    1175            1180            1185

Ile Pro Phe Gly Thr Phe Glu Lys Val Leu Ser Asp Gly Leu Asn
    1190            1195            1200

Lys Glu Val Ala Gln Ser Ile Glu Lys Leu Lys Ile Arg Leu Ala
    1205            1210            1215

Gln Glu Asp Phe Ser Ala Leu Gly Glu Ile Arg Lys Val Val Leu
    1220            1225            1230

Asn Leu Thr Ala Pro Met Gln Leu Val Asn Glu Leu Lys Glu Arg
    1235            1240            1245

Met Leu Gly Ser Gly Met Pro Trp Pro Gly Asp Glu Gly Asp Lys
    1250            1255            1260

Arg Trp Glu Gln Ala Trp Met Ala Ile Lys Lys Val Trp Ala Ser
    1265            1270            1275

Lys Trp Asn Glu Arg Ala Tyr Phe Ser Thr Arg Lys Val Lys Leu
    1280            1285            1290

Asp His Glu Tyr Leu Ser Met Ala Val Leu Val Gln Glu Val Val
    1295            1300            1305

Asn Ala Asp Tyr Ala Phe Val Ile His Thr Thr Asn Pro Ser Ser
    1310            1315            1320

Gly Asp Ser Ser Glu Ile Tyr Ala Glu Val Val Lys Gly Leu Gly
    1325            1330            1335
```

```
Glu Thr Leu Val Gly Ala Tyr Pro Gly Arg Ala Met Ser Phe Val
    1340                1345                1350

Cys Lys Lys Asp Asp Leu Asp Ser Pro Lys Leu Leu Gly Tyr Pro
    1355                1360                1365

Ser Lys Pro Ile Gly Leu Phe Ile Arg Gln Ser Ile Ile Phe Arg
    1370                1375                1380

Ser Asp Ser Asn Gly Glu Asp Leu Glu Gly Tyr Ala Gly Ala Gly
    1385                1390                1395

Leu Tyr Asp Ser Val Pro Met Asp Glu Glu Asp Glu Val Val Leu
    1400                1405                1410

Asp Tyr Thr Thr Asp Pro Leu Ile Val Asp Arg Gly Phe Arg Ser
    1415                1420                1425

Ser Ile Leu Ser Ser Ile Ala Arg Ala Gly His Ala Ile Glu Glu
    1430                1435                1440

Leu Tyr Gly Ser Pro Gln Asp Val Glu Gly Val Val Lys Asp Gly
    1445                1450                1455

Lys Ile Tyr Val Val Gln Thr Arg Pro Gln Met
    1460                1465
```

```
<210> SEQ ID NO 44
<211> LENGTH: 1469
<212> TYPE: PRT
<213> ORGANISM: Sorghum bicolor
<220> FEATURE:
<221> NAME/KEY: MISC_FEATURE
<222> LOCATION: (1)..(1469)
<223> OTHER INFORMATION: SbGWD

<400> SEQUENCE: 44

Met Thr Gly Phe Ser Ala Ala Ser Ala Ala Ala Ala Ala Glu Arg
1               5                   10                  15

Cys Ala Leu Ala Ile Arg Ala Arg Pro Ala Ala Ser Ser Pro Ala Lys
                20                  25                  30

Arg Gln Gln Gln Ser Ala Ser Leu Arg Arg Ser Gly Gly Gln Arg Arg
        35                  40                  45

Pro Thr Thr Leu Ala Ala Ser Arg Arg Ser Pro Val Val Val Pro Arg
    50                  55                  60

Ala Ile Ala Thr Ser Ala Asp Arg Ala Ser His Asp Leu Val Gly Lys
65                  70                  75                  80

Phe Thr Leu Asp Ser Asn Ser Glu Leu Leu Val Ala Val Asn Pro Ala
                85                  90                  95

Pro Gln Gly Leu Val Ser Val Ile Gly Leu Glu Val Thr Asn Thr Ser
            100                 105                 110

Gly Ser Leu Ile Leu His Trp Gly Val Leu Arg Pro Asp Lys Arg Asp
        115                 120                 125

Trp Ile Leu Pro Ser Arg Gln Pro Asp Gly Thr Thr Val Tyr Lys Asn
    130                 135                 140

Arg Ala Leu Arg Thr Pro Phe Val Lys Ser Gly Asp Asn Ser Thr Leu
145                 150                 155                 160

Arg Ile Glu Ile Asp Asp Pro Ala Val Gln Ala Ile Glu Phe Leu Ile
                165                 170                 175

Phe Gly Glu Thr Gln Asn Lys Trp Phe Lys Asn Asn Gly Gln Asn Phe
            180                 185                 190

Gln Ile Gln Leu Gln Ser Ser Arg His Gln Gly Asn Gly Ala Ser Gly
        195                 200                 205
```

```
Ala Ser Ser Ala Thr Ser Thr Leu Val Pro Glu Asp Leu Val Gln
    210             215                 220

Ile Gln Ala Tyr Leu Arg Trp Glu Arg Lys Gly Lys Gln Ser Tyr Thr
225             230                 235                 240

Pro Glu Gln Glu Lys Glu Glu Tyr Ala Ala Arg Ala Glu Leu Ile
                245                 250                 255

Glu Glu Leu Asn Arg Gly Val Ser Leu Glu Lys Leu Arg Ala Lys Leu
            260                 265                 270

Thr Lys Thr Pro Glu Ala Pro Glu Ser Asp Glu Arg Lys Ser Pro Ala
        275                 280                 285

Ser Arg Met Pro Val Asp Lys Leu Pro Glu Asp Leu Val Gln Val Gln
    290                 295                 300

Ala Tyr Ile Arg Trp Glu Lys Ala Gly Lys Pro Asn Tyr Pro Pro Glu
305             310                 315                 320

Lys Gln Leu Val Glu Leu Glu Ala Arg Lys Glu Leu Gln Ala Glu
                325                 330                 335

Val Asp Lys Gly Ile Ser Ile Asp Gln Leu Arg Gln Lys Ile Leu Lys
            340                 345                 350

Gly Asn Ile Glu Ser Lys Val Ser Lys Gln Leu Lys Asn Lys Lys Tyr
        355                 360                 365

Phe Ser Val Glu Arg Ile Gln Arg Lys Lys Arg Asp Ile Met Gln Leu
370             375                 380

Leu Ser Lys His Lys His Thr Val Met Glu Glu Lys Val Glu Val Ala
385             390                 395                 400

Pro Lys Gln Pro Thr Val Leu Asp Leu Phe Thr Lys Ser Leu His Glu
                405                 410                 415

Lys Asp Gly Cys Glu Val Leu Ser Arg Lys Leu Phe Lys Phe Gly Asp
            420                 425                 430

Lys Glu Ile Leu Ala Ile Ser Thr Lys Val Gln Asn Lys Thr Glu Val
        435                 440                 445

His Leu Ala Thr Asn His Thr Glu Pro Leu Ile Leu His Trp Ser Leu
    450                 455                 460

Ala Lys Lys Ala Gly Glu Trp Lys Ala Pro Pro Ser Asn Ile Leu Pro
465             470                 475                 480

Ser Gly Ser Lys Leu Leu Asp Met Ala Cys Glu Thr Glu Phe Thr Arg
                485                 490                 495

Ser Glu Leu Asp Gly Leu Cys Tyr Gln Val Val Glu Ile Glu Leu Asp
            500                 505                 510

Asp Gly Gly Tyr Lys Gly Met Pro Phe Val Leu Arg Ser Gly Glu Thr
        515                 520                 525

Trp Ile Lys Asn Asn Gly Ser Asp Phe Phe Leu Asp Phe Ser Thr Arg
    530                 535                 540

Asp Thr Arg Asn Ile Lys Leu Lys Asp Asn Gly Asp Ala Gly Lys Gly
545             550                 555                 560

Thr Ala Lys Ala Leu Leu Glu Arg Ile Ala Asp Leu Glu Glu Asp Ala
                565                 570                 575

Gln Arg Ser Leu Met His Arg Phe Asn Ile Ala Ala Asp Leu Ala Asp
            580                 585                 590

Glu Ala Arg Asp Ala Gly Leu Gly Ile Val Gly Leu Phe Val Trp
        595                 600                 605

Ile Arg Phe Met Ala Thr Arg Gln Leu Thr Trp Asn Lys Asn Tyr Asn
610             615                 620

Val Lys Pro Arg Glu Ile Ser Lys Ala Gln Asp Arg Phe Thr Asp Asp
```

```
625                 630                 635                 640
Leu Glu Asn Met Tyr Arg Thr Tyr Pro Gln Tyr Arg Glu Ile Leu Arg
                645                 650                 655
Met Ile Met Ala Ala Val Gly Arg Gly Gly Glu Gly Asp Val Gly Gln
                660                 665                 670
Arg Ile Arg Asp Glu Ile Leu Val Ile Gln Arg Asn Asn Asp Cys Lys
                675                 680                 685
Gly Gly Met Met Glu Glu Trp His Gln Lys Leu His Asn Asn Thr Ser
                690                 695                 700
Pro Asp Asp Val Val Ile Cys Gln Ala Leu Ile Asp Tyr Ile Lys Asn
705                 710                 715                 720
Asp Phe Asp Ile Ser Val Tyr Trp Asp Thr Leu Asn Lys Asn Gly Ile
                725                 730                 735
Thr Lys Glu Arg Leu Leu Ser Tyr Asp Arg Ala Ile His Ser Glu Pro
                740                 745                 750
Asn Phe Arg Ser Glu Gln Lys Glu Gly Leu Leu Arg Asp Leu Gly Asn
                755                 760                 765
Tyr Met Arg Ser Leu Lys Ala Val His Ser Gly Ala Asp Leu Glu Ser
                770                 775                 780
Ala Ile Ala Thr Cys Met Gly Tyr Lys Ser Glu Gly Glu Gly Phe Met
785                 790                 795                 800
Val Gly Val Gln Ile Asn Pro Val Lys Gly Leu Pro Ser Gly Phe Pro
                805                 810                 815
Glu Leu Leu Glu Phe Val Leu Asp His Val Glu Asp Lys Ser Ala Glu
                820                 825                 830
Pro Leu Leu Glu Gly Leu Leu Glu Ala Arg Val Asp Leu Arg Pro Leu
                835                 840                 845
Leu Leu Asp Ser Pro Glu Arg Met Lys Asp Leu Ile Phe Leu Asp Ile
                850                 855                 860
Ala Leu Asp Ser Thr Phe Arg Thr Ala Ile Glu Arg Ser Tyr Glu Glu
865                 870                 875                 880
Leu Asn Asp Ala Ala Pro Glu Lys Ile Met Tyr Phe Ile Ser Leu Val
                885                 890                 895
Leu Glu Asn Leu Ala Phe Ser Ile Asp Asp Asn Glu Asp Ile Leu Tyr
                900                 905                 910
Cys Leu Lys Gly Trp Asn Gln Ala Leu Glu Met Ala Lys Gln Lys Asp
                915                 920                 925
Asp Gln Trp Ala Leu Tyr Ala Lys Ala Phe Leu Asp Arg Ile Arg Leu
                930                 935                 940
Ala Leu Ala Ser Lys Gly Glu Gln Tyr His Asn Met Met Gln Pro Ser
945                 950                 955                 960
Ala Glu Tyr Leu Gly Ser Leu Leu Ser Ile Asp Lys Trp Ala Val Asn
                965                 970                 975
Ile Phe Thr Glu Glu Ile Ile Arg Gly Gly Ser Ala Thr Leu Ser
                980                 985                 990
Ala Leu Leu Asn Arg Phe Asp Pro Val Leu Arg Asn Val Ala Asn Leu
                995                 1000                1005
Gly Ser Trp Gln Val Ile Ser Pro Val Glu Val Ser Gly Tyr Val
                1010                1015                1020
Val Val Val Asp Glu Leu Ala Val Gln Asn Lys Ser Tyr Asp
                1025                1030                1035
Lys Pro Thr Ile Leu Val Ala Lys Ser Val Lys Gly Glu Glu Glu
                1040                1045                1050
```

```
Ile Pro Asp Gly Val Val Gly Val Ile Thr Pro Asp Met Pro Asp
    1055                1060                1065

Val Leu Ser His Val Ser Val Arg Ala Arg Asn Ser Lys Val Leu
    1070                1075                1080

Phe Ala Thr Cys Phe Asp His Thr Thr Leu Ser Glu Leu Glu Gly
    1085                1090                1095

Tyr Asp Gln Lys Leu Leu Ser Phe Lys Pro Thr Ser Ala Asp Ile
    1100                1105                1110

Thr Tyr Arg Glu Ile Thr Glu Ser Glu Leu Gln Gln Ser Ser Ser
    1115                1120                1125

Pro Asn Ala Glu Val Gly His Ala Val Pro Ser Ile Ser Leu Ala
    1130                1135                1140

Lys Lys Lys Phe Leu Gly Lys Tyr Ala Ile Ser Ala Glu Glu Phe
    1145                1150                1155

Thr Glu Glu Met Val Gly Ala Lys Ser Arg Asn Ile Ala Tyr Leu
    1160                1165                1170

Lys Gly Lys Val Pro Ser Trp Val Gly Val Pro Thr Ser Val Ala
    1175                1180                1185

Ile Pro Phe Gly Thr Phe Glu Lys Val Leu Ser Asp Gly Leu Asn
    1190                1195                1200

Lys Glu Val Ala Gln Thr Ile Glu Lys Leu Lys Ile Arg Leu Ala
    1205                1210                1215

Gln Glu Asp Phe Ser Ala Leu Gly Glu Ile Arg Lys Ala Val Leu
    1220                1225                1230

Asn Leu Thr Ala Pro Met Gln Leu Val Asn Glu Leu Lys Glu Arg
    1235                1240                1245

Met Leu Gly Ser Gly Met Pro Trp Pro Gly Asp Glu Gly Asn Arg
    1250                1255                1260

Arg Trp Glu Gln Ala Trp Met Ala Ile Lys Lys Val Trp Ala Ser
    1265                1270                1275

Lys Trp Asn Glu Arg Ala Tyr Phe Ser Thr Arg Lys Val Lys Leu
    1280                1285                1290

Asn His Glu Tyr Leu Ser Met Ala Val Leu Val Gln Glu Val Val
    1295                1300                1305

Asn Ala Asp Tyr Ala Phe Val Ile His Thr Thr Asn Pro Ser Ser
    1310                1315                1320

Gly Asp Ser Ser Glu Ile Tyr Ala Glu Val Val Lys Gly Leu Gly
    1325                1330                1335

Glu Thr Leu Val Gly Ala Tyr Pro Gly Arg Ala Met Ser Phe Val
    1340                1345                1350

Cys Lys Lys Asp Asp Leu Asp Ser Pro Lys Leu Leu Gly Tyr Pro
    1355                1360                1365

Ser Lys Pro Ile Gly Leu Phe Ile Arg Arg Ser Ile Ile Phe Arg
    1370                1375                1380

Ser Asp Ser Asn Gly Glu Asp Leu Glu Gly Tyr Ala Gly Ala Gly
    1385                1390                1395

Leu Tyr Asp Ser Val Pro Met Asp Glu Glu Asp Glu Val Val Leu
    1400                1405                1410

Asp Tyr Thr Thr Asp Pro Leu Ile Val Asp Arg Gly Phe Arg Asn
    1415                1420                1425

Ser Ile Leu Ser Ser Ile Ala Arg Ala Gly His Ala Ile Glu Glu
    1430                1435                1440
```

Leu Tyr Gly Ser Pro Gln Asp Val Glu Gly Val Val Lys Asp Gly
        1445                1450                1455

Lys Ile Tyr Val Val Gln Thr Arg Pro Gln Met
        1460                1465

<210> SEQ ID NO 45
<211> LENGTH: 74
<212> TYPE: PRT
<213> ORGANISM: Zea mays
<220> FEATURE:
<221> NAME/KEY: MISC_FEATURE
<222> LOCATION: (1)..(74)
<223> OTHER INFORMATION: ZmGWD_M1_aa_1040-1120

<400> SEQUENCE: 45

Pro Thr Ile Leu Val Ala Lys Ser Val Lys Gly Glu Glu Glu Ile Pro
1               5                   10                  15

Asp Gly Val Val Gly Arg Asn Thr Pro Asp Met Pro Asp Val Leu Ser
            20                  25                  30

His Val Ser Val Arg Pro Thr Ile Leu Val Ala Lys Ser Val Lys Gly
        35                  40                  45

Glu Glu Glu Ile Pro Asp Gly Val Val Gly Arg Asn Thr Pro Asp Met
    50                  55                  60

Pro Asp Val Leu Ser His Val Ser Val Arg
65                  70

<210> SEQ ID NO 46
<211> LENGTH: 79
<212> TYPE: PRT
<213> ORGANISM: Zea mays
<220> FEATURE:
<221> NAME/KEY: MISC_FEATURE
<222> LOCATION: (1)..(79)
<223> OTHER INFORMATION: ZmGWD_M2 _1040-1120)

<400> SEQUENCE: 46

Pro Thr Ile Leu Val Ala Lys Ser Val Lys Gly Glu Glu Glu Ile Pro
1               5                   10                  15

Asp Gly Val Val Val Thr Pro Asp Met Pro Asp Val Leu Ser His Val
            20                  25                  30

Ser Val Arg Ala Arg Asn Ser Lys Val Leu Phe Ala Thr Cys Phe Asp
        35                  40                  45

His Thr Thr Leu Ser Glu Leu Glu Gly Tyr Asp Gln Lys Leu Phe Ser
    50                  55                  60

Phe Lys Pro Thr Ser Ala Asp Ile Thr Tyr Arg Glu Ile Thr Glu
65                  70                  75

<210> SEQ ID NO 47
<211> LENGTH: 76
<212> TYPE: PRT
<213> ORGANISM: Zea mays
<220> FEATURE:
<221> NAME/KEY: MISC_FEATURE
<222> LOCATION: (1)..(76)
<223> OTHER INFORMATION: ZmGWD_M3 _aa1040-1120

<400> SEQUENCE: 47

Pro Thr Ile Leu Val Ala Lys Ser Val Lys Gly Glu Glu Glu Ile Pro
1               5                   10                  15

Asp Gly Ala Pro Asp Met Pro Asp Val Leu Ser His Val Ser Val Arg
            20                  25                  30

Ala Arg Asn Ser Lys Val Leu Phe Ala Thr Cys Phe Asp His Thr Thr

```
                 35                  40                  45
Leu Ser Glu Leu Glu Gly Tyr Asp Gln Lys Leu Phe Ser Phe Lys Pro
 50                  55                  60

Thr Ser Ala Asp Ile Thr Tyr Arg Glu Ile Thr Glu
 65                  70                  75
```

<210> SEQ ID NO 48
<211> LENGTH: 78
<212> TYPE: PRT
<213> ORGANISM: Zea mays
<220> FEATURE:
<221> NAME/KEY: MISC_FEATURE
<222> LOCATION: (1)..(78)
<223> OTHER INFORMATION: ZmGWD_M4 _aa_1040-1120

<400> SEQUENCE: 48

```
Pro Thr Ile Leu Val Ala Lys Ser Val Lys Gly Glu Glu Glu Ile Pro
  1               5                  10                  15

Asp Gly Val Ile Thr Pro Asp Met Pro Asp Val Leu Ser His Val Ser
                 20                  25                  30

Val Arg Ala Arg Asn Ser Lys Val Leu Phe Ala Thr Cys Phe Asp His
             35                  40                  45

Thr Thr Leu Ser Glu Leu Glu Gly Tyr Asp Gln Lys Leu Phe Ser Phe
 50                  55                  60

Lys Pro Thr Ser Ala Asp Ile Thr Tyr Arg Glu Ile Thr Glu
 65                  70                  75
```

<210> SEQ ID NO 49
<211> LENGTH: 95
<212> TYPE: PRT
<213> ORGANISM: Zea mays
<220> FEATURE:
<221> NAME/KEY: MISC_FEATURE
<222> LOCATION: (1)..(95)
<223> OTHER INFORMATION: ZmGWD_M5_aa_1040-1120

<400> SEQUENCE: 49

```
Pro Thr Ile Leu Val Ala Lys Ser Val Lys Gly Glu Glu Glu Ile Pro
  1               5                  10                  15

Asp Gly Val Val Ala Glu Leu Leu Asn Ser Phe Ile Ile Glu Leu Tyr
                 20                  25                  30

Asp Asp Ala Leu Leu Asp Cys Ile Ile Leu Met Leu Asn His Ile Leu
             35                  40                  45

Met Ile Val Gly Thr Cys Ser Pro Met Gln Gly Asp Pro Thr Gly Val
 50                  55                  60

Cys Arg Asn Val Asn Arg Val Phe Ala Arg Asp Gly Asn Ser Ser Val
 65                  70                  75                  80

Asn Leu Ala Ser His Gly His Cys Ala Gly Val Phe Asn Tyr Thr
                 85                  90                  95
```

<210> SEQ ID NO 50
<211> LENGTH: 73
<212> TYPE: PRT
<213> ORGANISM: Zea mays
<220> FEATURE:
<221> NAME/KEY: MISC_FEATURE
<222> LOCATION: (1)..(73)
<223> OTHER INFORMATION: ZmGWD_M6 _aa_1040-1120

<400> SEQUENCE: 50

```
Pro Thr Ile Leu Val Ala Lys Ser Val Lys Gly Glu Glu Glu Ile Pro
  1               5                  10                  15
```

Asp Gly Val Val Gly Lys Leu His Leu Ile Cys Gln Met Phe Cys Leu
            20                  25                  30

Met Cys Gln Ser Glu Gln Gly Ile Ala Arg Tyr Cys Leu Arg Pro Val
        35                  40                  45

Leu Thr Thr Pro Leu Tyr Leu Asn Leu Lys Asp Met Ile Arg Asn Cys
    50                  55                  60

Phe Pro Ser Ser Leu Leu Leu Gln Ile
65                  70

<210> SEQ ID NO 51
<211> LENGTH: 72
<212> TYPE: PRT
<213> ORGANISM: Zea mays
<220> FEATURE:
<221> NAME/KEY: MISC_FEATURE
<222> LOCATION: (1)..(72)
<223> OTHER INFORMATION: ZmGWD_M7 _aa_1040-1120

<400> SEQUENCE: 51

Pro Thr Ile Leu Val Ala Lys Ser Val Lys Gly Glu Glu Glu Ile Pro
1               5                   10                  15

Asp Gly Val Val Gly Leu His Leu Ile Cys Gln Met Phe Cys Leu Met
            20                  25                  30

Cys Gln Ser Glu Gln Gly Ile Ala Arg Tyr Cys Leu Arg Pro Val Leu
        35                  40                  45

Thr Thr Pro Leu Tyr Leu Asn Leu Lys Asp Met Ile Arg Asn Cys Phe
    50                  55                  60

Pro Ser Ser Leu Leu Leu Gln Ile
65                  70

<210> SEQ ID NO 52
<211> LENGTH: 79
<212> TYPE: PRT
<213> ORGANISM: Zea mays
<220> FEATURE:
<221> NAME/KEY: MISC_FEATURE
<222> LOCATION: (1)..(79)
<223> OTHER INFORMATION: ZmGWD_M8 _aa_1040-1120

<400> SEQUENCE: 52

Pro Thr Ile Leu Val Ala Lys Ser Val Lys Gly Glu Glu Glu Ile Pro
1               5                   10                  15

Asp Gly Val Val Gly Met Pro Asp Met Pro Asp Val Leu Ser His Val
            20                  25                  30

Ser Val Arg Ala Arg Asn Ser Lys Val Leu Phe Ala Thr Cys Phe Asp
        35                  40                  45

His Thr Thr Leu Ser Glu Leu Glu Gly Tyr Asp Gln Lys Leu Phe Ser
    50                  55                  60

Phe Lys Pro Thr Ser Ala Asp Ile Thr Tyr Arg Glu Ile Thr Glu
65                  70                  75

<210> SEQ ID NO 53
<211> LENGTH: 76
<212> TYPE: PRT
<213> ORGANISM: Zea mays
<220> FEATURE:
<221> NAME/KEY: MISC_FEATURE
<222> LOCATION: (1)..(76)
<223> OTHER INFORMATION: ZmGWD_M9_aa_1040-1120

<400> SEQUENCE: 53

```
Pro Thr Ile Leu Val Ala Lys Ser Val Lys Gly Glu Glu Ile Pro
1               5                   10                  15

Asp Gly Val Val Gly Met Pro Val Leu Ser His Val Ser Val Arg
            20                  25                  30

Ala Arg Asn Ser Lys Val Leu Phe Ala Thr Cys Phe Asp His Thr Thr
        35                  40                  45

Leu Ser Glu Leu Glu Gly Tyr Asp Gln Lys Leu Phe Ser Phe Lys Pro
    50                  55                  60

Thr Ser Ala Asp Ile Thr Tyr Arg Glu Ile Thr Glu
65                  70                  75

<210> SEQ ID NO 54
<211> LENGTH: 25
<212> TYPE: PRT
<213> ORGANISM: Zea mays
<220> FEATURE:
<221> NAME/KEY: MISC_FEATURE
<223> OTHER INFORMATION: ZmGWD_M10 _aa_1040-1120

<400> SEQUENCE: 54

Pro Thr Ile Leu Val Ala Lys Ser Val Lys Gly Glu Glu Ile Pro
1               5                   10                  15

Asp Gly Val Val Gly Val Asn Tyr Thr
            20                  25

<210> SEQ ID NO 55
<211> LENGTH: 34
<212> TYPE: PRT
<213> ORGANISM: Zea mays
<220> FEATURE:
<221> NAME/KEY: MISC_FEATURE
<222> LOCATION: (1)..(34)
<223> OTHER INFORMATION: ZmGWD_M11_aa_1040-1120

<400> SEQUENCE: 55

Pro Thr Ile Leu Val Ala Lys Ser Val Lys Gly Glu Glu Ile Pro
1               5                   10                  15

Asp Gly Val Val Gly Val Arg Cys Ser Val Ser Cys Val Ser Pro Ser
            20                  25                  30

Lys Glu

<210> SEQ ID NO 56
<211> LENGTH: 27
<212> TYPE: PRT
<213> ORGANISM: Zea mays
<220> FEATURE:
<221> NAME/KEY: MISC_FEATURE
<222> LOCATION: (1)..(27)
<223> OTHER INFORMATION: ZmGWD_M12 _1040-1120

<400> SEQUENCE: 56

Pro Thr Ile Leu Val Ala Lys Ser Val Lys Gly Glu Glu Ile Pro
1               5                   10                  15

Asp Gly Val Val Gly Val Ser Pro Ser Lys Glu
            20                  25

<210> SEQ ID NO 57
<211> LENGTH: 60
<212> TYPE: PRT
<213> ORGANISM: Zea mays
<220> FEATURE:
<221> NAME/KEY: MISC_FEATURE
<222> LOCATION: (1)..(60)
<223> OTHER INFORMATION: ZmGWD_M13 _aa_1040-1120
```

<400> SEQUENCE: 57

```
Pro Thr Ile Leu Val Ala Lys Ser Val Lys Gly Glu Glu Ile Pro
1               5                   10                  15

Asp Val Leu Ser His Val Ser Val Arg Ala Arg Asn Ser Lys Val Leu
            20                  25                  30

Phe Ala Thr Cys Phe Asp His Thr Thr Leu Ser Glu Leu Glu Gly Tyr
        35                  40                  45

Asp Gln Lys Leu Phe Ser Phe Lys Pro Thr Ser Ala
    50                  55                  60
```

<210> SEQ ID NO 58
<211> LENGTH: 65
<212> TYPE: PRT
<213> ORGANISM: Zea mays
<220> FEATURE:
<221> NAME/KEY: MISC_FEATURE
<222> LOCATION: (1)..(65)
<223> OTHER INFORMATION: ZmGWD_M14_aa_1040-1120

<400> SEQUENCE: 58

```
Pro Thr Ile Leu Val Ala Lys Ser Val Lys Gly Glu Glu Leu His
1               5                   10                  15

Leu Ile Cys Gln Met Phe Cys Leu Met Cys Gln Ser Glu Gln Gly Ile
            20                  25                  30

Ala Arg Tyr Cys Leu Arg Pro Val Leu Thr Thr Pro Leu Tyr Leu Asn
        35                  40                  45

Leu Lys Asp Met Ile Arg Asn Cys Phe Pro Ser Ser Leu Leu Leu Gln
    50                  55                  60

Ile
65
```

<210> SEQ ID NO 59
<211> LENGTH: 11
<212> TYPE: PRT
<213> ORGANISM: Zea mays
<220> FEATURE:
<221> NAME/KEY: MISC_FEATURE
<222> LOCATION: (1)..(11)
<223> OTHER INFORMATION: ZmGWD_M15_aa_1040-1120

<400> SEQUENCE: 59

```
Pro Thr Ile Leu Val Ala Lys Ser Asn Tyr Thr
1               5                   10
```

<210> SEQ ID NO 60
<211> LENGTH: 10
<212> TYPE: PRT
<213> ORGANISM: Zea mays
<220> FEATURE:
<221> NAME/KEY: MISC_FEATURE
<222> LOCATION: (1)..(10)
<223> OTHER INFORMATION: ZmGWD_M16_aa_1040-1120

<400> SEQUENCE: 60

```
Pro Arg Glu Arg Lys Lys Tyr Gln Met Glu
1               5                   10
```

<210> SEQ ID NO 61
<211> LENGTH: 15
<212> TYPE: PRT
<213> ORGANISM: Zea mays
<220> FEATURE:
<221> NAME/KEY: MISC_FEATURE

```
<222> LOCATION: (1)..(15)
<223> OTHER INFORMATION: ZmGWD_M17_aa_1040-1120

<400> SEQUENCE: 61

Pro Thr Ile Leu Val Ala Arg Glu Arg Lys Lys Tyr Gln Met Glu
1               5                   10                  15

<210> SEQ ID NO 62
<211> LENGTH: 18
<212> TYPE: PRT
<213> ORGANISM: Zea mays
<220> FEATURE:
<221> NAME/KEY: MISC_FEATURE
<222> LOCATION: (1)..(18)
<223> OTHER INFORMATION: ZmGWD_M18_aa_1040-1120

<400> SEQUENCE: 62

Pro Thr Ile Leu Val Ala Arg Val Ser Arg Glu Arg Lys Lys Tyr Gln
1               5                   10                  15

Met Glu

<210> SEQ ID NO 63
<211> LENGTH: 71
<212> TYPE: PRT
<213> ORGANISM: Zea mays
<220> FEATURE:
<221> NAME/KEY: MISC_FEATURE
<222> LOCATION: (1)..(71)
<223> OTHER INFORMATION: ZmGWD_M19 _aa_1040-1120

<400> SEQUENCE: 63

Pro Thr Ile Leu Val Ala Lys Ser Val Lys Gly Glu Glu Ile Pro
1               5                   10                  15

Asp Gly Val Val Gly Val His Leu Ile Cys Gln Met Phe Cys Leu Met
                20                  25                  30

Cys Gln Ser Glu Gln Gly Ile Ala Arg Tyr Cys Leu Arg Pro Val Leu
            35                  40                  45

Thr Thr Pro Leu Tyr Leu Asn Leu Lys Asp Met Ile Arg Asn Cys Phe
        50                  55                  60

Pro Ser Ser Leu Leu Gln
65                  70

<210> SEQ ID NO 64
<211> LENGTH: 73
<212> TYPE: PRT
<213> ORGANISM: Zea mays
<220> FEATURE:
<221> NAME/KEY: MISC_FEATURE
<222> LOCATION: (1)..(73)
<223> OTHER INFORMATION: ZmGWD_M20_aa_1040-1120

<400> SEQUENCE: 64

Pro Thr Ile Leu Val Ala Lys Ser Val Lys Gly Glu Glu Ile Pro
1               5                   10                  15

Asp Gly Val Val Gly Val Leu His Leu Ile Cys Gln Met Phe Cys Leu
                20                  25                  30

Met Cys Gln Ser Glu Gln Gly Ile Ala Arg Tyr Cys Leu Arg Pro Val
            35                  40                  45

Leu Thr Thr Pro Leu Tyr Leu Asn Leu Lys Asp Met Ile Arg Asn Cys
        50                  55                  60

Phe Pro Ser Ser Leu Leu Gln Ile
65                  70
```

```
<210> SEQ ID NO 65
<211> LENGTH: 12
<212> TYPE: PRT
<213> ORGANISM: Zea mays
<220> FEATURE:
<221> NAME/KEY: MISC_FEATURE
<222> LOCATION: (1)..(12)
<223> OTHER INFORMATION: ZmGWD_M21_aa_1040-1120

<400> SEQUENCE: 65

Pro Thr Ile Leu Val Ala Lys Ser Val Lys Ile Leu
1               5                   10

<210> SEQ ID NO 66
<211> LENGTH: 70
<212> TYPE: PRT
<213> ORGANISM: Zea mays
<220> FEATURE:
<221> NAME/KEY: MISC_FEATURE
<222> LOCATION: (1)..(70)
<223> OTHER INFORMATION: ZmGWD_M22_aa_1040-1120

<400> SEQUENCE: 66

Pro Thr Ile Leu Val Ala Lys Ser Val Lys Gly Glu Glu Ile Pro
1               5                   10                  15

Asp Gly Val Val Gly Val Ile Cys Gln Met Phe Cys Leu Met Cys Gln
                20                  25                  30

Ser Glu Gln Gly Ile Ala Arg Tyr Cys Leu Arg Pro Val Leu Thr Thr
            35                  40                  45

Pro Leu Tyr Leu Asn Leu Lys Asp Met Ile Arg Asn Cys Phe Pro Ser
    50                  55                  60

Ser Leu Leu Leu Gln Ile
65                  70

<210> SEQ ID NO 67
<211> LENGTH: 27
<212> TYPE: PRT
<213> ORGANISM: Zea mays
<220> FEATURE:
<221> NAME/KEY: MISC_FEATURE
<222> LOCATION: (1)..(27)
<223> OTHER INFORMATION: ZmGWD_M23_aa_1040-1120

<400> SEQUENCE: 67

Pro Thr Ile Leu Val Ala Lys Ser Val Lys Gly Glu Glu Ile Pro
1               5                   10                  15

Asp Gly Val Val Gly Lys Asp Lys Pro Cys Thr
                20                  25

<210> SEQ ID NO 68
<211> LENGTH: 73
<212> TYPE: PRT
<213> ORGANISM: Zea mays
<220> FEATURE:
<221> NAME/KEY: MISC_FEATURE
<222> LOCATION: (1)..(73)
<223> OTHER INFORMATION: ZmGWD_M24_aa_1040-1120

<400> SEQUENCE: 68

Pro Thr Ile Leu Val Ala Lys Ser Val Lys Gly Glu Glu Ile Pro
1               5                   10                  15

Asp Gly Val Val Gly Glu Leu His Leu Ile Cys Gln Met Phe Cys Leu
                20                  25                  30

Met Cys Gln Ser Glu Gln Gly Ile Ala Arg Tyr Cys Leu Arg Pro Val
```

```
                35                  40                  45
Leu Thr Thr Pro Leu Tyr Leu Asn Leu Lys Asp Met Ile Arg Asn Cys
    50                  55                  60

Phe Pro Ser Ser Leu Leu Leu Gln Ile
65                  70
```

<210> SEQ ID NO 69
<211> LENGTH: 24
<212> TYPE: PRT
<213> ORGANISM: Zea mays
<220> FEATURE:
<221> NAME/KEY: MISC_FEATURE
<222> LOCATION: (1)..(24)
<223> OTHER INFORMATION: ZmGWD_M25 _aa_1040-1120

<400> SEQUENCE: 69

```
Pro Thr Ile Leu Val Ala Lys Ser Val Lys Gly Glu Glu Glu Ile Pro
1               5                   10                  15

Asp Gly Val Val Gly Asn Tyr Thr
                20
```

<210> SEQ ID NO 70
<211> LENGTH: 95
<212> TYPE: PRT
<213> ORGANISM: Zea mays
<220> FEATURE:
<221> NAME/KEY: MISC_FEATURE
<222> LOCATION: (1)..(95)
<223> OTHER INFORMATION: ZmGWD_M26_aa_1040-1120

<400> SEQUENCE: 70

```
Pro Thr Ile Leu Val Ala Lys Ser Val Lys Gly Glu Glu Glu Ile Pro
1               5                   10                  15

Asp Gly Ala Val Cys Ser Gly Thr Ala Ser Tyr Phe Asn Val Ser Ser
                20                  25                  30

Gly Arg Leu Thr Ser Met Phe Val Phe Phe Lys Cys Arg Asn Arg
            35                  40                  45

Glu Ser Ser Cys Lys Tyr Leu Leu Tyr Glu Lys Asp Ser Tyr Leu Glu
    50                  55                  60

Ile Cys Glu Gln Asn Tyr Pro Gln Leu Leu Gly Lys Thr Lys Lys Lys
65                  70                  75                  80

Val Pro Ser Asn Ile Tyr Ser Met Thr Thr Ser Val Tyr Tyr Thr
                85                  90                  95
```

<210> SEQ ID NO 71
<211> LENGTH: 13
<212> TYPE: PRT
<213> ORGANISM: Zea mays
<220> FEATURE:
<221> NAME/KEY: MISC_FEATURE
<222> LOCATION: (1)..(13)
<223> OTHER INFORMATION: ZmGWD_M27_aa_1040-1120

<400> SEQUENCE: 71

```
Pro Thr Ile Leu Val Ala Arg Glu Arg Tyr Gln Met Glu
1               5                   10
```

<210> SEQ ID NO 72
<211> LENGTH: 72
<212> TYPE: PRT
<213> ORGANISM: Zea mays
<220> FEATURE:
<221> NAME/KEY: MISC_FEATURE
<222> LOCATION: (1)..(72)

```
<223> OTHER INFORMATION: ZmGWD_M28_aa_1040-1120

<400> SEQUENCE: 72

Pro Thr Ile Leu Val Ala Lys Ser Val Lys Gly Glu Glu Thr Pro
1               5                   10                  15

Asp Met Pro Asp Val Leu Ser His Val Ser Val Arg Ala Arg Asn Ser
            20                  25                  30

Lys Val Leu Phe Ala Thr Cys Phe Asp His Thr Thr Leu Ser Glu Leu
                35                  40                  45

Glu Gly Tyr Asp Gln Lys Leu Phe Ser Phe Lys Pro Thr Ser Ala Asp
        50                  55                  60

Ile Thr Tyr Arg Glu Ile Thr Glu
65                  70

<210> SEQ ID NO 73
<211> LENGTH: 24
<212> TYPE: PRT
<213> ORGANISM: Zea mays
<220> FEATURE:
<221> NAME/KEY: MISC_FEATURE
<222> LOCATION: (1)..(24)
<223> OTHER INFORMATION: ZmGWD_M29 _aa_1040-1120

<400> SEQUENCE: 73

Pro Thr Ile Leu Val Ala Lys Ser Val Lys Gly Glu Glu Ile Pro
1               5                   10                  15

Asp Gly Val Val Gly Asn Tyr Thr
            20

<210> SEQ ID NO 74
<211> LENGTH: 1417
<212> TYPE: PRT
<213> ORGANISM: Streptococcus pyogenes
<220> FEATURE:
<221> NAME/KEY: MISC_FEATURE
<222> LOCATION: (1)..(1147)
<223> OTHER INFORMATION: Cas9 protein

<400> SEQUENCE: 74

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160
```

Ile Val Asp Glu Val Ala Tyr His Glu Lys Tyr Pro Thr Ile Tyr His
            165                 170                 175

Leu Arg Lys Lys Leu Val Asp Ser Thr Asp Lys Ala Asp Leu Arg Leu
        180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe

-continued

```
            580             585             590
Lys Thr Asn Arg Lys Val Thr Val Lys Gln Leu Lys Glu Asp Tyr Phe
            595             600             605
Lys Lys Ile Glu Cys Phe Asp Ser Val Glu Ile Ser Gly Val Glu Asp
            610             615             620
Arg Phe Asn Ala Ser Leu Gly Thr Tyr His Asp Leu Leu Lys Ile Ile
625             630             635             640
Lys Asp Lys Asp Phe Leu Asp Asn Glu Glu Asn Glu Asp Ile Leu Glu
            645             650             655
Asp Ile Val Leu Thr Leu Thr Leu Phe Glu Asp Arg Glu Met Ile Glu
            660             665             670
Glu Arg Leu Lys Thr Tyr Ala His Leu Phe Asp Asp Lys Val Met Lys
            675             680             685
Gln Leu Lys Arg Arg Arg Tyr Thr Gly Trp Gly Arg Leu Ser Arg Lys
            690             695             700
Leu Ile Asn Gly Ile Arg Asp Lys Gln Ser Gly Lys Thr Ile Leu Asp
705             710             715             720
Phe Leu Lys Ser Asp Gly Phe Ala Asn Arg Asn Phe Met Gln Leu Ile
            725             730             735
His Asp Asp Ser Leu Thr Phe Lys Glu Asp Ile Gln Lys Ala Gln Val
            740             745             750
Ser Gly Gln Gly Asp Ser Leu His Glu His Ile Ala Asn Leu Ala Gly
            755             760             765
Ser Pro Ala Ile Lys Lys Gly Ile Leu Gln Thr Val Lys Val Val Asp
            770             775             780
Glu Leu Val Lys Val Met Gly Arg His Lys Pro Glu Asn Ile Val Ile
785             790             795             800
Glu Met Ala Arg Glu Asn Gln Thr Thr Gln Lys Gly Gln Lys Asn Ser
            805             810             815
Arg Glu Arg Met Lys Arg Ile Glu Glu Gly Ile Lys Glu Leu Gly Ser
            820             825             830
Gln Ile Leu Lys Glu His Pro Val Glu Asn Thr Gln Leu Gln Asn Glu
            835             840             845
Lys Leu Tyr Leu Tyr Tyr Leu Gln Asn Gly Arg Asp Met Tyr Val Asp
            850             855             860
Gln Glu Leu Asp Ile Asn Arg Leu Ser Asp Tyr Asp Val Asp His Ile
865             870             875             880
Val Pro Gln Ser Phe Leu Lys Asp Asp Ser Ile Asp Asn Lys Val Leu
            885             890             895
Thr Arg Ser Asp Lys Asn Arg Gly Lys Ser Asp Asn Val Pro Ser Glu
            900             905             910
Glu Val Val Lys Lys Met Lys Asn Tyr Trp Arg Gln Leu Leu Asn Ala
            915             920             925
Lys Leu Ile Thr Gln Arg Lys Phe Asp Asn Leu Thr Lys Ala Glu Arg
            930             935             940
Gly Gly Leu Ser Glu Leu Asp Lys Ala Gly Phe Ile Lys Arg Gln Leu
945             950             955             960
Val Glu Thr Arg Gln Ile Thr Lys His Val Ala Gln Ile Leu Asp Ser
            965             970             975
Arg Met Asn Thr Lys Tyr Asp Glu Asn Asp Lys Leu Ile Arg Glu Val
            980             985             990
Lys Val Ile Thr Leu Lys Ser Lys  Leu Val Ser Asp Phe  Arg Lys Asp
            995             1000            1005
```

```
Phe Gln Phe Tyr Lys Val Arg Glu Ile Asn Asn Tyr His His Ala
    1010            1015            1020

His Asp Ala Tyr Leu Asn Ala Val Val Gly Thr Ala Leu Ile Lys
    1025            1030            1035

Lys Tyr Pro Lys Leu Glu Ser Glu Phe Val Tyr Gly Asp Tyr Lys
    1040            1045            1050

Val Tyr Asp Val Arg Lys Met Ile Ala Lys Ser Glu Gln Glu Ile
    1055            1060            1065

Gly Lys Ala Thr Ala Lys Tyr Phe Phe Tyr Ser Asn Ile Met Asn
    1070            1075            1080

Phe Phe Lys Thr Glu Ile Thr Leu Ala Asn Gly Glu Ile Arg Lys
    1085            1090            1095

Arg Pro Leu Ile Glu Thr Asn Gly Glu Thr Gly Glu Ile Val Trp
    1100            1105            1110

Asp Lys Gly Arg Asp Phe Ala Thr Val Arg Lys Val Leu Ser Met
    1115            1120            1125

Pro Gln Val Asn Ile Val Lys Lys Thr Glu Val Gln Thr Gly Gly
    1130            1135            1140

Phe Ser Lys Glu Ser Ile Leu Pro Lys Arg Asn Ser Asp Lys Leu
    1145            1150            1155

Ile Ala Arg Lys Lys Asp Trp Asp Pro Lys Lys Tyr Gly Gly Phe
    1160            1165            1170

Asp Ser Pro Thr Val Ala Tyr Ser Val Leu Val Val Ala Lys Val
    1175            1180            1185

Glu Lys Gly Lys Ser Lys Lys Leu Lys Ser Val Lys Glu Leu Leu
    1190            1195            1200

Gly Ile Thr Ile Met Glu Arg Ser Ser Phe Glu Lys Asn Pro Ile
    1205            1210            1215

Asp Phe Leu Glu Ala Lys Gly Tyr Lys Glu Val Lys Lys Asp Leu
    1220            1225            1230

Ile Ile Lys Leu Pro Lys Tyr Ser Leu Phe Glu Leu Glu Asn Gly
    1235            1240            1245

Arg Lys Arg Met Leu Ala Ser Ala Gly Glu Leu Gln Lys Gly Asn
    1250            1255            1260

Glu Leu Ala Leu Pro Ser Lys Tyr Val Asn Phe Leu Tyr Leu Ala
    1265            1270            1275

Ser His Tyr Glu Lys Leu Lys Gly Ser Pro Glu Asp Asn Glu Gln
    1280            1285            1290

Lys Gln Leu Phe Val Glu Gln His Lys His Tyr Leu Asp Glu Ile
    1295            1300            1305

Ile Glu Gln Ile Ser Glu Phe Ser Lys Arg Val Ile Leu Ala Asp
    1310            1315            1320

Ala Asn Leu Asp Lys Val Leu Ser Ala Tyr Asn Lys His Arg Asp
    1325            1330            1335

Lys Pro Ile Arg Glu Gln Ala Glu Asn Ile Ile His Leu Phe Thr
    1340            1345            1350

Leu Thr Asn Leu Gly Ala Pro Ala Ala Phe Lys Tyr Phe Asp Thr
    1355            1360            1365

Thr Ile Asp Arg Lys Arg Tyr Thr Ser Thr Lys Glu Val Leu Asp
    1370            1375            1380

Ala Thr Leu Ile His Gln Ser Ile Thr Gly Leu Tyr Glu Thr Arg
    1385            1390            1395
```

Ile Asp Leu Ser Gln Leu Gly Gly Asp Arg Pro Lys Lys Lys Arg
1400                1405                1410

Lys Val Gly Gly
    1415

<210> SEQ ID NO 75
<211> LENGTH: 4272
<212> TYPE: DNA
<213> ORGANISM: Artificial Sequence
<220> FEATURE:
<223> OTHER INFORMATION: Synthetic construct, ZmCas9

<400> SEQUENCE: 75

| | | | | | |
|---|---|---|---|---|---|
| ggatcctaaa | ccatggatta | caaggaccac | gacggcgatt | acaaggacca | cgacattgat | 60 |
| tacaaggacg | acgacgataa | gatggctccc | aagaagaaga | ggaaggttgg | catccacggg | 120 |
| gtgccggctg | ctgacaagaa | gtactcgatc | ggcctcgata | ttgggactaa | ctctgttggc | 180 |
| tgggccgtga | tcaccgacga | gtacaaggtg | ccctcgaaga | agttcaaggt | cctgggcaac | 240 |
| accgatcggc | attctatcaa | gaagaatctc | attggcgctc | tcctgttcga | ctcaggggag | 300 |
| accgctgagg | ctacgaggct | caagaggacc | gcccgcaggc | ggtacacgcg | caggaagaat | 360 |
| cgcatctgct | acctgcagga | gattttctcc | aacgagatgg | cgaaggttga | cgattctttc | 420 |
| ttccacaggc | tggaggagtc | attcctcgtg | gaggaggata | agaagcacga | gcggcatcca | 480 |
| atcttcggca | acattgtcga | cgaggttgcc | taccacgaga | agtaccctac | gatctaccat | 540 |
| ctgcggaaga | agctcgtgga | ctccacagat | aaggcggacc | tccgcctgat | ctacctcgct | 600 |
| ctggcccaca | tgattaagtt | cagggggcat | ttcctgatcg | aggggatctc | caacccggac | 660 |
| aatagcgatg | ttgacaagct | gttcatccag | ctcgtgcaga | cgtacaacca | gctcttcgag | 720 |
| gagaacccca | ttaatgcgtc | aggcgtcgac | gcgaaggcta | tcctgtccgc | tcgcctctcg | 780 |
| aagtctagga | ggctggagaa | cctgatcgcc | cagctgccgg | gcgagaagaa | gaacggcctg | 840 |
| ttcgggaatc | tcatcgctct | cagcctgggg | ctcacgccaa | acttcaagtc | gaatttcgat | 900 |
| ctcgctgagg | acgccaagct | gcagctctcc | aaggacacat | cgacgatga | cctggataac | 960 |
| ctcctggccc | agatcggcga | tcagtacgcg | gacctgttcc | tcgctgccaa | gaatctgtcg | 1020 |
| gacgccatcc | tcctgtctga | tattctcagg | gtgaacaccg | agattacgaa | ggctccgctc | 1080 |
| tcagcctcca | tgatcaagcg | ctacgacgag | caccatcagg | atctgaccct | cctgaaggcg | 1140 |
| ctggtcaggc | agcagctccc | cgagaagtac | aaggagattt | tcttcgatca | gtccaagaac | 1200 |
| ggctacgctg | gtacattga | cggcggggcc | agccaggagg | agttctacaa | gttcatcaag | 1260 |
| ccgattctgg | agaagatgga | cggcacggag | gagctcctgg | tgaagctcaa | tcgcgaggac | 1320 |
| ctcctgagga | agcagcggac | attcgataac | ggcagcatcc | cacaccagat | tcatctcggg | 1380 |
| gagctgcacg | ccatcctgag | gcggcaggag | gacttctacc | ctttcctcaa | ggataaccgc | 1440 |
| gagaagatcg | agaagattct | gaccttccgc | atcccgtact | acgtcggccc | actcgcccgc | 1500 |
| ggcaactccc | gcttcgcttg | gatgacccgc | aagtcagaga | gaccatcac | gccgtggaac | 1560 |
| ttcgaggagg | tggtcgacaa | gggcgctagc | gctcagtcgt | tcatcgagag | gatgacgaat | 1620 |
| ttcgacaaga | acctgccaaa | tgagaaggtg | ctccctaagc | actcgctcct | gtacgagtac | 1680 |
| ttcacagtct | acaacgagct | cactaaggtg | aagtatgtga | ccgagggcat | gaggaagccg | 1740 |
| gctttcctgt | ctggggagca | gaagaaggcc | atcgtggacc | tcctgttcaa | gaccaaccgg | 1800 |
| aaggtcacgg | ttaagcagct | caaggaggac | tacttcaaga | agattgagtg | cttcgattcg | 1860 |
| gtcgagatca | gcggcgttga | ggacaggttc | aacgcctccc | tggggaccta | ccacgatctc | 1920 |

```
ctgaagatca ttaaggataa ggacttcctg acaacgagg agaatgagga tatcctggag    1980
gacattgtgc tgacactcac tctgttcgag gaccgggaga tgatcgagga gcgcctgaag    2040
acttacgccc atctcttcga tgacaaggtc atgaagcagc tcaagaggag gaggtacacc    2100
ggctggggga ggctgagcag gaagctcatc aacggcattc gggacaagca gtccgggaag    2160
acgatcctcg acttcctgaa gagcgatggc ttcgcgaacc gcaatttcat gcagctgatt    2220
cacgatgaca gcctcacatt caaggaggat atccagaagg ctcaggtgag cggccagggg    2280
gactcgctgc acgagcatat cgcgaacctc gctggctcgc agctatcaa gaagggatt     2340
ctgcagaccg tgaaggttgt ggacgagctc gtgaaggtca tgggcaggca aagcctgag     2400
aacatcgtca ttgagatggc ccgcgagaat cagaccacgc agaagggcca agaactca      2460
cgcgagagga tgaagaggat cgaggagggc attaaggagc tggggtccca gatcctcaag    2520
gagcacccgg tggagaacac gcagctgcag aatgagaagc tctacctgta ctacctccag    2580
aatggccgcg atatgtatgt ggaccaggag ctggatatta caggctcag cgattacgac     2640
gtcgatcata tcgttccaca gtcattcctg aaggatgact ccattgacaa caaggtcctc    2700
accaggtcgg acaagaaccg gggcaagtct gataatgttc cttcagagga ggtcgttaag    2760
aagatgaaga actactggcg ccagctcctg aatgccaagc tgatcacgca gcggaagttc    2820
gataacctca caaaggctga gggggcgggc ctctctgagc tggacaaggc gggcttcatc    2880
aagaggcagc tggtcgagac acggcagatc actaagcacg ttgcgcagat tctcgactca    2940
cggatgaaca ctaagtacga tgagaatgac aagctgatcc gcgaggtgaa ggtcatcacc    3000
ctgaagtcaa agctcgtctc cgacttcagg aaggatttcc agttctacaa ggttcgggag    3060
atcaacaatt accaccatgc ccatgacgcg tacctgaacg cggtggtcgg cacagctctg    3120
atcaagaagt acccaaagct ggagtccgag ttcgtgtacg gggactacaa ggtttacgat    3180
gtgcgcaaga tgatcgccaa gtcggagcag gagattggca aggctaccgc caagtacttc    3240
ttctactcta acattatgaa tttcttcaag acagagatca ctctggccaa tggcgagatc    3300
cggaagcgcc ccctcattga gaccaacggc gagacggggg agatcgtgtg ggacaagggc    3360
agggatttcg cgaccgtcag gaaggttctc tccatgccac aagtgaatat cgtcaagaag    3420
acagaggtcc agactggcgg gttctctaag gagtcaattc tgcctaagcg aacagcgac     3480
aagctcatcg cccgcaagaa ggactgggac ccgaagaagt acggcgggtt cgacagcccc    3540
actgtggcct actcggtcct ggttgtggcg aaggttgaga agggcaagtc caagaagctc    3600
aagagcgtga aggagctcct ggggatcacg attatggaga ggtccagctt cgagaagaac    3660
ccgatcgatt tcctggaggc gaagggctac aaggaggtga agaaggacct gatcattaag    3720
ctccccaagt actcactctt cgagctggag aacggcagga gcggatgct ggcttccgct     3780
ggcgagctcc agaaggggaa tgagctcgct ctgccgtcca gtatgtgaa cttcctctac     3840
ctggcctccc actacgagaa gctcaaggc agccccgagg acaacgagca gaagcagctg     3900
ttcgtcgagc agcacaagca ttacctcgac gagatcattg agcagatttc gagttcagc     3960
aagcgcgtga tcctggccga cgcgaatctg gataaggtcc tcagcgcgta caacaagcac    4020
cgcgacaagc caatcaggga gcaggctgag aatatcatcc atctcttcac cctgacgaac    4080
ctcggcgccc ctgctgcttt caagtacttc gacacaacta tcgatcgcaa gaggtacaca    4140
tcgactaagg aggtcctgga cgcgaccctc atccaccagt ctattacagg cctgtacgag    4200
actcggattg atctgtcgca gctcggcggg gataggccca agaagaagag gaaggtcggc    4260
```

| ggctgaccta gg | 4272 |

<210> SEQ ID NO 76
<211> LENGTH: 1007
<212> TYPE: DNA
<213> ORGANISM: Zea mays
<220> FEATURE:
<221> NAME/KEY: misc_feature
<222> LOCATION: (1)..(1007)
<223> OTHER INFORMATION: MzU3.8

<400> SEQUENCE: 76

| gaattccatc taagtatctt ggtaaagcat ggattaattt ggatgctcac ttcaggtcta | 60 |
| tgcagctccg gtgccttgtg attgtgagtt gtgaccgatg ctcatgctat tttgcatttc | 120 |
| tgcgatgtat gatgctagta gatcttcaaa actaacagcg catgccatca tcatccactg | 180 |
| cttgatttta gtctcaccgc tggccaaaaa tgtgatgatg ccagaaacct caactacctt | 240 |
| gaatcaacac gggcccagca gtgtgatgac gacagaaacc aaaaaaaaat gagccaatag | 300 |
| ttcagaagga ggcactatgc agaaactaca tttctgaagg tgactaaaag gtgagcgtag | 360 |
| agtgtactta ctagtagttt agccaccatt acccaaatgc tttcgagctt gtattaagac | 420 |
| ttcctaagct gagcatcatc actgatctgc aggagggtcg cttcgctgcc aagatcaaca | 480 |
| gcaaccatgt ggcggcaaca tccagcattg cacatgggct aaagattgag ctctgtgcca | 540 |
| agtgtgagct gcaaccatct agggatcagc tgagtttatc agtctttcct ttttttcatt | 600 |
| ctggtgaggc atcaagctac tactgcctcg atcggttgga cttggacctg aagcccacat | 660 |
| gtaggatacc agaatggacc gacccaggac gtagtgccac ctcggttgtc acactgcgta | 720 |
| gaagccagct taaaaattta gctttggtga ctcacagcac gaccttactt gaacaggatc | 780 |
| tgttctatag gatcgtactg ttgcatcttt gattaataag aaggcaagta cttaaacctg | 840 |
| gttgatgaga atttgacctg tgggccagag cgtgatttaa cggccaggac tttgccttgg | 900 |
| tgcattgtct ggagctgcag atgatcgttc ttggccaggc ttaatgtctg gctagggtgg | 960 |
| cctacaggct gtttgacagg tttctcaatt ttttttgctct gctgcag | 1007 |

<210> SEQ ID NO 77
<211> LENGTH: 1501
<212> TYPE: DNA
<213> ORGANISM: Zea mays
<220> FEATURE:
<221> NAME/KEY: misc_feature
<222> LOCATION: (1)..(1501)
<223> OTHER INFORMATION: ZmU3

<400> SEQUENCE: 77

| tagttgtcta ttaataaatt ttatcatgtg tagctgactt aaaagacatg taatctagtg | 60 |
| cgcatgcaat ctcagcatgc aaacatatat atttttgaac ttgtgatatt tttatacagt | 120 |
| atatcataat agataaaatt agacaacaca gaactaaaat tataatatta atactaattt | 180 |
| ggaccatacc attaccaaat atgttgaact aaatcattct tgaagtcaat atgctttat | 240 |
| agtttgatat atccatgatt tctgaattcc atctaagtat gttggtaaag catggattaa | 300 |
| tttggatgcc cacttcaggt ctatgcagct ccggtgcctt gtgattgtga gttgtgaccg | 360 |
| atgctcatgc tattctgcat ttctgcgatg tatgtagcta gtagatcttc aaaactaaca | 420 |
| ccgcatgcca tcatcatcca ctgcttgatt ttagtctcac cgctggccaa aaatgtgatg | 480 |
| atgccagaaa cctcaactac cttgaatcaa cacgggccca acagtgtgat gacgacagaa | 540 |
| acaaaaaaaa atgagccaat agttcagaag gaggcactat gcagaaacta catttctgaa | 600 |

```
ggtgactaaa aggtgagcgt agagtgtaat tactagtagt ttagccacca ttacccaaat      660
gctttcgagc ttgtattaag atttcctaag ctgagcatca tcactgatct gcaggccacc      720
ctcgcttcgc tgccaagatc aacagcaacc atgtggcggc aacatccagc attgcacatg      780
ggctaaagat tgagctttgt gcctcgtcta gggatcagct gaggttatca gtctttcctt      840
tttttcatcc aggtgaggca tcaagctact actgcctcga ttggctggac ccgaagccca      900
catgtaggat accagaatgg gccgacccag gacgcagtat gttggccagt cccaccggtt      960
agtgccatct cggttgctca catgcgtaga agccagctta aaaatttagc tttggtaact     1020
cacagcacga ccttacttga acaggatctg ttctatagga tcgtactgtt gcatctttga     1080
ttaataagaa ggcaagtact taaacctggt tgatgagaat ttgacctgtg ggccagagcg     1140
tgattaacgg ccaggactct ttgccttggt gcattgtctg gagctgcaga tgatcgttct     1200
tggccaggct taatgtctgg ctagggtggc ctacaggctg tttgacaggt ctctcaattt     1260
ttttgctctg ctgcaggtga tcatttgact caacgccatt aatgattgac ttttgatct      1320 gtgctgcgtt tgaagaaacc tactccagct agcttttcct cagcatttgc actcaaatta     1380
agagggccag atatcttgct cgcttttgcc atcagtaata aagttttcct taggtgtgat     1440
gcatttgaag gggatttaag gaggttattt ctgtcaccag ctgttttgc ttagtgttgc      1500 t                                                                     1501

<210> SEQ ID NO 78
<211> LENGTH: 761
<212> TYPE: DNA
<213> ORGANISM: Zea mays
<220> FEATURE:
<221> NAME/KEY: misc_feature
<222> LOCATION: (1)..(761)
<223> OTHER INFORMATION: MzU3.8 promoter region

<400> SEQUENCE: 78
gaattccatc taagtatctt ggtaaagcat ggattaattt ggatgctcac ttcaggtcta       60
mtgcagctcc ggtgccttgt gattgtgagt tgtgaccgat gctcatgcta ttttgcattt      120
cmtgcgatgt atgatgctag tagatcttca aaactaacag cgcatgccat catcatccac      180
tgcttgattt tagtctcacc gctggccaaa aatgtgatga tgccagaaac ctcaactacc      240
ttgaatcaac acgggcccag cagtgtgatg acgacagaaa ccaaaaaaaa atgagccaat      300
agttcagaag gaggcactat gcagaaacta catttctgaa ggtgactaaa aggtgagcgt      360
agagtgtact tactagtagt ttagccacca ttacccaaat gctttcgagc ttgtattaag      420
acttcctaag ctgagcatca tcactgatct gcaggagggt cgcttcgctg ccaagatcaa      480
cagcaaccat gtgcggcaa catccagcat tgcacatggg ctaaagattg agctctgtgc      540
caagtgtgag ctgcaaccat ctagggatca gctgagttta tcagtctttc cttttttca      600 ttctggtgag gcatcaagct actactgcct cgatcggttg gacttggacc tgaagcccac      660
atgtaggata ccagaatgga ccgacccagg acgtagtgcc acctcggttg tcacactgcg      720
tagaagccag cttaaaaatt tagctttggt gactcacagc a                         761

<210> SEQ ID NO 79
<211> LENGTH: 764
<212> TYPE: DNA
<213> ORGANISM: Zea mays
<220> FEATURE:
<221> NAME/KEY: misc_feature
<222> LOCATION: (1)..(764)
```

<223> OTHER INFORMATION: ZmU3 promoter region

<400> SEQUENCE: 79

```
gaattccatc taagtatgtt ggtaaagcat ggattaattt ggatgcccac ttcaggtcta    60
tgcagctccg gtgccttgtg attgtgagtt gtgaccgatg ctcatgctat tctgcatttc   120
tgcgatgtat gtagctagta gatcttcaaa actaacaccg catgccatca tcatccactg   180
cttgatttta gtctcaccgc tggccaaaaa tgtgatgatg ccagaaacct caactacctt   240
gaatcaacac gggcccaaca gtgtgatgac gacagaaaca aaaaaaaatg agccaatagt   300
tcagaaggag gcactatgca gaaactacat ttctgaaggt gactaaaagg tgagcgtaga   360
gtgtaattac tagtagttta gccaccatta cccaaatgct ttcgagcttg tattaagatt   420
tcctaagctg agcatcatca ctgatctgca ggccaccctc gcttcgctgc caagatcaac   480
agcaaccatg tggcggcaac atccagcatt gcacatgggc taaagattga gctttgtgcc   540
tcgtctaggg atcagctgag gttatcagtc tttccttttt ttcatccagg tgaggcatca   600
agctactact gcctcgattg gctggacccg aagcccacat gtaggatacc agaatgggcc   660
gacccaggac gcagtatgtt ggccagtccc accggttagt gccatctcgg ttgctcacat   720
gcgtagaagc cagcttaaaa atttagcttt ggtaactcac agca               764
```

<210> SEQ ID NO 80
<211> LENGTH: 34
<212> TYPE: DNA
<213> ORGANISM: Artificial Sequence
<220> FEATURE:
<223> OTHER INFORMATION: Synthetic construct, ob 2297 forward primer

<400> SEQUENCE: 80

```
gcgatcgcca tctaagtatg ttggtaaagc atgg                              34
```

<210> SEQ ID NO 81
<211> LENGTH: 36
<212> TYPE: DNA
<213> ORGANISM: Artificial Sequence
<220> FEATURE:
<223> OTHER INFORMATION: Synthetic construct, ob2299 reverse primer

<400> SEQUENCE: 81

```
tgctgtgagt taccaaagct aaattttttaa gctggc                           36
```

<210> SEQ ID NO 82
<211> LENGTH: 758
<212> TYPE: DNA
<213> ORGANISM: Zea mays
<220> FEATURE:
<221> NAME/KEY: misc_feature
<222> LOCATION: (1)..(758)
<223> OTHER INFORMATION: ZmU3P1

<400> SEQUENCE: 82

```
catctaagta tgttggtaaa gcatggatta atttggatgc ccacttcagg tctatgcagc    60
tccggtgcct tgtgattgtg agttgtgacc gatgctcatg ctattctgca tttctgcgat   120
gtatgtagct agtagatctt caaaactaac accgcatgcc atcatcatcc actgcttgat   180
tttagtctca ccgctggcca aaaatgtgat gatgccagaa acctcaacta ccttgaatca   240
acacgggccc aacagtgtga tgacgacaga aacaaaaaaa aatgagccaa tagttcagaa   300
ggaggcacta tgcagaaact acatttctga aggtgactaa aaggtgagcg tagagtgtaa   360
ttactagtag tttagccacc attacccaaa tgctttcgag cttgtattaa gatttcctaa   420
```

```
gctgagcatc atcactgatc tgcaggccac cctcgcttcg ctgccaagat caacagcaac    480
catgtggcgg caacatccag cattgcacat gggctaaaga ttgagctttg tgcctcgtct    540
agggatcagc tgaggttatc agtctttcct ttttttcatc caggtgaggc atcaagctac    600
tactgcctcg attggctgga cccgaagccc acatgtagga taccagaatg ggccgaccca    660
ggacgcagta tgttggccag tcccaccggt tagtgccatc tcggttgctc acatgcgtag    720
aagccagctt aaaaatttag ctttggtaac tcacagca                            758

<210> SEQ ID NO 83
<211> LENGTH: 33
<212> TYPE: DNA
<213> ORGANISM: Artificial Sequence
<220> FEATURE:
<223> OTHER INFORMATION: Synthetic construct, ob2343 forward primer

<400> SEQUENCE: 83
gcgatcgcag tttagccacc attacccaaa tgc                                 33

<210> SEQ ID NO 84
<211> LENGTH: 398
<212> TYPE: DNA
<213> ORGANISM: Zea mays
<220> FEATURE:
<221> NAME/KEY: misc_feature
<222> LOCATION: (1)..(398)
<223> OTHER INFORMATION: ZmU3P2

<400> SEQUENCE: 84
gcgatcgcag tttagccacc attacccaaa tgctttcgag cttgtattaa gatttcctaa    60
gctgagcatc atcactgatc tgcaggccac cctcgcttcg ctgccaagat caacagcaac    120
catgtggcgg caacatccag cattgcacat gggctaaaga ttgagctttg tgcctcgtct    180
agggatcagc tgaggttatc agtctttcct ttttttcatc caggtgaggc atcaagctac    240
tactgcctcg attggctgga cccgaagccc acatgtagga taccagaatg ggccgaccca    300
ggacgcagta tgttggccag tcccaccggt tagtgccatc tcggttgctc acatgcgtag    360
aagccagctt aaaaatttag ctttggtaac tcacagca                            398

<210> SEQ ID NO 85
<211> LENGTH: 35
<212> TYPE: DNA
<213> ORGANISM: Artificial Sequence
<220> FEATURE:
<223> OTHER INFORMATION: Synthetic construct, ob2351 forward primer

<400> SEQUENCE: 85
cgatttaaat agtttagcca ccattaccca aatgc                               35

<210> SEQ ID NO 86
<211> LENGTH: 308
<212> TYPE: DNA
<213> ORGANISM: Zea mays
<220> FEATURE:
<221> NAME/KEY: misc_feature
<222> LOCATION: (1)..(308)
<223> OTHER INFORMATION: ZmU3.8P

<400> SEQUENCE: 86
gcgatcgcgc ttcgctgcca agatcaacag caaccatgtg gcggcaacat ccagcattgc    60
acatgggcta aagattgagc tctgtgccaa gtgtgagctg caaccatcta gggatcagct    120
```
gagtttatca gtctttcctt tttttcattc tggtgaggca tcaagctact actgcctcga    180
tcggttggac ttggacctga agcccacatg taggatacca gaatggaccg acccaggacg    240
tagtgccacc tcggttgtca cactgcgtag aagccagctt aaaaatttag ctttggtgac    300
tcacagca                                                              308

<210> SEQ ID NO 87
<211> LENGTH: 42
<212> TYPE: DNA
<213> ORGANISM: Streptococcus pyogenes
<220> FEATURE:
<221> NAME/KEY: misc_feature
<222> LOCATION: (1)..(42)
<223> OTHER INFORMATION: Cas9 handle hairpin

<400> SEQUENCE: 87
gttttagagc tagaaatagc aagttaaaat aaggctagtc cg                        42

<210> SEQ ID NO 88
<211> LENGTH: 41
<212> TYPE: DNA
<213> ORGANISM: Streptococcus pyogenes
<220> FEATURE:
<221> NAME/KEY: misc_feature
<222> LOCATION: (1)..(41)
<223> OTHER INFORMATION: S. pyogenes terminator

<400> SEQUENCE: 88
ttatcaactt gaaaaagtgg caccgagtcg gtgcttttt t                          41

<210> SEQ ID NO 89
<211> LENGTH: 37
<212> TYPE: DNA
<213> ORGANISM: Zea mays
<220> FEATURE:
<221> NAME/KEY: misc_feature
<222> LOCATION: (1)..(37)
<223> OTHER INFORMATION: ZmU3T

<400> SEQUENCE: 89
gctctgctgc aggtgatcat ttgactcaac gccatta                              37

<210> SEQ ID NO 90
<211> LENGTH: 120
<212> TYPE: DNA
<213> ORGANISM: Artificial Sequence
<220> FEATURE:
<223> OTHER INFORMATION: Synthetic construct, sgRNA scaffold

<400> SEQUENCE: 90
gttttagagc tagaaatagc aagttaaaat aaggctagtc cgttatcaac ttgaaaaagt     60
ggcaccgagt cggtgctttt tttgctctgc tgcaggtgat catttgactc aacgccatta    120

<210> SEQ ID NO 91
<211> LENGTH: 19
<212> TYPE: DNA
<213> ORGANISM: Artificial Sequence
<220> FEATURE:
<223> OTHER INFORMATION: Synthetic construct, GWDe1a antisense

<400> SEQUENCE: 91
ggcatgaggt gcttacgtc                                                  19

<210> SEQ ID NO 92
<211> LENGTH: 19

```
<212> TYPE: DNA
<213> ORGANISM: Artificial Sequence
<220> FEATURE:
<223> OTHER INFORMATION: Synthetic construct, GWDe24b antisense

<400> SEQUENCE: 92
cataacctga tacttcaac                                                   19

<210> SEQ ID NO 93
<211> LENGTH: 19
<212> TYPE: DNA
<213> ORGANISM: Artificial Sequence
<220> FEATURE:
<223> OTHER INFORMATION: Synthetic construct, GWDe24c sense

<400> SEQUENCE: 93
tctggctcct gctatcagt                                                   19

<210> SEQ ID NO 94
<211> LENGTH: 19
<212> TYPE: DNA
<213> ORGANISM: Artificial Sequence
<220> FEATURE:
<223> OTHER INFORMATION: Synthetic construct, GWDe25a antisense

<400> SEQUENCE: 94
tctgcagaag taggcttga                                                   19

<210> SEQ ID NO 95
<211> LENGTH: 911
<212> TYPE: DNA
<213> ORGANISM: Artificial Sequence
<220> FEATURE:
<223> OTHER INFORMATION: Synthetic construct, ZmU3P1:sgRNA_GWDe24b

<400> SEQUENCE: 95
gcgatcgcca tctaagtatg ttggtaaagc atggattaat ttggatgccc acttcaggtc       60
tatgcagctc cggtgccttg tgattgtgag ttgtgaccga tgctcatgct attctgcatt      120
tctgcgatgt atgtagctag tagatcttca aaactaacac cgcatgccat catcatccac      180
tgcttgattt tagtctcacc gctggccaaa aatgtgatga tgccagaaac ctcaactacc      240
ttgaatcaac acgggcccaa cagtgtgatg acgacagaaa caaaaaaaaa tgagccaata      300
gttcagaagg aggcactatg cagaaactac atttctgaag gtgactaaaa ggtgagcgta      360
gagtgtaatt actagtagtt tagccaccat tacccaaatg ctttcgagct tgtattaaga      420
tttcctaagc tgagcatcat cactgatctg caggccaccc tcgcttcgct gccaagatca      480
acagcaacca tgtggcggca acatccagca ttgcacatgg gctaaagatt gagctttgtg      540
cctcgtctag ggatcagctg aggttatcag tctttccttt ttttcatcca ggtgaggcat      600
caagctacta ctgcctcgat tggctggacc cgaagcccac atgtaggata ccagaatggg      660
ccgacccagg acgcagtatg ttggccagtc ccaccggtta gtgccatctc ggttgctcac      720
atgcgtagaa gccagcttaa aaatttagct ttggtaactc acagcacata acctgatact      780
tcaacgtttt agagctagaa atagcaagtt aaaataaggc tagtccgtta tcaacttgaa      840
aaagtggcac cgagtcggtg cttttttttgc tctgctgcag gtgatcattt gactcaacgc      900
cattatacgt a                                                           911

<210> SEQ ID NO 96
<211> LENGTH: 543
<212> TYPE: DNA
```

<213> ORGANISM: Artificial Sequence
<220> FEATURE:
<223> OTHER INFORMATION: Synthetic construct, ZmU3P2:sgRNA_GWDe24b

<400> SEQUENCE: 96

```
gcgatcgcag tttagccacc attacccaaa tgctttcgag cttgtattaa gatttcctaa      60
gctgagcatc atcactgatc tgcaggccac cctcgcttcg ctgccaagat caacagcaac     120
catgtggcgg caacatccag cattgcacat gggctaaaga ttgagctttg tgcctcgtct     180
agggatcagc tgaggttatc agtctttcct ttttttcatc caggtgaggc atcaagctac     240
tactgcctcg attggctgga cccgaagccc acatgtagga taccagaatg ggccgaccca     300
ggacgcagta tgttggccag tcccaccggt tagtgccatc tcggttgctc acatgcgtag     360
aagccagctt aaaaatttag ctttggtaac tcacagcaca taacctgata cttcaacgtt     420
ttagagctag aaatagcaag ttaaaataag gctagtccgt tatcaacttg aaaaagtggc     480
accgagtcgg tgcttttttt gctctgctgc aggtgatcat ttgactcaac gccattatac     540
gta                                                                    543
```

<210> SEQ ID NO 97
<211> LENGTH: 453
<212> TYPE: DNA
<213> ORGANISM: Artificial Sequence
<220> FEATURE:
<223> OTHER INFORMATION: Synthetic construct, ZmU3.8P:sgRNA_GWDe24b

<400> SEQUENCE: 97

```
gcgatcgcgc ttcgctgcca agatcaacag caaccatgtg gcggcaacat ccagcattgc      60
acatgggcta agattgagc tctgtgccaa gtgtgagctg caaccatcta gggatcagct     120
gagtttatca gtctttcctt tttttcattc tggtgaggca tcaagctact actgcctcga     180
tcggttggac ttggacctga agcccacatg taggatacca gaatggaccg acccaggacg     240
tagtgccacc tcggttgtca cactgcgtag aagccagctt aaaaatttag ctttggtgac     300
tcacagcaca taacctgata cttcaacgtt ttagagctag aaatagcaag ttaaaataag     360
gctagtccgt tatcaacttg aaaaagtggc accgagtcgg tgcttttttt gctctgctgc     420
aggtgatcat ttgactcaac gccattatac gta                                   453
```

<210> SEQ ID NO 98
<211> LENGTH: 543
<212> TYPE: DNA
<213> ORGANISM: Artificial Sequence
<220> FEATURE:
<223> OTHER INFORMATION: Synthetic construct, ZmU3P2:sgRNA_GWDe24c

<400> SEQUENCE: 98

```
gcgatcgcag tttagccacc attacccaaa tgctttcgag cttgtattaa gatttcctaa      60
gctgagcatc atcactgatc tgcaggccac cctcgcttcg ctgccaagat caacagcaac     120
catgtggcgg caacatccag cattgcacat gggctaaaga ttgagctttg tgcctcgtct     180
agggatcagc tgaggttatc agtctttcct ttttttcatc caggtgaggc atcaagctac     240
tactgcctcg attggctgga cccgaagccc acatgtagga taccagaatg ggccgaccca     300
ggacgcagta tgttggccag tcccaccggt tagtgccatc tcggttgctc acatgcgtag     360
aagccagctt aaaaatttag ctttggtaac tcacagcatc tggctcctgc tatcagtgtt     420
ttagagctag aaatagcaag ttaaaataag gctagtccgt tatcaacttg aaaaagtggc     480
accgagtcgg tgcttttttt gctctgctgc aggtgatcat ttgactcaac gccattatac     540
```

```
gta                                                                  543
```

<210> SEQ ID NO 99
<211> LENGTH: 545
<212> TYPE: DNA
<213> ORGANISM: Artificial Sequence
<220> FEATURE:
<223> OTHER INFORMATION: Synthetic construct, ZmU3P2:sgRNA_GWDe24a

<400> SEQUENCE: 99

```
atttaaatag tttagccacc attacccaaa tgctttcgag cttgtattaa gatttcctaa    60
gctgagcatc atcactgatc tgcaggccac cctcgcttcg ctgccaagat caacagcaac   120
catgtggcgg caacatccag cattgcacat gggctaaaga ttgagctttg tgcctcgtct   180
agggatcagc tgaggttatc agtctttcct ttttttcatc caggtgaggc atcaagctac   240
tactgcctcg attggctgga cccgaagccc acatgtagga taccagaatg ggccgaccca   300
ggacgcagta tgttggccag tcccaccggt tagtgccatc tcggttgctc acatgcgtag   360
aagccagctt aaaaatttag ctttggtaac tcacagcatc tgcagaagta ggcttgagtt   420
ttagagctag aaatagcaag ttaaaataag gctagtccgt tatcaacttg aaaaagtggc   480
accgagtcgg tgcttttttt gctctgctgc aggtgatcat ttgactcaac gccattaggc   540
gcgcc                                                               545
```

<210> SEQ ID NO 100
<211> LENGTH: 543
<212> TYPE: DNA
<213> ORGANISM: Artificial Sequence
<220> FEATURE:
<223> OTHER INFORMATION: Synthetic construct, ZmU3P2:sgRNA_GWDe1a

<400> SEQUENCE: 100

```
gcgatcgcag tttagccacc attacccaaa tgctttcgag cttgtattaa gatttcctaa    60
gctgagcatc atcactgatc tgcaggccac cctcgcttcg ctgccaagat caacagcaac   120
catgtggcgg caacatccag cattgcacat gggctaaaga ttgagctttg tgcctcgtct   180
agggatcagc tgaggttatc agtctttcct ttttttcatc caggtgaggc atcaagctac   240
tactgcctcg attggctgga cccgaagccc acatgtagga taccagaatg ggccgaccca   300
ggacgcagta tgttggccag tcccaccggt tagtgccatc tcggttgctc acatgcgtag   360
aagccagctt aaaaatttag ctttggtaac tcacagcagg catgaggtgc ttacgtcgtt   420
ttagagctag aaatagcaag ttaaaataag gctagtccgt tatcaacttg aaaaagtggc   480
accgagtcgg tgcttttttt gctctgctgc aggtgatcat ttgactcaac gccattatac   540
gta                                                                 543
```

<210> SEQ ID NO 101
<211> LENGTH: 23
<212> TYPE: DNA
<213> ORGANISM: Artificial Sequence
<220> FEATURE:
<223> OTHER INFORMATION: Synthetic construct, GWDe24b-F primer

<400> SEQUENCE: 101

```
ctcacagcac ataacctgat act                                            23
```

<210> SEQ ID NO 102
<211> LENGTH: 17
<212> TYPE: DNA

```
<213> ORGANISM: Artificial Sequence
<220> FEATURE:
<223> OTHER INFORMATION: Syntehtic construct, sgRNA-R primer

<400> SEQUENCE: 102
cgactcggtg ccacttt                                                     17

<210> SEQ ID NO 103
<211> LENGTH: 20
<212> TYPE: DNA
<213> ORGANISM: Artificial Sequence
<220> FEATURE:
<223> OTHER INFORMATION: Synthetic construct, ZmCas9-F primer

<400> SEQUENCE: 103
agaatcagac cacgcagaag                                                  20

<210> SEQ ID NO 104
<211> LENGTH: 22
<212> TYPE: DNA
<213> ORGANISM: Artificial Sequence
<220> FEATURE:
<223> OTHER INFORMATION: Synthetic construct, ZmCas9-R primer

<400> SEQUENCE: 104
gctcctggtc cacatacata tc                                               22

<210> SEQ ID NO 105
<211> LENGTH: 21
<212> TYPE: DNA
<213> ORGANISM: Artificial Sequence
<220> FEATURE:
<223> OTHER INFORMATION: Synthetic construct, GWDex23-F primer

<400> SEQUENCE: 105
tgctcttctg aaccgatttg a                                                21

<210> SEQ ID NO 106
<211> LENGTH: 227
<212> TYPE: DNA
<213> ORGANISM: Artificial Sequence
<220> FEATURE:
<223> OTHER INFORMATION: Synthetic construct, Sb4715_1 (WT+INS)_Exon24

<400> SEQUENCE: 106
ttggcaggtt ataagcccag ttgaagtatc aggttatgtg gttgtggttg atgagttact       60
tgctgtccag aacaaatctt atgataaacc aaccatcctt gtggagtagt tggtgtagtt      120
ggtgtatcaa gggagaggaa gaaataccag atggagtagt tggtgtaatt acacctgata     180
tgccagatgt tctgtcccat gtgtcagtcc gagcaaggaa tagcaag                    227

<210> SEQ ID NO 107
<211> LENGTH: 202
<212> TYPE: DNA
<213> ORGANISM: Artificial Sequence
<220> FEATURE:
<223> OTHER INFORMATION: Synthetic construct, Sb4715_2(WT+del)_Exon24

<400> SEQUENCE: 107
ttggcaggtt ataagcccag ttgaagtatc aggttatgtg gttgtggttg atgagttact       60
tgctgtccag aacaaatctt atgataaacc aaccatcctt gtggcaaaga gtgtcaaggg      120
agaggaagaa ataccagatg gagttacacc tgatatgcca gatgttctgt cccatgtgtc     180
agtccgagca aggaatagca ag                                               202
```

<210> SEQ ID NO 108
<211> LENGTH: 1095
<212> TYPE: DNA
<213> ORGANISM: Artificial Sequence
<220> FEATURE:
<223> OTHER INFORMATION: Synthetic construct, meganuclease 4715

<400> SEQUENCE: 108

```
atggcaccga agaagaagcg caaggtgcat atgaatacaa aatataataa agagttctta      60
ctctacttag cagggtttgt agacggtgac ggttccatct ttgccaggat caggccttct     120
caatctcgga agttcaagca ccagctgacg ctcgagttca aggtcactca gaagacacag     180
cgccgttggt tcctcgacaa gctggtggac gagatcggtg tgggttacgt gacggacgat     240
ggcagcgtct ccttttactc tctgtcccag atcaagcctt tgcataattt tttaacacaa     300
ctacaacctt ttctaaaact aaaacaaaaa caagcaagtt tagttttaaa aattattgag     360
caacttccgt cagcaaaaga atccccggac aaattcttag aagtttgtac atgggtggat     420
caaattgcag ctctgaatga ttcgaagacg cgtaaaacaa cttctgaaac cgttcgtgct     480
gtgctagaca gttaccagg atccgtggga ggtctatcgc catctcaggc atccagcgcc     540
gcatcctcgg cttcctcaag cccgggttca gggatctccg aagcactcag agctggagca     600
ggttccggca ctggatacaa caaggaattc ctgctctacc tggcgggctt cgtcgacggg     660
gacggctcca tctatgccac tatcaggccg aggcagtcgg tgaagttcaa gcactttctg     720
gagctcagtt tcgctgtcta tcagaagaca cagcgccgtt ggttcctcga caagctggtg     780
gacgagatcg gtgtgggtta cgtgtatgac agtggcagta cttcccggta cctgctgtcc     840
gagatcaagc tctgcacaa cttcctgacc cagctccagc ccttcctgaa gctcaagcag     900
aagcaggcca acctcgtgct gaagatcatc gagcagctgc cctccgctaa ggaatccccg     960
gacaagttcc tggaggtgtg cacctgggtg gaccagatcg ccgctctgaa cgactccaag    1020
acccgcaaga ccacttccga aaccgtccgc gccgttctag acagtctctc cgagaagaag    1080
aagtcgtccc cctaa                                                      1095
```

<210> SEQ ID NO 109
<211> LENGTH: 1095
<212> TYPE: DNA
<213> ORGANISM: Artificial Sequence
<220> FEATURE:
<223> OTHER INFORMATION: Synthetic construct, meganuclease 4716

<400> SEQUENCE: 109

```
atggcaccga agaagaagcg caaggtgcat atgaatacaa aatataataa agagttctta      60
ctctacttag cagggtttgt agacggtgac ggttccatct atgcctcgat cacgcctagt     120
caacatctga agttcaagca ccagctgagg ctctggttcg atgtcgctca gaagacacag     180
cgccgttggc tcctcgacaa gctggtggac gagatcggtg tgggttacgt gtatgaccag     240
ggcagcgtct cctattaccg tctgtccgag atcaagcctt tgcataattt tttaacacaa     300
ctacaacctt ttctaaaact aaaacaaaaa caagcaaatt tagttttaaa aattattgaa     360
caacttccgt cagcaaaaga atccccggac aaattcttag aagtttgtac atgggtggat     420
caaattgcag ctctgaatga ttcgaagacg cgtaaaacaa cttctgaaac cgttcgtgct     480
gtgctagaca gttaccagg atccgtggga ggtctatcgc catctcaggc atccagcgcc     540
gcatcctcgg cttcctcaag cccgggttca gggatctccg aagcactcag agctggagca     600
```

```
ggttccggca ctggatacaa caaggaattc ctgctctacc tggcgggctt cgtcgacggg    660
gacggctcca tctatgcctg tatccatcct gatcaagcta ataagttcaa gcaccggctg    720
cggctctatt tcattgtcag tcagaagaca cagcgccgtt ggttcctcga caagctggtg    780
gacgagatcg tgtgggtta cgtgtatgac aggggcggcg tctcccatta ccagctgtcc     840
cagatcaagc tctgcacaa cttcctgacc cagctccagc ccttcctgaa gctcaagcag     900
aagcaggcca acctcgtgct gaagatcatc gagcagctgc cctccgccaa ggaatccccg    960
gacaagttcc tggaggtgtg cacctgggtg gaccagatcg ccgctctgaa cgactccaag   1020
acccgcaaga ccacttccga aaccgtccgc gccgttctag acagtctctc cgagaagaag   1080
aagtcgtccc cctaa                                                    1095
```

<210> SEQ ID NO 110
<211> LENGTH: 21
<212> TYPE: DNA
<213> ORGANISM: Artificial Sequence
<220> FEATURE:
<223> OTHER INFORMATION: Synthetic construct, GWDe24a-F

<400> SEQUENCE: 110

```
tgcagaagta ggcttgagtt t                                               21
```

<210> SEQ ID NO 111
<211> LENGTH: 20
<212> TYPE: DNA
<213> ORGANISM: Artificial Sequence
<220> FEATURE:
<223> OTHER INFORMATION: Synthetic construct, 2856 forward primer

<400> SEQUENCE: 111

```
gaagggatt ggagaggaag                                                  20
```

<210> SEQ ID NO 112
<211> LENGTH: 21
<212> TYPE: DNA
<213> ORGANISM: Artificial Sequence
<220> FEATURE:
<223> OTHER INFORMATION: Synthetic construct, 2858 reverse primer

<400> SEQUENCE: 112

```
catgacgttc aaatagcctc a                                               21
```

<210> SEQ ID NO 113
<211> LENGTH: 21
<212> TYPE: DNA
<213> ORGANISM: Artificial Sequence
<220> FEATURE:
<223> OTHER INFORMATION: Synthetic construct, 429 reverse primer

<400> SEQUENCE: 113

```
gcagaagtag gcttgaagga a                                               21
```

<210> SEQ ID NO 114
<211> LENGTH: 77
<212> TYPE: DNA
<213> ORGANISM: Artificial Sequence
<220> FEATURE:
<223> OTHER INFORMATION: Synthetic construct, M32

<400> SEQUENCE: 114

```
gctcctgcta tcagttggca ggttataagc ccggtttgaa gtatcaggtt atgtggttgt     60
ggttgatgag ttacttg                                                   77
```

-continued

<210> SEQ ID NO 115
<211> LENGTH: 74
<212> TYPE: DNA
<213> ORGANISM: Artificial Sequence
<220> FEATURE:
<223> OTHER INFORMATION: Synthetic construct, M33

<400> SEQUENCE: 115
gctcctgcta tcagttggca ggttataagc ccggttagta tcaggttatg tggttgtggt    60
tgatgagtta cttg                                                      74

<210> SEQ ID NO 116
<211> LENGTH: 73
<212> TYPE: DNA
<213> ORGANISM: Artificial Sequence
<220> FEATURE:
<223> OTHER INFORMATION: Synthetic construct, M34

<400> SEQUENCE: 116
gctcctgcta tcagttggca ggttataagc ccggttgtat caggttatgt ggttgtggtt    60
gatgagttac ttg                                                       73

<210> SEQ ID NO 117
<211> LENGTH: 75
<212> TYPE: DNA
<213> ORGANISM: Artificial Sequence
<220> FEATURE:
<223> OTHER INFORMATION: Synthetic construct, M35

<400> SEQUENCE: 117
gctcctgcta tcagttggca ggttataagc ccggtgaagt atcaggttat gtggttgtgg    60
ttgatgagtt acttg                                                     75

<210> SEQ ID NO 118
<211> LENGTH: 39
<212> TYPE: DNA
<213> ORGANISM: Artificial Sequence
<220> FEATURE:
<223> OTHER INFORMATION: Synthetic construct, M36

<400> SEQUENCE: 118
gctcctgcta tcagttggtt gtggttgatg agttacttg                           39

<210> SEQ ID NO 119
<211> LENGTH: 19
<212> TYPE: DNA
<213> ORGANISM: Artificial Sequence
<220> FEATURE:
<223> OTHER INFORMATION: Syntehtic construct, e25a - 48

<400> SEQUENCE: 119
cactctatct gcagatata                                                 19

<210> SEQ ID NO 120
<211> LENGTH: 68
<212> TYPE: DNA
<213> ORGANISM: Artificial Sequence
<220> FEATURE:
<223> OTHER INFORMATION: Synthetic construct, e25a+1

<400> SEQUENCE: 120
cactctatct gaacttgaag gatatgatca gaaactgttt tccttcacag cctacttctg    60
cagatata                                                                      68

<210> SEQ ID NO 121
<211> LENGTH: 7
<212> TYPE: PRT
<213> ORGANISM: Artificial Sequence
<220> FEATURE:
<223> OTHER INFORMATION: Synthetic construct, M32 peptide

<400> SEQUENCE: 121

Trp Gln Val Ile Ser Pro Val
1               5

<210> SEQ ID NO 122
<211> LENGTH: 15
<212> TYPE: PRT
<213> ORGANISM: Artificial Sequence
<220> FEATURE:
<223> OTHER INFORMATION: Synthetic construct, M33 peptide

<400> SEQUENCE: 122

Trp Gln Val Ile Ser Pro Val Ser Ile Arg Leu Cys Gly Cys Gly
1               5                   10                  15

<210> SEQ ID NO 123
<211> LENGTH: 46
<212> TYPE: PRT
<213> ORGANISM: Artificial Sequence
<220> FEATURE:
<223> OTHER INFORMATION: Synthetic construct, M34 peptide

<400> SEQUENCE: 123

Trp Gln Val Ile Ser Pro Val Val Ser Gly Tyr Val Val Val Asp
1               5                   10                  15

Glu Leu Leu Ala Val Gln Asn Lys Ser Tyr Asp Lys Pro Thr Ile Leu
            20                  25                  30

Val Ala Lys Ser Val Lys Gly Glu Glu Glu Ile Pro Asp Gly
        35                  40                  45

<210> SEQ ID NO 124
<211> LENGTH: 47
<212> TYPE: PRT
<213> ORGANISM: Artificial Sequence
<220> FEATURE:
<223> OTHER INFORMATION: Synthetic construct, M35 peptide

<400> SEQUENCE: 124

Trp Gln Val Ile Ser Pro Val Lys Tyr Gln Val Met Trp Leu Trp Leu
1               5                   10                  15

Met Ser Tyr Leu Leu Ser Arg Thr Asn Leu Met Ile Asn Gln Pro Ser
            20                  25                  30

Leu Trp Gln Arg Val Ser Arg Glu Arg Lys Lys Tyr Gln Met Glu
        35                  40                  45

<210> SEQ ID NO 125
<211> LENGTH: 35
<212> TYPE: PRT
<213> ORGANISM: Artificial Sequence
<220> FEATURE:
<223> OTHER INFORMATION: Synthetic construct, M36 peptide

<400> SEQUENCE: 125

Trp Leu Trp Leu Met Ser Tyr Leu Leu Ser Arg Thr Asn Leu Met Ile
1               5                   10                  15

```
Asn Gln Pro Ser Leu Trp Gln Arg Val Ser Arg Glu Arg Lys Lys Tyr
            20                  25                  30

Gln Met Glu
        35

<210> SEQ ID NO 126
<211> LENGTH: 19
<212> TYPE: PRT
<213> ORGANISM: Artificial Sequence
<220> FEATURE:
<223> OTHER INFORMATION: Synthetic construct, M38 peptide

<400> SEQUENCE: 126

Val Leu Phe Ala Thr Cys Phe Asp His Thr Thr Leu Ser Ala Asp Ile
1               5                   10                  15

Thr Tyr Arg

<210> SEQ ID NO 127
<211> LENGTH: 34
<212> TYPE: PRT
<213> ORGANISM: Artificial Sequence
<220> FEATURE:
<223> OTHER INFORMATION: Synthetic construct, M39 peptide

<400> SEQUENCE: 127

Val Leu Phe Ala Thr Cys Phe Asp His Thr Thr Leu Ser Glu Leu Glu
1               5                   10                  15

Gly Tyr Asp Gln Lys Leu Phe Ser Phe Thr Ala Tyr Phe Cys Arg Tyr
            20                  25                  30

Asn Leu

<210> SEQ ID NO 128
<211> LENGTH: 32
<212> TYPE: PRT
<213> ORGANISM: Artificial Sequence
<220> FEATURE:
<223> OTHER INFORMATION: Synthetic construct, NLS 1 protein

<400> SEQUENCE: 128

Met Pro Thr Glu Glu Arg Val Arg Lys Arg Lys Glu Ser Asn Arg Glu
1               5                   10                  15

Ser Ala Arg Arg Ser Arg Tyr Arg Lys Ala Ala His Leu Lys Glu Leu
            20                  25                  30

<210> SEQ ID NO 129
<211> LENGTH: 27
<212> TYPE: PRT
<213> ORGANISM: Artificial Sequence
<220> FEATURE:
<223> OTHER INFORMATION: Synthetic construct, NLS3 protein

<400> SEQUENCE: 129

Met Ala Arg Lys Arg Lys Glu Ser Asn Arg Glu Ser Ala Arg Arg Ser
1               5                   10                  15

Arg Tyr Arg Lys Ala Ala His Leu Lys Glu Leu
            20                  25

<210> SEQ ID NO 130
<211> LENGTH: 24
<212> TYPE: PRT
<213> ORGANISM: Artificial Sequence
<220> FEATURE:
<223> OTHER INFORMATION: Synthetic construct, NLS4 protein
```

<400> SEQUENCE: 130

Met Ala Arg Lys Arg Lys Glu Ser Asn Arg Glu Ser Ala Arg Ser
1               5                   10                  15

Arg Arg Ser Arg Tyr Arg Lys Val
            20

<210> SEQ ID NO 131
<211> LENGTH: 54
<212> TYPE: DNA
<213> ORGANISM: Artificial Sequence
<220> FEATURE:
<223> OTHER INFORMATION: Synthetic construct, M40

<400> SEQUENCE: 131
gaaataccag atggagtagt tgtaattaca cctgatatgc cagatgttct gtct        54

<210> SEQ ID NO 132
<211> LENGTH: 58
<212> TYPE: DNA
<213> ORGANISM: Artificial Sequence
<220> FEATURE:
<223> OTHER INFORMATION: Synthetic construct, M41

<400> SEQUENCE: 132
gaaataccag atggagtagt tggtataaat tacacctgat atgccagatg ttctgtct    58

<210> SEQ ID NO 133
<211> LENGTH: 56
<212> TYPE: DNA
<213> ORGANISM: Artificial Sequence
<220> FEATURE:
<223> OTHER INFORMATION: Synthetic construct, M42

<400> SEQUENCE: 133
gaaataccag atggagtagt tggtgtatta cacctgatat gccagatgtt ctgtct      56

<210> SEQ ID NO 134
<211> LENGTH: 62
<212> TYPE: DNA
<213> ORGANISM: Artificial Sequence
<220> FEATURE:
<223> OTHER INFORMATION: Synthetic construct, M43

<400> SEQUENCE: 134
gaaataccag atggagtagt tggtgtagag taataacacc tgatatgcca gatgttctgt  60
ct                                                                62

<210> SEQ ID NO 135
<211> LENGTH: 33
<212> TYPE: DNA
<213> ORGANISM: Artificial Sequence
<220> FEATURE:
<223> OTHER INFORMATION: Synthetic construct, M44

<400> SEQUENCE: 135
gaaataccag atggagtagt tgtgttctg tct                                33

<210> SEQ ID NO 136
<211> LENGTH: 21
<212> TYPE: DNA
<213> ORGANISM: Artificial Sequence
<220> FEATURE:
<223> OTHER INFORMATION: Synthetic construct, M45

<400> SEQUENCE: 136

```
gaaataccag atgttctgtc t                                              21

<210> SEQ ID NO 137
<211> LENGTH: 67
<212> TYPE: DNA
<213> ORGANISM: Artificial Sequence
<220> FEATURE:
<223> OTHER INFORMATION: Synthetic construct, M46

<400> SEQUENCE: 137
gaaataccag atggagtagt tggtgtatga acacgtaatt acacctgata tgccagatgt    60
tctgtct                                                              67

<210> SEQ ID NO 138
<211> LENGTH: 28
<212> TYPE: DNA
<213> ORGANISM: Artificial Sequence
<220> FEATURE:
<223> OTHER INFORMATION: Synthetic construct, M47

<400> SEQUENCE: 138
gaaataccag atggagtagt tggtgtct                                       28

<210> SEQ ID NO 139
<211> LENGTH: 54
<212> TYPE: DNA
<213> ORGANISM: Artificial Sequence
<220> FEATURE:
<223> OTHER INFORMATION: Synthetic construct, M48

<400> SEQUENCE: 139
gaaataccag atggagtagt tggtgttaca cctgatatgc cagatgttct gtct          54

<210> SEQ ID NO 140
<211> LENGTH: 58
<212> TYPE: DNA
<213> ORGANISM: Artificial Sequence
<220> FEATURE:
<223> OTHER INFORMATION: Synthetic construct, M49

<400> SEQUENCE: 140
gaaataccag atggagtagt tggtgtaaat tacacctgat atgccagatg ttctgtct      58

<210> SEQ ID NO 141
<211> LENGTH: 35
<212> TYPE: DNA
<213> ORGANISM: Artificial Sequence
<220> FEATURE:
<223> OTHER INFORMATION: Synthetic construct, M50

<400> SEQUENCE: 141
gaaataccag atgggatatg ccagatgttc tgtct                               35

<210> SEQ ID NO 142
<211> LENGTH: 76
<212> TYPE: DNA
<213> ORGANISM: Artificial Sequence
<220> FEATURE:
<223> OTHER INFORMATION: Synthetic construct, M51

<400> SEQUENCE: 142
gaaataccag atggagtagt tggtgtctca tgccagatgt gaagaaatta cacctgatat    60
gccagatgtt ctgtct                                                    76
```

<210> SEQ ID NO 143
<211> LENGTH: 36
<212> TYPE: DNA
<213> ORGANISM: Artificial Sequence
<220> FEATURE:
<223> OTHER INFORMATION: Synthetic construct, M52

<400> SEQUENCE: 143
gaaataccag atggagtagt tggtgatgtt ctgtct                          36

<210> SEQ ID NO 144
<211> LENGTH: 49
<212> TYPE: DNA
<213> ORGANISM: Artificial Sequence
<220> FEATURE:
<223> OTHER INFORMATION: Synthetic construct, M53

<400> SEQUENCE: 144
gaaataccag atggagtagt tggtgtcaga tatgccagat gttctgtct            49

<210> SEQ ID NO 145
<211> LENGTH: 167
<212> TYPE: DNA
<213> ORGANISM: Artificial Sequence
<220> FEATURE:
<223> OTHER INFORMATION: Synthetic construct, M54

<400> SEQUENCE: 145
gaaataccag atggagtagt tggtgcattt actcatattt tctgtgattg aatattcttt   60
tccagatgga gtgtcaaggg agaggaagaa ataccagatg gagtgtcaag ggagaggaag  120
aaataccaga tgaaggaaat acacctgata tgccagatgt tctgtct              167

<210> SEQ ID NO 146
<211> LENGTH: 38
<212> TYPE: DNA
<213> ORGANISM: Artificial Sequence
<220> FEATURE:
<223> OTHER INFORMATION: Synthetic construct, M55

<400> SEQUENCE: 146
gaaataccag atggagttac acctgatatg ccagatgt                        38

<210> SEQ ID NO 147
<211> LENGTH: 27
<212> TYPE: PRT
<213> ORGANISM: Artificial Sequence
<220> FEATURE:
<223> OTHER INFORMATION: Synthetic construct, M40 pepide

<400> SEQUENCE: 147

Ile Pro Asp Gly Val Val Val Ile Thr Pro Asp Met Pro Asp Val Leu
1               5                   10                  15

Ser His Val Ser Val Arg Ala Arg Asn Ser Lys
            20                  25

<210> SEQ ID NO 148
<211> LENGTH: 11
<212> TYPE: PRT
<213> ORGANISM: Artificial Sequence
<220> FEATURE:
<223> OTHER INFORMATION: Synthetic construct, M41 peptide

<400> SEQUENCE: 148

Ile Pro Asp Gly Val Val Gly Ile Asn Tyr Thr

```
1               5                  10
```

<210> SEQ ID NO 149
<211> LENGTH: 57
<212> TYPE: PRT
<213> ORGANISM: Artificial Sequence
<220> FEATURE:
<223> OTHER INFORMATION: Synthetic construct, M42 peptide

<400> SEQUENCE: 149

```
Ile Pro Asp Gly Val Val Gly Val Leu His Leu Ile Cys Gln Met Phe
1               5                  10                  15

Cys Leu Met Cys Gln Ser Glu Gln Gly Ile Ala Arg Tyr Cys Leu Arg
            20                  25                  30

Pro Val Leu Thr Thr Pro Leu Tyr Leu Asn Leu Lys Asp Met Ile Arg
        35                  40                  45

Asn Cys Phe Pro Ser Ser Leu Leu Leu
    50                  55
```

<210> SEQ ID NO 150
<211> LENGTH: 9
<212> TYPE: PRT
<213> ORGANISM: Artificial Sequence
<220> FEATURE:
<223> OTHER INFORMATION: Synthetic construct, M43 peptide

<400> SEQUENCE: 150

```
Ile Pro Asp Gly Val Val Gly Val Glu
1               5
```

<210> SEQ ID NO 151
<211> LENGTH: 20
<212> TYPE: PRT
<213> ORGANISM: Artificial Sequence
<220> FEATURE:
<223> OTHER INFORMATION: Synthetic construct, M44 peptide

<400> SEQUENCE: 151

```
Ile Pro Asp Gly Val Val Gly Val Leu Ser His Val Ser Val Arg Ala
1               5                  10                  15

Arg Asn Ser Lys
            20
```

<210> SEQ ID NO 152
<211> LENGTH: 16
<212> TYPE: PRT
<213> ORGANISM: Artificial Sequence
<220> FEATURE:
<223> OTHER INFORMATION: Synthetic construct, M45 peptide

<400> SEQUENCE: 152

```
Ile Pro Asp Val Leu Ser His Val Ser Val Arg Ala Arg Asn Ser Lys
1               5                  10                  15
```

<210> SEQ ID NO 153
<211> LENGTH: 8
<212> TYPE: PRT
<213> ORGANISM: Artificial Sequence
<220> FEATURE:
<223> OTHER INFORMATION: Synthetic construct, M46 peptide

<400> SEQUENCE: 153

```
Ile Pro Asp Gly Val Val Gly Val
1               5
```

<210> SEQ ID NO 154
<211> LENGTH: 16
<212> TYPE: PRT
<213> ORGANISM: Artificial Sequence
<220> FEATURE:
<223> OTHER INFORMATION: Synthetic construct, M47 peptide

<400> SEQUENCE: 154

Ile Pro Asp Gly Val Val Gly Val Ser Cys Val Ser Pro Ser Lys Glu
1               5                   10                  15

<210> SEQ ID NO 155
<211> LENGTH: 27
<212> TYPE: PRT
<213> ORGANISM: Artificial Sequence
<220> FEATURE:
<223> OTHER INFORMATION: Synthetic construct, M48 peptide

<400> SEQUENCE: 155

Ile Pro Asp Gly Val Val Gly Val Thr Pro Asp Met Pro Asp Val Leu
1               5                   10                  15

Ser His Val Ser Val Arg Ala Arg Asn Ser Lys
            20                  25

<210> SEQ ID NO 156
<211> LENGTH: 11
<212> TYPE: PRT
<213> ORGANISM: Artificial Sequence
<220> FEATURE:
<223> OTHER INFORMATION: Synthetic construct, M49 peptide

<400> SEQUENCE: 156

Ile Pro Asp Gly Val Val Gly Val Asn Tyr Thr
1               5                   10

<210> SEQ ID NO 157
<211> LENGTH: 52
<212> TYPE: PRT
<213> ORGANISM: Artificial Sequence
<220> FEATURE:
<223> OTHER INFORMATION: Synthetic construct, M50 peptide

<400> SEQUENCE: 157

Ile Pro Asp Gly Ile Cys Gln Met Phe Cys Leu Met Phe Gln Ser Glu
1               5                   10                  15

Gln Gly Ile Ala Arg Tyr Cys Leu Arg Pro Val Leu Thr Thr Pro Leu
            20                  25                  30

Tyr Leu Asn Leu Lys Asp Met Ile Arg Asn Cys Phe Pro Ser Ser Leu
        35                  40                  45

Leu Leu Gln Ile
    50

<210> SEQ ID NO 158
<211> LENGTH: 12
<212> TYPE: PRT
<213> ORGANISM: Artificial Sequence
<220> FEATURE:
<223> OTHER INFORMATION: Synthetic construct, M51 peptide

<400> SEQUENCE: 158

Ile Pro Asp Gly Val Val Gly Val Ser Cys Gln Met
1               5                   10

<210> SEQ ID NO 159

```
<211> LENGTH: 21
<212> TYPE: PRT
<213> ORGANISM: Artificial Sequence
<220> FEATURE:
<223> OTHER INFORMATION: Synthetic construct, M52 peptide

<400> SEQUENCE: 159

Ile Pro Asp Gly Val Val Gly Asp Val Leu Ser His Val Ser Val Arg
1               5                   10                  15

Ala Arg Asn Ser Lys
            20

<210> SEQ ID NO 160
<211> LENGTH: 23
<212> TYPE: PRT
<213> ORGANISM: Artificial Sequence
<220> FEATURE:
<223> OTHER INFORMATION: Synthetic construct, M53 peptide

<400> SEQUENCE: 160

Ile Pro Asp Gly Val Val Gly Val Arg Tyr Ala Arg Cys Ser Val Ser
1               5                   10                  15

Cys Val Ser Pro Ser Lys Glu
            20

<210> SEQ ID NO 161
<211> LENGTH: 15
<212> TYPE: PRT
<213> ORGANISM: Artificial Sequence
<220> FEATURE:
<223> OTHER INFORMATION: Synthetic construct, M54 peptide

<400> SEQUENCE: 161

Ile Pro Asp Gly Val Val Gly Ala Phe Thr His Ile Phe Cys Asp
1               5                   10                  15

<210> SEQ ID NO 162
<211> LENGTH: 24
<212> TYPE: PRT
<213> ORGANISM: Artificial Sequence
<220> FEATURE:
<223> OTHER INFORMATION: Synthetic construct, M55 peptide

<400> SEQUENCE: 162

Ile Pro Asp Gly Val Thr Pro Asp Met Pro Asp Val Leu Ser His Val
1               5                   10                  15

Ser Val Arg Ala Arg Asn Ser Lys
            20

<210> SEQ ID NO 163
<211> LENGTH: 21
<212> TYPE: DNA
<213> ORGANISM: Artificial Sequence
<220> FEATURE:
<223> OTHER INFORMATION: Synthetic construct, SV40 NLS coding sequence

<400> SEQUENCE: 163
ccgaagaaga agcgcaaggt g                                           21

<210> SEQ ID NO 164
<211> LENGTH: 96
<212> TYPE: DNA
<213> ORGANISM: Artificial Sequence
<220> FEATURE:
<223> OTHER INFORMATION: Synthetic construct, NLS1 coding sequence
```

<400> SEQUENCE: 164

```
atgcctaccg aggaaagagt gaggaaaaga aaggaatcca atagagaatc agccagacgc    60
tccagataca ggaaagccgc tcacctgaaa gaactg                              96
```

<210> SEQ ID NO 165
<211> LENGTH: 81
<212> TYPE: DNA
<213> ORGANISM: Artificial Sequence
<220> FEATURE:
<223> OTHER INFORMATION: Synthetic construct, NLS3 coding sequence

<400> SEQUENCE: 165

```
atggccagga aagaaagga atccaataga gaatcagcca gacgctccag atacaggaaa    60
gccgctcacc tgaaagaact g                                              81
```

<210> SEQ ID NO 166
<211> LENGTH: 72
<212> TYPE: DNA
<213> ORGANISM: Artificial Sequence
<220> FEATURE:
<223> OTHER INFORMATION: Synthetic construct, NLS4 coding sequence

<400> SEQUENCE: 166

```
atggccagga aagaaagga atccaataga gaatcagcca gacgctccag acgctccaga    60
tacaggaagg tg                                                        72
```

<210> SEQ ID NO 167
<211> LENGTH: 30
<212> TYPE: DNA
<213> ORGANISM: Artificial Sequence
<220> FEATURE:
<223> OTHER INFORMATION: Synthetic construct, NLS5 coding sequence

<400> SEQUENCE: 167

```
atgtcggagc gaaagcgacg agagaagctc                                     30
```

<210> SEQ ID NO 168
<211> LENGTH: 39
<212> TYPE: DNA
<213> ORGANISM: Artificial Sequence
<220> FEATURE:
<223> OTHER INFORMATION: Synthetic construct, NLS6 coding sequence

<400> SEQUENCE: 168

```
atgatcagcg aggctcttcg caaagctata gggaagcgg                           39
```

<210> SEQ ID NO 169
<211> LENGTH: 10
<212> TYPE: PRT
<213> ORGANISM: Artificial Sequence
<220> FEATURE:
<223> OTHER INFORMATION: Synthetic construct, NLS5 peptide

<400> SEQUENCE: 169

```
Met Ser Glu Arg Lys Arg Arg Glu Lys Leu
1               5                   10
```

<210> SEQ ID NO 170
<211> LENGTH: 13
<212> TYPE: PRT
<213> ORGANISM: Artificial Sequence
<220> FEATURE:
<223> OTHER INFORMATION: Synthetic construct, NLS6 peptide

<400> SEQUENCE: 170

Met Ile Ser Glu Ala Leu Arg Lys Ala Ile Gly Lys Arg
1               5                   10

<210> SEQ ID NO 171
<211> LENGTH: 204
<212> TYPE: DNA
<213> ORGANISM: Zea mays
<220> FEATURE:
<221> NAME/KEY: misc_feature
<222> LOCATION: (1)..(204)
<223> OTHER INFORMATION: T1_ZmGWDmega-2F-2R

<400> SEQUENCE: 171

| | | |
|---|---|---|
| ggttataagc ccggttgaag tatcaggtta tgtggttgtg gttgatgagt tacttgctgt | 60 |
| ccagaacaaa tcttatgata aaccaaccat ccttgtggca aagagtgtca agggagagga | 120 |
| agaaatacca gatggagtag ttggtgtaat tacacctgat atgccagatg ttctgtctca | 180 |
| tgtgtcagtc cgagcaagga atag | 204 |

<210> SEQ ID NO 172
<211> LENGTH: 560
<212> TYPE: DNA
<213> ORGANISM: Zea mays
<220> FEATURE:
<221> NAME/KEY: misc_feature
<222> LOCATION: (1)..(560)
<223> OTHER INFORMATION: T2_GWDex23-F + ZmGWDmega-2R

<400> SEQUENCE: 172

| | | |
|---|---|---|
| tgctcttctg aaccgatttg atcctgtttt aaggaatgtt gctcacctcg gaaggtaaaa | 60 |
| atgtaaaatc tatgactgct gttgaacttc ttttactttg tatccccagt atatgaacac | 120 |
| ataattctaa ggactacttt gggaactcaa atccccttcg ggattgaagg ggattggaga | 180 |
| ggaagttagt ttattttcac ctcaatcctc tcctatcccg aaggggattt gaggttccca | 240 |
| aagtagccct aaaagtgata ctagtgaccc tctccacaat tttatgcgaa ccacagaaat | 300 |
| taataatata ttctattact ctgcacctga catctggctc ctgctatcag ttggcaggtt | 360 |
| ataagcccgg ttgaagtatc aggttatgtg ttgtggttg atgagttact tgctgtccag | 420 |
| aacaaatctt atgataaacc aaccatcctt gtggcaaaga gtgtcaaggg agaggaagaa | 480 |
| ataccagatg gagtagttgg tgtaattaca cctgatatgc cagatgttct gtctcatgtg | 540 |
| tcagtccgag caaggaatag | 560 |

<210> SEQ ID NO 173
<211> LENGTH: 613
<212> TYPE: DNA
<213> ORGANISM: Zea mays
<220> FEATURE:
<221> NAME/KEY: misc_feature
<222> LOCATION: (1)..(613)
<223> OTHER INFORMATION: T3_2856 + 2858

<400> SEQUENCE: 173

| | | |
|---|---|---|
| gaagggatt ggagaggaag ttagtttatt tcacctcaa tcctctccta tcccgaaggg | 60 |
| gatttgaggt tcccaaagta gccctaaaag tgatactagt gaccctctcc acaatttat | 120 |
| gcgaaccaca gaaattaata atatattcta ttactctgca cctgacatct ggctcctgct | 180 |
| atcagttggc aggttataag cccggttgaa gtatcaggtt atgtggttgt ggttgatgag | 240 |
| ttacttgctg tccagaacaa atcttatgat aaaccaacca ccttgtggc aaagagtgtc | 300 |

```
aagggagagg aagaaatacc agatggagta gttggtgtaa ttacacctga tatgccagat    360
gttctgtctc atgtgtcagt ccgagcaagg aatagcaagg tttatcttca cagctatgtt    420
gcaagatttc ttgaattttt tctcttgtat tgatgttgac atactagctt tttcctaatg    480
aaggtactgt ttgcgacctg ttttgaccac accactctat ctgaacttga aggatatgat    540
cagaaactgt tttccttcaa gcctacttct gcagatataa cctataggta cttgaggcta    600
tttgaacgtc atg                                                      613
```

<210> SEQ ID NO 174
<211> LENGTH: 381
<212> TYPE: DNA
<213> ORGANISM: Zea mays
<220> FEATURE:
<221> NAME/KEY: misc_feature
<222> LOCATION: (1)..(381)
<223> OTHER INFORMATION: T4_ZmGWDmega-2F + 429

<400> SEQUENCE: 174

```
ggttataagc ccggttgaag tatcaggtta tgtggttgtg gttgatgagt tacttgctgt     60
ccagaacaaa tcttatgata aaccaaccat ccttgtggca aagagtgtca agggagagga    120
agaaatacca gatggagtag ttggtgtaat tacacctgat atgccagatg ttctgtctca    180
tgtgtcagtc cgagcaagga atagcaaggt ttatcttcac agctatgttg caagatttct    240
tgaatttttt ctcttgtatt gatgttgaca tactagcttt ttcctaatga aggtactgtt    300
tgcgacctgt tttgaccaca ccactctatc tgaacttgaa ggatatgatc agaaactgtt    360
ttccttcaag cctacttctg c                                              381
```

<210> SEQ ID NO 175
<211> LENGTH: 737
<212> TYPE: DNA
<213> ORGANISM: Zea mays
<220> FEATURE:
<221> NAME/KEY: misc_feature
<222> LOCATION: (1)..(737)
<223> OTHER INFORMATION: T5_GWDex23-F + 429

<400> SEQUENCE: 175

```
tgctcttctg aaccgatttg atcctgtttt aaggaatgtt gctcacctcg aaggtaaaa     60 atgtaaaatc tatgactgct gttgaacttc ttttactttg tatccccagt atatgaacac    120
ataattctaa ggactacttt gggaactcaa atcccccttcg ggattgaagg ggattggaga   180
ggaagttagt ttattttcac ctcaatcctc tcctatcccg aaggggattt gaggttccca    240
aagtagccct aaaagtgata ctagtgaccc tctccacaat tttatgcgaa ccacagaaat    300
taataatata ttctattact ctgcacctga catctggctc ctgctatcag ttggcaggtt    360
ataagcccgg ttgaagtatc aggttatgtg gttgtggttg atgagttact tgctgtccag    420
aacaaatctt atgataaacc aaccatcctt gtggcaaaga gtgtcaaggg agaggaagaa    480
ataccagatg gagtagttgg tgtaattaca cctgatatgc cagatgttct gtctcatgtg    540
tcagtccgag caaggaatag caaggtttat cttcacagct atgttgcaag atttcttgaa    600
ttttttctct tgtattgatg ttgacatact agcttttttcc taatgaaggt actgtttgcg    660
acctgttttg accacaccac tctatctgaa cttgaaggat atgatcagaa actgttttcc    720
ttcaagccta cttctgc                                                   737
```

<210> SEQ ID NO 176
<211> LENGTH: 778

```
<212> TYPE: DNA
<213> ORGANISM: Zea mays
<220> FEATURE:
<221> NAME/KEY: misc_feature
<222> LOCATION: (1)..(778)
<223> OTHER INFORMATION: T6_GWDex23-F + 2858

<400> SEQUENCE: 176
tgctcttctg aaccgatttg atcctgtttt aaggaatgtt gctcacctcg gaaggtaaaa      60
atgtaaaatc tatgactgct gttgaacttc ttttactttg tatccccagt atatgaacac     120
ataattctaa ggactacttt gggaactcaa atccccttcg ggattgaagg ggattggaga     180
ggaagttagt ttattttcac ctcaatcctc tcctatcccg aagggattt gaggttccca      240
aagtagccct aaaagtgata ctagtgaccc tctccacaat tttatgcgaa ccacagaaat     300
taataatata ttctattact ctgcacctga catctggctc ctgctatcag ttggcaggtt     360
ataagcccgg ttgaagtatc aggttatgtg gttgtggttg atgagttact tgctgtccag     420
aacaaatctt atgataaacc aaccatcctt gtggcaaaga gtgtcaaggg agaggaagaa     480
ataccagatg gagtagttgg tgtaattaca cctgatatgc cagatgttct gtctcatgtg     540
tcagtccgag caaggaatag caaggtttat cttcacagct atgttgcaag atttcttgaa     600
tttttctct tgtattgatg ttgacatact agcttttcc taatgaaggt actgtttgcg       660
acctgttttg accacaccac tctatctgaa cttgaaggat atgatcagaa actgttttcc     720
ttcaagccta cttctgcaga tataacctat aggtacttga ggctatttga acgtcatg      778

<210> SEQ ID NO 177
<211> LENGTH: 395
<212> TYPE: DNA
<213> ORGANISM: Zea mays
<220> FEATURE:
<221> NAME/KEY: misc_feature
<222> LOCATION: (1)..(395)
<223> OTHER INFORMATION: T7_2856 + ZmGWDmega-2R

<400> SEQUENCE: 177 gaagggatt ggagaggaag ttagtttatt ttcacctcaa tcctctccta tcccgaaggg       60
gatttgaggt tcccaaagta gccctaaaag tgatactagt gaccctctcc acaatttat     120
gcgaaccaca gaaattaata atatattcta ttactctgca cctgacatct ggctcctgct    180
atcagttggc aggttataag cccggttgaa gtatcaggtt atgtggttgt ggttgatgag    240
ttacttgctg tccagaacaa atcttatgat aaaccaacca tccttgtggc aaagagtgtc    300
aagggagagg aagaaatacc agatggagta gttggtgtaa ttacacctga tatgccagat    360
gttctgtctc atgtgtcagt ccgagcaagg aatag                               395

<210> SEQ ID NO 178
<211> LENGTH: 572
<212> TYPE: DNA
<213> ORGANISM: Zea mays
<220> FEATURE:
<221> NAME/KEY: misc_feature
<222> LOCATION: (1)..(572)
<223> OTHER INFORMATION: T8_2856 + 429

<400> SEQUENCE: 178 gaagggatt ggagaggaag ttagtttatt ttcacctcaa tcctctccta tcccgaaggg       60
gatttgaggt tcccaaagta gccctaaaag tgatactagt gaccctctcc acaatttat     120
gcgaaccaca gaaattaata atatattcta ttactctgca cctgacatct ggctcctgct    180
```
atcagttggc aggttataag cccggttgaa gtatcaggtt atgtggttgt ggttgatgag    240
ttacttgctg tccagaacaa atcttatgat aaaccaacca tccttgtggc aaagagtgtc    300
aagggagagg aagaaatacc agatggagta gttggtgtaa ttacacctga tatgccagat    360
gttctgtctc atgtgtcagt ccgagcaagg aatagcaagg tttatcttca cagctatgtt    420
gcaagatttc ttgaattttt tctcttgtat tgatgttgac atactagctt tttcctaatg    480
aaggtactgt ttgcgacctg ttttgaccac accactctat ctgaacttga aggatatgat    540
cagaaactgt tttccttcaa gcctacttct gc                                   572

<210> SEQ ID NO 179
<211> LENGTH: 381
<212> TYPE: DNA
<213> ORGANISM: Zea mays
<220> FEATURE:
<221> NAME/KEY: misc_feature
<222> LOCATION: (1)..(381)
<223> OTHER INFORMATION: T9_ZmGWDmega-2F+429

<400> SEQUENCE: 179
ggttataagc ccggttgaag tatcaggtta tgtggttgtg gttgatgagt tacttgctgt     60
ccagaacaaa tcttatgata aaccaaccat ccttgtggca aagagtgtca agggagagga    120
agaaatacca gatggagtag ttggtgtaat tacacctgat atgccagatg ttctgtctca    180
tgtgtcagtc cgagcaagga atagcaaggt ttatcttcac agctatgttg caagatttct    240 tgaattttt ctcttgtatt gatgttgaca tactagcttt ttcctaatga aggtactgtt    300
tgcgacctgt tttgaccaca ccactctatc tgaacttgaa ggatatgatc agaaactgtt    360
ttccttcaag cctacttctg c                                              381

<210> SEQ ID NO 180
<211> LENGTH: 422
<212> TYPE: DNA
<213> ORGANISM: Zea mays
<220> FEATURE:
<221> NAME/KEY: misc_feature
<222> LOCATION: (1)..(422)
<223> OTHER INFORMATION: T10_ZmGWDmega-2F+ 2858

<400> SEQUENCE: 180
ggttataagc ccggttgaag tatcaggtta tgtggttgtg gttgatgagt tacttgctgt     60
ccagaacaaa tcttatgata aaccaaccat ccttgtggca aagagtgtca agggagagga    120
agaaatacca gatggagtag ttggtgtaat tacacctgat atgccagatg ttctgtctca    180
tgtgtcagtc cgagcaagga atagcaaggt ttatcttcac agctatgttg caagatttct    240 tgaattttt ctcttgtatt gatgttgaca tactagcttt ttcctaatga aggtactgtt    300
tgcgacctgt tttgaccaca ccactctatc tgaacttgaa ggatatgatc agaaactgtt    360
ttccttcaag cctacttctg cagatataac ctataggtac ttgaggctat tgaacgtca    420 tg                                                                   422

<210> SEQ ID NO 181
<211> LENGTH: 208
<212> TYPE: DNA
<213> ORGANISM: Sorghum bicolor
<220> FEATURE:
<221> NAME/KEY: misc_feature
<222> LOCATION: (1)..(208)
<223> OTHER INFORMATION: T11_SbGWDmega-2F + ZmGWDmega-2R

<400> SEQUENCE: 181

```
ggcaggttat aagcccagtt gaagtatcag gttatgtggt tgtggttgat gagttacttg    60
ctgtccagaa caaatcttat gataaaccaa ccatccttgt ggcaaagagt gtcaagggag   120
aggaagaaat accagatgga gtagttggtg taattacacc tgatatgcca gatgttctgt   180
cccatgtgtc agtccgagca aggaatag                                      208
```

<210> SEQ ID NO 182
<211> LENGTH: 214
<212> TYPE: DNA
<213> ORGANISM: Zea mays
<220> FEATURE:
<221> NAME/KEY: misc_feature
<222> LOCATION: (1)..(214)
<223> OTHER INFORMATION: Zm GWD Exon 24

<400> SEQUENCE: 182

```
ttggcaggtt ataagcccgg ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tgtaattaca cctgatatgc cagatgttct   180
gtctcatgtg tcagtccgag caaggaatag caag                               214
```

<210> SEQ ID NO 183
<211> LENGTH: 214
<212> TYPE: DNA
<213> ORGANISM: Sorghum bicolor
<220> FEATURE:
<221> NAME/KEY: misc_feature
<222> LOCATION: (1)..(214)
<223> OTHER INFORMATION: SbGWD Exon 24

<400> SEQUENCE: 183

```
ttggcaggtt ataagcccag ttgaagtatc aggttatgtg gttgtggttg atgagttact    60
tgctgtccag aacaaatctt atgataaacc aaccatcctt gtggcaaaga gtgtcaaggg   120
agaggaagaa ataccagatg gagtagttgg tgtaattaca cctgatatgc cagatgttct   180
gtcccatgtg tcagtccgag caaggaatag caag                               214
```

<210> SEQ ID NO 184
<211> LENGTH: 234
<212> TYPE: DNA
<213> ORGANISM: Sorghum bicolor
<220> FEATURE:
<221> NAME/KEY: misc_feature
<222> LOCATION: (1)..(234)
<223> OTHER INFORMATION: SbGWD Exon 7

<400> SEQUENCE: 184

```
gaggagtatg aagctgcacg agctgagtta atagaggaat taaatagagg tgtttctttta   60 gagaagcttc gagctaaatt gacaaaaaca cctgaagcac ctgagtcaga tgaacgtaaa   120
tctcctgcat ctcgaatgcc cgttgataaa cttccagagg accttgtaca ggtgcaggct   180
tatataaggt gggagaaagc gggcaagcca aattatcctc ctgagaagca actg          234
```

<210> SEQ ID NO 185
<211> LENGTH: 81
<212> TYPE: PRT
<213> ORGANISM: Zea mays
<220> FEATURE:
<221> NAME/KEY: MISC_FEATURE
<222> LOCATION: (1)..(81)
<223> OTHER INFORMATION: ZmGWD aa1040-1120

<400> SEQUENCE: 185

Pro Thr Ile Leu Val Ala Lys Ser Val Lys Gly Glu Glu Ile Pro
1               5                   10                  15

Asp Gly Val Val Gly Val Ile Thr Pro Asp Met Pro Asp Val Leu Ser
            20                  25                  30

His Val Ser Val Arg Ala Arg Asn Ser Lys Val Leu Phe Ala Thr Cys
        35                  40                  45

Phe Asp His Thr Thr Leu Ser Glu Leu Glu Gly Tyr Asp Gln Lys Leu
    50                  55                  60

Phe Ser Phe Lys Pro Thr Ser Ala Asp Ile Thr Tyr Arg Glu Ile Thr
65                  70                  75                  80

Glu

<210> SEQ ID NO 186
<211> LENGTH: 76
<212> TYPE: DNA
<213> ORGANISM: Zea mays
<220> FEATURE:
<221> NAME/KEY: misc_feature
<222> LOCATION: (1)..(76)
<223> OTHER INFORMATION: WT ZmGWD_nt 81-160 Exon 24

<400> SEQUENCE: 186
gctcctgcta tcagttggca ggttataagc ccggttgaag tatcaggtta tgtggttgtg    60
gttgatgagt tacttg                                                    76

<210> SEQ ID NO 187
<211> LENGTH: 76
<212> TYPE: DNA
<213> ORGANISM: Zea mays
<220> FEATURE:
<221> NAME/KEY: misc_feature
<222> LOCATION: (1)..(76)
<223> OTHER INFORMATION: Wt ZmGWD Exon 24
<220> FEATURE:
<221> NAME/KEY: misc_feature
<222> LOCATION: (1)..(76)
<223> OTHER INFORMATION: Wt ZmGWD Exon 24_nt 81-160

<400> SEQUENCE: 187
gctcctgcta tcagttggca ggttataagc ccggttgaag tatcaggtta tgtggttgtg    60
gttgatgagt tacttg                                                    76

<210> SEQ ID NO 188
<211> LENGTH: 77
<212> TYPE: DNA
<213> ORGANISM: Artificial Sequence
<220> FEATURE:
<223> OTHER INFORMATION: Synthetic construct, M37

<400> SEQUENCE: 188
gctcctgcta tctagttggc aggttataag cccggttgaa gtatcaggtt atgtggttgt    60
ggttgatgag ttacttg                                                   77

<210> SEQ ID NO 189
<211> LENGTH: 67
<212> TYPE: DNA
<213> ORGANISM: Zea mays
<220> FEATURE:
<221> NAME/KEY: misc_feature
<222> LOCATION: (1)..(67)
<223> OTHER INFORMATION: Wt ZmGWD Exon 25

<400> SEQUENCE: 189
cactctatct gaacttgaag gatatgatca gaaactgttt tccttcaagc ctacttctgc    60
agatata    67

<210> SEQ ID NO 190
<211> LENGTH: 47
<212> TYPE: PRT
<213> ORGANISM: Zea mays
<220> FEATURE:
<221> NAME/KEY: MISC_FEATURE
<222> LOCATION: (1)..(47)
<223> OTHER INFORMATION: Wt ZmGWD aa 1011-1057

<400> SEQUENCE: 190

Trp Gln Val Ile Ser Pro Val Glu Val Ser Gly Tyr Val Val Val
1               5                   10                  15

Asp Glu Leu Leu Ala Val Gln Asn Lys Ser Tyr Asp Lys Pro Thr Ile
            20                  25                  30

Leu Val Ala Lys Ser Val Lys Gly Glu Glu Ile Pro Asp Gly
        35                  40                  45

<210> SEQ ID NO 191
<211> LENGTH: 35
<212> TYPE: PRT
<213> ORGANISM: Zea mays
<220> FEATURE:
<221> NAME/KEY: MISC_FEATURE
<222> LOCATION: (1)..(35)
<223> OTHER INFORMATION: Wt ZmGWD aa 1082-1116

<400> SEQUENCE: 191

Val Leu Phe Ala Thr Cys Phe Asp His Thr Thr Leu Ser Glu Leu Glu
1               5                   10                  15

Gly Tyr Asp Gln Lys Leu Phe Ser Phe Lys Pro Thr Ser Ala Asp Ile
            20                  25                  30

Thr Tyr Arg
        35

<210> SEQ ID NO 192
<211> LENGTH: 57
<212> TYPE: DNA
<213> ORGANISM: Zea mays
<220> FEATURE:
<221> NAME/KEY: misc_feature
<222> LOCATION: (1)..(57)
<223> OTHER INFORMATION: Wt ZmGWD_nt 3157-3213

<400> SEQUENCE: 192
gaaataccag atggagtagt tggtgtaatt acacctgata tgccagatgt tctgtct    57

<210> SEQ ID NO 193
<211> LENGTH: 28
<212> TYPE: PRT
<213> ORGANISM: Zea mays
<220> FEATURE:
<221> NAME/KEY: MISC_FEATURE
<222> LOCATION: (1)..(28)
<223> OTHER INFORMATION: Wt ZmGDW_aa1054-1081

<400> SEQUENCE: 193

Ile Pro Asp Gly Val Val Gly Val Ile Thr Pro Asp Met Pro Asp Val
1               5                   10                  15

Leu Ser His Val Ser Val Arg Ala Arg Asn Ser Lys
            20                  25

<210> SEQ ID NO 194
<211> LENGTH: 1045
<212> TYPE: PRT
<213> ORGANISM: Sorghum bicolor
<220> FEATURE:
<221> NAME/KEY: MISC_FEATURE
<222> LOCATION: (1)..(1045)
<223> OTHER INFORMATION: Sb4715_2 WT + del

<400> SEQUENCE: 194

```
Met Thr Gly Phe Ser Ala Ala Ser Ala Ala Ala Ala Glu Arg
1               5                   10                  15

Cys Ala Leu Ala Ile Arg Ala Arg Pro Ala Ala Ser Ser Pro Ala Lys
                20                  25                  30

Arg Gln Gln Gln Ser Ala Ser Leu Arg Arg Ser Gly Gly Gln Arg Arg
            35                  40                  45

Pro Thr Thr Leu Ala Ala Ser Arg Arg Ser Pro Val Val Pro Arg
50                  55                  60

Ala Ile Ala Thr Ser Ala Asp Arg Ala Ser His Asp Leu Val Gly Lys
65                  70                  75                  80

Phe Thr Leu Asp Ser Asn Ser Glu Leu Leu Val Ala Val Asn Pro Ala
                85                  90                  95

Pro Gln Gly Leu Val Ser Val Ile Gly Leu Glu Val Thr Asn Thr Ser
            100                 105                 110

Gly Ser Leu Ile Leu His Trp Gly Val Leu Arg Pro Asp Lys Arg Asp
        115                 120                 125

Trp Ile Leu Pro Ser Arg Gln Pro Asp Gly Thr Thr Val Tyr Lys Asn
130                 135                 140

Arg Ala Leu Arg Thr Pro Phe Val Lys Ser Gly Asp Asn Ser Thr Leu
145                 150                 155                 160

Arg Ile Glu Ile Asp Asp Pro Ala Val Gln Ala Ile Glu Phe Leu Ile
                165                 170                 175

Phe Gly Glu Thr Gln Asn Lys Trp Phe Lys Asn Asn Gly Gln Asn Phe
            180                 185                 190

Gln Ile Gln Leu Gln Ser Ser Arg His Gln Gly Asn Gly Ala Ser Gly
        195                 200                 205

Ala Ser Ser Ser Ala Thr Ser Thr Leu Val Pro Glu Asp Leu Val Gln
210                 215                 220

Ile Gln Ala Tyr Leu Arg Trp Glu Arg Lys Gly Lys Gln Ser Tyr Thr
225                 230                 235                 240

Pro Glu Gln Glu Lys Glu Glu Tyr Glu Ala Ala Arg Ala Glu Leu Ile
                245                 250                 255

Glu Glu Leu Asn Arg Gly Val Ser Leu Glu Lys Leu Arg Ala Lys Leu
            260                 265                 270

Thr Lys Thr Pro Glu Ala Pro Glu Ser Asp Glu Arg Lys Ser Pro Ala
        275                 280                 285

Ser Arg Met Pro Val Asp Lys Leu Pro Glu Asp Leu Val Gln Val Gln
290                 295                 300

Ala Tyr Ile Arg Trp Glu Lys Ala Gly Lys Pro Asn Tyr Pro Pro Glu
305                 310                 315                 320

Lys Gln Leu Val Glu Leu Glu Glu Ala Arg Lys Glu Leu Gln Ala Glu
                325                 330                 335

Val Asp Lys Gly Ile Ser Ile Asp Gln Leu Arg Gln Lys Ile Leu Lys
            340                 345                 350
```

-continued

Gly Asn Ile Glu Ser Lys Val Ser Lys Gln Leu Lys Asn Lys Lys Tyr
            355                 360                 365
Phe Ser Val Glu Arg Ile Gln Arg Lys Lys Arg Asp Ile Met Gln Leu
    370                 375                 380
Leu Ser Lys His Lys His Thr Val Met Glu Glu Lys Val Glu Val Ala
385                 390                 395                 400
Pro Lys Gln Pro Thr Val Leu Asp Leu Phe Thr Lys Ser Leu His Glu
                405                 410                 415
Lys Asp Gly Cys Glu Val Leu Ser Arg Lys Leu Phe Lys Phe Gly Asp
            420                 425                 430
Lys Glu Ile Leu Ala Ile Ser Thr Lys Val Gln Asn Lys Thr Glu Val
        435                 440                 445
His Leu Ala Thr Asn His Thr Glu Pro Leu Ile Leu His Trp Ser Leu
    450                 455                 460
Ala Lys Lys Ala Gly Glu Trp Lys Ala Pro Ser Asn Ile Leu Pro
465                 470                 475                 480
Ser Gly Ser Lys Leu Leu Asp Met Ala Cys Glu Thr Glu Phe Thr Arg
                485                 490                 495
Ser Glu Leu Asp Gly Leu Cys Tyr Gln Val Val Glu Ile Glu Leu Asp
            500                 505                 510
Asp Gly Gly Tyr Lys Gly Met Pro Phe Val Leu Arg Ser Gly Glu Thr
        515                 520                 525
Trp Ile Lys Asn Asn Gly Ser Asp Phe Phe Leu Asp Phe Ser Thr Arg
    530                 535                 540
Asp Thr Arg Asn Ile Lys Leu Lys Asp Asn Gly Asp Ala Gly Lys Gly
545                 550                 555                 560
Thr Ala Lys Ala Leu Leu Glu Arg Ile Ala Asp Leu Glu Glu Asp Ala
                565                 570                 575
Gln Arg Ser Leu Met His Arg Phe Asn Ile Ala Ala Asp Leu Ala Asp
            580                 585                 590
Glu Ala Arg Asp Ala Gly Leu Leu Gly Ile Val Gly Leu Phe Val Trp
        595                 600                 605
Ile Arg Phe Met Ala Thr Arg Gln Leu Thr Trp Asn Lys Asn Tyr Asn
    610                 615                 620
Val Lys Pro Arg Glu Ile Ser Lys Ala Gln Asp Arg Phe Thr Asp Asp
625                 630                 635                 640
Leu Glu Asn Met Tyr Arg Thr Tyr Pro Gln Tyr Arg Glu Ile Leu Arg
                645                 650                 655
Met Ile Met Ala Ala Val Gly Arg Gly Glu Gly Asp Val Gly Gln
            660                 665                 670
Arg Ile Arg Asp Glu Ile Leu Val Ile Gln Arg Asn Asn Asp Cys Lys
        675                 680                 685
Gly Gly Met Met Glu Glu Trp His Gln Lys Leu His Asn Asn Thr Ser
    690                 695                 700
Pro Asp Asp Val Val Ile Cys Gln Ala Leu Ile Asp Tyr Ile Lys Asn
705                 710                 715                 720
Asp Phe Asp Ile Ser Val Tyr Trp Asp Thr Leu Asn Lys Asn Gly Ile
                725                 730                 735
Thr Lys Glu Arg Leu Leu Ser Tyr Asp Arg Ala Ile His Ser Glu Pro
            740                 745                 750
Asn Phe Arg Ser Glu Gln Lys Glu Gly Leu Leu Arg Asp Leu Gly Asn
        755                 760                 765
Tyr Met Arg Ser Leu Lys Ala Val His Ser Gly Ala Asp Leu Glu Ser

```
                770             775             780
Ala Ile Ala Thr Cys Met Gly Tyr Lys Ser Glu Gly Glu Gly Phe Met
785             790             795             800

Val Gly Val Gln Ile Asn Pro Val Lys Gly Leu Pro Ser Gly Phe Pro
            805             810             815

Glu Leu Leu Glu Phe Val Leu Asp His Val Glu Asp Lys Ser Ala Glu
            820             825             830

Pro Leu Leu Glu Gly Leu Leu Glu Ala Arg Val Asp Leu Arg Pro Leu
            835             840             845

Leu Leu Asp Ser Pro Glu Arg Met Lys Asp Leu Ile Phe Leu Asp Ile
            850             855             860

Ala Leu Asp Ser Thr Phe Arg Thr Ala Ile Glu Arg Ser Tyr Glu Glu
865             870             875             880

Leu Asn Asp Ala Ala Pro Glu Lys Ile Met Tyr Phe Ile Ser Leu Val
            885             890             895

Leu Glu Asn Leu Ala Phe Ser Ile Asp Asp Asn Glu Asp Ile Leu Tyr
            900             905             910

Cys Leu Lys Gly Trp Asn Gln Ala Leu Glu Met Ala Lys Gln Lys Asp
            915             920             925

Asp Gln Trp Ala Leu Tyr Ala Lys Ala Phe Leu Asp Arg Ile Arg Leu
            930             935             940

Ala Leu Ala Ser Lys Gly Glu Gln Tyr His Asn Met Met Gln Pro Ser
945             950             955             960

Ala Glu Tyr Leu Gly Ser Leu Leu Ser Ile Asp Lys Trp Ala Val Asn
            965             970             975

Ile Phe Thr Glu Glu Ile Ile Arg Gly Gly Ser Ala Ala Thr Leu Ser
            980             985             990

Ala Leu Leu Asn Arg Phe Asp Pro Val Leu Arg Asn Val Ala Asn Leu
            995            1000            1005

Gly Ser Trp Gln Val Ile Ser Pro Val Glu Val Ser Gly Tyr Val
        1010            1015            1020

Val Val Val Asp Glu Leu Leu Ala Val Gln Asn Lys Ser Tyr Asp
        1025            1030            1035

Lys Pro Thr Ile Leu Val Glu
        1040            1045

<210> SEQ ID NO 195
<211> LENGTH: 840
<212> TYPE: PRT
<213> ORGANISM: Sorghum bicolor
<220> FEATURE:
<221> NAME/KEY: MISC_FEATURE
<222> LOCATION: (1)..(840)
<223> OTHER INFORMATION: Sb4715_2 WT + del

<400> SEQUENCE: 195

Val Val Pro Arg Ala Ile Ala Thr Ser Ala Asp Arg Ala Ser His Asp
1               5               10              15

Leu Val Gly Lys Phe Thr Leu Asp Ser Asn Ser Glu Leu Leu Val Ala
            20              25              30

Val Asn Pro Ala Pro Gln Gly Leu Val Ser Val Ile Gly Leu Glu Val
            35              40              45

Thr Asn Thr Ser Gly Ser Leu Ile Leu His Trp Gly Val Leu Arg Pro
            50              55              60

Asp Lys Arg Asp Trp Ile Leu Pro Ser Arg Gln Pro Asp Gly Thr Thr
65              70              75              80
```

```
Val Tyr Lys Asn Arg Ala Leu Arg Thr Pro Phe Val Lys Ser Gly Asp
                85                  90                  95

Asn Ser Thr Leu Arg Ile Glu Ile Asp Asp Pro Ala Val Gln Ala Ile
            100                 105                 110

Glu Phe Leu Ile Phe Gly Glu Thr Gln Asn Lys Trp Phe Lys Asn Asn
        115                 120                 125

Gly Gln Asn Phe Gln Ile Gln Leu Gln Ser Ser Arg His Gln Gly Asn
    130                 135                 140

Gly Ala Ser Gly Ala Ser Ser Ala Thr Ser Thr Leu Val Pro Glu
145                 150                 155                 160

Asp Leu Val Gln Ile Gln Ala Tyr Leu Arg Trp Glu Arg Lys Gly Lys
                165                 170                 175

Gln Ser Tyr Thr Pro Glu Gln Glu Lys Glu Glu Tyr Glu Ala Ala Arg
            180                 185                 190

Ala Glu Leu Ile Glu Glu Leu Asn Arg Gly Val Ser Leu Glu Lys Leu
        195                 200                 205

Arg Ala Lys Leu Thr Lys Thr Pro Glu Ala Pro Glu Ser Asp Glu Arg
    210                 215                 220

Lys Ser Pro Ala Ser Arg Met Pro Val Asp Lys Leu Pro Glu Asp Leu
225                 230                 235                 240

Val Gln Val Gln Ala Tyr Ile Arg Trp Glu Lys Ala Gly Lys Pro Asn
                245                 250                 255

Tyr Pro Pro Glu Lys Gln Leu Val Glu Leu Glu Ala Arg Lys Glu
            260                 265                 270

Leu Gln Ala Glu Val Asp Lys Gly Ile Ser Ile Asp Gln Leu Arg Gln
        275                 280                 285

Lys Ile Leu Lys Gly Asn Ile Glu Ser Lys Val Ser Lys Gln Leu Lys
    290                 295                 300

Asn Lys Lys Tyr Phe Ser Val Glu Arg Ile Gln Arg Lys Arg Asp
305                 310                 315                 320

Ile Met Gln Leu Leu Ser Lys His Lys His Thr Val Met Glu Glu Lys
                325                 330                 335

Val Glu Val Ala Pro Lys Gln Pro Thr Val Leu Asp Leu Phe Thr Lys
            340                 345                 350

Ser Leu His Glu Lys Asp Gly Cys Glu Val Leu Ser Arg Lys Leu Phe
        355                 360                 365

Lys Phe Gly Asp Lys Glu Ile Leu Ala Ile Ser Thr Lys Val Gln Asn
    370                 375                 380

Lys Thr Glu Val His Leu Ala Thr Asn His Thr Glu Pro Leu Ile Leu
385                 390                 395                 400

His Trp Ser Leu Ala Lys Lys Ala Gly Glu Trp Lys Ala Pro Pro Ser
                405                 410                 415

Asn Ile Leu Pro Ser Gly Ser Lys Leu Leu Asp Met Ala Cys Glu Thr
            420                 425                 430

Glu Phe Thr Arg Ser Glu Leu Asp Gly Leu Cys Tyr Gln Val Val Glu
        435                 440                 445

Ile Glu Leu Asp Asp Gly Gly Tyr Lys Gly Met Pro Phe Val Leu Arg
    450                 455                 460

Ser Gly Glu Thr Trp Ile Lys Asn Asn Gly Ser Asp Phe Phe Leu Asp
465                 470                 475                 480

Phe Ser Thr Arg Asp Thr Arg Asn Ile Lys Leu Lys Asp Asn Gly Asp
                485                 490                 495
```

```
Ala Gly Lys Gly Thr Ala Lys Ala Leu Leu Glu Arg Ile Ala Asp Leu
            500                 505                 510
Glu Glu Asp Ala Gln Arg Ser Leu Met His Arg Phe Asn Ile Ala Ala
            515                 520                 525
Asp Leu Ala Asp Glu Ala Arg Asp Ala Gly Leu Leu Gly Ile Val Gly
            530                 535                 540
Leu Phe Val Trp Ile Arg Phe Met Ala Thr Arg Gln Leu Thr Trp Asn
545                 550                 555                 560
Lys Asn Tyr Asn Val Lys Pro Arg Glu Ile Ser Lys Ala Gln Asp Arg
                565                 570                 575
Phe Thr Asp Asp Leu Glu Asn Met Tyr Arg Thr Tyr Pro Gln Tyr Arg
                580                 585                 590
Glu Ile Leu Arg Met Ile Met Ala Ala Val Gly Arg Gly Gly Glu Gly
                595                 600                 605
Asp Val Gly Gln Arg Ile Arg Asp Glu Ile Leu Val Ile Gln Arg Asn
                610                 615                 620
Asn Asp Cys Lys Gly Gly Met Met Glu Glu Trp His Gln Lys Leu His
625                 630                 635                 640
Asn Asn Thr Ser Pro Asp Asp Val Val Ile Cys Gln Ala Leu Ile Asp
                645                 650                 655
Tyr Ile Lys Asn Asp Phe Asp Ile Ser Val Tyr Trp Asp Thr Leu Asn
                660                 665                 670
Lys Asn Gly Ile Thr Lys Glu Arg Leu Leu Ser Tyr Asp Arg Ala Ile
                675                 680                 685
His Ser Glu Pro Asn Phe Arg Ser Glu Gln Lys Glu Gly Leu Leu Arg
            690                 695                 700
Asp Leu Gly Asn Tyr Met Arg Ser Leu Lys Ala Val His Ser Gly Ala
705                 710                 715                 720
Asp Leu Glu Ser Ala Ile Ala Thr Cys Met Gly Tyr Lys Ser Glu Gly
                725                 730                 735
Glu Gly Phe Met Val Gly Val Gln Ile Asn Pro Val Lys Gly Leu Pro
                740                 745                 750
Ser Gly Phe Pro Glu Leu Leu Glu Phe Val Leu Asp His Val Glu Asp
                755                 760                 765
Lys Ser Ala Glu Pro Leu Leu Glu Gly Leu Leu Glu Ala Arg Val Asp
                770                 775                 780
Leu Arg Pro Leu Leu Leu Asp Ser Pro Glu Arg Met Lys Asp Leu Ile
785                 790                 795                 800
Phe Leu Asp Ile Ala Leu Asp Ser Thr Phe Arg Thr Ala Ile Glu Arg
                805                 810                 815
Ser Tyr Glu Glu Leu Asn Asp Ala Ala Pro Glu Lys Ile Met Tyr Phe
                820                 825                 830
Ile Ser Leu Val Leu Glu Asn Leu
            835                 840

<210> SEQ ID NO 196
<211> LENGTH: 7
<212> TYPE: PRT
<213> ORGANISM: Artificial Sequence
<220> FEATURE:
<223> OTHER INFORMATION: Synthetic construct, SV NLS peptide

<400> SEQUENCE: 196

Pro Lys Lys Lys Arg Lys Val
1               5
```